(12) United States Patent
Attie

(10) Patent No.: US 10,487,144 B2
(45) Date of Patent: Nov. 26, 2019

(54) METHODS FOR TREATING ULCERS IN A HEMOGLOBINOPATHY ANEMIA WITH A SOLUBLE ACTRIIB POLYPEPTIDE

(71) Applicant: Acceleron Pharma Inc., Cambridge, MA (US)

(72) Inventor: Kenneth M. Attie, Boston, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 15/818,974

(22) Filed: Nov. 21, 2017

(65) Prior Publication Data

US 2018/0194834 A1 Jul. 12, 2018

Related U.S. Application Data

(62) Division of application No. 14/738,761, filed on Jun. 12, 2015, now Pat. No. 9,850,298.

(60) Provisional application No. 62/045,808, filed on Sep. 4, 2014, provisional application No. 62/012,109, filed on Jun. 13, 2014.

(51) Int. Cl.
| | |
|---|---|
| *A61P 17/02* | (2006.01) |
| *A61P 7/06* | (2006.01) |
| *A61K 38/00* | (2006.01) |
| *C07K 16/22* | (2006.01) |
| *A61K 38/17* | (2006.01) |
| *A61K 38/45* | (2006.01) |
| *C07K 14/475* | (2006.01) |
| *A61K 38/18* | (2006.01) |
| *A61K 45/06* | (2006.01) |
| *A61K 31/16* | (2006.01) |
| *A61K 31/17* | (2006.01) |
| *A61K 31/4196* | (2006.01) |
| *A61K 31/4422* | (2006.01) |
| *C07K 14/71* | (2006.01) |
| *C07K 14/715* | (2006.01) |

(52) U.S. Cl.
CPC .............. *C07K 16/22* (2013.01); *A61K 31/16* (2013.01); *A61K 31/17* (2013.01); *A61K 31/4196* (2013.01); *A61K 31/4422* (2013.01); *A61K 38/179* (2013.01); *A61K 38/1793* (2013.01); *A61K 38/1816* (2013.01); *A61K 38/45* (2013.01); *A61K 45/06* (2013.01); *A61P 7/06* (2018.01); *A61P 17/02* (2018.01); *C07K 14/475* (2013.01); *A61K 38/00* (2013.01); *C07K 14/71* (2013.01); *C07K 14/715* (2013.01); *C07K 2317/31* (2013.01); *C07K 2317/52* (2013.01); *C07K 2317/76* (2013.01); *C07K 2319/30* (2013.01); *C07K 2319/31* (2013.01); *C07K 2319/32* (2013.01); *C12Y 207/1103* (2013.01)

(58) Field of Classification Search
None
See application file for complete search history.

(56) References Cited

U.S. PATENT DOCUMENTS

| | | | |
|---|---|---|---|
| 4,973,577 | A | 11/1990 | Vale, Jr. et al. |
| 5,118,667 | A | 6/1992 | Adams et al. |
| 5,658,876 | A | 8/1997 | Crowley et al. |
| 5,703,043 | A | 12/1997 | Celeste et al. |
| 5,760,010 | A | 6/1998 | Klein |
| 5,808,007 | A | 9/1998 | Lee et al. |
| 5,824,637 | A | 10/1998 | Crowley et al. |
| 5,847,078 | A | 12/1998 | Eto et al. |
| 5,885,794 | A | 3/1999 | Mathews et al. |
| 6,004,780 | A | 12/1999 | Soppet et al. |
| 6,034,062 | A | 3/2000 | Thies et al. |
| 6,093,547 | A | 7/2000 | Jin et al. |
| 6,132,988 | A | 10/2000 | Sugino et al. |
| 6,162,896 | A | 12/2000 | Mathews et al. |
| 6,287,816 | B1 | 9/2001 | Rosen et al. |
| 6,440,930 | B1 | 8/2002 | Rinella, Jr. |
| 6,451,334 | B2 | 9/2002 | Perrine |
| 6,537,966 | B1 | 3/2003 | Duan et al. |
| 6,548,634 | B1 | 4/2003 | Ballinger et al. |
| 6,599,876 | B2 | 7/2003 | Kojima |
| 6,605,699 | B1 | 8/2003 | Ni et al. |
| 6,632,180 | B1 | 10/2003 | Laragh |
| 6,656,475 | B1 | 12/2003 | Lee et al. |
| 6,656,708 | B1 | 12/2003 | Yu et al. |
| 6,692,925 | B1 | 2/2004 | Miyazono et al. |
| 6,696,260 | B1 | 2/2004 | Lee et al. |

(Continued)

FOREIGN PATENT DOCUMENTS

| | | |
|---|---|---|
| EP | 1174149 A1 | 1/2002 |
| EP | 1 362 062 A1 | 11/2003 |

(Continued)

OTHER PUBLICATIONS

Abaza, M.S.I., et al., Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin, Journal of Protein Chemistry, 11(5):433-444 (1992).

(Continued)

*Primary Examiner* — Zachary C Howard
(74) *Attorney, Agent, or Firm* — White & Case LLP

(57) ABSTRACT

The present disclosure provides compositions and methods for treating or preventing ulcers in subjects having low red blood cell levels and/or hemoglobin levels (e.g. anemia). In some embodiments, the compositions of the disclosure may be used to treat or prevent ulcers associated with anemia.

21 Claims, 49 Drawing Sheets
(27 of 49 Drawing Sheet(s) Filed in Color)
Specification includes a Sequence Listing.

(56) References Cited

U.S. PATENT DOCUMENTS

| | | |
|---|---|---|
| 6,777,205 B1 | 8/2004 | Carcagno et al. |
| 6,835,544 B2 | 12/2004 | Mathews et al. |
| 6,891,082 B2 | 5/2005 | Lee et al. |
| 6,914,128 B1 | 7/2005 | Salfeld et al. |
| 7,052,873 B2 | 5/2006 | Tsuchiya |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Dunham et al. |
| 7,560,441 B2 | 7/2009 | Wolfman et al. |
| 7,612,041 B2 | 11/2009 | Knopf et al. |
| 7,709,605 B2 | 5/2010 | Knopf et al. |
| 7,842,663 B2 | 11/2010 | Knopf et al. |
| 7,893,213 B2 | 2/2011 | Mathews et al. |
| 7,919,296 B2 | 4/2011 | Wang |
| 7,947,646 B2 | 5/2011 | Sun et al. |
| 7,951,771 B2 | 5/2011 | Knopf et al. |
| 7,968,091 B2 | 6/2011 | Woolf et al. |
| 7,988,973 B2 | 8/2011 | Sherman |
| 8,007,809 B2 | 8/2011 | Sherman |
| 8,058,229 B2 | 11/2011 | Seehra et al. |
| 8,067,360 B2 | 11/2011 | Knopf et al. |
| 8,110,355 B2 | 2/2012 | Atwood et al. |
| 8,124,830 B2 | 2/2012 | Lee et al. |
| 8,128,933 B2 | 3/2012 | Knopf et al. |
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,236 B2 | 10/2012 | Lin et al. |
| 8,293,881 B2 | 10/2012 | Seehra et al. |
| 8,309,082 B2 | 11/2012 | Han et al. |
| 8,343,933 B2 | 1/2013 | Knopf et al. |
| 8,388,968 B2 | 3/2013 | Berger et al. |
| 8,410,043 B2 | 4/2013 | Sun et al. |
| 8,435,948 B2 | 5/2013 | Zaidi et al. |
| 8,501,678 B2 | 8/2013 | Sun et al. |
| 8,629,109 B2 | 1/2014 | Knopf et al. |
| 8,637,023 B2 | 1/2014 | Lin et al. |
| 8,703,694 B2 | 4/2014 | Knopf et al. |
| 8,703,927 B2 | 4/2014 | Seehra et al. |
| 8,716,459 B2 | 5/2014 | Sun et al. |
| 8,753,627 B2 | 6/2014 | Han et al. |
| 8,765,663 B2 | 7/2014 | Seehra et al. |
| 8,822,411 B2 | 9/2014 | Lee et al. |
| 8,865,168 B2 | 10/2014 | Lin et al. |
| 8,895,016 B2 | 11/2014 | Sherman et al. |
| 8,987,203 B2 | 3/2015 | Van Leeuwen et al. |
| 8,999,917 B2 | 4/2015 | Sun et al. |
| 2001/0039036 A1 | 11/2001 | Mathews et al. |
| 2003/0082233 A1 | 5/2003 | Lyons et al. |
| 2003/0083251 A1 | 5/2003 | Westenfelder |
| 2003/0118556 A1 | 6/2003 | Kaspar et al. |
| 2003/0144203 A1 | 7/2003 | Bowen |
| 2003/0215913 A1 | 11/2003 | Alvarez et al. |
| 2003/0224397 A1 | 12/2003 | Lowman et al. |
| 2003/0224501 A1 | 12/2003 | Young et al. |
| 2004/0033511 A1 | 2/2004 | Pfizenmaier et al. |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0239070 A1 | 10/2005 | Von Knebel-Doeberitz et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0172347 A1 | 8/2006 | Mellor et al. |
| 2006/0178316 A1 | 8/2006 | Klaus et al. |
| 2006/0210657 A1 | 9/2006 | Chou |
| 2007/0048830 A1 | 3/2007 | Gilbert et al. |
| 2007/0117130 A1 | 5/2007 | Han et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2008/0261879 A1 | 10/2008 | Melton et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2009/0202471 A1 | 8/2009 | Khetani et al. |
| 2009/0226460 A1 | 9/2009 | Phillips et al. |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0113327 A1 | 5/2010 | Van Leeuwen et al. |
| 2010/0125099 A1 | 5/2010 | 't Hoen et al. |
| 2010/0183624 A1 | 7/2010 | Seehra et al. |
| 2010/0272734 A1 | 10/2010 | Berger et al. |
| 2010/0279409 A1 | 11/2010 | Robson et al. |
| 2010/0316644 A1 | 12/2010 | Seehra et al. |
| 2011/0038831 A1 | 2/2011 | Seehra et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2011/0286998 A1 | 11/2011 | Gregory et al. |
| 2011/0293526 A1 | 12/2011 | Plikus et al. |
| 2012/0003218 A1 | 1/2012 | Sherman et al. |
| 2012/0015877 A1 | 1/2012 | Seehra et al. |
| 2012/0052067 A1 | 3/2012 | Sherman |
| 2012/0148588 A1 | 6/2012 | Knopf et al. |
| 2012/0156204 A1 | 6/2012 | Seehra et al. |
| 2012/0232021 A1 | 9/2012 | Martini et al. |
| 2012/0237521 A1 | 9/2012 | Berger et al. |
| 2013/0004489 A1 | 1/2013 | Knopf et al. |
| 2013/0065299 A1 | 3/2013 | Knopf et al. |
| 2013/0071393 A1 | 3/2013 | Seehra et al. |
| 2013/0108650 A1 | 5/2013 | Kumar et al. |
| 2013/0177559 A1 | 7/2013 | Seehra et al. |
| 2013/0184210 A1 | 7/2013 | Knopf et al. |
| 2013/0195862 A1 | 8/2013 | Knopf et al. |
| 2013/0225484 A1 | 8/2013 | Sun et al. |
| 2013/0243743 A1 | 9/2013 | Seehra et al. |
| 2013/0244324 A1 | 9/2013 | Seehra et al. |
| 2013/0287765 A1 | 10/2013 | Zaidi et al. |
| 2013/0303068 A1 | 11/2013 | Hall et al. |
| 2013/0344091 A1 | 12/2013 | Berger et al. |
| 2014/0056902 A1 | 2/2014 | Shimizu et al. |
| 2014/0079700 A1 | 3/2014 | Knopf et al. |
| 2014/0194355 A1 | 7/2014 | Sun et al. |
| 2014/0220033 A1 | 8/2014 | Han et al. |
| 2014/0303068 A1 | 10/2014 | OHehir et al. |
| 2014/0348827 A1 | 11/2014 | Sun et al. |
| 2015/0072927 A1 | 3/2015 | Lin et al. |
| 2015/0086556 A1 | 3/2015 | Han et al. |
| 2015/0111248 A1 | 4/2015 | Bancel et al. |
| 2015/0139983 A1 | 5/2015 | Karni et al. |
| 2015/0231206 A1 | 8/2015 | Sun et al. |
| 2015/0258120 A1 | 9/2015 | Zarnitsyn et al. |
| 2015/0266950 A1 | 9/2015 | Sung et al. |
| 2015/0276766 A1 | 10/2015 | Sung et al. |

(56) References Cited

U.S. PATENT DOCUMENTS

| | | |
|---|---|---|
| 2015/0283209 A1 | 10/2015 | Sung et al. |
| 2015/0328249 A1 | 11/2015 | Gonzalez-Cadavid et al. |
| 2016/0185836 A1 | 6/2016 | Kumar et al. |

FOREIGN PATENT DOCUMENTS

| | | |
|---|---|---|
| EP | 1 416 273 A1 | 5/2004 |
| JP | 2007099764 | 4/2007 |
| WO | WO-9204913 A1 | 4/1992 |
| WO | WO-1992/20793 A1 | 11/1992 |
| WO | WO-93/00432 A1 | 1/1993 |
| WO | WO-1994/15965 A1 | 7/1994 |
| WO | WO-94/26893 A1 | 11/1994 |
| WO | WO-1995/10611 A1 | 4/1995 |
| WO | WO-1995/29685 A1 | 11/1995 |
| WO | WO-1997/023613 A2 | 7/1997 |
| WO | WO-9818926 A1 | 5/1998 |
| WO | WO-1999/06559 A1 | 2/1999 |
| WO | WO-00/18932 A2 | 4/2000 |
| WO | WO-0025807 A1 | 5/2000 |
| WO | WO-2000/43781 A2 | 7/2000 |
| WO | WO-00/62809 A1 | 10/2000 |
| WO | WO-0136001 A2 | 5/2001 |
| WO | WO-0143763 A1 | 6/2001 |
| WO | WO-01/87329 A1 | 11/2001 |
| WO | WO-2002/10214 A2 | 2/2002 |
| WO | WO-0222680 A2 | 3/2002 |
| WO | WO-02/40501 A2 | 5/2002 |
| WO | WO-2002/036152 A1 | 5/2002 |
| WO | WO-02/43759 A2 | 6/2002 |
| WO | WO-02074340 A1 | 9/2002 |
| WO | WO-2002085306 A2 | 10/2002 |
| WO | WO-02/094852 A2 | 11/2002 |
| WO | WO-2003/006057 A1 | 1/2003 |
| WO | WO-2003/053219 A2 | 7/2003 |
| WO | WO-2003/072808 A1 | 9/2003 |
| WO | WO-2003087162 A2 | 10/2003 |
| WO | WO-2004/012759 A2 | 2/2004 |
| WO | WO-2004016639 A1 | 2/2004 |
| WO | WO-2004/039948 | 5/2004 |
| WO | WO-2004/069237 A1 | 8/2004 |
| WO | WO-2004/092199 A2 | 10/2004 |
| WO | WO-2004086953 A2 | 10/2004 |
| WO | WO-2004/108157 A2 | 12/2004 |
| WO | WO-2005003158 A2 | 1/2005 |
| WO | WO-2005009460 A2 | 2/2005 |
| WO | WO-2005014650 A2 | 2/2005 |
| WO | WO-2005028517 A2 | 3/2005 |
| WO | WO-2005/053795 A2 | 6/2005 |
| WO | WO-2005070967 A2 | 8/2005 |
| WO | WO-2005/094871 A2 | 10/2005 |
| WO | WO-2005/097825 A2 | 10/2005 |
| WO | WO-2005/113590 A2 | 12/2005 |
| WO | WO-2006002387 A2 | 1/2006 |
| WO | WO-2006012627 A2 | 2/2006 |
| WO | WO-2006020884 A2 | 2/2006 |
| WO | WO-2006039400 A2 | 4/2006 |
| WO | WO-2006083183 A1 | 8/2006 |
| WO | WO-2006088972 | 8/2006 |
| WO | WO-2006115274 A1 | 11/2006 |
| WO | WO-2007/024715 A2 | 3/2007 |
| WO | WO-2007038703 A2 | 4/2007 |
| WO | WO-2007053775 A1 | 5/2007 |
| WO | WO-2007062188 | 5/2007 |
| WO | WO-2007067616 A2 | 6/2007 |
| WO | WO-2007071023 A1 | 6/2007 |
| WO | WO-2007075702 A2 | 7/2007 |
| WO | WO-2007076127 A2 | 7/2007 |
| WO | WO-2007087505 A2 | 8/2007 |
| WO | WO-2007101060 A2 | 9/2007 |
| WO | WO-2008/015383 A2 | 2/2008 |
| WO | WO-2008031061 | 3/2008 |
| WO | WO-2008/060139 A1 | 5/2008 |
| WO | WO-2008/072723 A1 | 6/2008 |
| WO | WO-2008/073292 A2 | 6/2008 |
| WO | WO-2008/076437 A2 | 6/2008 |
| WO | WO-2008076437 A2 | 6/2008 |
| WO | WO-2008094708 A2 | 8/2008 |
| WO | WO-2008097541 A2 | 8/2008 |
| WO | WO-2008100384 A2 | 8/2008 |
| WO | WO-2008/109167 A2 | 9/2008 |
| WO | WO-2008151078 A1 | 12/2008 |
| WO | WO-2009009059 A1 | 1/2009 |
| WO | WO-2009019504 A1 | 2/2009 |
| WO | WO-2009019505 A2 | 2/2009 |
| WO | WO-2009021747 A2 | 2/2009 |
| WO | WO-2009025651 A1 | 2/2009 |
| WO | WO-2009/058346 A1 | 5/2009 |
| WO | WO-2009/070243 | 6/2009 |
| WO | WO-2009114180 A1 | 9/2009 |
| WO | WO-2009137075 A1 | 11/2009 |
| WO | WO-2009137613 A2 | 11/2009 |
| WO | WO-2009/158015 A2 | 12/2009 |
| WO | WO-2009/158033 A2 | 12/2009 |
| WO | WO-2009158015 A2 | 12/2009 |
| WO | WO-2009158025 A2 | 12/2009 |
| WO | WO-2010/019261 A1 | 2/2010 |
| WO | WO-2010083034 A1 | 7/2010 |
| WO | WO-2010/125003 A1 | 11/2010 |
| WO | WO-2010144452 A1 | 12/2010 |
| WO | WO-2010151426 A1 | 12/2010 |
| WO | WO-2011/020045 A1 | 2/2011 |
| WO | WO-2011020045 | 2/2011 |
| WO | WO-2011031901 A1 | 3/2011 |
| WO | WO-2012/027065 A2 | 3/2012 |
| WO | WO-2012027065 A2 | 3/2012 |
| WO | WO-2013006437 A1 | 1/2013 |
| WO | WO-2013059347 A1 | 4/2013 |
| WO | WO-2013/063536 A1 | 5/2013 |
| WO | WO-2013063536 A1 | 5/2013 |
| WO | WO-2014064292 A1 | 5/2014 |
| WO | WO-2014066487 A2 | 5/2014 |
| WO | WO-2014152940 A1 | 9/2014 |
| WO | WO-2015017576 A1 | 2/2015 |
| WO | WO-2015022658 A2 | 2/2015 |
| WO | WO-2015089575 A1 | 6/2015 |
| WO | WO-2015108972 A1 | 7/2015 |
| WO | WO-2015111008 A2 | 7/2015 |
| WO | WO-2015/161220 A1 | 10/2015 |
| WO | WO-2015152183 A1 | 10/2015 |
| WO | WO-2015162590 A1 | 10/2015 |
| WO | WO-2015192127 A2 | 12/2015 |
| WO | WO-2016/183280 A1 | 11/2016 |

OTHER PUBLICATIONS

Abbiotec: ACTR-IIA Antibody: Catalog No. 251303 (http://www.abbiotec.com) Jun. 3, 2010.
Abrahams, B. And Ertel, S., 'Acceleron Pharma at Wells Fargo Healthcare Conference—Final', published on Jun 17, 2014, Fair Disclosure Wire (Quarterly Earnings Reports), Accession No. 32U3101469591FDW.
ACCELERON, 'Corporate Overview', considered published in Jul. 31, 2014, Retrieved on Aug. 20, 2015 from the Internet.
Acceleron Pharma Presents Positive Phase 1 Results Demonstrating ACE-011 Increases Markers of Bone Formation, Acceleron Pharma, pp. 1-2, Downloaded from the Internet on Feb. 17, 2009.
ACCELERON, 'Review of the Data Presented at the European Hematology Association 19th Annual Meeting', considered published on Jun 16, 2014; Retrieved on Aug. 20, 2015 from the Internet.
Acta Cryst.,"The CCP4 suite: programs for protein crystallography: Collaborative Computational Project, No. 4," D50: 760-763 (1994).
Akel, S., et al "Neutralization of Autocrine Transforming Growth Factor -β," Stem Cells, 21:557-567 (2003).
Akpan, I., et al., "The effects of a soluble activin type IIB receptor on obesity and insulin sensitivity," International Journal of Obesity, 33(11):1265-1273 (2009).
Allendorph, G.P., et al., "Structure of the ternary signaling complex of a TGF-β superfamily member," PNAS, 103(20):7643-7648 (2006).
Anonymous "Learning about Thalassemia" <http://www.genome.gov/10001221> Accessed on Internet Jul. 9, 2013. Published Jun. 28, 2010.

(56) References Cited

OTHER PUBLICATIONS

Anonymous "Iron and Thalassemia," Accessed on the Internet Apr. 3, 2014 at <sickle.bwh.harvard.edu/thaliron.html>. Published Aug. 25, 1997.
Anti-ActRIIA Antibodies: Commercial Monoclonal Antibodies Against Human ActRIIA (2010).
"Anti-human Activin RIIA Antibody," R&D Systems, Catalog No. AF340 (Feb. 14, 2006).
Antibodies for ACVR2A: http://www.genecards.org/cgi-bin/carddisp.pl?gene=Acvr2a (Jun. 8, 2010).
Attie et al., "A Single Ascending-Dose Study of Muscle Regulator Ace-031 in Healthy volunteers," Muscle & Nerve, pp. 1-8 (2012).
Banks, G.B., et al., "The Value of Mammalian Models for Duchenne Muscular Dystrophy in Developing Therapeutic Strategies," Current Topics in Developmental Biology, 84:431-453 (2008).
Benny Klimek, Margaret E., et al., "Acute inhibition of myostatin-family proteins preserves skeletal muscle in mouse models of cancer cachexia," Biochemical and Biophysical Research Communications, 391:1548-1554 (2010).
Berenson, J.R., "Multiple Myeloma," Multiple Myeloma: Plasma Cell Disorders: Merck Manual Professional, pp. 1-5, Jul. 2008.
Bhatia et al., Protein Glycosylation: Implications for In Vivo Functions and Therapeutic Applications. Advances in Biochemical Engineering/Biotechnology, vol. 64: 155-201 (1998).
Binkert, et al., "Cloning, sequence analysis and expression of a cDNA encoding a novel insulin-like growth factor binding protein (IGFBP-2)," The EMBO Journal, 8(9):2497-2502 (1989).
BIOSIS Accession No. 2015:276893 & PIGA, A. et al., 'ACE-536 Increases Hemoglobin and Decreases Transfusion Burden and Serum Ferritin in Adults with Beta-Thalassemia: Preliminary Results from a Phase 2 Study', Blood, vol. 124(21): p. 53 (2014).
Bodey, B., et al., "Failure of Cancer Vaccines: The Significant Limitations of this Approach to Immunotherapy," Anticancer Research, 20:2665-2676 (2000).
Bogdanovich, S., et al., "Functional improvement of dystrophic muscle by myostatin blockade," Nature, 420:418-421 (2002).
Bork, "Powers and Pitfalls in Sequence Analysis: The 70% Hurdle," Genome Research, 10:398-400 (2000).
Bowie, J.U., et al., "Deciphering the Message in Protein Sequences: Tolerance to Amino Acid Substitutions," Science, 257:1306-1310 (1990).
Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).
Burdette, J.E., et al., "Activin A mediates growth inhibition and cell cycle arest through Smads in human breast cancer cells," Cancer Research, 65(17):7968-7975 (2005).
Burgess, W.H., et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," J. Cell Biol., 111:2129-2138 (1990).
Cadena, S.M., et al., "Administration of a Soluble Activin Type IIB Receptor Promotes Skeletal Muscle Growth Independent of Fiber Type," Journal of Applied Physiology, 109:635-642 (2010).
Cannon and Nedergaard, "Neither fat nor flesh," Nature, vol. 454(7207): 947-948 (2008).
Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).
Carrancio, S. et al. "An activin receptor IIA ligand trap promotes erythropoiesis resulting in a rapid induction of red blood cells and haemoglobin," British Journal of Haematology, vol. 165: 870-882 (2014).
Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2010).
Centrella, M., et al., "Activin-A Binding and Biochemical Effects in Osteoblast-Enriched Cultures from Fetal-Rat Parietal Bone," Molecular and Cellular Biology, 11(1):250-58 (1991).
Chamberlain, R.S., et al., "Innovations and strategies for the development of anticancer vaccines," Expert Opinion on Pharmacotherapy, 1(4):603-614 (2000).
Chamow, S.M., and Ashkenazi, A., "Immunoadhesins: Principles and Applications," TIBTECH, 14: 52-60 (1996).
Chantry et al., "Inhibiting Activin-A Signaling Stimulates Bone Formation and Prevents Cancer-Induced Bone Destruction in Vivo," Journal of Bone and Mineral Research, vol. 25(12): 2357-2370 (2010).
Chang, Sam S., "Exploring the Effects of Luteinizing Hormone-Releasing Hormone Agonist Therapy on Bone Health: Implications in the Management of Prostate Cancer," Urology, vol. 52: 29-35 (2003).
Chapman, B., et al., "Effect of intron A from human cytomegalovirus (Towne) immediate-early gene on heterologous expression in mammalian cells," Nucleic Acids Research, 19(14):3979-3986 (1991).
Chardès et al., "Efficient amplification and direct sequencing of mouse variable regions from any immunoglobulin gene family," FEBS Lett. vol. 452(3): 386-394 (1999).
Chavez-Tapia, Norberto-C et al., "Insulin sensitizers in treatment of nonalcoholic fatty liver disease: Systematic review," World Journal of Gastroenterology, vol. 12(48): 7826-7831 (2006).
Chen, Y.G., et al. "Regulation of Cell Proliferation, Apoptosis, and Carcinogenesis by Activin," Exp. Biol. Med., 227(2):75-87 (2002).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Cirillo, M., et al., "Hematocrit, Blood Pressure, and Hypertension. The Gubbio Population Study," Hypertension, 20(3):319-326 (1992).
Coerver, K.A., et al., "Activin Signaling through Activin Receptor Type II Causes the Cachexia-Like Symptoms in Inhibin-Deficient Mice," Molecular Endocrinology, 10(5):534-543 (1996).
Collins, C.D., "Multidisciplinary Symposium: Haematological Malignancies," Cancer Imaging 5:S119-S126 (2005).
Colman, P.M., et al., "Effects of amino acid sequence changes on antibody-antigen interactions," Research of Immunology, 145(1):33-36 (1994).
Crisan et al., "A Reservoir of Brown Adipocyte Progenitors in Human Skeletal Muscle," Stem Cells, vol. 26(9): 2425-2433 (2008).
Daluiski, A., et al., "Bone Morphogenetic Protein-3 is a Negative Regulator of Bone Density," Nature Genetics, 27:84-88 (2001).
Database Geneseq [Online], "Variable heavy chain of anti-human Fas ligand antibody NOK-4," retrieved from EBI accession No. GSP:AAW00829; Database accession No. AAW00829; abstract, sequence (1997).
Database Geneseq [Online]; "Monoclonal antibody 10D4 HMGB1 Vkappa domain," retrieved from EBI accession No. GSP:ADY85028, Database accession No. GSP:ADY85028; abstract, sequence (2005).
Datta-Mannan et al, Addendum to "An Engineered Human Follistatin Variant: Insights into the Pharmacokinetic and Pharmacodynamic Relationships of a Novel Molecule with Broad Therapeutic Potential," The Journal of Pharmacology and Experimental Therapeutics, 1 page (2013).
Deal, C., "Potential New Drug Targets for Osteoporosis," Nature Clinical Practice, 5(1):20-27 (2009).
Deconinck, N., et al., "Pathophysiology of Duchenne Muscular Dystrophy: Current Hypotheses," Pediatr. Neurol., 36:1-7 (2007).
Delogu, G., Et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).
del Re, E., et al., "Reconstitution and Analysis of Soluble Inhibin and Activin Receptor Complexes in a Cell-free System," The Journal of Biological Chemistry, 279(51):53126-53135 (2004).
DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).

(56) References Cited

OTHER PUBLICATIONS

Donald et al., "SDR: a database of predicted specificity-determining residues in proteins," Nucleic Acids Research, vol. 37: D191-D194 (2009).

Donaldson, C.J., et al., "Activin and inhibin binding to the soluble extracellular domain of activin receptor II," Endocrinology, 140(4):1760-1766 (1999).

Donaldson, C.J., et al., "Molecular Cloning and Binding Properties of the Human Type II Activin Receptor," Biochemical and Biophysical Research Communications, 184(1):310-316 (1992).

Donaldson et al., GenBank: BAA06548.1: activin typeII A receptor precursor [Homo sapiens] (1992).

Dussiot et al., "An activin receptor IIA ligand trap corrects ineffective erythropoiesis in B-thalassemia," Nature Medicine, vol. 20: 398-407 (2014).

Ear et al., "RAP-011 Efficiently Rescues Erthropoiesis in Zebrafish Models of Diamond Blackfan Anemia," 55 ASH Annual Meeting and Exposition. Abstract #3702 (2013).

Elliot et al., "Enhancement of therapeutic protein in vivo activities through glycoengineering," Nature Biotechnology, vol. 21: 414-421 (2003).

Eijken, M., "The Activin A-Follistatin System: Potent Regulator of Human Extracellular Matrix Mineralization," The FASEB Journal, 21:2949-2960 (2007).

Fafioffe, A., et al.,"Activin and inhibin receptor gene expression in the ewe pituitary throughout the oestrous cycle," Journal of Endocrinology, 182:55-68 (2004).

Fajardo, R. J., et al., "Treatment with a Soluble Receptor for Activin Improves Bone Mass and Structure in the Axial and Appendicular Skeleton of Female Cynomolgus Macaques (Macaca fascicularis)," Bone, 46:64-71 (2010).

Fan, et al., "Preclinical evaluation of Hematide, a novel erythropoiesis stimulating agent, for the treatment of anemia," Experimental Hematology; vol. 34(10): 1303-1311 (2006).

Farmer, Stephen R., "Brown Fat and Skeletal Muscle: Unlikely Cousins?," Cell, vol. 134(5): 726-727 (2008).

Ferguson et al., "The role of effectors of the activin signalling pathway, activin receptors IIA and IIB, and Smad2, in patterning of tooth development," Development, vol. 128: 4605-4613 (2001).

Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).

Foucar, K., Myelodysplastic/ Myeloproliferative Neoplasms, Am J Clin Pathol, vol. 132: 281-289 (2009).

Frankel et al., "Characterization of diphtheria fusion proteins targeted to the human interleukin-3 receptor," Protein Engineering, vol. 13(8): 575-581 (2000).

Frigon, N.L., et al, "Regulation of Globin Gene Expression in Human K562 Cells by Recombinant Activin A," Blood, 79(3):765-772 (1992).

Fuller, K., et al., "Activin A is an Essential Cofactor for Osteoclast Induction," Biochemical and Biophysical Research Communications, 268:2-7 (2000).

Funaba, M., et al., "Expression and Localization of Activin Receptors During Endochondral Bone Development," European Journal of Endocrinology, 144:63-71 (2001).

Gaddy-Kurten, D., et al., "Inhibin Suppresses and Activin Stimulates Osteoblastogenesis and Osteoclastogenesis in Murine Bone Marrow Cultures," Endocrinology, 143(1):74-83 (2002).

Gamer, L.W., et al., "BMP-3 is a Novel Inhibitor of Both Activin and BMP-4 Signaling in Xenopus Embryos," Developmental Biology, 285:156-168 (2005).

Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).

GenBank NM_001106, Homo sapiens activin A receptor, type IIB (ACVR2B), mRNA, http://www.ncbi.nlm.nih.gov/entrez/viewer.fcgi?db=nucleotide&val=116734707 (Downloaded on Jan. 29, 2007).

GenBank NP_001607.1, Activin A Type II receptor precursor [Homo sapiens], http://www.ncbi.nlm.nih.gov/protein/4501897?sat=34 &satkey=10571517 (Apr. 22, 2005); downloaded Nov. 24, 2015).

Gilbert, R., et al., "Prolonged dystrophin expression and functional correction of mdx mouse muscle following gene transfer with a helper-dependent (gutted) adenovirencoding murine dystrophin," Human Molecular Genetics, 12(11):1287-1299 (2003).

Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998). (D4 PE2-003).

Gonzalez-Cadavid, N.F., et al., "Organization of the human myostatin gene and expression in healthy men and HIV-infected men with muscle wasting," PNAS, 95:14938-14943 (1998).

Gray, P.C., et al., "Identification of a binding site on the type II activin receptor for activin and inhibin", Journal of Biological Chemistry, 275(5):3206-3212 (2000). (D2 PE2-003).

Greenspan, N.S., et al., "Defining epitopes: It's not as easy as it seems," Nature Biotechnology, 17:936-937 (1999).

Greenwald, J., et al., "The BMP7/ActRII Extracellular Domain Complex Provides New Insights into the Cooperative Nature of Receptor Assembly," Molecular Cell, 11:605-617 (2003).

Greenwald, J., et al., "Three-finger toxin fold for the extracellular ligand-binding domain of the type II activin receptor serine kinase," Nature Structural Biology, 6(1):18-22 (1999).

Greenwald, et al., "Characterization of the Extracellular Ligand-Binding Domain of the Type II Activin Receptor," Biochemistry, 37(47):16711-16718 (1998).

Gregoriadis, G., et al., "Polysialic acids: potential in drug delivery," FEBS, 315(3):271-276 (1993).

Gupta, V., et al., "Transforming Growth Factor-b Superfamily: Evaluation as Breast Cancer Biomarkers and Preventive Agents," Current Cancer Drug Targets, 4:165-182 (2004).

Guo, et al., Protein Tolerance to Random Amino Acid Change. Proc. Natl. Acad. Sci. USA, 101(25):9205-9210 (Jun. 22, 2004). Epub Jun. 14, 2004.

Gura, T., "Cancer Models: Systems for Identifying New Drugs are Often Faulty," Science, 278(5340):1041-1042 (1997).

Haidar et al., "Paraspinal extramedullary hematopoiesis in patients with thalassemia intermedia," Eur Spine J., vol. 19: 871-878 (2010).

Hamrick et al., "Bone Mineral Content and Density in the Humerus of Adult Myostatin-Deficient Mice," Calcified Tissue International, 71:63-68 (2002).

Hamrick, "Increased Bone Mineral Density in the Femora of GDF8 Knockout Mice," The Anatomical Record, Part A 272A:388-391 (2003).

Hamrick, M.W., et al., "Femoral Morphology and Cross-sectional Geometry of Adult Myostatin-deficient Mice," Bone, 27(3):343-349 (2000).

Harrison, C.A., et al., "An Activin Mutant with Disrupted ALK4 Binding Blocks Signaling via Type II Receptors," The Journal of Biological Chemistry, 279(27):28036-28044 (2004).

Harrison, C.A., et al., "Antagonists of activin signaling: mechanisms and potential biological applications," Trends in Endocrinology and Metabolism, 16(2):73-78 (2005).

Harousseau et al., "Multiple Myeloma," American Society of Hematology, pp. 237-256 (2004).

Hashimoto, M., et al., "Functional Regulation of Osteoblastic Cells by the Interaction of Activin-A with Follistatin," The Journal of Biological Chemistry, 267(7):4999-5004 (1992).

Hemmati-Brivanlou, A., et al., "A truncated activin receptor inhibits mesoderm induction and formation of axial structures in Xenopus embryos," Nature, 359:609-614 (1992).

Herbert, W.J., et al., The Dictionary of Immunology, Academic Press, 3rd Edition, London, pp. 58-59 (1985).

Hilden, K., et al., "Expression of Type II Activin Receptor Genes During Differentiation of Human K562 Cells and cDNA Cloning of the Human Type IIB Activin Receptor," Blood, 83(8):2163-2170 (1994).

Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).

(56) References Cited

OTHER PUBLICATIONS

Holm et al., "Functional mapping and single chain construction of the anti-cytokeratin 8 monoclonal antibody TS1," ScienceDirect; Molecular Immunology, vol. 44(6): 1075-1084 (2007).
Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).
"Human Activin RIIA Antibody," R&D Systems, Tools for Cell Biology Research, Catalog No. MAB340 (Mar. 22, 2011).
Ikenoue, T., et al., "Inhibitory Effects of Activin-A on Osteoblast Differentiation During Cultures of Fetal Rat Calvarial Cells," Journal of Cellular Biochemistry, 75:206-214 (1999).
"The Illustrated Guide to Bone Marrow Diagnosis Second Edition," Ed. By G. Kumar. Originally published 2003.
Ito et al., "Presence of activin signal transduction in normal ovarian cells and epithelial ovarian carcinoma," British Journal of Cancer, vol. 82(8): 1415-1420 (2000).
International Search Report, PCT/US2010/000080, dated Mar. 29, 2010.
Kaiser, J., "First Pass at Cancer Genome Reveals Complex Landscape," Science, 313:1370 (2006).
Kanemitsu, Fusae, "Clinical application of subforms of creatine kinase MM and macro creatine kinases," Journal of Chromatography, vol. 526: 423-438 (1990).
Kaspar, B.K., et al., "Retrograde Viral Delivery of IGF-1 Prolongs Survival in a Mouse ALS Model," Science, 301:839-842 (2003).
Keutmann et al, "The Role of Follistatin Domains in Follistatin Biological Action," Molecular Endocrinology, Jan.; 18(1) pp. 228-240 (2003).
Kim, K.T., et al., "ACE-011, a Soluble Activin Receptor Type IIa IgG-Fc Fusion Protein, Increases Hemoglobin and Hematocrit Levels in Postmenopausal Healthy Women," Blood, 112(11):1316 (2008).
Knight, "Roles of Inhibins, Activins, and Follistatin in the Female Reproductive System," Frontiers in Neuroendocrinology, 17:476-509 (1996).
Koncarevic et al., "A Soluble Activin Receptor Type IIB Prevents the Effects of Angdrogen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF-b Family in Osteoclastogenesis Induced by RANKL," Cellular Signaling, 14:31-36 (2002).
Krag, T.O.B., et al., "Heregulin ameliorates the dystrophic phenotype in mdx mice," PNAS, 101(38):13856-13860 (2004).
Krneta, J., et al., "Dissociation of Angiogenesis and Tumorigenesis in Follistatin- and Activin-Expressing Tumors," Cancer Research, 66(11):5686-5695 (2006).
Krystal et al., "Transforming Growth Factor β1 is an Inducer of Erythroid Differentiation," J. Exp. Med., 180:851-860 (1994).
Kubanek, B., "Introduction: The Role of the Microenvironment and Cytokines on the Modulation of Erythropoiesis," Annals New York Academy of Sciences, 257-258 (1994).
Kumar, T.R., et al., "Regulation of FSHbeta and GnRH Receptor Gene Expression in Activin Receptor II Knockout Male Mice," Mol. Cell. Endocrinol., 212(1-2):19-27 (2003).
Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-based strategies for drug design and discovery," Science, 257(5073):1078-1082 (1992).

Kwiatkowski, J.L. et al., "Iron chelation therapy in sickle-cell disease and other transfusion-dependent anemias," Hematol Oncol Clin N Am., vol. 18: 1355-1377 (2004).
Lazar, E., et al., "Transforming Growth Factor α: Mutation of Aspartic Acid 47 and Leucine 48 Results in Different Biological Activities," Molecular and Cellular Biology, 8(3):1247-1252 (1988).
Lazar, Mitchell A., "How Now, Brown Fat?" Science, vol. 321(5892): 1048-1049 (2008).
Lebrun, J.J., et al, "Activin and Inhibin Have Antagonistic Effects on Ligand-Dependent Heterodimerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23(2):117-122 (2006).
Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Lifespan Biosciences, Activin Receptor Type 2A (ACVR2A) Mouse anti-Human Monoclonal Antibody—LS-C33835—LifeSpan Biosciences, (2010).
Liu et al., "Characterization of isoforms of activin receptor-interacting protein 2 that augment activin signaling," Journal of Endocrinology, vol. 189: 409-421 (2006).
Lotinun, S., et al., "A Soluble Activin Receptor Type IIA Fusion Protein (ACE-011) Increases Bone Mass Via a Dual Anabolic-Antiresorptive Effect in Cynomolgus Monkeys," Bone, 46:1082-1088 (2010).
Lu, S., et al., "Simian Immunodeficiency Virus DNA Vaccine Trial in Macaques," Journal of Virology, 70(6):3978-3991 (1996).
Ludlow, H., et al., "Development of a new antibody to the human inhibin/activin βB subunit and its application to improved inhibin B ELISAs," J. Immunol. Methods, 329:102-111 (2008).
Ma, "Animal Models of Disease," Modern Drug Discovery, 30-36 (2004).
MacCallum et al., "Antibody-antigen Interactions: Contact Analysis and Binding site Topography," J. Mol. Biol, vol. 262: 732-745 (1996).
MacLennan et al., "Multiple Myeloma," BMJ, vol. 308:1033-1036 (1994).
Maguer-Satta, V., et al, "A Novel Role for Fibronectin Type 1 Domain in the Regulation of Human Hematopoietic Cell Adhesiveness Through Binding to Follistatin Domains of FLRG and Follistatin," Experimental Cell Research, Academic Press, 312(4):434-442 (2006).
Maguer-Satta, V., et al., "FLRG, Member of the Follistatin Family, a New Player in Hematopoiesis," Molecular and Cellular Endocrinology, Elsevier Ireland Ltd., 225(1-2):109-118 (2004).
Maguer-Satta, V., et al, "Regulation of human erythropoiesis by activin A, BMP2, and BMP4, members of the TGFβ family," Experimental Cell Research, 282:110-120 (2003).
Marri et al, Human Biochemistry, Moscow, "Mir", vol. 1: 34-35 (1993).
Mathews, L.S., et al., "Expression Cloning of an Activin Receptor, a Predicted Transmembrane Serine Kinase," Cell, 65(6):973-982 (1991).
Matzuk et al., "Cloning of the human activin receptor cDNA reveals high evolutionary conservation," Biochim Biophys Acta, 1130(1):105-108 (1992).
Matzuk et al., "Different phenotypes for mice deficient in either activins or activin receptor type II," Nature, 374:356-360 (1995).
McCarthy et al., Monoclonal antibodies that recognize the type-2 activin receptor, ACTR2, Hybridoma, vol. 13(3): 199-203 (1994) (abstract).
McNally, E.M., "Powerful Genes—Myostatin Regulation of Human Muscle Mass," N. Engl. J. Med., 350(26):2642-2644 (2004).

(56) References Cited

OTHER PUBLICATIONS

McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).
McPherron, A.C., et al., "Regulation of Skeletal Muscle Mass in Mice by a Bew TGF-β Superfamily Member," Nature, 387:83-90 (1997).
McPherron and Lee, "Suppression of body fat accumulation in myostatin-deficient mice," The Journal of Clinical Investigation, vol. 109(5): 595-601 (2002).
McPherson, S.J., et al., "Growth inhibitory response to activin A and B by human prostate tumour cell lines LNCaP and DU1465," Journal of Endocrinology, 154:535-545 (1997).
Menstruation: Absent Periods (Amenorrhea), downloaded on Jun. 14, 2010, <http//:adam.about.com/reports/000101_2.htm?p=1> (11 pages).
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.
Merck Manual. Iron-Utilization Anemias (Sideroblastic Anemias), pp. 1150-1151 (1992).
The Merck Manual of Diagnosis and Therapy, 17th Edition. Nyelodysplastic Syndrome, pp. 865 and 963-955 (1999).
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d. html> pp. 1-4.
Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).
Mickle, J.E., et al., "Genotype-Phenotype Relationships in Cystic Fibrosis," Med. Clin. North Am., 84(3):597-607 (2000).
Miller et al., Ligand binding to proteins: the binding landscape model. Protein Sci., 6(10):2166-79 (1997).
Miura, P., et al., "Utrophin upregulation for treating Duchenne or Becker muscular dystrophy: how close are we?," Trends in Molecular Medicine, 12(3):122-129 (2006).
Monoclonal Anti-human Activin RII Antibody, R&D Systems, Catalog No. MAB3391 (Feb. 18, 2009).
Moore et al., "Molecular Basis of Bone Morphogenetic Protein-15 Signaling in Granulosa Cells*," The Journal of Biological Chemistry, vol. 278(1): 304-310 (2003).
Morrison et al., "A soluble activin type IIB receptor improves function in a mouse model of amyotrophic lateral sclerosis," Experimental Neurology vol. 217: 258-268 (2009).
Mosekilde, L., et al., "Emerging Anabolic Treatments in Osteoporosis," Current Drug Safety, 6:62-74 (2011).
The website downloaded Oct. 28, 2014 from the Multiple Myeloma Research Foundation, themmrf.org/multiple-myeloma/symptoms/bone-lesions/, 2 pages total.
Murase et al., "Possible Involvement of Protein Kinases and Smad2 Signaling Pathways on Osteoclast Differentiation Enhanced by Activin A," Journal of Cellular Physiology, 188:236-242 (2001).
Murata, T., et al., "Anti-activin A Antibody (IgY) Specifically Neutralizes Various Activin A Activities," Proceedings of the Society for Experimental Biology & Medicine, 211(1):100-107 (1996).
Nagamine et al., "Immunohistochemical Detection of Activin A, Follistatin, and Activin Receptors during Fracture Healing in the Rat," Journal of Orthopaedic Research, 16:314-321 (1998).
Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Nemeth, E., "Hepcidin in β-thalassemia," Annals of the New York Academy of Sciences, vol. 1202: 31-35. Published Aug. 2, 2010.
Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).
NIH website downloaded May 28, 2014 from: web.archive.org/web/20030409091558/http://www.cc.nih.gov/ccc/patient_education/pepubs/subq.pdf; Patient Information Publications: Giving a Subcutaneous Injection ( 6 pages total).
Nolan, V.G., et al, 'Sickle Cell Leg Ulcers: Associations with Haemolysis and SNPs in Klotho, TEK and Genes of the TGF-β/BMP Pathway:-Sickle Cell Leg Ulcers, Genetics and Haemolysis', British Journal of Haematology, 133(5), pp. 570-578 (2006).
Ogawa et al., "Bovine Bone Activin Enhances Bone Morphogenetic Protein-Induced Ectopic Bone Formation," The Journal of Biological Chemistry, 267(20):14233-14237 (1992).
Oh, S.P., et al., "Activin type IIA and IIB receptors mediate Gdf11 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Padlan et al., "Identification of specificity-determining residues in antibodies," The FASEB Journal, vol. 9: 133-139 (1995).
Pak et al., "Suppression of hepcidin during anemia requires erythropoietic activity," Blood, vol. 108(12): 3730-3735 (2006).
Pakula and Sauer, "Genetic analysis of protein stability and function," Annu. Rev. Genet., vol. 23: 289-310 (1989).
Patel, K., et al., "The function of Myostatin and strategies of Myostatin blockade—new hope for therapies aimed at promoting growth of skeletal muscle," Neuromuscular Disorders, 15:117-126 (2005).
Paul, William E., Fundamental Immunology, 3rd edition, Raven Press, New York, 1003: 292-295 (1999).
Paulson, Robert F., "Targeting a new regulator of erythropoiesis to alleviate anemia," Nature Medicine, News and Views, vol. 20(4) (2 pages) (2014).
Pearsall, et al., "A Soluble Activin Receptor Type IIA (ACTRIIA) Acts as a Novel Bone Anabolic Agent," The Official Journal of the European Calcified Tissue Society, 34th Europena Symposium on Calcified Tissues (2007).
Pearsall, et al., "Treatment with a Soluble Activin Type II Receptor Reverses Bone Loss in Ovariectomized Mice," Journal of Bone and Mineral Research 2006 Abstracts, 21(1):s1-5530 (2006).
Pearsall et al., An investigative pharmacology study of a Gdf-8 (myostatin) inhibitor, ACE-031, in the common Marmoset (Callithrix jacchus), Database Biosis, Biosciences Information Service, Accession No. PREV201200750016; Faseb Journal, vol. 22, Experimental Biology Annual Meeting, San Diego, CA Apr. 5-9 (2008) (Abstract).
Pearsall, R.S., et al., "A soluble activin Type IIA receptor induces bone formation and improves skeletal integrity," PNAS, 105(19):7082-7087 (2008).
Pennucci et al., Multiplexed evaluation of a cell-based assay for the detection of antidrug neutralilzing antibodies to Panitumumab in human serum using automated fluorescent microsopy,: J. Biomol. Sceen. vol. 15: 644-652 (2010).
Perrien, D. S., et al., "Inhibin A is an Endocrine Stimulator of Bone Mass and Strength," Endocrinology, 148(4):1654-1665 (2007).
Phillips, A.J., "The challenge of gene therapy and DNA delivery," J. Pharm. Pharmacology, 53:1169-1174 (2001).
Pirollo, K.F., et al., "Targeted Delivery of Small Interfering RNA: Approaching Effective Cancer Therapies," Cancer Res., 68(5):1247-1250 (2008).
Qi, Z., et al., "Blockade of type β transforming growth factor signaling prevents liver fibrosis and dysfunction in the rat," PNAS, 96:2345-2349 (1999).
Raju, T.S., "Glycosylation in the Fc domain of IgG increases resistance to proteolytic cleavage by papain," Biochemical and Biophysical Research Communications, 341:797-803 (2006).
R&D Systems Catalogue No. AF339 Datasheet: Human Activin RIIB Antibody [retrieved on Feb. 13, 2013] Retrieved from the Internet: http://www.rndsystems.com/pdf/af339.pdf.
R&D Systems, "Antibody Reference Guide and Catalog Instructions," [retrieved on Feb. 13, 2013]; http://web.archive.org/web/

(56) References Cited

OTHER PUBLICATIONS

20090220022132/http://rndsystems.com/DAM_public/5658.pdf; published Mar. 14, 2009 as per the Wayback Engine. See, in particular: p. 3.
Rebbapragada, et al., "Myostatin Signals Through a Transforming Growth Fact b-Like Signaling Pathway to Block Adipogenesis," Molecular and Cellular Biology, 23(20):7230-7242 (2003).
"Recombinant Human Activin RIIB/FC Chimera," R&D Systems 339-RB/CF (Aug. 27, 2003).
"Recombinant Human Activin RIIA/FC Chimera," R&D Systems 340-R2 (Aug. 27, 2003).
Reis, F.M., et al., "Activin, Inhibin and the Human Breast," Molecular and Cellular Edocrinology, 225:77-82 (2004).
Risbridger, G.P, et al., "Activins and Inhibins in Endocrine and Other Tumors," Endocrine Reviews, 22(6):836-858 (2001).
Robinson, G.W., et al., "Inhibins and Activins Regulate Mammary Epithelial Cell Differentiation Through Mesenchymal-epithelial Interactions," Development, 124:2701-2708 (1997).
Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).
Rosenzweig et al., "Cloning and characterization of a human type II receptor for bone morphogenetic proteins," PNAS, 92:7632-7636 (1995).
Ruckle et al., "Single-Dose, Randomized, Double-Blind, Pacebo-Controlled Study of ACE-011 (ACTRIIA-IgG1) in Postmenopausal Women," Journal of Bone and Mineral Research, vol. 24(4):744-752 (2009).
Ruzek et al., "Minimal Effects on Immune Parameters Following Chronic Anti-TGF-β Monoclonal Antibody Administration to Normal Mice," Immunopharmacology and Immunotoxicology 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., "The Measurement of Activin/EDF in Mouse Serum: Evidence for Extragonadal Production," Biochemical and Biophysical Research Communications, 188(2):921-926 (1992).
Sakai, et al., "Osteogenic Activity of Activin in Young Normal Rats and Young Adult and Aged Rats after Ovarlectomy," Bone, 23:S467 (1998).
Sako, D., et al., "Characterization of the Ligand Binding Functionality of the Extracellular Domain of Activin Receptor Type IIB," The Journal of Biological Chemistry, 285(27):21037-21048 (2010).
Satoh, K., et al., "Hemodynamic changes by recombinant erythropoietin therapy in hemodialyzed patients," Hypertension, 15(3):262-266 (1990).
Schmelzer, C.H., et al., "Purification and Characterization of Recombinant Human Activin B," Biochimica et Biophysica Acta, 1039(2):135-141 (1990).
Schuelke, M., et al., "Myostatin Mutation Associated with Gross Muscle Hypertrophy in a Child," New England Journal of Medicine, 350(26):2682-2688 (2004).
Seale et al., "PRDM16 controls a brown fat/skeletal muscle switch," Nature, vol. 454(7207): 961-967 (2008).
Shao, L., et al., "Effect of Activin A on Globin Gene Expression in Purified Human Erythroid Progenitors," Blood, 79(3):773-781 (1992).

Shao, L., et al., "Efficient synthesis of globoside and isogloboside tetrasaccharides by using beta (1A3) N-acetylgalactosaminyltransferase/ UDP-N-acetyglucosamine C4 epimerase fusion protein," Chem Commun.: 1422-1423 (2003).
Shapiro et al., "Side Effects of Adjuvant Treatment of Breast Cancer," New England Journal of Medicine, vol. 344: 1997-2008 (2001).
Shav-Tal, Y., et al., "The Role of Activin A in Regulation of Hemopoiesis," Stem Cells, 20:493-500 (2002).
Shi et al., "Energy Balance, Myostatin, and GILZ: Factors Regulating Adipocyte Differentiation in Belly and Bone," PPAR Research, pp. 1-12 (2007).
Shiozaki, M., et al, "Activin A: A Commitment Factor in Erythroid Differentiation," Biochemical and Biophysical Research Communications, 242:631-635 (1998).
Shiozaki, M., et al, "Evidence for the participation of endogenous activin A/erythroid differentiation factor in the regulation of erythropoiesis," Proc. Natl. Acad. Sci. USA, 89:1553-1556 (1992).
Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shoji et al., "Identification and Characterization of a PDZ Protein That Interacts with Activin Type II Receptors," The Journal of Biological Chemistry, vol. 275(8): 5485-5492 (2000).
Shuto et al., "Osteoblasts Express Types I and II Activin Receptors During Early Intramembranous and Endochondral Bone Formation," Journal of Bone Mineral Research, 12(3):403-411 (1997).
Sirskyj et al., Detection of influenza A and B neutralizing antibodies in vaccinated ferrets and macaques using specific biotinstreptavidin conjugated antibodies, J. Virol. Methods. vol. 163: 459-464 (2010).
Smith, L. et al., The Status, Quality, and Expansion of the NIH Full-Length cDNA Project: The Mammalian Gene Collection (MGC), Genome Res., vol. 14(10b),: 2127-2127 (2004).
Smith, L. et al., "The analysis of doxorubicin resistance in human breast cancer cells using antibody microarrays," Mol. Cancer Therapy, vol. 5: 2115-2120 (2006).
Song, J., et al., "The Type II Activin Receptors are Essential for Egg Cylinder Growth, Gastrulation, and Rostral Head Development in Mice," Development Biology, 213:157-169 (1999).
Springer, et al., "Seventh European Congress on Clinical and Economic Aspects of Osteoporosis and Osteoarthritis," Osteoporosis International, 18(1):S29-S75 (2007).
Sun, et al., "FSH Directly Regulates Bone Mass," Cell, 125:247-260 (2006).
Sun Shuhan et al., "Chromosome, Gene, and Disesase," Science Press (2009).
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010. (abstract).
Suragani et al., "Transforming growth factor-? superfamily ligand trap ACE-536 corrects anemia by promoting late-stage erythropoiesis," Letters, Nature Medicine, Advance Online Publication (44 pages) (2014).
Swanson et al., "Use of Biosensors to Monitor the Immune Response," Biologics, vol. 109: 71-78 (2000).
Swanson, S. J., "New Technologies for the Detection of Antibodies to Therapeutic Proteins," Immunogenicity of Therapeutics Biological Products, vol. 112: 127-133 (2003).
Tanno, T. and Miller, J.L., "Iron Loading and Overloading due to Ineffective Erythropoiesis," Advances in Hematology, Article ID 358283, Chapter 2 (Abstract) (2010). (orig ISR 060-WO1).
Thompson, T.B., et al., "Beta A versus beta B: is it merely a matter of express?," Molecular and Cellular Endocrinology, 225:9-17 (2004).
Thompson, T.B., et al., "Structures of an ActRIIB: activin A complex reveal a novel binding mode for TGF-beta ligand: receptor interactions," EMBO, 22(7):1555-1566 (2003).
Thorpe and Swanson, "Current methods for Detecting Antibodies against Erythropoietin and Other Recombinant Proteins," Clinical and Diagnostic Laboratory Immunology, vol. 12(1): 28-39 (2005).

(56) References Cited

OTHER PUBLICATIONS

Tinsley, J., et al., "Expression of full-length utrophin prevents muscular dystrophy in mdx mice," Nature Medicine, 4(12):1441-1444 (1998).
Tisdale, M.J., "Cachexia in Cancer Patients," Nat. Rev. Cancer, 2:862-871 (2002).
Tokuriki, N., et al., "Stability effects of mutations and protein evolvability," Current Opinion in Structural Biology, 19:596-604 (2009).
Trivedi, R., et al., "Investigational Anabolic Therapies for Osteoporosis," Expert Opin. Investig. Drugs, 19(8):995-1005 (2010).
Truksa et al., "Bone morphogenetic proteins 2, 4, and 9 stimulate murine hepcidin 1 expression independently of Hfe, transferrin receptor 2 (Tfr2), and IL-6," PNAS, vol. 103(27): 10289-10293 (2006).
Tseng, Yu-Hua et al., "New role of bone morphogenetic protein 7 in brown adipogenesis and energy expenditure," Nature: International Weekly Journal of Science (and Supplementary Information), vol. 454(7207): 1000-1004 (2008).
Tsuchida, et al., "Activin isoforms signal through type I receptor serine/threonine kinase ALK7," Molecular and Cellular Endocrinology, 220:59-65 (2004).
Tu, P., et al., "Genetic Disruption of Myostatin Reduces the Development of Proatherogenic Dyslipidemia and Atherogenic Lesions in Ldlr Null Mice," Diabetes, 58:1739-1748 (2009).
Type 2 Diabetes, PubMed Health, Diseases and Conditions, U.S. National Library of Medicine, Bethesda, MD (online), Jun. 28, 2011 retrieved on Jun. 6, 2012. Retrieved from the Internet:<URL:http://www.ncbi.nlm.nih.gov/pubmedhealth/PMH0001356/>.
Ukkola, et al., "Adiponectin: A Link Between Excess Adiposity and Associated Comorbidities?", Journal of Molecular Medicine, 80(11):696-702 (2002).
U.S. Biological Technical Data Sheet for A0856-10A, accessed on Feb. 20, 2013.
U.S. Biological, Activin Receptor Type IIA (RIIA) A0856-05E www.usbio.net/technicalsheet.php?item=A0856-05E dated Jun. 8, 2010.
Utzschneider, et al., The Role of Insulin Resistance in Nonalcoholic Fatty Liver Disease, J. Clin. Endocrinol. Metab., 91(12):4753-4761 (Dec. 2006). Epub Sep. 12, 2006.
Vallet, S., et al., "Activin A promotes multiple myeloma-induced osteolysis and is a promising target for myeloma bone disease," PNAS, 107(11):5124-5129 (2010).
Vidal, L., et al., "Making sense of antisense," European Journal of Cancer, 41:2812-2818 (2005).
Wagner, K.R., et al., "Loss of Myostatin Attenuates Severity of Muscular Dystrophy in mdx Mice," Ann. Neurol., 52:832-836 (2002).
Wagner, K.R., et al., "Muscle regeneration in the prolonged absence of myostatin," PNAS, 102(7):2519-2524 (2005).
Wagner, K.R., et al., "A Phase I/II trial of MYO-029 in Adult Subjects with Muscular Dystrophy," Ann. Neurol., 63:561-571 (2008).
Walsh, F. S, et al., "Myostatin: a modulator of skeletal-muscle stems cells," Biochemical Society Transactions, 33(Pt.6):1513-1517 (2005).
Wang, et al., A single amino acid determines lysophospholipid specificity of the S1P1 (EDG1) and LPA1 (EDG2) phospholipid growth factor receptors. JBC 276:49213-49220 (2001).
Wang, W., et al., "GDF-3 is an adipogenic cytokine under high fat dietary condition," Biochemical and Biophysical Research Comm., 321(4):1024-1031 (2004).
Ware, Russell E., "How I use hydroxyurea to treat young patients with sickle cell anemia," Blood, vol. 115(26): 5300-5311 (2010).
Ward, R., "An update on disordered iron metabolism and iron overload," Hematology, vol. 15(5): 311-317 (2010).
Weber, et al., "A slient H-bond can be mutationally activated for high-affinity interaction of BMP-2 and activin type IIB receptor," BMC Structural Biology, 7(6):1-20 (2007).
Wells, J.A., "Additivity of Mutational Effects in Proteins," Biochemistry, 29(37):8509-8517 (1990).
Welt, C.K., et al., "Activin: an endocrine or panacrine agent?," European Journal of Endocrinology, 139:469-471 (1998).
Wiater, et al., "Inhibin is an Antagonist of Bone Morphogenetic Protein Signaling," The Journal of Biological Chemistry, 278(10):7934-7941 (2003).
Winkler et al., "Sclerostin Inhibition of Wnt-3a-induced C3H10T1/2 Cell Differentiation is Indirect and Mediated by Bone Morphogenetic Proteins," vol. 280(4): 2498-2502 (2005).
Wolfman, N.M., et al., "Activation of latent myostatin by the BMP-1/tolloid family of metalloproteinases," PNAS, 100(26):15842-15846 (2003).
Wong et al., "Validation parameters for a novel biosensor assay which simultaneously measures serum concentrations of a humanized monoclonal antibody and detects induced antibodies," Journal of Immunological Methods, vol. 209: 1-15 (1997).
Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567 (2012). (translated and original).
Yokota, T., et al., "Isolation and characterization of a mouse cDNA clone that expresses mast-cell growth-factor activity in monkey cells," Proc. Natl. Acad. Sci. USA, 81:1070-1074 (1984).
Yu, J., et al., "Importance of FSH-releasing protein and inhibin in erythrodifferentiation," Nature, 330:765-767 (1987).
Yu, J., et al., "Specific roles of activin/inhibin in human erythropoiesis in vitro," Annals New York Academy of Sciences, 20(10):1243-1246 (1991).
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhang et al., Effects of Activin A on the Activities of the Mouse Peritoneal Macrophages, Cellular & Molecular Immunology, vol. 2(1): 63-67 (2005).
Zhao, B., et al., "Transgenic expression of myostatin propeptide prevents diet-induced obesity and insulin resistance," Biochemical and Biophysical Research Communications, vol. 337:248-255 (2005).
ACTR-II (149/1): sc-57022, Santa Cruz Biotechnology, Inc.: http://datasheets.scbt.com/sc-57022.pdf, dated Jun. 3, 2010.
ACTR-II (H-65): sc-25451, Santa Cruz Biotechnology, Inc.: http://datasheets.sebt.com/sc-25451.pdf, dated Jun. 3, 2010.
ACTR-II (D-15): sc-5669, Santa Cruz Biotechnology, Inc.: http://datasheets.scbt.com/sc-5669.pdf, dated Jun. 3, 2010.
ACTR-IIA (A-24): sc-130679, Santa Cruz Biotechnology, Inc.: http://datasheets.scbt.com/sc-130679.pdf, dated Jun. 3, 2010.
ACTR-IIA (N-17): sc-5667, Santa Cruz Biotechnology, Inc.: http://datasheets.scbt.com/sc-5667.pdf, dated Jun. 3, 2010.
ACCELERON, 'Corporate Overview', considered published in Jul. 31, 2014,; Retrieved on Aug. 20, 2015 from the Internet at URL:; http://files.shareholder.com/downloads/AMDA-23MZWJ/0x0x773202/925b82ab-5576-;43a4-9f75-15d69fa35685/Xlrn%20Corp%20Overview%20-%20July%202014.pdf.
ACCELERON, 'Review of the Data Presented at the European Hematology Association; 19th Annual Meeting', considered published on Jun. 16, 2014; Retrieved on Aug. 20, 2015 from the Internet at URL:; http://files.shareholder.com/downloads/Amda-23MZWJ/0x0x762136/20a51a29-0a0f-;4a35-965e-;4e299efd7d12/v11%20EHA%20Investor%20Call%20June%2016%202014.pdf.
Anonymous "Ferritin" www.webmd.com/a-to-z-guides/ferritin?p.=2 originally published 2008.
Attie et al., "A phase 1 study of Ace-536, a regulator of erythroid differentiation, in healthy volunteers," American Journal of Hematology, vol. 89(7): 766-770 (2014).
Beutler et al., Williams Hematology, 6th Edition. McGraw Hill, p. 561, published 2001.
Mallat et al., "Potential mechanisims for renal demage in beta-thalassemia," J. Nephrol, vol. 26(5): 821-828 (2013).
Kumar and Tiwari, "Iron Overload in Beta Thalassaemia Major and Intermedia Patients," MAEDICA—Journal of Clinical Medicine, vol. 8(4): 328-332 (2013).

(56) References Cited

OTHER PUBLICATIONS

Martens et al., "Inhibin Interferes with Activin Signaling at the Level of the Activin Receptor Complex in Chinese Hamster Ovary Cells," Endocrinology, vol. 138(7): 2928-2936 (1997).
Rund and Rachmilewitz," Medical Progress Beta-Thalassemia," N. England J. Medicine, vol. 35: 1135-1146 (2005).
International Search Report dated Sep. 3, 2015 in connection with PCT/US2015/035706.
Guerra et al., "Lack of GDF11 Does Not Ameliorate Erythropoiesis in β-Thalassemia and Does Not Prevent the Activity of the Trap-Ligand RAP—536," Blood, vol. 132:165 (6 pages) 2018.
Cappellini et al., "An overview of current treatment strategies for β-thalassemia", Expert Opinion on Orphan Drugs, vol. 2(7): 665-679 (2014).

```
ActRIIa     ILGRSETQEC LFFNANWEKD RTNQTGVEPC YGDKDKRRHC FATWKNISGS
ActRIIb     GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
            IELVKKGCWL DDFNCYDRQE CVATEENPQV YFCCCEGNFC NERFTHLPEA

EVTQPTSNPV TPKPPT
            GGPEVTYEPP PTAPT
```

FIGURE 1

Figure 3A
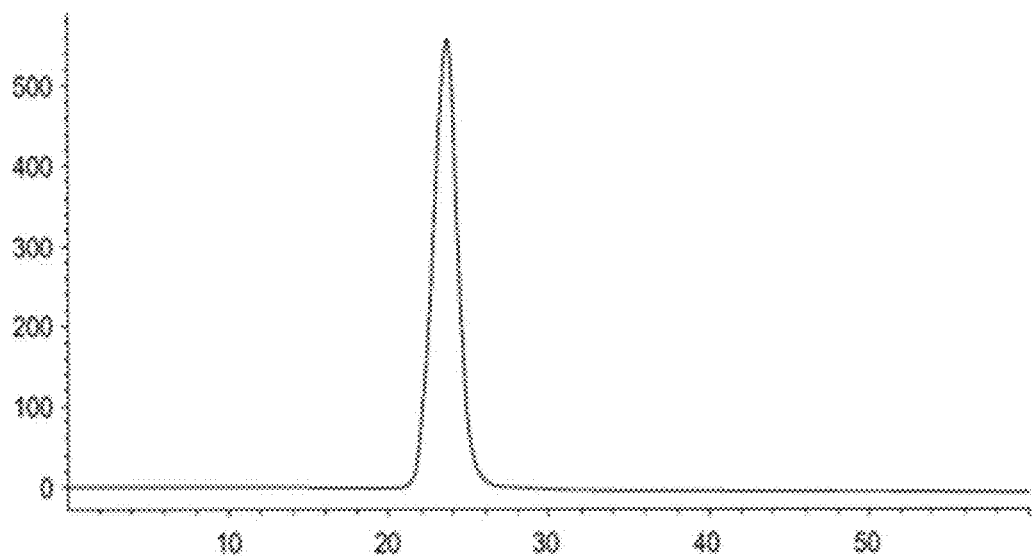
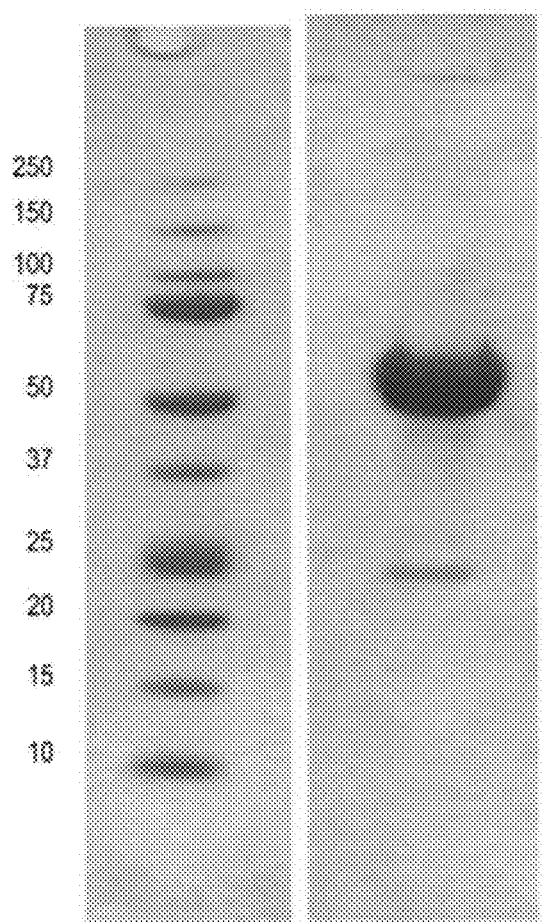
Figure 3B

Kd 5 e-12 M

Kd 9.96 e-9 M

```
  1  MDAMKRGLCC VLLLCGAVFV SPGAS RGEA ETRECIYYNA NWELERTNQS
 51  GLERCEGEQD KRLHCYASWR NSSGTIELVK KGCW DDFNC YDRQECVATE
101  ENPQVYFCCC EGNFCNERFT HLPEAGGPEV TYEPPPTAPT GGGTHTCPPC
151  PAPELLGGPS VFLFPPKPKD TLMISRTPEV TCVVVDVSHE DPEVKFNWYV
201  DGVEVHNAKT KPREEQYNST YRVVSVLTVL HQDWLNGKEY KCKVSNKALP
251  APIEKTISKA KGQPREPQVY TLPPSREEMT KNQVSLTCLV KGFYPSDIAV
301  EWESNGQPEN NYKTTPPVLD SDGSFFLYSK LTVDKSRWQQ GNVFSCSVMH
351  EALHNHYTQK SLSLSPGK (SEQ ID NO:38)
```

FIGURE 16

| | | | | |
|---|---|---|---|---|
| 1 | ATGGATGCAA | TGAAGAGAGG | GCTCTGCTGT | GTGCTGCTGC | TGTGTGGAGC |
| | TACCTACGTT | ACTTCTCTCC | CGAGACGACA | CACGACGACG | ACACACCTCG |
| 51 | AGTCTTCGTT | TCGCCCGGCG | CCTCTGGGCG | TGGGGAGGCT | GAGACACGGG |
| | TCAGAAGCAA | AGCGGGCCGC | GGAGACCCGC | ACCCCTCCGA | CTCTGTGCCC |
| 101 | AGTGCATCTA | CTACAACGCC | AACTGGGAGC | TGGAGCGCAC | CAACCAGAGC |
| | TCACGTAGAT | GATGTTGCGG | TTGACCCTCG | ACCTCGCGTG | GTTGGTCTCG |
| 151 | GGCCTGGAGC | GCTGCGAAGG | CGAGCAGGAC | AAGCGGCTGC | ACTGCTACGC |
| | CCGGACCTCG | CGACGCTTCC | GCTCGTCCTG | TTCGCCGACG | TGACGATGCG |
| 201 | CTCCTGGCGC | AACAGCTCTG | GCACCATCGA | GCTCGTGAAG | AAGGGCTGCT |
| | GAGGACCGCG | TTGTCGAGAC | CGTGGTAGCT | CGAGCACTTC | TTCCCGACGA |
| 251 | GGGATGATGA | CTTCAACTGC | TACGATAGGC | AGGAGTGTGT | GGCCACTGAG |
| | CCCTACTACT | GAAGTTGACG | ATGCTATCCG | TCCTCACACA | CCGGTGACTC |
| 301 | GAGAACCCCC | AGGTGTACTT | CTGCTGCTGT | GAAGGCAACT | TCTGCAACGA |
| | CTCTTGGGGG | TCCACATGAA | GACGACGACA | CTTCCGTTGA | AGACGTTGCT |
| 351 | GCGCTTCACT | CATTTGCCAG | AGGCTGGGGG | CCCGGAAGTC | ACGTACGAGC |
| | CGCGAAGTGA | GTAAACGGTC | TCCGACCCCC | GGGCCTTCAG | TGCATGCTCG |
| 401 | CACCCCCGAC | AGCCCCCACC | GGTGGTGGAA | CTCACACATG | CCCACCGTGC |
| | GTGGGGGCTG | TCGGGGGTGG | CCACCACCTT | GAGTGTGTAC | GGGTGGCACG |
| 451 | CCAGCACCTG | AACTCCTGGG | GGGACCGTCA | GTCTTCCTCT | TCCCCCCAAA |
| | GGTCGTGGAC | TTGAGGACCC | CCCTGGCAGT | CAGAAGGAGA | AGGGGGGTTT |
| 501 | ACCCAAGGAC | ACCCTCATGA | TCTCCCGGAC | CCCTGAGGTC | ACATGCGTGG |
| | TGGGTTCCTG | TGGGAGTACT | AGAGGGCCTG | GGGACTCCAG | TGTACGCACC |
| 551 | TGGTGGACGT | GAGCCACGAA | GACCCTGAGG | TCAAGTTCAA | CTGGTACGTG |
| | ACCACCTGCA | CTCGGTGCTT | CTGGGACTCC | AGTTCAAGTT | GACCATGCAC |
| 601 | GACGGCGTGG | AGGTGCATAA | TGCCAAGACA | AAGCCGCGGG | AGGAGCAGTA |
| | CTGCCGCACC | TCCACGTATT | ACGGTTCTGT | TTCGGCGCCC | TCCTCGTCAT |
| 651 | CAACAGCACG | TACCGTGTGG | TCAGCGTCCT | CACCGTCCTG | CACCAGGACT |
| | GTTGTCGTGC | ATGGCACACC | AGTCGCAGGA | GTGGCAGGAC | GTGGTCCTGA |
| 701 | GGCTGAATGG | CAAGGAGTAC | AAGTGCAAGG | TCTCCAACAA | AGCCCTCCCA |
| | CCGACTTACC | GTTCCTCATG | TTCACGTTCC | AGAGGTTGTT | TCGGGAGGGT |
| 751 | GCCCCCATCG | AGAAAACCAT | CTCCAAAGCC | AAAGGGCAGC | CCCGAGAACC |
| | CGGGGGTAGC | TCTTTTGGTA | GAGGTTTCGG | TTTCCCGTCG | GGGCTCTTGG |

FIGURE 17A

```
 801    ACAGGTGTAC  ACCCTGCCCC  CATCCCGGGA  GGAGATGACC  AAGAACCAGG
        TGTCCACATG  TGGGACGGGG  GTAGGGCCCT  CCTCTACTGG  TTCTTGGTCC

851    TCAGCCTGAC  CTGCCTGGTC  AAAGGCTTCT  ATCCCAGCGA  CATCGCCGTG
        AGTCGGACTG  GACGGACCAG  TTTCCGAAGA  TAGGGTCGCT  GTAGCGGCAC

901    GAGTGGGAGA  GCAATGGGCA  GCCGGAGAAC  AACTACAAGA  CCACGCCTCC
        CTCACCCTCT  CGTTACCCGT  CGGCCTCTTG  TTGATGTTCT  GGTGCGGAGG

951    CGTGCTGGAC  TCCGACGGCT  CCTTCTTCCT  CTATAGCAAG  CTCACCGTGG
        GCACGACCTG  AGGCTGCCGA  GGAAGAAGGA  GATATCGTTC  GAGTGGCACC

1001    ACAAGAGCAG  GTGGCAGCAG  GGGAACGTCT  TCTCATGCTC  CGTGATGCAT
        TGTTCTCGTC  CACCGTCGTC  CCCTTGCAGA  AGAGTACGAG  GCACTACGTA

1051    GAGGCTCTGC  ACAACCACTA  CACGCAGAAG  AGCCTCTCCC  TGTCCCCGGG
        CTCCGAGACG  TGTTGGTGAT  GTGCGTCTTC  TCGGAGAGGG  ACAGGGGCCC

1101    TAAATGA     (SEQ ID NO:39)
        ATTTACT     (SEQ ID NO:40)
```

FIGURE 17B

```
  1  MDAMKRGLCC VLLLCGAVFV SPGAA TREC IYYNANWELE RTNQSGLERC
 51  EGEQDKRLHC YASWRNSSGT IELVKKGCW  DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK (SEQ ID NO: 41)
```

FIGURE 18

```
  1  ATGGATGCAA TGAAGAGAGG GCTCTGCTGT GTGCTGCTGC TGTGTGGAGC
     TACCTACGTT ACTTCTCTCC CGAGACGACA CACGACGACG ACACACCTCG

E  T  R  E  C  I  Y  Y
 51  AGTCTTCGTT TCGCCCGGCG CCGCTGAGAC ACGGGAGTGC ATCTACTACA
     TCAGAAGCAA AGCGGGCCGC GGCGACTCTG TGCCCTCACG TAGATGATGT

N  A  N  W  E  L  E  R  T  N  Q  S  G  L  E  R  C
101  ACGCCAACTG GGAGCTGGAG CGCACCAACC AGAGCGGCCT GGAGCGCTGC
     TGCGGTTGAC CCTCGACCTC GCGTGGTTGG TCTCGCCGGA CCTCGCGACG

E  G  E  Q  D  K  R  L  H  C  Y  A  S  W  R  N  S
151  GAAGGCGAGC AGGACAAGCG GCTGCACTGC TACGCCTCCT GGCGCAACAG
     CTTCCGCTCG TCCTGTTCGC CGACGTGACG ATGCGGAGGA CCGCGTTGTC

S  G  T  I  E  L  V  K  G  C  W  D  D  D  F
201  CTCTGGCACC ATCGAGCTCG TGAAGAAGGG CTGCTGGGAC GATGACTTCA
     GAGACCGTGG TAGCTCGAGC ACTTCTTCCC GACGACCCTG CTACTGAAGT

N  C  Y  D  R  Q  E  C  V  A  T  E  E  N  P  Q  V
251  ACTGCTACGA TAGGCAGGAG TGTGTGGCCA CTGAGGAGAA CCCCCAGGTG
     TGACGATGCT ATCCGTCCTC ACACACCGGT GACTCCTCTT GGGGGTCCAC

Y  F  C  C  C  E  G  N  F  C  N  E  R  F  T  H  L
301  TACTTCTGCT GCTGTGAAGG CAACTTCTGC AACGAGCGCT TCACTCATTT
     ATGAAGACGA CGACACTTCC GTTGAAGACG TTGCTCGCGA AGTGAGTAAA

P  E  A  G  G  P  E  V  T  Y  E  P  P  P  T
351  GCCAGAGGCT GGGGGCCCGG AAGTCACGTA CGAGCCACCC CCGACAGGTG
     CGGTCTCCGA CCCCCGGGCC TTCAGTGCAT GCTCGGTGGG GGCTGTCCAC

401  GTGGAACTCA CACATGCCCA CCGTGCCCAG CACCTGAACT CCTGGGGGGA
     CACCTTGAGT GTGTACGGGT GGCACGGGTC GTGGACTTGA GGACCCCCCT

451  CCGTCAGTCT TCCTCTTCCC CCCAAAACCC AAGGACACCC TCATGATCTC
     GGCAGTCAGA AGGAGAAGGG GGGTTTTGGG TTCCTGTGGG AGTACTAGAG

501  CCGGACCCCT GAGGTCACAT GCGTGGTGGT GGACGTGAGC CACGAAGACC
     GGCCTGGGGA CTCCAGTGTA CGCACCACCA CCTGCACTCG GTGCTTCTGG

551  CTGAGGTCAA GTTCAACTGG TACGTGGACG GCGTGGAGGT GCATAATGCC
     GACTCCAGTT CAAGTTGACC ATGCACCTGC CGCACCTCCA CGTATTACGG
```

FIGURE 19A

```
601  AAGACAAAGC CGCGGGAGGA GCAGTACAAC AGCACGTACC GTGTGGTCAG
     TTCTGTTTCG GCGCCCTCCT CGTCATGTTG TCGTGCATGG CACACCAGTC

651  CGTCCTCACC GTCCTGCACC AGGACTGGCT GAATGGCAAG GAGTACAAGT
     GCAGGAGTGG CAGGACGTGG TCCTGACCGA CTTACCGTTC CTCATGTTCA

701  GCAAGGTCTC CAACAAAGCC CTCCCAGCCC CCATCGAGAA AACCATCTCC
     CGTTCCAGAG GTTGTTTCGG GAGGGTCGGG GGTAGCTCTT TTGGTAGAGG

751  AAAGCCAAAG GGCAGCCCCG AGAACCACAG GTGTACACCC TGCCCCCATC
     TTTCGGTTTC CCGTCGGGGC TCTTGGTGTC CACATGTGGG ACGGGGGTAG

801  CCGGGAGGAG ATGACCAAGA ACCAGGTCAG CCTGACCTGC CTGGTCAAAG
     GGCCCTCCTC TACTGGTTCT TGGTCCAGTC GGACTGGACG GACCAGTTTC

851  GCTTCTATCC CAGCGACATC GCCGTGGAGT GGGAGAGCAA TGGGCAGCCG
     CGAAGATAGG GTCGCTGTAG CGGCACCTCA CCCTCTCGTT ACCCGTCGGC

901  GAGAACAACT ACAAGACCAC GCCTCCCGTG CTGGACTCCG ACGGCTCCTT
     CTCTTGTTGA TGTTCTGGTG CGGAGGGCAC GACCTGAGGC TGCCGAGGAA

951  CTTCCTCTAT AGCAAGCTCA CCGTGGACAA GAGCAGGTGG CAGCAGGGGA
     GAAGGAGATA TCGTTCGAGT GGCACCTGTT CTCGTCCACC GTCGTCCCCT

1001 ACGTCTTCTC ATGCTCCGTG ATGCATGAGG CTCTGCACAA CCACTACACG
     TGCAGAAGAG TACGAGGCAC TACGTACTCC GAGACGTGTT GGTGATGTGC

1051 CAGAAGAGCC TCTCCCTGTC CCGGGTAAA TGA (SEQ ID NO: 42)
     GTCTTCTCGG AGAGGGACAG GGCCCATTT ACT (SEQ ID NO: 43)
```

FIGURE 19B

1    TRECIYYNA NWELERTNQS GLERCEGEQD KRLHCYASWR NSSGTIELVK

51   KGCW DDFNC YDRQECVATE ENPQVYFCCC EGNFCNERFT HLPEAGGPEV

101  TYEPPPTGGG THTCPPCPAP ELLGGPSVFL FPPKPKDTLM ISRTPEVTCV

151  VVDVSHEDPE VKFNWYVDGV EVHNAKTKPR EEQYNSTYRV VSVLTVLHQD

201  WLNGKEYKCK VSNKALPAPI EKTISKAKGQ PREPQVYTLP PSREEMTKNQ

251  VSLTCLVKGF YPSDIAVEWE SNGQPENNYK TTPPVLDSDG SFFLYSKLTV

301  DKSRWQQGNV FSCSVMHEAL HNHYTQKSLS LSPGK (SEQ ID NO: 44)

FIGURE 20

1   ETRECIYYNA NWELERTNQS GLERCEGEQD KRLHCYASWR NSSGTIELVK

51   KGCWLDDFNC YDRQECVATE ENPQVYFCCC EGNFCNERFT HLPEAGGPEV

101   TYEPPPT   (SEQ ID NO: 45)

FIGURE 21

```
  1    ATGGATGCAA TGAAGAGAGG GCTCTGCTGT GTGCTGCTGC TGTGTGGAGC
       TACCTACGTT ACTTCTCTCC CGAGACGACA CACGACGACG ACACACCTCG

E  T  R  E  C  I  Y  Y
 51    AGTCTTCGTT TCGCCCGGCG CCGCCGAAAC CCGGGAATGT ATTTATTACA
       TCAGAAGCAA AGCGGGCCGC GGCGGCTTTG GGCCCTTACA TAAATAATGT

N  A  N  W  E  L  E  R  T  N  Q  S  G  L  E  R  C
101    AGCTAATTG GGAACTGGAA CGGACAAACC AGTCGGGCT GAACGGTG
       TACGATTAAC CCTTGAGCTT GCCTGCTTGG TTAGGCCCGA GCTTGCCACA

E  G  E  Q  D  K  R  L  H  C  Y  A  S  W  R  N  S
151    GAGGGGAAC AGGAAAACG CTCATGC TAGCTCT GGGAACT
       CTCCCCCTTG TCCTATTTGC GGAGGTAACG ATACGCAGCA CCTCCTTGAG

S  G  T  I  E  L  V  K  G  C  W  D  D  F
201    CTCGGACT ATGACTG TAAGAAGG GTGCTGGAC GAGATTCA
       GAGGCCCTGC TAACTTGACC AGTTCTTTCC CACGACCCTG CTGCTAAAGT

N  C  Y  D  R  Q  E  C  V  A  T  E  E  N  P  Q  V
251    ATGTTATGA GGCAGGAA TGTGTGCA CGAGAGAA CCCAGGT
       TAACAATACT GGCGGTCCTT ACACAGCGCT GGCTTCTCTT AGGCGTCCAG

Y  F  C  C  E  G  N  F  C  N  E  R  F  T  H  L
301    TATTCTGT GTGGAGG AATTCTG AAGACGT TACCACT
       ATAAAGACAA CAACGCTCCC CTTAAAGACA TTACTTGCCA AATGGGTGGA

P  E  A  G  G  P  E  V  T  Y  E  P  P  P  T
351    CCCGAAGC GGGGGCCG AGGTACTA TGACCCC CCACGGTG
       GGGGCTTCGG CCGCCCGGGC TCCACTGGAT ACTTGGGGC GGGTGGCCAC

401    GTGGAACTCA CACATGCCCA CCGTGCCCAG CACCTGAACT CCTGGGGGGA
       CACCTTGAGT GTGTACGGGT GGCACGGGTC GTGGACTTGA GGACCCCCCT

451    CCGTCAGTCT TCCTCTTCCC CCCAAAACCC AAGGACACCC TCATGATCTC
       GGCAGTCAGA AGGAGAAGGG GGGTTTTGGG TTCCTGTGGG AGTACTAGAG

501    CCGGACCCCT GAGGTCACAT GCGTGGTGGT GGACGTGAGC CACGAAGACC
       GGCCTGGGGA CTCCAGTGTA CGCACCACCA CCTGCACTCG GTGCTTCTGG

551    CTGAGGTCAA GTTCAACTGG TACGTGGACG GCGTGGAGGT GCATAATGCC
       GACTCCAGTT CAAGTTGACC ATGCACCTGC CGCACCTCCA CGTATTACGG

601    AAGACAAAGC CGCGGGAGGA GCAGTACAAC AGCACGTACC GTGTGGTCAG
       TTCTGTTTCG GCGCCCTCCT CGTCATGTTG TCGTGCATGG CACACCAGTC

651    CGTCCTCACC GTCCTGCACC AGGACTGGCT GAATGGCAAG GAGTACAAGT
       GCAGGAGTGG CAGGACGTGG TCCTGACCGA CTTACCGTTC CTCATGTTCA
```

FIGURE 22A

```
701    GCAAGGTCTC CAACAAAGCC CTCCCAGCCC CCATCGAGAA AACCATCTCC
       CGTTCCAGAG GTTGTTTCGG GAGGGTCGGG GGTAGCTCTT TTGGTAGAGG

751    AAAGCCAAAG GGCAGCCCCG AGAACCACAG GTGTACACCC TGCCCCCATC
       TTTCGGTTTC CCGTCGGGGC TCTTGGTGTC CACATGTGGG ACGGGGGTAG

801    CCGGGAGGAG ATGACCAAGA ACCAGGTCAG CCTGACCTGC CTGGTCAAAG
       GGCCCTCCTC TACTGGTTCT TGGTCCAGTC GGACTGGACG GACCAGTTTC

851    GCTTCTATCC CAGCGACATC GCCGTGGAGT GGGAGAGCAA TGGGCAGCCG
       CGAAGATAGG GTCGCTGTAG CGGCACCTCA CCCTCTCGTT ACCCGTCGGC

901    GAGAACAACT ACAAGACCAC GCCTCCCGTG CTGGACTCCG ACGGCTCCTT
       CTCTTGTTGA TGTTCTGGTG CGGAGGGCAC GACCTGAGGC TGCCGAGGAA

951    CTTCCTCTAT AGCAAGCTCA CCGTGGACAA GAGCAGGTGG CAGCAGGGGA
       GAAGGAGATA TCGTTCGAGT GGCACCTGTT CTCGTCCACC GTCGTCCCCT

1001   ACGTCTTCTC ATGCTCCGTG ATGCATGAGG CTCTGCACAA CCACTACACG
       TGCAGAAGAG TACGAGGCAC TACGTACTCC GAGACGTGTT GGTGATGTGC

1051   CAGAAGAGCC TCTCCCTGTC CCCGGGTAAA TGA (SEQ ID NO: 46)
       GTCTTCTCGG AGAGGGACAG GGGCCCATTT ACT (SEQ ID NO: 47)
```

FIGURE 22B

```
GA_AC _CG_GA_TG_ AT_TA_TACA A_GC_AA_TG GGA_CT_GA_ CG_AC_AACC

A_T_CGG_CT _GA_CG_TG_ GA_GG_GA_C AGGA_AA_CG _CT_CA_TGC TA_GC_TC_T

GG_G_AAC__ CTC_GG_AC_ AT_GA_CT_G T_AAGAA_GG _TGCTGGAC GA_GA_TTCA

A_TG_TA_GA _CG_CAGGA_ TGTGT_GC_A C_GA_GAGAA _CC_CAGGT_ TA_TTCTG_T

G_TG_GA_GG _AA_TTCTG_ AA_GA_CG_T T_AC_CA_C_T _CC_GA_GC_ GG_GG_CC_G

A_GT_AC_TA _GA_CC_CC_ CC_AC_     (SEQ ID NO: 48)
```

FIGURE 23

# # P≤0.001 vs Wild type mice, *** P≤0.001 vs vehicle control, N=5 per treatment group

METHODS FOR TREATING ULCERS IN A HEMOGLOBINOPATHY ANEMIA WITH A SOLUBLE ACTRIIB POLYPEPTIDE

RELATED APPLICATIONS

This application is a divisional of U.S. application Ser. No. 14/738,761, filed on Jun. 12, 2015, which claims the benefit of priority to U.S. Provisional Application Ser. No. 62/012,109, filed Jun. 13, 2014, and 62/045,808, filed Sep. 4, 2014. The disclosures of each of the foregoing applications are hereby incorporated in their entirety.

SEQUENCE LISTING

The instant application contains a Sequence Listing which has been submitted electronically in ASCII format and is hereby incorporated by reference in its entirety. Said ASCII copy, created on Nov. 20, 2017, is named 1848179-0002-079-102_Seq.txt and is 109,962 bytes in size.

BACKGROUND OF THE INVENTION

The mature red blood cell, or erythrocyte, is responsible for oxygen transport in the circulatory systems of vertebrates. Red blood cells contain high concentrations of hemoglobin, a protein that binds to oxygen in the lungs at relatively high partial pressure of oxygen ($pO_2$) and delivers oxygen to areas of the body with a relatively low $pO_2$.

Mature red blood cells are produced from pluripotent hematopoietic stem cells in a process termed erythropoiesis. Postnatal erythropoiesis occurs primarily in the bone marrow and in the red pulp of the spleen. The coordinated action of various signaling pathways controls the balance of cell proliferation, differentiation, survival, and death. Under normal conditions, red blood cells are produced at a rate that maintains a constant red cell mass in the body, and production may increase or decrease in response to various stimuli, including increased or decreased oxygen tension or tissue demand. The process of erythropoiesis begins with the formation of lineage committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates.

In general, anemia is a condition that develops when a subject's blood lacks enough healthy red blood cells or less than the normal quantity of hemoglobin. Anemia may also be diagnosed when there is decreased oxygen-binding capacity of red blood cells, which may result from a deformity in one or more hemoglobin subunits. As human cells depend on oxygen for survival, anemia can result in a wide range of clinical complications including, e.g., tissue damage. For example, it has been reported that ulcers are the one of most common cutaneous manifestation of chronic anemia disorders, particularly in hemolytic anemias such as sickle-cell disease and thalassemia. See, e.g., Keast et al. (2004) Ostomy Wound Manage., 50(10): 64-70; Trent et al. (2004) Adv Skin Wound Care, 17(8): 410-416; J. R. Eckman (1996) Hematol Oncol Clin North Am., 10(6): 1333-1344; and Rassi et al. (2008) Pediatric Annals 37(5): 322-328. The underlying mechanism for ulcer formation in anemic patients has not been completely defined. However, it is believed that multiple complications of anemia contribute to ulcer development including, for example, ischemia, decreased nitric oxide bioavailability, vascular obstruction, thrombosis, and hypoxia. Id.

Ulcer healing in anemic patients is typically a slow process, and such patients are also at a high risk of recurrent ulceration. See, e.g., Keast et al. (2004) Ostomy Wound Manage., 50(10): 64-70; Trent et al. (2004) Adv Skin Wound Care, 17(8): 410-416; J. R. Eckman (1996) Hematol Oncol Clin North Am., 10(6): 1333-1344; and Rassi et al. (2008) Pediatric Annals 37(5): 322-328. Furthermore, most therapies have had limited success in the treatment of ulcers occurring in anemic patients.

Thus, it is an object of the present disclosure to provide alternative methods for treating or preventing ulcers associated with anemia.

SUMMARY OF THE INVENTION

In part, the present disclosure demonstrates that ActRII antagonists can be used to alter various blood parameters (e.g., red blood cell levels, hemoglobin levels, iron levels, bilirubin levels, nitrogen levels, etc.) in patients that have anemia as well as treat complications associated with anemia including, for example, ulcers. In particular, the disclosure demonstrates that administration of a GDF Trap polypeptide, which is soluble form of an ActRIIB polypeptide having an acidic amino acid at position 79 with respect to instant SEQ ID NO:1, increases red blood cell levels and/or hemoglobin levels in patients having various types of hemolytic anemia, particularly the hemoglobinopathic anemias, thalassemia and sickle-cell disease. Surprisingly, in addition to directly affecting various red blood cell parameters, the disclosed ActRII antagonist ameliorates other complications associated with anemia. For example, treatment with a GDF Trap protein was shown to increase hemoglobin levels and promote wound healing of a cutaneous (skin) ulcer in a human patient having thalassemia. In some instances, amelioration of these associated complications is of equal or greater importance to patient health and quality of life as the treatment of the underlying anemia. Therefore, in certain embodiments, the disclosure provides methods of using one or more ActRII antagonists to increase red blood cell levels and/or hemoglobin levels in patients in need thereof and to treat or prevent one or more complications associated with low red blood cell levels and/or hemoglobin levels in these patients. In particular, the disclosure provides methods for treating or preventing an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria] by administering one or more ActRII antagonists. In some embodiments, the disclosure provides methods for treating an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria] by administering one or more ActRII antagonists. In some embodiments, the disclosure provides methods for preventing an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria] by administering one or more ActRII antagonists. In some embodiments, the methods of the disclosure relate to treating or preventing an ulcer, particularly a cutaneous ulcer, in a subject that has a hemolytic anemia by administering one or more ActRII antagonists. In some embodiments, the methods of the disclosure relate to treating an ulcer, particularly a cutaneous ulcer, in a subject that has a hemolytic anemia by administering one or more ActRII antagonists. In some embodiments, the methods of the disclosure relate to preventing an ulcer, particularly a cutaneous ulcer, in a subject that has a hemolytic anemia by administering one or more ActRII antagonists. In particular, the methods of the disclosure relate, in part, to methods of treating or preventing an ulcer, particularly a cutaneous ulcer, in a subject that has a hemoglobinopathy anemia by administering one or more ActRII antagonists. In some embodiments, the methods of the disclosure relate to methods of treating an ulcer, particularly a cutaneous ulcer, in a subject that has a hemoglobinopathy anemia by administering one or more ActRII antagonists. In some embodiments, the methods of the disclosure relate to methods of preventing an ulcer, particularly a cutaneous ulcer, in a subject that has a hemoglobinopathy anemia by administering one or more ActRII antagonists. For example, the present disclosure relates, in part, to methods of treating or preventing an ulcer, particularly a cutaneous ulcer, in a subject that has a thalassemia syndrome by administering one or more ActRII antagonists. In some embodiments, the present disclosure relates to methods of treating an ulcer, particularly a cutaneous ulcer, in a subject that has a thalassemia syndrome by administering one or more ActRII antagonists. In some embodiments, the present disclosure relates to methods of preventing an ulcer, particularly a cutaneous ulcer, in a subject that has a thalassemia syndrome by administering one or more ActRII antagonists. In some embodiments, the present disclosure relates to methods of treating or preventing an ulcer, particularly a cutaneous ulcer, in a subject that has sickle-cell disease by administering one or more ActRII antagonists. In some embodiments, the present disclosure relates to methods of treating an ulcer, particularly a cutaneous ulcer, in a subject that has sickle-cell disease by administering one or more ActRII antagonists. In some embodiments, the present disclosure relates to methods of preventing an ulcer, particularly a cutaneous ulcer, in a subject that has sickle-cell disease by administering one or more ActRII antagonists. In certain aspects, one or more ActRII antagonists can be used in combination with one or more existing supportive therapies for treating or preventing ulcers and/or treating anemia (e.g., supportive therapies for treating sickle-cell disease, thalassemia, etc.). Examples of such supportive therapies are well known in the art and also described herein. In some embodiments, the subject is a transfusion dependent subject having anemia. In some embodiments, the subject is a non-transfusion dependent subject having anemia.

In part, the disclosure provides methods of treating ulcers associated with anemia, particularly treating or preventing cutaneous (skin) ulcers, with one or more ActRII antagonists. In some embodiments, the disclosure provides methods of treating ulcers associated with anemia, particularly treating cutaneous (skin) ulcers, with one or more ActRII antagonists. In part, the disclosure provides methods of preventing ulcers associated with anemia, particularly preventing cutaneous (skin) ulcers, with one or more ActRII antagonists. ActRII antagonists of the disclosure include, for example, agents that can inhibit ActRII receptor (e.g., an ActRIIA and/or ActRIIB receptor) mediated activation of a signal transduction pathway (e.g., activation of signal transduction via intracellular mediators, such as SMAD 1, 2, 3, 5, and/or 8); agents that can inhibit one or more ActRII ligands (e.g., activin A, activin B, activin AB, activin C, activin E, GDF11, GDF8, BMP6, BMP7, Nodal, etc.) from, e.g., binding to and/or activating an ActRII receptor; agents that inhibit expression (e.g., transcription, translation, cellular secretion, or combinations thereof) of an ActRII ligand and/or an ActRII receptor; and agents that can inhibit one or more intracellular mediators of the ActRII signaling pathway (e.g., SMADs 1, 2, 3, 5, and/or 8).

In certain embodiments, the disclosure relates to one or more ActRII antagonists for use in a method to increase red blood cell levels and/or hemoglobin levels in patients in need thereof and to treat or prevent one or more complications associated with low red blood cell levels and/or hemoglobin levels in these patients. In particular, the disclosure provides ActRII antagonists for use in treating or preventing an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria]. In some embodiments, the disclosure provides ActRII antagonists for use in treating an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria]. In some embodiments, the disclosure provides ActRII antagonists for use in preventing an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria]. In some embodiments, the ActRII antagonists of the disclosure are for use in treating or preventing an ulcer, particularly a cutaneous ulcer, in a subject that has a hemolytic anemia. In some embodiments, the ActRII antagonists of the disclosure are for use in treating an ulcer, particularly a cutaneous ulcer, in a subject that has a hemolytic anemia. In some embodiments, the ActRII antagonists of the disclosure are for use in preventing an ulcer, particularly a cutaneous ulcer, in a subject that has a hemolytic anemia. In particular, the ActRII antagonists of the disclosure are for use in, in part, treating or preventing an ulcer, particularly a cutaneous ulcer, in a subject that has a hemoglobinopathy anemia. In some embodiments, the ActRII antagonists of the disclosure are for use in treating an ulcer, particularly a cutaneous ulcer, in a subject that has a hemoglobinopathy anemia. In some embodiments, the ActRII antagonists of the disclosure are for use in preventing an ulcer, particularly a cutaneous ulcer, in a subject that has a hemoglobinopathy anemia. For example, the present disclosure relates, in part, to one or more ActRII antagonists for use in treating or preventing an ulcer, particularly a cutaneous ulcer, in a subject that has a thalassemia syndrome. In some embodiments, the present disclosure relates to one or more ActRII antagonists for use in treating an ulcer, particularly a cutaneous ulcer, in a subject that has a thalassemia syndrome. In some embodiments, the present disclosure relates to one or more ActRII antagonists for use in preventing an ulcer, particularly a cutaneous ulcer, in a subject that has a thalassemia syndrome. In some embodiments, the present disclosure relates to one or more ActRII antagonists for use in treating or preventing an ulcer, particularly a cutaneous ulcer, in a subject that has sickle-cell disease. In some embodiments, the present disclosure relates to one or more ActRII antagonists for use in treating an ulcer, particularly a cutaneous ulcer, in a subject that has sickle-cell disease. In some embodiments, the present disclosure relates to one or more ActRII antagonists for use in preventing an ulcer, particularly a cutaneous ulcer, in a subject that has sickle-cell disease. In certain aspects, one or more ActRII antagonists can be used in combination with one or more existing supportive therapies for treating or preventing ulcers and/or treating anemia (e.g., supportive therapies for treating sickle-cell disease, thalassemia, etc.). Examples of such supportive therapies are well known in the art and also described herein.

In part, the disclosure provides one or more ActRII antagonists for use in treating ulcers associated with anemia, particularly treating or preventing cutaneous (skin) ulcers. In some embodiments, the disclosure provides one or more ActRII antagonists for use in treating ulcers associated with anemia, particularly treating cutaneous (skin) ulcers, with one or more ActRII antagonists. In part, the disclosure provides one or more ActRII antagonists for use in preventing ulcers associated with anemia, particularly preventing cutaneous (skin) ulcers. ActRII antagonists of the disclosure include, for example, agents that can inhibit ActRII receptor (e.g., an ActRIIA and/or ActRIIB receptor) mediated activation of a signal transduction pathway (e.g., activation of signal transduction via intracellular mediators, such as SMAD 1, 2, 3, 5, and/or 8); agents that can inhibit one or more ActRII ligands (e.g., activin A, activin B, activin AB, activin C, activin E, GDF11, GDF8, BMP6, BMP7, Nodal, etc.) from, e.g., binding to and/or activating an ActRII receptor; agents that inhibit expression (e.g., transcription, translation, cellular secretion, or combinations thereof) of an ActRII ligand and/or an ActRII receptor; and agents that can inhibit one or more intracellular mediators of the ActRII signaling pathway (e.g., SMADs 1, 2, 3, 5, and/or 8).

In certain embodiments, the disclosure relates to the use of one or more ActRII antagonists in the manufacture of a medicament for increasing red blood cell levels and/or hemoglobin levels in patients in need thereof and for treating or preventing one or more complications associated with low red blood cell levels and/or hemoglobin levels in these patients. In particular, the disclosure provides the use of one or more ActRII antagonists in the manufacture of a medicament for treating or preventing an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria]. In some embodiments, the disclosure provides the use of one or more ActRII antagonists in the manufacture of a medicament for treating an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria]. In some embodiments, the disclosure provides the use of one or more ActRII antagonists in the manufacture of a medicament for preventing an ulcer, particularly a cutaneous ulcer, in a subject in need thereof that has low levels of red blood cells and/or hemoglobin or is otherwise classified as a subject having an anemia [e.g., hereditary spherocytosis, hereditary elliptocytosis, hereditary stomacytosis, glucose6-phosphate dehydrogenase deficiency, sickle-cell disease, thalassemia (both alpha and beta), and paroxysmal nocturnal hemoglobinuria]. In some embodiments, the disclosure provides the use of one or more ActRII antagonists in the manufacture of a medicament for treating or preventing an ulcer, particularly a cutaneous ulcer, in a subject that has a hemolytic anemia. In some embodiments, the disclosure provides the use of one or more ActRII antagonists in the manufacture of a medicament for treating an ulcer, particularly a cutaneous ulcer, in a subject that has a hemolytic anemia. In some embodiments, the disclosure provides the use of one or more ActRII antagonists in the manufacture of a medicament for preventing an ulcer, particularly a cutaneous ulcer, in a subject that has a hemolytic anemia. In particular, the disclosure provides the use of one or more ActRII antagonists in the manufacture of a medicament for, in part, treating or preventing an ulcer, particularly a cutaneous ulcer, in a subject that has a hemoglobinopathy anemia. In some embodiments, the disclosure provides the use of one or more ActRII antagonists in the manufacture of a medicament for treating an ulcer, particularly a cutaneous ulcer, in a subject that has a hemoglobinopathy anemia. In some embodiments, the disclosure provides the use of one or more ActRII antagonists in the manufacture of a medicament for preventing an ulcer, particularly a cutaneous ulcer, in a subject that has a hemoglobinopathy anemia. For example, the present disclosure relates, in part, to the use of one or more ActRII antagonists in the manufacture of a medicament for treating or preventing an ulcer, particularly a cutaneous ulcer, in a subject that has a thalassemia syndrome. In some embodiments, the disclosure provides the use of one or more ActRII antagonists in the manufacture of a medicament for treating an ulcer, particularly a cutaneous ulcer, in a subject that has a thalassemia syndrome by administering one or more ActRII antagonists. In some embodiments, the disclosure provides the use of one or more ActRII antagonists in the manufacture of a medicament for preventing an ulcer, particularly a cutaneous ulcer, in a subject that has a thalassemia syndrome. In some embodiments, the disclosure provides the use of one or more ActRII antagonists in the manufacture of a medicament for treating or preventing an ulcer, particularly a cutaneous ulcer, in a subject that has sickle-cell disease. In some embodiments, the disclosure provides the use of one or more ActRII antagonists in the manufacture of a medicament for treating an ulcer, particularly a cutaneous ulcer, in a subject that has sickle-cell disease. In some embodiments, the disclosure provides the use of one or more ActRII antagonists in the manufacture of a medicament for preventing an ulcer, particularly a cutaneous ulcer, in a subject that has sickle-cell disease. In certain aspects, one or more ActRII antagonists can be used in combination with one or more existing supportive therapies for treating or preventing ulcers and/or treating anemia (e.g., supportive therapies for treating sickle-cell disease, thalassemia, etc.). Examples of such supportive therapies are well known in the art and also described herein.

In part, the disclosure provides the use of one or more ActRII antagonists in the manufacture of a medicament for treating ulcers associated with anemia, particularly treating or preventing cutaneous (skin) ulcers. In some embodiments, the disclosure provides the use of one or more ActRII antagonists in the manufacture of a medicament for treating ulcers associated with anemia, particularly treating cutaneous (skin) ulcers, with one or more ActRII antagonists. In part, the disclosure provides the use of one or more ActRII antagonists in the manufacture of a medicament for preventing ulcers associated with anemia, particularly preventing cutaneous (skin) ulcers. ActRII antagonists of the disclosure include, for example, agents that can inhibit ActRII receptor (e.g., an ActRIIA and/or ActRIIB receptor) mediated activation of a signal transduction pathway (e.g., activation of signal transduction via intracellular mediators, such as SMAD 1, 2, 3, 5, and/or 8); agents that can inhibit one or more ActRII ligands (e.g., activin A, activin B, activin AB, activin C, activin E, GDF11, GDF8, BMP6, BMP7, Nodal, etc.) from, e.g., binding to and/or activating an ActRII receptor; agents that inhibit expression (e.g., transcription, translation, cellular secretion, or combinations thereof) of an ActRII ligand and/or an ActRII receptor; and agents that can inhibit one or more intracellular mediators of the ActRII signaling pathway (e.g., SMADs 1, 2, 3, 5, and/or 8).

In certain embodiments, ActRII antagonists to be used in accordance with the methods disclosed herein are agents that bind to and/or inhibit GDF11 and/or GDF8 (e.g., an agent that inhibits GDF11- and/or GDF8-mediated activation of ActRIIA and/or ActRIIB signaling transduction, such as SMAD 2/3 signaling). Such agents are referred to collectively as GDF-ActRII antagonists. Optionally, such GDF-ActRII antagonists may further inhibit one or more of activin A, activin B, activin AB, activin C, activin E, BMP6, BMP7, and Nodal. Therefore, in some embodiments, the disclosure provides methods of using one or more ActRII antagonists, including, for example, soluble ActRIIA polypeptides, soluble ActRIIB polypeptides, GDF Trap polypeptides, anti-ActRIIA antibodies, anti-ActRIIB antibodies, anti-ActRII ligand antibodies (e.g, anti-GDF11 antibodies, anti-GDF8 antibodies, anti-activin A antibodies, anti-activin B antibodies, anti-activin AB antibodies, anti-activin C antibodies, anti-activin E antibodies, anti-BMP6 antibodies, anti-BMP7 antibodies, and anti-Nodal antibodies), small molecule inhibitors of ActRIIA, small molecule inhibitors of ActRIIB, small molecule inhibitors of one or more ActRII ligands (e.g., activin A, activin B, activin AB, activin C, activin E, GDF11, GDF8, BMP6, BMP7, Nodal, etc.), inhibitor nucleotides of ActRIIA, inhibitor nucleotides of ActRIIB, inhibitor nucleotides of one or more ActRII ligands (e.g., activin A, activin B, activin AB, activin C, activin E, GDF11, GDF8, BMP6, BMP7, Nodal, etc.), or combinations thereof, to increase red blood cell levels and/or hemoglobin levels in a subject in need thereof, treat or prevent an anemia in a subject in need thereof, and/or treat or prevent ulcers, particularly cutaneous ulcers, in a subject that has anemia. In certain embodiments, ActRII antagonists to be used in accordance with the methods disclosed herein bind activin A or acitivin B. In certain embodiments, ActRII antagonists to be used in accordance with the methods disclosed herein bind activin A. In certain embodiments, ActRII antagonists to be used in accordance with the methods disclosed herein bind activin B. In certain embodiments, ActRII antagonists to be used in accordance with the methods disclosed herein do not substantially bind to and/or inhibit activin A (e.g., activin A-mediated activation of ActRIIA and/or ActRIIB signaling transduction, such as SMAD 2/3 signaling).

In part, the present disclosure demonstrates that an ActRII antagonist comprising a variant, extracellular (soluble) ActRIIB domain that binds to and inhibits GDF11 activity (e.g., GDF11-mediated ActRIIA and/or ActRIIB signaling transduction, such as SMAD 2/3 signaling) may be used to increase red blood cell levels in vivo, treat anemia resulting from various conditions/disorders, and treat a cutaneous ulcer in a patient with anemia. Therefore, in certain embodiments, ActRII antagonists to be used in accordance with the methods disclosed herein [e.g., methods of increasing red blood cell levels in a subject in need thereof, methods of treating anemia in a subject in need thereof, methods of treating or preventing one or more complications of anemia (particularly ulcers) in subject in need thereof, etc.] are soluble ActRII polypeptides (e.g., soluble ActRIIA or ActRIIB polypeptides) that bind to and/or inhibit GDF11 (e.g., GDF11-mediated activation of ActRIIA and/or ActRIIB signaling transduction, such as SMAD 2/3 signaling). While soluble ActRIIA and soluble ActRIIB ActRII antagonists may affect red blood cell formation and ulcers through a mechanism other than GDF11 antagonism, the disclosure nonetheless demonstrates that desirable therapeutic agents, with respect to the methods disclosed herein, may be selected on the basis of GDF11 antagonism or ActRII antagonism or both. Optionally, such soluble ActRII polypeptide antagonists may further bind to and/or inhibit GDF8 (e.g. inhibit GDF8-mediated activation of ActRIIA and/or ActRIIB signaling transduction, such as SMAD 2/3 signaling). In some embodiments, soluble ActRIIA and ActRIIB polypeptides of the disclosure that bind to and/or inhibit GDF11 and/or GDF8 may further bind to and/or inhibit one or more additional ActRII ligands selected from: activin A, activin B, activin AB, activin C, activin E, BMP6, BMP7, and Nodal.

In certain aspects, the present disclosure provides GDF Traps that are variant ActRII polypeptides (e.g., ActRIIA and ActRIIB polypeptides), including ActRII polypeptides having amino- and carboxy-terminal truncations and/or other sequence alterations (one or more amino acid substitutions, additions, deletions, or combinations thereof). Optionally, GDF Traps of the invention may be designed to preferentially antagonize one or more ligands of ActRII receptors, such as GDF8 (also called myostatin), GDF11, Nodal, BMP6, and BMP7 (also called OP-1). As disclosed herein, examples of GDF Traps include a set of variants derived from ActRIIB that have greatly diminished affinity for activin, particularly activin A. These variants exhibit desirable effects on red blood cells while reducing effects on other tissues. Examples of such variants include those having an acidic amino acid [e.g., aspartic acid (D) or glutamic acid (E)] at the position corresponding to position 79 of SEQ ID NO:1. In certain embodiments, GDF Traps to be used in accordance with the methods disclosed herein [e.g., methods of increasing red blood cell levels in a subject in need thereof, methods of treating anemia in a subject in need thereof, methods of treating or preventing one or more complications of anemia (particularly ulcers) in subject in need thereof, etc.] bind to and/or inhibit GDF11. Optionally, such GDF Traps may further bind to and/or inhibit GDF8. In some embodiments, GDF Traps that bind to and/or inhibit GDF11 and/or GDF8 may further bind to and/or inhibit one or more additional ActRII ligands (e.g., activin B, activin E, BMP6, BMP7, and Nodal). In some embodiments, GDF Traps to be used in accordance with the methods disclosed herein do not substantially bind to and/or inhibit activin A (e.g., activin A-mediated activation of ActRIIA and/or ActRIIB signaling transduction, such as SMAD 2/3 signaling). In certain embodiments, a GDF Trap polypeptide comprises an amino acid sequence that comprises, consists of, or consists essentially of, the amino acid sequence of SEQ ID NOs: 36, 37, 41, 44, 45, 50 or 51, and polypeptides that are at least 80%, 85%, 90%, 95%, 96%, 97%, 98%, or 99% identical to any of the foregoing. In other embodiments, a GDF Trap polypeptide comprises an amino acid sequence that comprises, consists of, or consists essentially of the amino acid sequence of SEQ ID NOs: 2, 3, 4, 5, 6, 10, 11, 22, 26, 28, 29, 31, or 49, and polypeptides that are at least 80%, 85%, 90%, 95%, 96%, 97%, 98%, or 99% identical to any of the foregoing. In still other embodiments, a GDF Trap polypeptide comprises an amino acid sequence that comprises of the amino acid sequence of SEQ ID NOs: 2, 3, 4, 5, 6, 29, 31, or 49, and polypeptides that are at least 80%, 85%, 90%, 95%, 96%, 97%, 98%, or 99% identical to any of the foregoing, wherein the position corresponding to 79 in SEQ ID NO: 1, 4, or 50 is an acidic amino acid. A GDF Trap may include a functional fragment of a natural ActRII polypeptide, such as one comprising at least 10, 20, or 30 amino acids of a sequence selected from SEQ ID NOs: 1, 2, 3, 4, 5, 6, 9, 10, 11, or 49 or a sequence of SEQ ID NO: 2, 5, 10, 11, or 49 lacking the C-terminal 1, 2, 3, 4, 5 or 10 to 15 amino acids and lacking 1, 2, 3, 4 or 5 amino acids at the N-terminus. In some embodiments, a polypeptide will comprise a truncation relative to SEQ ID NO: 2 or 5 of between 2 and 5 amino acids at the N-terminus and no more than 3 amino acids at the C-terminus. In some embodiments, a GDF Trap for use in accordance with the methods disclosed herein consists of, or consists essentially of, the amino acid sequence of SEQ ID NO:36.

Optionally, a GDF Trap comprising an altered ActRII ligand-binding domain has a ratio of $K_d$ for activin A binding to $K_d$ for GDF11 and/or GDF8 binding that is at least 2-, 5-, 10-, 20, 50-, 100- or even 1000-fold greater relative to the ratio for the wild-type ligand-binding domain. Optionally, the GDF Trap comprising an altered ligand-binding domain has a ratio of $IC_{50}$ for inhibiting activin A to $IC_{50}$ for inhibiting GDF11 and/or GDF8 that is at least 2-, 5-, 10-, 20-, 25-50-, 100- or even 1000-fold greater relative to the wild-type ActRII ligand-binding domain. Optionally, the GDF Trap comprising an altered ligand-binding domain inhibits GDF11 and/or GDF8 with an $IC_{50}$ at least 2, 5, 10, 20, 50, or even 100 times less than the $IC_{50}$ for inhibiting activin A. These GDF Traps can be fusion proteins that include an immunoglobulin Fc domain (either wild-type or mutant). In certain cases, the subject soluble GDF Traps are antagonists (inhibitors) of GDF8 and/or GDF11.

In certain aspects, the disclosure provides GDF Traps which are soluble ActRIIB polypeptides comprising an altered ligand-binding (e.g., GDF11-binding) domain. GDF Traps with altered ligand-binding domains may comprise, for example, one or more mutations at amino acid residues such as E37, E39, R40, K55, R56, Y60, A64, K74, W78, L79, D80, F82 and F101 of human ActRIIB (numbering is relative to SEQ ID NO: 1). Optionally, the altered ligand-binding domain can have increased selectivity for a ligand such as GDF8/GDF11 relative to a wild-type ligand-binding domain of an ActRIIB receptor. To illustrate, these mutations are demonstrated herein to increase the selectivity of the altered ligand-binding domain for GDF11 (and therefore, presumably, GDF8) over activin: K74Y, K74F, K74I, L79D, L79E, and D80I. The following mutations have the reverse effect, increasing the ratio of activin binding over GDF11: D54A, K55A, L79A and F82A. The overall (GDF11 and activin) binding activity can be increased by inclusion of the "tail" region or, presumably, an unstructured linker region, and also by use of a K74A mutation. Other mutations that caused an overall decrease in ligand binding affinity include: R40A, E37A, R56A, W78A, D80K, D80R, D80A, D80G, D80F, D80M and D80N. Mutations may be combined to achieve desired effects. For example, many of the mutations that affect the ratio of GDF11:Activin binding have an overall negative effect on ligand binding, and therefore, these may be combined with mutations that generally increase ligand binding to produce an improved binding protein with ligand selectivity. In an exemplary embodiment, a GDF Trap is an ActRIIB polypeptide comprising an L79D or L79E mutation, optionally in combination with additional amino acid substitutions, additions or deletions.

In certain embodiments, ActRII antagonists to be used in accordance with the methods disclosed herein are ActRIIB polypeptides or ActRIIB-based GDF Trap polypeptides. In general such ActRIIB polypeptides and ActRIIB-based GDF Trap polypeptides are soluble polypeptides that comprise a portion/domain derived from the ActRIIB sequence of SEQ ID NO:1, 4, or 49, particularly an extracellular, ligand-binding portion/domain derived from the ActRIIB sequence of SEQ ID NO:1, 4, or 49. In some embodiments, the portion derived from ActRIIB corresponds to a sequence beginning at any one of amino acids 21-29 (e.g., 21, 22, 23, 24, 25, 26, 27, 28, or 29) of SEQ ID NO:1 or 4 [optionally beginning at 22-25 (e.g., 22, 23, 24, or 25) of SEQ ID NO:1 or 4] and ending at any one of amino acids 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-29 (e.g., 20, 21, 22, 23, 24, 25, 26, 27, 28, or 29) of SEQ ID NO: 1 or 4 [optionally beginning at 22-25 (e.g., 22, 23, 24, or 25) of SEQ ID NO:1 or 4] and ending at any one of amino acids 109-133 (e.g., 109, 110, 111, 112, 113, 114, 115, 116, 117, 118, 119, 120, 121, 122, 123, 124, 125, 126, 127, 128, 129, 130, 131, 132, or 133) of SEQ ID NO: 1 or 4. In some embodiments, the portion derived from ActRIIB corresponds to a sequence beginning at any one of amino acids 20-24 (e.g., 20, 21, 22, 23, or 24) of SEQ ID NO: 1 or 4 [optionally beginning at 22-25 (e.g., 22, 23, 24, or 25) of SEQ ID NO:1 or 4] and ending at any one of amino acids 109-133 (e.g., 109, 110, 111, 112, 113, 114, 115, 116, 117, 118, 119, 120, 121, 122, 123, 124, 125, 126, 127, 128, 129, 130, 131, 132, or 133) of SEQ ID NO: 1 or 4. In some embodiments, the portion derived from ActRIIB corresponds to a sequence beginning at any one of amino acids 21-24 (e.g., 21, 22, 23, or 24) of SEQ ID NO: 1 or 4 and ending at any of amino acids 109-134 (e.g., 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-24 (e.g., 20, 21, 22, 23, or 24) of SEQ ID NO: 1 or 4 and ending at any one of amino acids 118-133 (e.g., 118, 119, 120, 121, 122, 123, 124, 125, 126, 127, 128, 129, 130, 131, 132, or 133) of SEQ ID NO: 1 or 4. In some embodiments, the portion derived from ActRIIB corresponds to a sequence beginning at any one of amino acids 21-24 (e.g., 21, 22, 23, or 24) of SEQ ID NO: 1 or 4 and ending at any one of amino acids 118-134 (e.g., 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-24 (e.g., 20, 21, 22, 23, or 24) of SEQ ID NO: 1 or 4 and ending at any one of amino acids 128-133 (e.g., 128, 129, 130, 131, 132, or 133) of SEQ ID NO: 1 or 4. In some embodiments, the portion derived from ActRIIB corresponds to a sequence beginning at any of amino acids 20-24 (e.g., 20, 21, 22, 23, or 24) of SEQ ID NO: 1 or 39 and ending at any of amino acids 128-133 (e.g., 128, 129, 130, 131, 132, or 133) of SEQ ID NO: 1 or 39. In some embodiments, the portion derived from ActRIIB corresponds to a sequence beginning at any one of amino acids 21-29 (e.g., 21, 22, 23, 24, 25, 26, 27, 28, or 29) of SEQ ID NO: 1 or 4 and ending at any one of amino acids 118-134 (e.g., 118, 119, 120, 121, 122, 123, 124, 125, 126, 127, 128, 129, 130, 131, 132, 133, or 134) of SEQ ID NO: 1 or 4. In some embodiments, the portion derived from ActRIIB corresponds to a sequence beginning at any one of amino acids 20-29 (e.g., 20, 21, 22, 23, 24, 25, 26, 27, 28, or 29) of SEQ ID NO: 1 or 4 and ending at any one of amino acids 118-133 (e.g., 118, 119, 120, 121, 122, 123, 124, 125, 126, 127, 128, 129, 130, 131, 132, or 133) of SEQ ID NO: 1 or 4. In some embodiments, the portion derived from ActRIIB corresponds to a sequence beginning at one any of amino acids 21-29 (e.g., 21, 22, 23, 24, 25, 26, 27, 28, or 29) of SEQ ID NO: 1 or 4 and ending at any one of amino acids 128-134 (e.g., 128, 129, 130, 131, 132, 133, or 134) of SEQ ID NO: 1 or 4. In some embodiments, the portion derived from ActRIIB corresponds to a sequence beginning at any one of amino acids 20-29 (e.g., 20, 21, 22, 23, 24, 25, 26, 27, 28, or 29) of SEQ ID NO: 1 or 4 and ending at any one of amino acids 128-133 (e.g., 128, 129, 130, 131, 132, or 133) of SEQ ID NO: 1 or 4. Surprisingly, ActRIIB and ActRIIB-based GDF Trap constructs beginning at 22-25 (e.g., 22, 23, 24, or 25) of SEQ ID NO: 1 or 4 have activity levels greater than proteins having the full extracellular domain of human ActRIIB. In some embodiments, the ActRIIB polypeptides and ActRIIB-based GDF Trap polypeptides comprises, consists essentially of, or consists of, an amino acid sequence beginning at amino acid position 25 of SEQ ID NO: 1 or 4 and ending at amino acid position 131 of SEQ ID NO: 1 or 4. Any of the foregoing ActRIIB polypeptide or ActRIIB-based GDF Trap polypeptides may be produced as a homodimer. Any of the foregoing ActRIIB polypeptide or ActRIIB-based GDF Trap polypeptides may further comprise a heterologous portion that comprises a constant region from an IgG heavy chain, such as an Fc domain. Any of the above ActRIIB-based GDF Trap polypeptides may comprise an acidic amino acid at the position corresponding to position 79 of SEQ ID NO: 1, optionally in combination with one or more additional amino acid substitutions, deletions, or insertions relative to SEQ ID NO: 1. Any of the above ActRIIB polypeptides ActRIIB-based GDF Trap polypeptides, including homodimer and/or fusion proteins thereof, may bind to and/or inhibit signaling by activin (e.g., activin A, activin B, activin C, or activin AB) in a cell-based assay. Any of the above ActRIIB polypeptides ActRIIB-based GDF Trap polypeptides, including homodimer and/or fusion proteins thereof, may bind to and/or inhibit signaling by GDF11 and/or GDF8 in a cell based assay. Optionally, any of the above ActRIIB polypeptides ActRIIB-based GDF Trap polypeptides, including homodimer and/or fusion proteins thereof, may bind to and/or inhibit signaling of one or more of activin B, activin C, activin E, BMP6, BMP7, and Nodal in a cell-based assay.

Other ActRIIB polypeptides and ActRIIB-based GDF Trap polypeptides are contemplated, such as the following. An ActRIIB polypeptide or GDF Trap polypeptide comprising an amino acid sequence that is at least 80% (e.g., 85%, 90%, 95%, 96%, 97%, 98%, 99%, or 100%) identical to the sequence of amino acids 29-109 of SEQ ID NO: 1 or 4, wherein the position corresponding to 64 of SEQ ID NO: 1 is an R or K, and wherein the ActRIIB polypeptide or ActRIIB-based GDF Trap polypeptide inhibits signaling by activin, GDF8, and/or GDF11 in a cell-based assay. The ActRIIB polypeptide or ActRIIB-based GDF Trap polypeptide as above, wherein at least one alteration with respect to the sequence of SEQ ID NO: 1 or 4 is positioned outside of the ligand-binding pocket. The ActRIIB polypeptide or ActRIIB-based GDF Trap polypeptide as above, wherein at least one alteration with respect to the sequence of SEQ ID NO: 1 or 4 is a conservative alteration positioned within the ligand-binding pocket. The ActRIIB polypeptide or ActRIIB-based GDF Trap polypeptide as above, wherein at least one alteration with respect to the sequence of SEQ ID NO: 1 or 4 is an alteration at one or more positions selected from the group consisting of K74, R40, Q53, K55, F82, and L79.

Other ActRIIB polypeptides and ActRIIB-based GDF Trap polypeptides are contemplated, such as the following. An ActRIIB polypeptide or ActRIIB-based GDF Trap polypeptide comprising an amino acid sequence that is at least 80% (e.g., 85%, 90%, 95%, 96%, 97%, 98%, 99%, or 100%) identical to the sequence of amino acids 29-109 of SEQ ID NO: 1 or 4, and wherein the protein comprises at least one N-X-S/T sequence at a position other than an endogenous N-X-S/T sequence of ActRIIB, and at a position outside of the ligand binding pocket. The ActRIIB polypeptide or ActRIIB-based GDF Trap polypeptide as above, wherein the ActRIIB polypeptide or ActRIIB-based GDF Trap polypeptide comprises an N at the position corresponding to position 24 of SEQ ID NO: 1 or 4 and an S or T at the position corresponding to position 26 of SEQ ID NO: 1 or 4, and wherein the ActRIIB polypeptide or ActRIIB-based GDF Trap polypeptide inhibits signaling by activin, GDF8, and/or GDF11 in a cell-based assay. The ActRIIB polypeptide or ActRIIB-based GDF Trap polypeptide as above, wherein the ActRIIB polypeptide or ActRIIB-based GDF Trap polypeptide comprises an R or K at the position corresponding to position 64 of SEQ ID NO: 1 or 4. The ActRIIB polypeptide or ActRIIB-based GDF Trap polypeptide as above, wherein ActRIIB polypeptide or ActRIIB-based GDF Trap polypeptide comprises a D or E at the position corresponding to position 79 of SEQ ID NO: 1 or 4, and wherein the ActRIIB polypeptide or ActRIIB-based GDF Trap polypeptide inhibits signaling by activin, GDF8, and/or GDF11 in a cell-based assay. The ActRIIB polypeptide or ActRIIB-based GDF Trap polypeptide as above, wherein at least one alteration with respect to the sequence of SEQ ID NO: 1 or 4 is a conservative alteration positioned within the ligand-binding pocket. The ActRIIB polypeptide or ActRIIB-based GDF Trap polypeptide as above, wherein at least one alteration with respect to the sequence of SEQ ID NO: 1 or 4 is an alteration at one or more positions selected from the group consisting of K74, R40, Q53, K55, F82, and L79. The ActRIIB polypeptide or ActRIIB-based GDF Trap polypeptide above, wherein the ActRIIB polypeptide or ActRIIB-based GDF Trap polypeptide is a fusion protein further comprising one or more heterologous portion. Any of the above ActRIIB polypeptides or ActRIIB-based GDF Trap polypeptides, or fusion proteins thereof, may be produced as a homodimer. Any of the above ActRIIB fusion proteins or ActRIIB-based GDF Trap fusion proteins may have a heterologous portion that comprises a constant region from an IgG heavy chain, such as an Fc domain.

In certain embodiments, an ActRIIB polypeptide, for use in accordance with the methods disclosed herein, comprises an amino acid sequence that comprises, consists of, or consists essentially of, the amino acid sequence of SEQ ID NOs: 2, 3, 5, 6, 29, 31, or 49, and polypeptides that are at least 80%, 85%, 90%, 95%, 96%, 97%, 98%, or 99% identical to any of the foregoing. An ActRIIB polypeptide may include a functional fragment of a natural ActRIIB polypeptide, such as one comprising at least 10, 20 or 30 amino acids of a sequence selected from SEQ ID NOs: 2, 3, 5, 6, 29, 31, or 49 or a sequence of SEQ ID NO: 2 or 5, lacking the C-terminal 1, 2, 3, 4, 5 or 10 to 15 amino acids and lacking 1, 2, 3, 4 or 5 amino acids at the N-terminus. In some embodiments, a polypeptide will comprise a truncation relative to SEQ ID NO: 2 or 5 of between 2 and 5 amino acids at the N-terminus and no more than 3 amino acids at the C-terminus. In some embodiments, a GDF Trap for use in accordance with the methods described herein consists of, or consists essentially of, the amino acid sequence of SEQ ID NO:29.

A general formula for an active (e.g., ligand binding) ActRIIA polypeptide is one that comprises a polypeptide that starts at amino acid 30 and ends at amino acid 110 of SEQ ID NO:9. Accordingly, ActRIIA polypeptides and ActRIIA-based GDF Traps of the present disclosure may comprise, consist, or consist essentially of a polypeptide that is at least 80%, 85%, 90%, 95%, 96%, 97%, 98%, 99%, or 100% identical to amino acids 30-110 of SEQ ID NO:9. Optionally, ActRIIA polypeptides and ActRIIA-based GDF Trap polypeptides of the present disclosure comprise, consists, or consist essentially of a polypeptide that is at least 80%, 85%, 90%, 95%, 96%, 97%, 98%, 99%, or 100% identical to amino acids amino acids 12-82 of SEQ ID NO:9 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115) or SEQ ID NO:9, respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO:9. Any of the foregoing ActRIIA polypeptide or ActRIIA-based GDF Trap polypeptides may be produced as a homodimer. Any of the foregoing ActRIIA polypeptide or ActRIIA-based GDF Trap polypeptides may further comprise a heterologous portion that comprises a constant region from an IgG heavy chain, such as an Fc domain. Any of the above ActRIIA polypeptides ActRIIA-based GDF Trap polypeptides, including homodimer and/or fusion proteins thereof, may bind to and/or inhibit signaling by activin (e.g., activin A, activin B, activin C, or activin AB) in a cell-based assay. Any of the above ActRIIA polypeptides ActRIIA-based GDF Trap polypeptides, including homodimer and/or fusion proteins thereof, may bind to and/or inhibit signaling by GDF11 and/or GDF8 in a cell based assay. Optionally, any of the above ActRIIA polypeptides ActRIIB-based GDF Trap polypeptides, including homodimer and/or fusion proteins thereof, may bind to and/or inhibit signaling of one or more of activin B, activin C, activin E, GDF7, and Nodal in a cell-based assay.

In certain embodiments, ActRIIA polypeptides and ActRIIA-based GDF-Trap polypeptides, for use in accordance with the methods disclosed herein, comprises an amino acid sequence that comprises, consists of, or consists essentially of, the amino acid sequence of SEQ ID NOs: 9, 10, 22, 26, or 28, and polypeptides that are at least 80%, 85%, 90%, 95%, 96%, 97%, 98%, or 99% identical to any of the foregoing. An ActRIIA polypeptide or ActRIIA-based GDF-Trap polypeptide may include a functional fragment of a natural ActRIIA polypeptide, such as one comprising at least 10, 20 or 30 amino acids of a sequence selected from SEQ ID NOs: 9, 10, 22, 26, or 28 or a sequence of SEQ ID NO:10, lacking the C-terminal 1, 2, 3, 4, 5 or 10 to 15 amino acids and lacking 1, 2, 3, 4 or 5 amino acids at the N-terminus. In some embodiments, a polypeptide will comprise a truncation relative to SEQ ID NO:10 of between 2 and 5 amino acids at the N-terminus and no more than 3 amino acids at the C-terminus. In some embodiments, an ActRIIA polypeptide for use in the methods described herein consists of, or consists essentially of, the amino acid sequence of SEQ ID NO: 26 or 28.

An ActRII polypeptide (e.g. an ActRIIA or ActRIIB polypeptide) or GDF Trap polypeptide of the disclosure may include one or more alterations (e.g., amino acid additions, deletions, substitutions, or combinations thereof) in the amino acid sequence of an ActRII polypeptide (e.g., in the ligand-binding domain) relative to a naturally occurring ActRII polypeptide. The alteration in the amino acid sequence may, for example, alter glycosylation of the polypeptide when produced in a mammalian, insect, or other eukaryotic cell or alter proteolytic cleavage of the polypeptide relative to the naturally occurring ActRII polypeptide.

Optionally, ActRII polypeptides (e.g. an ActRIIA or ActRIIB polypeptides) and GDF Trap polypeptides of the disclosure comprise one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

In some embodiments, an ActRII polypeptide (e.g. an ActRIIA or ActRIIB polypeptide) or GDF Trap polypeptide of the disclosure may be a fusion protein that has, as one domain, an ActRII polypeptide or GDF Trap polypeptide (e.g., a ligand-binding domain of an ActRII receptor, optionally with one or more sequence variations) and one or more additional heterologous domains that provide a desirable property, such as improved pharmacokinetics, easier purification, targeting to particular tissues, etc. For example, a domain of a fusion protein may enhance one or more of in vivo stability, in vivo half-life, uptake/administration, tissue localization or distribution, formation of protein complexes, multimerization of the fusion protein, and/or purification. ActRII polypeptide and GDF Trap fusion proteins may include a heterologous polypeptide domain such as but not limited to, an immunoglobulin Fc domain (wild-type or mutant) or a serum albumin. In some embodiments, the immunoglobulin Fc domain is an IgG1 Fc domain. In some embodiments, the IgG1 Fc domain is a human IgG1 Fc domain. In some embodiments, the IgG1 Fc domain is a mouse IgG1 Fc domain. In certain embodiments, an ActRII polypeptide and GDF Trap polypeptide fusion protein comprises a relatively unstructured linker positioned between the ActRII or GDF Trap polypeptide domain and the heterologous domain. In certain embodiments, an ActRII polypeptide and GDF Trap fusion protein comprises a relatively unstructured linker positioned between the Fc domain and the ActRII or GDF Trap domain. This unstructured linker may correspond to the roughly 15 amino acid unstructured region at the C-terminal end of the extracellular domain of ActRII or GDF Trap (the "tail"), or it may be an artificial sequence of between 3 and 5, 15, 20, 30, 50 or more amino acids that are relatively free of secondary structure. A linker may be rich in glycine and proline residues and may, for example, contain repeating sequences of threonine/serine and glycines [e.g., TG$_4$ (SEQ ID NO:52), SG$_4$ (SEQ ID NO:54), or TG$_3$ (SEQ ID NO:53) singlets or repeats] or a series of three glycines. A fusion protein may include a purification subsequence, such as an epitope tag, a FLAG tag, a polyhistidine sequence, and a GST fusion. In certain embodiments, an ActRII fusion protein or GDF Trap fusion comprises a leader sequence. The leader sequence may be a native ActRII leader sequence (e.g., a native ActRIIA or ActRIIB leader sequence) or a heterologous leader sequence. In certain embodiments, the leader sequence is a Tissue Plasminogen Activator (TPA) leader sequence. In some embodiments, an ActRII fusion protein or GDF Trap fusion protein comprises an amino acid sequence as set forth in the formula A-B-C. The B portion is an N- and C-terminally truncated ActRII or GDF Trap polypeptide as described herein. The A and C portions may be independently zero, one or more than one amino acids, and both A and C portions are heterologous to B. The A and/or C portions may be attached to the B portion via a linker sequence.

Optionally, ActRII polypeptides (e.g., ActRIIA and ActRIIB polypeptides) GDF Trap polypeptides, including variants and fusion proteins thereof, to be used in accordance with the methods disclosed herein bind to one or more ActRIIB ligand (e.g., activin A, activin B, activin AB, activin C, activin E, GDF11, GDF8, BMP6, BMP7, and/or Nodal) with a Kd less than 10 micromolar, less than 1 micromolar, less than 100 nanomolar, less than 10 nanomolar, or less than 1 nanomolar. Optionally, such ActRII polypeptides GDF Trap polypeptides inhibit ActRII signaling, such as ActRIIA and/or ActRIIB intracellular signal transduction events triggered by an ActRII ligand (e.g., SMAD 2/3 and/or SMAD 1/5/8 signaling).

In certain aspects, the disclosure provides pharmaceutical preparations or compositions comprising an ActRII antagonist of the present disclosure (e.g., an ActRIIA polypeptide, and ActRIIB polypeptide, a GDF Trap polypeptide) and a pharmaceutically acceptable carrier. A pharmaceutical preparation or composition may also include one or more additional compounds such as a compound that is used to treat a disorder or condition described herein (e.g., an addition compound that increases red blood cell levels and/or hemoglobin levels in a subject in need thereof, treats or prevents anemia in a subject in need thereof, treat or prevents an ulcer, particularly a cutaneous ulcer, a subject in need thereof). Preferably, a pharmaceutical preparation or composition of the disclosure is substantially pyrogen-free.

In general, it is preferable that an ActRIIA polypeptide, and ActRIIB polypeptide, or a GDF Trap polypeptide be expressed in a mammalian cell line that mediates suitably natural glycosylation of the polypeptide so as to diminish the likelihood of an unfavorable immune response in a patient. Human and CHO cell lines have been used successfully, and it is expected that other common mammalian expression vectors will be useful. In some embodiments, preferable ActRIIA polypeptides, ActRIIB polypeptides, and GDF Trap polypeptides are glycosylated and have a glycosylation pattern that is obtainable from a mammalian cell, preferably a CHO cell.

In certain embodiments, the disclosure provides packaged pharmaceuticals comprising a pharmaceutical preparation or composition described herein and labeled for use in one or more of increasing red blood cell levels and/or hemoglobin in a mammal (preferably a human), treating or preventing anemia in a mammal (preferably a human), treating or preventing sickle cell disease in a mammal (preferably a human), and/or treating or preventing one or more complications of sickle-cell disease (e.g., anemia, vaso-occlusive crisis, ulcers (such as cutaneous ulcers), etc.) in a mammal (preferably a human). In certain embodiments, the disclosure provides packaged pharmaceuticals comprising a pharmaceutical preparation or composition described herein and labeled for use in treating anemia in a mammal (preferably a human), treating sickle cell disease in a mammal (preferably a human), and/or treating one or more complications of sickle-cell disease (e.g., anemia, vaso-occlusive crisis, ulcers (such as cutaneous ulcers), etc.) in a mammal (preferably a human). In certain embodiments, the disclosure provides packaged pharmaceuticals comprising a pharmaceutical preparation or composition described herein and labeled for use in preventing anemia in a mammal (preferably a human), preventing sickle cell disease in a mammal (preferably a human), and/or treating or preventing one or more complications of sickle-cell disease (e.g., anemia, vaso-occlusive crisis, ulcers (such as cutaneous ulcers), etc.) in a mammal (preferably a human).

In certain aspects, the disclosure provides nucleic acids encoding an ActRII polypeptide (e.g., an ActRIIA or ActRIIB polypeptide) or GDF Trap polypeptide. An isolated polynucleotide may comprise a coding sequence for a soluble ActRII polypeptide or GDF Trap polypeptide, such as described herein. For example, an isolated nucleic acid may include a sequence coding for an ActRII polypeptide or GDF Trap comprising an extracellular domain (e.g., ligand-binding domain) of an ActRII polypeptide having one or more sequence variations and a sequence that would code for part or all of the transmembrane domain and/or the cytoplasmic domain of an ActRII polypeptide, but for a stop codon positioned within the transmembrane domain or the cytoplasmic domain, or positioned between the extracellular domain and the transmembrane domain or cytoplasmic domain. For example, an isolated polynucleotide coding for a GDF Trap may comprise a full-length ActRII polynucleotide sequence such as SEQ ID NO: 1, 4, or 9 or having one or more variations, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRII. Nucleic acids disclosed herein may be operably linked to a promoter for expression, and the disclosure provides cells transformed with such recombinant polynucleotides. Preferably the cell is a mammalian cell, such as a CHO cell.

In certain aspects, the disclosure provides methods for making an ActRII polypeptide or GDF Trap. Such a method may include expressing any of the nucleic acids disclosed herein (e.g., SEQ ID NO: 8, 13, 27, 32, 39, 42, 46, or 48) in a suitable cell, such as a Chinese hamster ovary (CHO) cell. Such a method may comprise: a) culturing a cell under conditions suitable for expression of the GDF Trap polypeptide, wherein said cell is transformed with a GDF Trap expression construct; and b) recovering the GDF Trap polypeptide so expressed. GDF Trap polypeptides may be recovered as crude, partially purified or highly purified fractions using any of the well-known techniques for obtaining protein from cell cultures.

In certain aspects, the present disclosure relates to an antibody, or combination of antibodies, that antagonize ActRII activity (e.g., inhibition of ActRIIA and/or ActRIIB signaling transduction, such as SMAD 2/3 and/or SMAD 1/5/8 signaling). In particular, the disclosure provides methods of using an antibody ActRII antagonist, or combination of antibody ActRII antagonists, to, e.g., increase red blood cell levels in a subject in need thereof, treat or prevent an anemia in a subject in need thereof, and/or treat or prevent an ulcer, particularly a cutaneous ulcer, in a subject that has anemia. In some embodiments, the disclosure provides methods of using an antibody ActRII antagonist, or combination of antibody ActRII antagonists to treat an ulcer, particularly a cutaneous ulcer, in a subject that has anemia. In some embodiments, the disclosure provides methods of using an antibody ActRII antagonist, or combination of antibody ActRII antagonists to prevent an ulcer, particularly a cutaneous ulcer, in a subject that has anemia.

In certain embodiments, an antibody ActRII antagonist of the disclosure is an antibody, or combination of antibodies, that binds to and/or inhibits activity of at least GDF11 (e.g., GDF11-mediated activation of ActRIIA and/or ActRIIB signaling transduction, such as SMAD 2/3 signaling). Optionally, the antibody, or combination of antibodies, further binds to and/or inhibits activity of GDF8 (e.g., GDF8-mediated activation of ActRIIA and/or ActRIIB signaling transduction, such as SMAD 2/3 signaling), particularly in the case of a multi-specific antibody that has binding affinity for both GDF11 and GDF8 or in the context of a combination of one or more anti-GDF11 antibody and one or more anti-GDF8 antibody. Optionally, an antibody, or combination of antibodies, of the disclosure does not substantially bind to and/or inhibit activity of activin A (e.g., activin A-mediated activation of ActRIIA or ActRIIB signaling transduction, such as SMAD 2/3 signaling). In some embodiments, an antibody, or combination of antibodies, of the disclosure that binds to and/or inhibits the activity of GDF11 and/or GDF8 further binds to and/or inhibits activity of one of more of activin A, activin B, activin AB, activin C, activin E, BMP6, BMP7, and Nodal (e.g., activation of ActRIIA or ActRIIB signaling transduction, such as SMAD 2/3 and/or SMAD 1/5/8 signaling), particularly in the case of a multi-specific antibody that has binding affinity for multiple ActRII ligands or in the context of a combination multiple antibodies—each having binding affinity for a different ActRII ligand.

In part, the disclosure demonstrates that ActRII antagonists may be used in combination (e.g., administered at the same time or different times, but generally in such a manner as to achieve overlapping pharmacological effects) with EPO receptor activators to increase red blood cell levels (erythropoiesis) or treat anemia in patients in need thereof. In part, the disclosure demonstrates that a GDF Trap can be administered in combination with an EPO receptor activator to synergistically increase formation of red blood cells in a patient, particularly in sickle-cell patients. Thus, the effect of this combined treatment can be significantly greater than the sum of the effects of the ActRII antagonists and the EPO receptor activator when administered separately at their respective doses. In certain embodiments, this synergism may be advantageous since it enables target levels of red blood cells to be attained with lower doses of an EPO receptor activator, thereby avoiding potential adverse effects or other problems associated with higher levels of EPO receptor activation. Accordingly, in certain embodiments, the methods of the present disclosure (e.g., methods of increasing red blood cell levels and/or hemoglobin in a subject in need thereof, treating or preventing anemia in a subject in need thereof, and/or treating or preventing an ulcer in a subject that has anemia) comprise administering a patient in need thereof one or more ActRII antagonists (e.g., ActRIIA polypeptides, ActRIIB polypeptides, and/or GDF Trap polypeptides) in combination with one or more EPO receptor activators.

An EPO receptor activator may stimulate erythropoiesis by directly contacting and activating EPO receptor. In certain embodiments, the EPO receptor activator is one of a class of compounds based on the 165 amino-acid sequence of native EPO and generally known as erythropoiesis-stimulating agents (ESAs), examples of which are epoetin alfa, epoetin beta (NeoRecormon®), epoetin delta (Dynepo™), and epoetin omega. In other embodiments, ESAs include synthetic EPO proteins (SEPs) and EPO derivatives with nonpeptidic modifications conferring desirable pharmacokinetic properties (lengthened circulating half-life), examples of which are darbepoetin alfa (Aranesp®) and methoxy-polyethylene-glycol epoetin beta (Mircera®). In certain embodiments, an EPO receptor activator may be an EPO receptor agonist that does not incorporate the EPO polypeptide backbone or is not generally classified as an ESA. Such EPO receptor agonists may include, but are not limited to, peptidic and nonpeptidic mimetics of EPO, agonistic antibodies targeting EPO receptor, fusion proteins comprising an EPO mimetic domain, and erythropoietin receptor extended-duration limited agonists (EREDLA).

In certain embodiments, an EPO receptor activator may stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. In part, the disclosure provides increased erythropoiesis in a patient by combined treatment with a GDF Trap and an indirect EPO receptor activator with HIF stabilizing properties, such as a prolyl hydroxylase inhibitor.

ActRII antagonists, particularly ActRII polypeptides and GDF Trap polypeptides, may also be used for treating or preventing other disorders and conditions such as promoting muscle growth and/or treating or preventing a muscle-related disorder, promoting bone growth and/or treating or preventing a bone-related disorder, treating or preventing cancer (particularly multiple myeloma and/or breast cancer). See, e.g., U.S. Pat. Nos. 7,612,041; 8,173,601; 7,842,663 as well as U.S. Patent Application Publication No. U.S. 2009/0074768. In certain instances, when administering a GDF Trap polypeptide for these other therapeutic indications, it may be desirable to monitor the effects on red blood cells during administration of the ActRII antagonist, or to determine or adjust the dosing of the ActRII antagonist, in order to reduce undesired effects on red blood cells. For example, increases in red blood cell levels, hemoglobin levels, or hematocrit levels may cause increases in blood pressure.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

FIG. 1 shows an alignment of extracellular domains of human ActRIIA (SEQ ID NO:56) and human ActRIIB (SEQ ID NO:2) with the residues that are deduced herein, based on composite analysis of multiple ActRIIB and ActRIIA crystal structures, to directly contact ligand indicated with boxes.

FIGS. 3A and 3B shows the purification of ActRIIA-hFc expressed in CHO cells. The protein purifies as a single, well-defined peak as visualized by sizing column (top panel) and Coomassie stained SDS-PAGE (bottom panel) (left lane: molecular weight standards; right lane: ActRIIA-hFc).

FIG. 5A shows red blood cell (RBC) counts. FIG. 5B shows hemoglobin levels. Statistical significance is relative to baseline for each treatment group. At day 57, two monkeys remained in each group.

FIG. 6A shows red blood cell (RBC) counts. FIG. 6B shows hemoglobin levels. Statistical significance is relative to baseline for each treatment group. At day 57, two monkeys remained in each group.

FIG. 7A shows absolute reticulocyte counts. FIG. 7B shows the percentage of reticulocytes relative to RBCs. Statistical significance is relative to baseline for each group. At day 57, two monkeys remained in each group.

FIG. 8A shows absolute reticulocyte counts. FIG. 8B shows the percentage of reticulocytes relative to RBCs. Statistical significance is relative to baseline for each group. At day 57, two monkeys remained in each group.

FIG. 16 shows the full amino acid sequence for the GDF Trap ActRIIB(L79D 20-134)-hFc (SEQ ID NO:38), including the TPA leader sequence (double underlined), ActRIIB extracellular domain (residues 20-134 in SEQ ID NO: 1; underlined), and hFc domain. The aspartate substituted at position 79 in the native sequence is double underlined and highlighted, as is the glycine revealed by sequencing to be the N-terminal residue in the mature fusion protein.

FIGS. 17A and 17B show a nucleotide sequence encoding ActRIIB(L79D 20-134)-hFc. SEQ ID NO:39 corresponds to the sense strand, and SEQ ID NO:40 corresponds to the antisense strand. The TPA leader (nucleotides 1-66) is double underlined, and the ActRIIB extracellular domain (nucleotides 76-420) is underlined.

FIG. 18 shows the full amino acid sequence for the truncated GDF Trap ActRIIB(L79D 25-131)-hFc (SEQ ID NO:41), including the TPA leader (double underlined), truncated ActRIIB extracellular domain (residues 25-131 in SEQ ID NO:1; underlined), and hFc domain. The aspartate substituted at position 79 in the native sequence is double underlined and highlighted, as is the glutamate revealed by sequencing to be the N-terminal residue in the mature fusion protein.

FIGS. 19A and 19B show a nucleotide sequence encoding ActRIIB(L79D 25-131)-hFc. SEQ ID NO:42 corresponds to the sense strand, and SEQ ID NO:43 corresponds to the antisense strand. The TPA leader (nucleotides 1-66) is double underlined, and the truncated ActRIIB extracellular domain (nucleotides 76-396) is underlined. The amino acid sequence for the ActRIIB extracellular domain (residues 25-131 in SEQ ID NO: 1) is also shown (SEQ ID NO:45).

FIG. 20 shows the amino acid sequence for the truncated GDF Trap ActRIIB(L79D 25-131)-hFc without a leader (SEQ ID NO:44). The truncated ActRIIB extracellular domain (residues 25-131 in SEQ ID NO:1) is underlined. The aspartate substituted at position 79 in the native sequence is double underlined and highlighted, as is the glutamate revealed by sequencing to be the N-terminal residue in the mature fusion protein.

FIG. 21 shows the amino acid sequence for the truncated GDF Trap ActRIIB(L79D 25-131) without the leader, hFc domain, and linker (SEQ ID NO:45). The aspartate substituted at position 79 in the native sequence is underlined and highlighted, as is the glutamate revealed by sequencing to be the N-terminal residue in the mature fusion protein.

FIGS. 22A and 22B show an alternative nucleotide sequence encoding ActRIIB(L79D 25-131)-hFc. SEQ ID NO:46 corresponds to the sense strand, and SEQ ID NO:47 corresponds to the antisense strand. The TPA leader (nucleotides 1-66) is double underlined, the truncated ActRIIB extracellular domain (nucleotides 76-396) is underlined, and substitutions in the wild-type nucleotide sequence of the extracellular domain are double underlined and highlighted (compare with SEQ ID NO:42, FIG. 19). The amino acid sequence for the ActRIIB extracellular domain (residues 25-131 in SEQ ID NO:1) is also shown (SEQ ID NO:45).

FIG. 23 shows nucleotides 76-396 (SEQ ID NO:48) of the alternative nucleotide sequence shown in FIG. 22 (SEQ ID NO:46). The same nucleotide substitutions indicated in FIG.

22 are also underlined and highlighted here. SEQ ID NO:48 encodes only the truncated ActRIIB extracellular domain (corresponding to residues 25-131 in SEQ ID NO:1) with a L79D substitution, e.g., ActRIIB(L79D 25-131).

Figure 24:
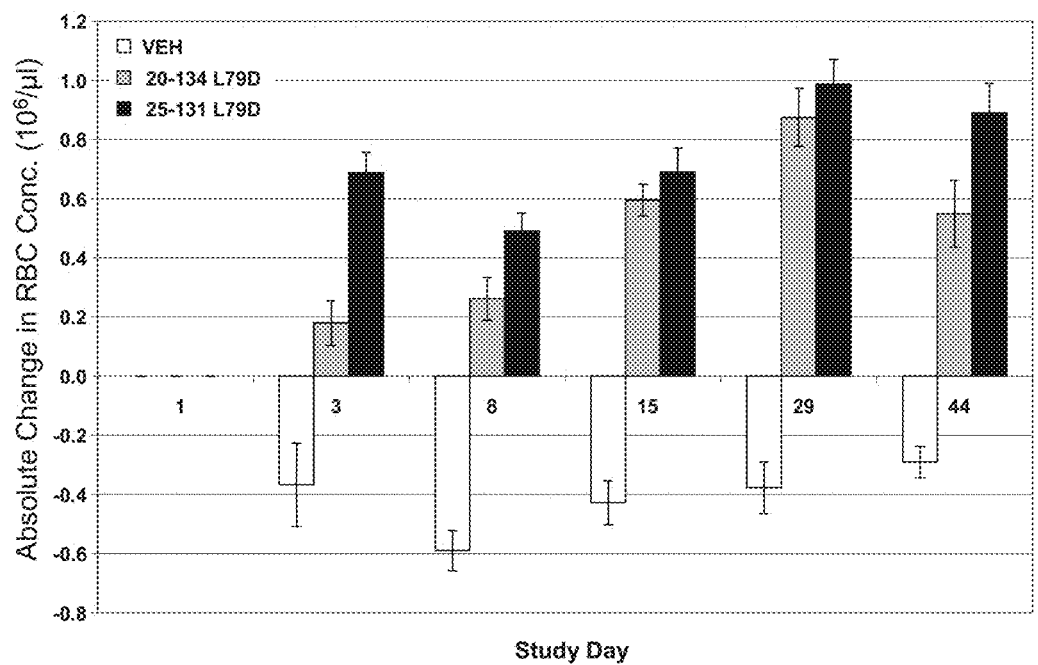

FIG. 24 shows the effect of treatment with ActRIIB(L79D 20-134)-hFc (gray) or ActRIIB(L79D 25-131)-hFc (black) on the absolute change in red blood cell concentration from baseline in cynomolgus monkey. VEH=vehicle. Data are means±SEM. n=4-8 per group.

Figure 25:
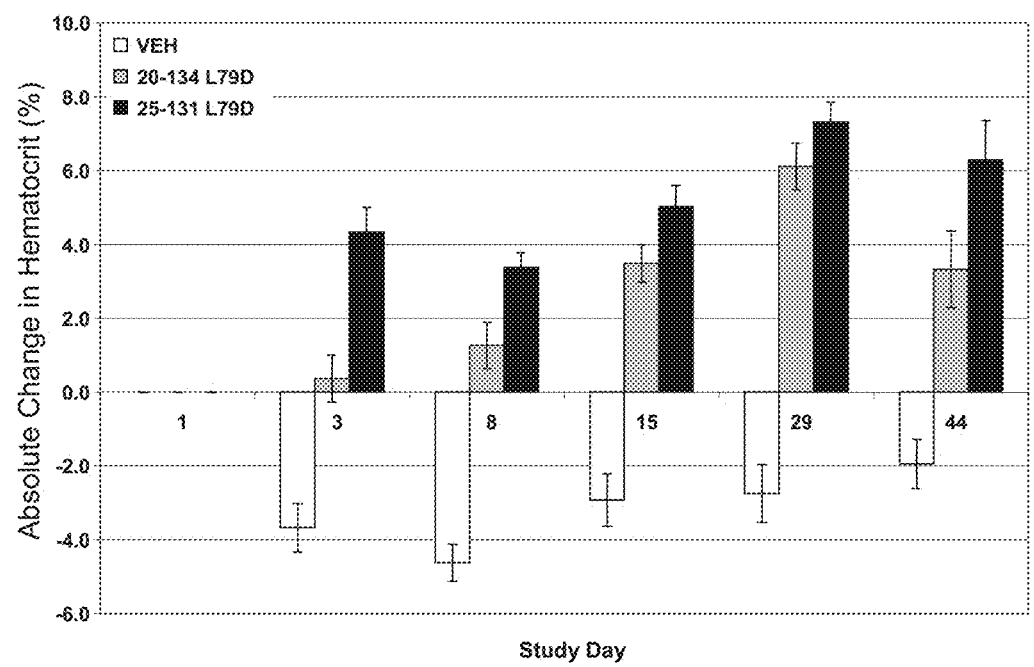

FIG. 25 shows the effect of treatment with ActRIIB(L79D 20-134)-hFc (gray) or ActRIIB(L79D 25-131)-hFc (black) on the absolute change in hematocrit from baseline in cynomolgus monkey. VEH=vehicle. Data are means±SEM. n=4-8 per group.

Figure 26:
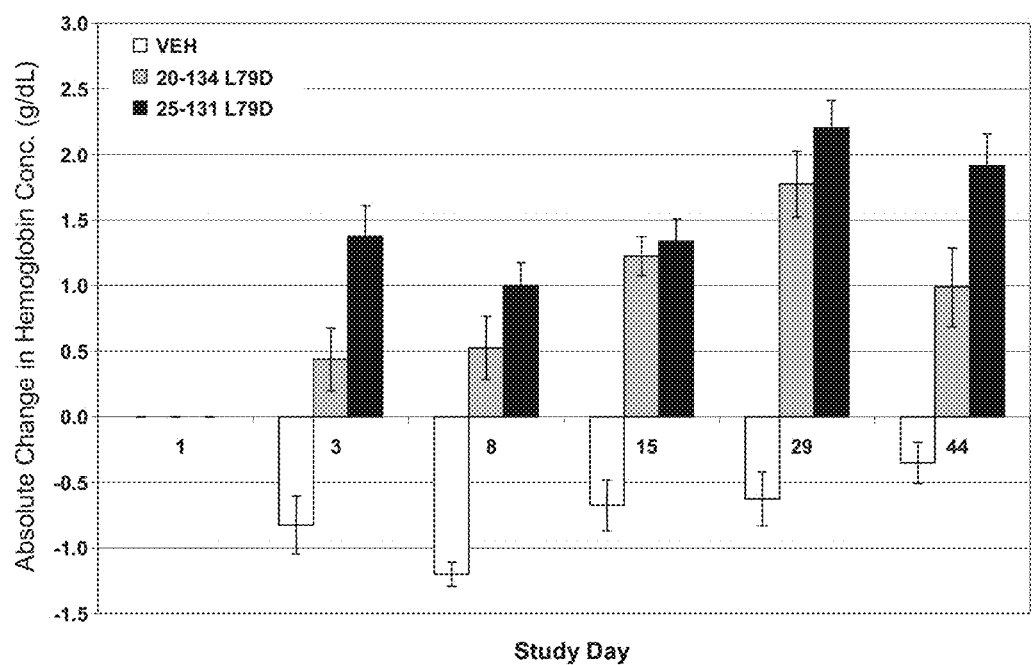

FIG. 26 shows the effect of treatment with ActRIIB(L79D 20-134)-hFc (gray) or ActRIIB(L79D 25-131)-hFc (black) on the absolute change in hemoglobin concentration from baseline in cynomolgus monkey. VEH=vehicle. Data are means±SEM. n=4-8 per group.

Figure 27:
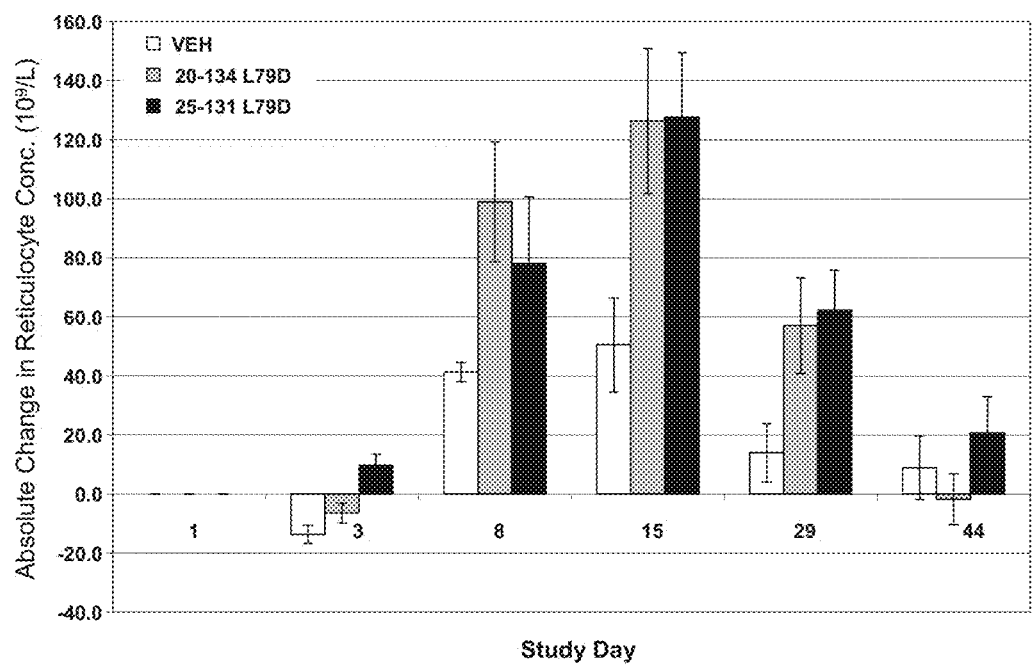

FIG. 27 shows the effect of treatment with ActRIIB(L79D 20-134)-hFc (gray) or ActRIIB(L79D 25-131)-hFc (black) on the absolute change in circulating reticulocyte concentration from baseline in cynomolgus monkey. VEH=vehicle. Data are means±SEM. n=4-8 per group.

Figure 28:
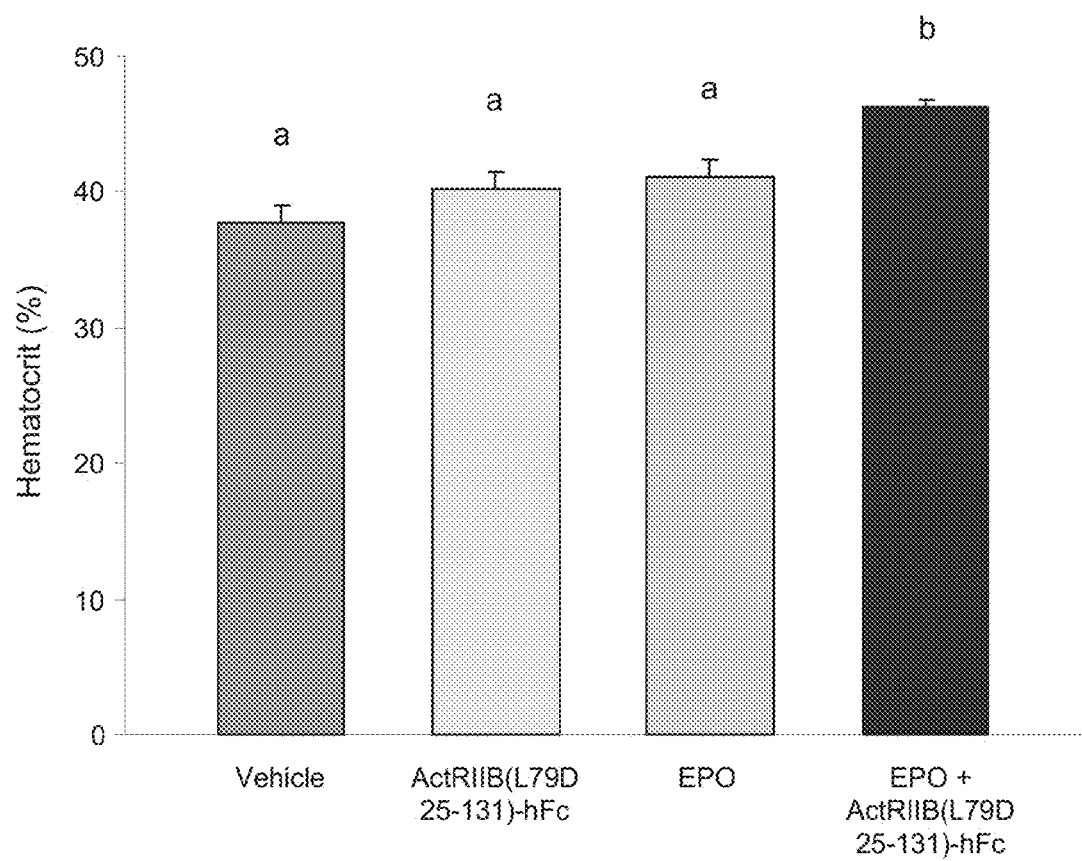

FIG. 28 shows the effect of combined treatment with erythropoietin (EPO) and ActRIIB(L79D 25-131)-hFc for 72 hours on hematocrit in mice. Data are means±SEM (n=4 per group), and means that are significantly different from each other ($p<0.05$, unpaired t-test) are designated by different letters. Combined treatment increased hematocrit by 23% compared to vehicle, a synergistic increase greater than the sum of the separate effects of EPO and ActRIIB(L79D 25-131)-hFc.

Figure 29:
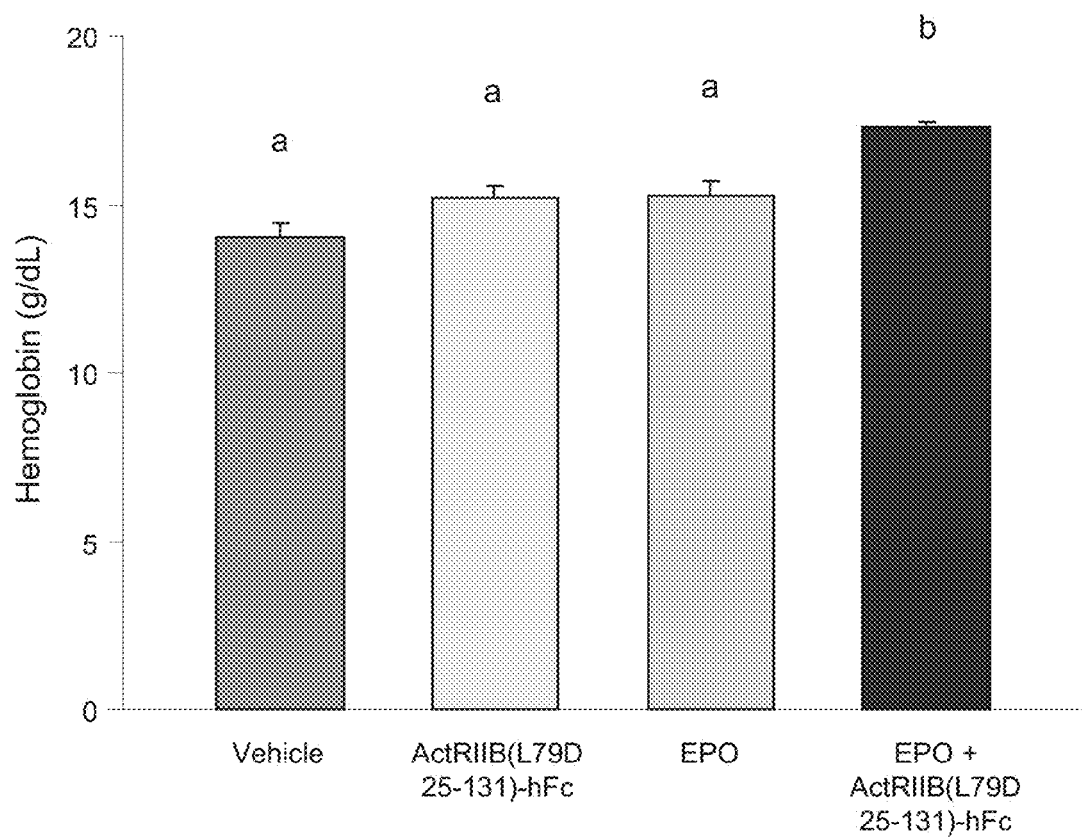

FIG. 29 shows the effect of combined treatment with EPO and ActRIIB(L79D 25-131)-hFc for 72 hours on hemoglobin concentrations in mice. Data are means±SEM (n=4 per group), and means that are significantly different from each other ($p<0.05$) are designated by different letters. Combined treatment increased hemoglobin concentrations by 23% compared to vehicle, which was also a synergistic effect.

Figure 30:
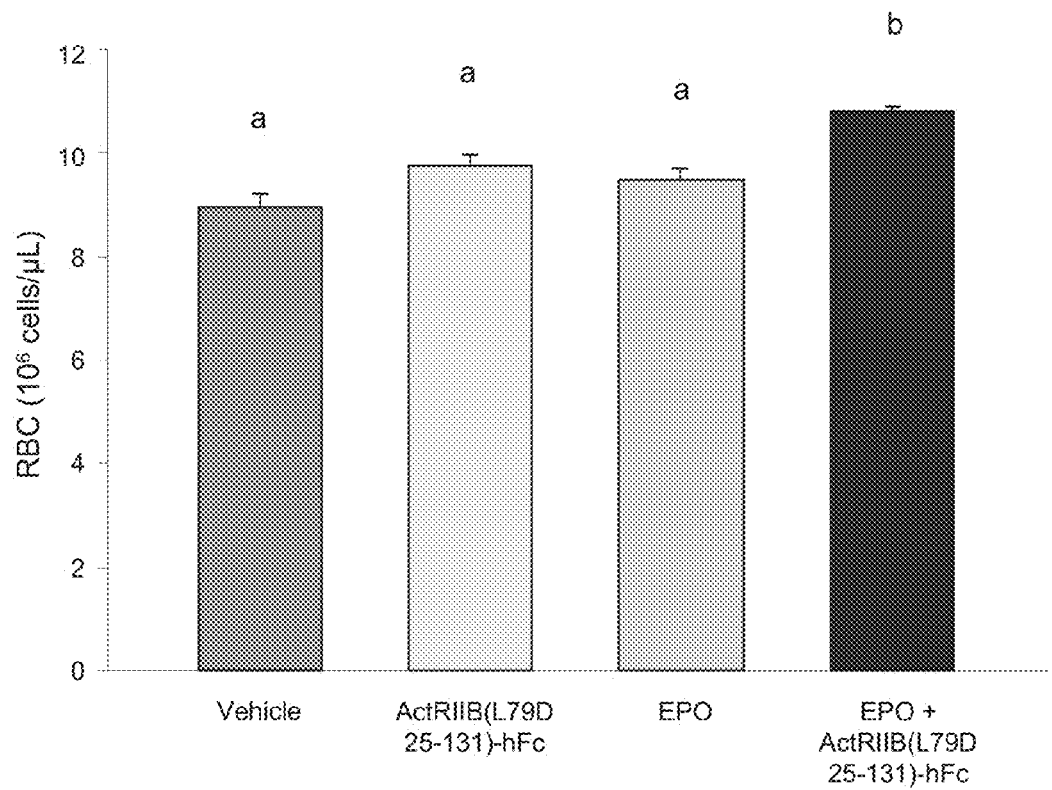

FIG. 30 shows the effect of combined treatment with EPO and ActRIIB(L79D 25-131)-hFc for 72 hours on red blood cell concentrations in mice. Data are means±SEM (n=4 per group), and means that are significantly different from each other ($p<0.05$) are designated by different letters. Combined treatment increased red blood cell concentrations by 20% compared to vehicle, which was also a synergistic effect.

Figure 31:
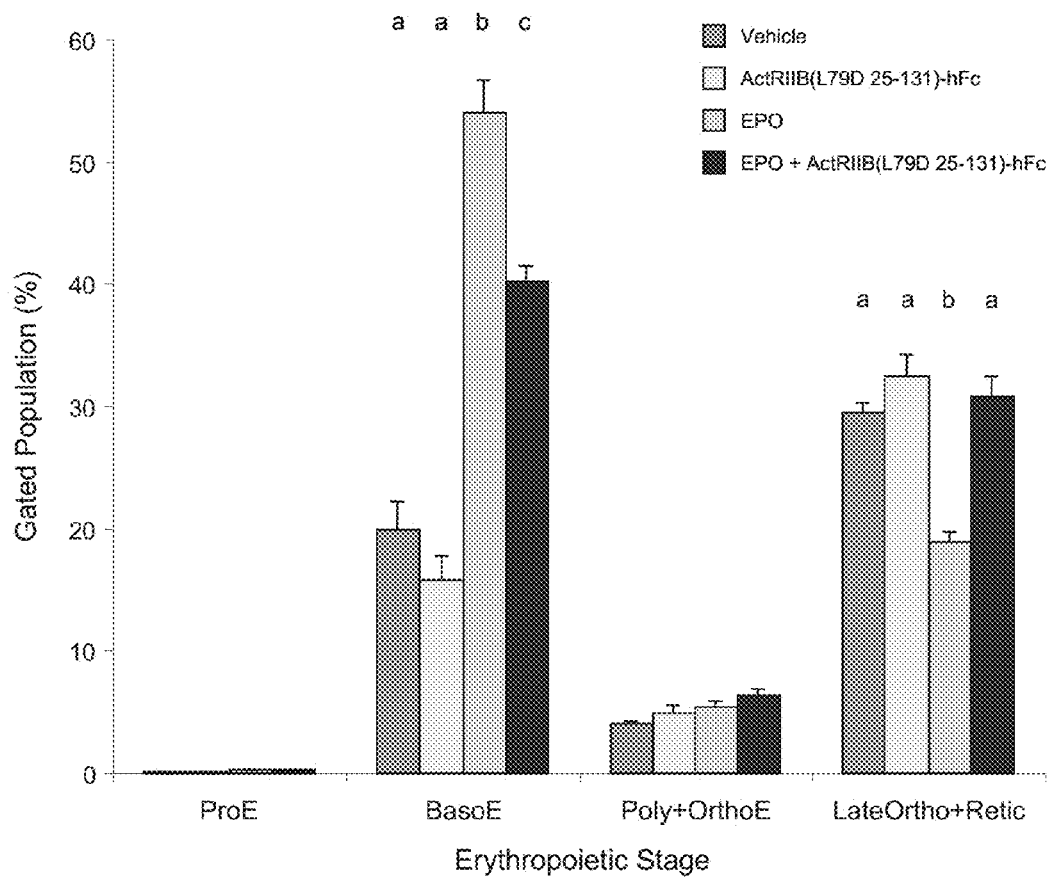

FIG. 31 shows the effect of combined treatment with EPO and ActRIIB(L79D 25-131)-hFc for 72 hours on numbers of erythropoietic precursor cells in mouse spleen. Data are means±SEM (n=4 per group), and means that are significantly different from each other ($p<0.01$) are designated by different letters. Whereas EPO alone increased the number of basophilic erythroblasts (BasoE) dramatically at the expense of late-stage precursor maturation, combined treatment increased BasoE numbers to a lesser but still significant extent while supporting undiminished maturation of late-stage precursors.

Figure 32A:
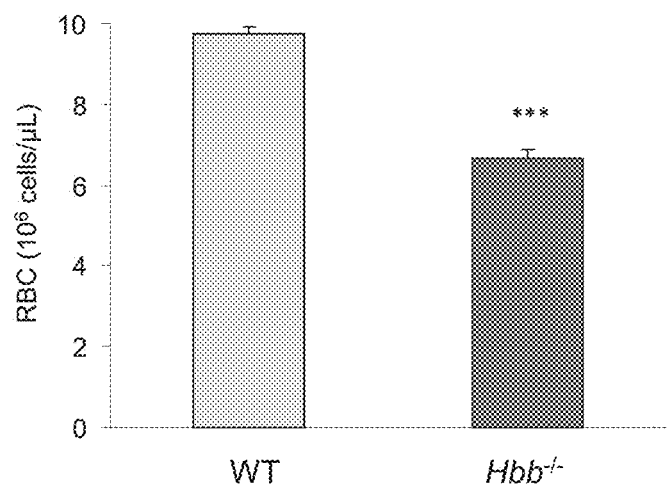
Figure 32B:
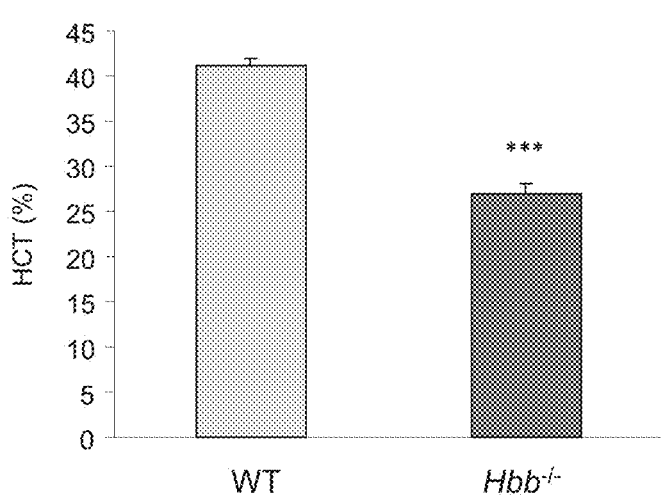
Figure 32C:
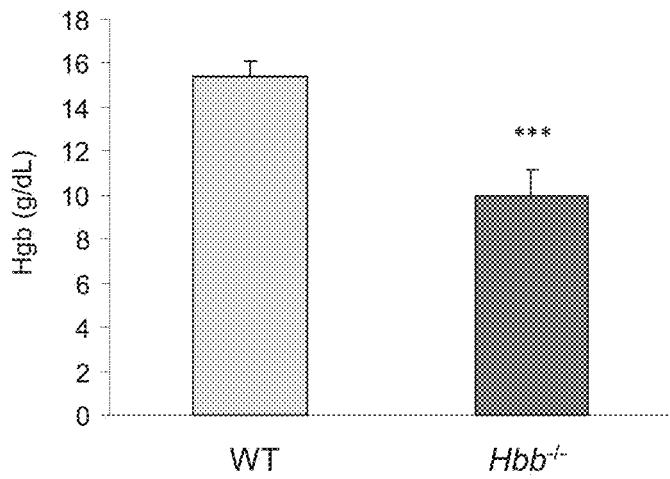

FIGS. 32A-C compares RBC parameters in an $Hbb^{-/-}$ mouse model of β-thalassemia with those in wildtype (WT) mice. Blood samples from untreated mice at 2-6 months of age were analyzed to determine red blood cell number (RBC; A), hematocrit (HCT; B), and hemoglobin concentration (Hgb; C). Data are means±SEM (n=4 per group), ***, $p<0.001$. $Hbb^{-/-}$ mice were confirmed to be severely anemic.

Figure 33:
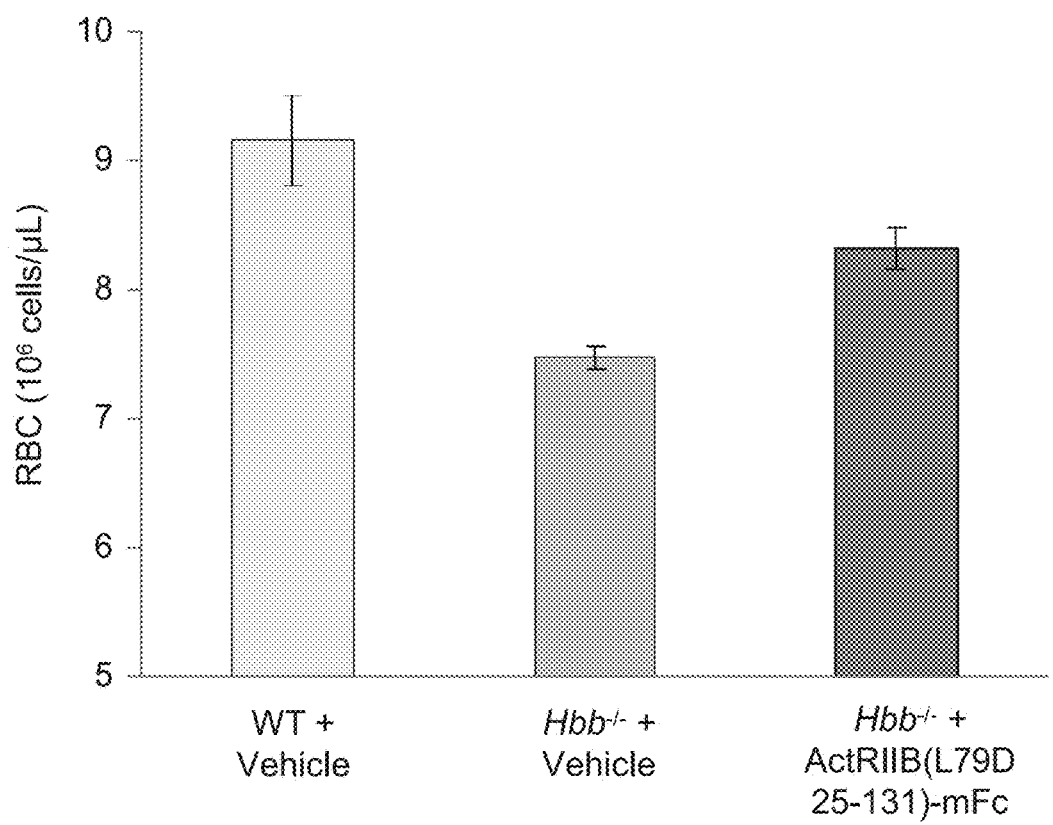

FIG. 33 shows the effect of ActRIIB(L79D 25-131)-mFc on RBC number in an $Hbb^{-/-}$ mouse model of β-thalassemia. Blood samples were collected after 4 weeks of treatment. Data are means of 2 per group, with bars indicating the range. Treatment with ActRIIB(L79D 25-131)-mFc reduced by half the RBC deficit present in $Hbb^{-/-}$ mice.

Figure 34:
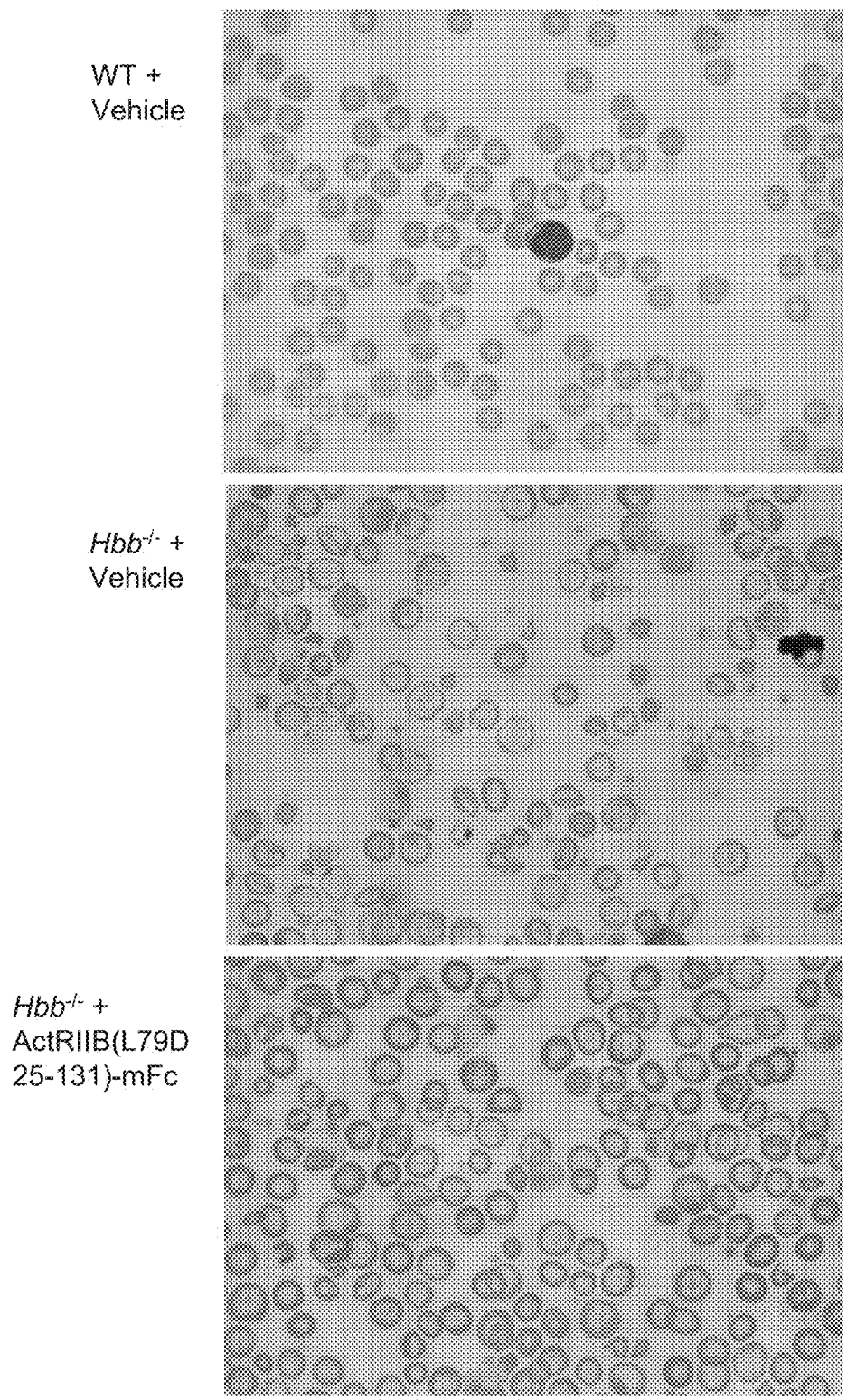

FIG. 34 shows the effect of ActRIIB(L79D 25-131)-mFc on RBC morphology in an $Hbb^{-/-}$ mouse model of β-thalassemia. Images of Giemsa-stained blood smears from mice treated for 4 weeks were obtained at 100× magnification. Note hemolysis, cellular debris, and many small or irregularly shaped RBCs in blood from the vehicle-treated $Hbb^{-/-}$ mouse. By comparison, ActRIIB(L79D 25-131)-mFc treatment greatly reduced hemolysis, debris, and the occurrence of irregularly shaped RBCs while increasing the number of normally shaped RBCs.

Figure 35:
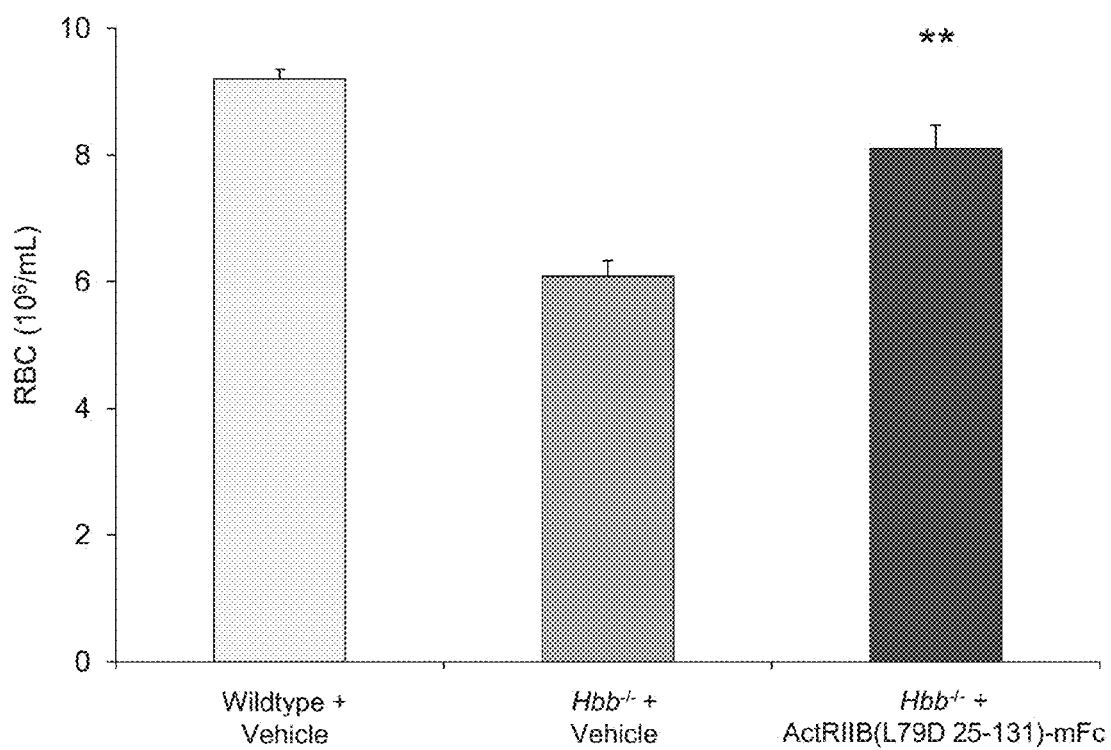

FIG. 35 shows the effect of ActRIIB(L79D 25-131)-mFc treatment for 2 months on RBC number in an $Hbb^{-/-}$ mouse model of β-thalassemia, with data from vehicle-dosed wildtype mice included for comparison. Data are means±SEM; n=7 per group. **, $P<0.01$ vs. vehicle-treated $Hbb^{-/-}$ mice. Treatment with ActRIIB(L79D 25-131)-mFc reduced the mean RBC deficit in $Hbb^{-/-}$ mice by more than 50%.

Figure 36:
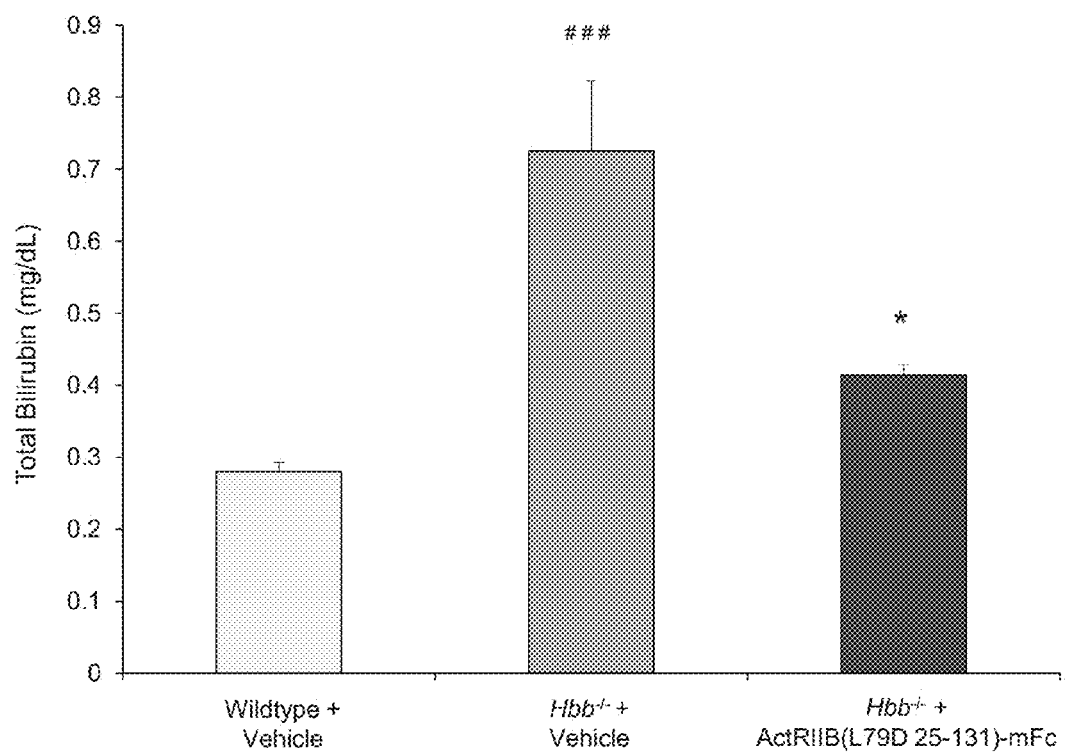

FIG. 36 shows the effect of ActRIIB(L79D 25-131)-mFc treatment for 2 months on serum bilirubin levels in an $Hbb^{-/-}$ mouse model of β-thalassemia, with data from vehicle-dosed wildtype mice included for comparison. Data are means±SEM. # # #, $P<0.001$ vs. vehicle-treated wildtype mice; *, $P<0.05$ vs. vehicle-treated $Hbb^{-/-}$ mice. Treatment with ActRIIB(L79D 25-131)-mFc reduced total bilirubin levels significantly in $Hbb^{-/-}$ mice.

Figure 37:
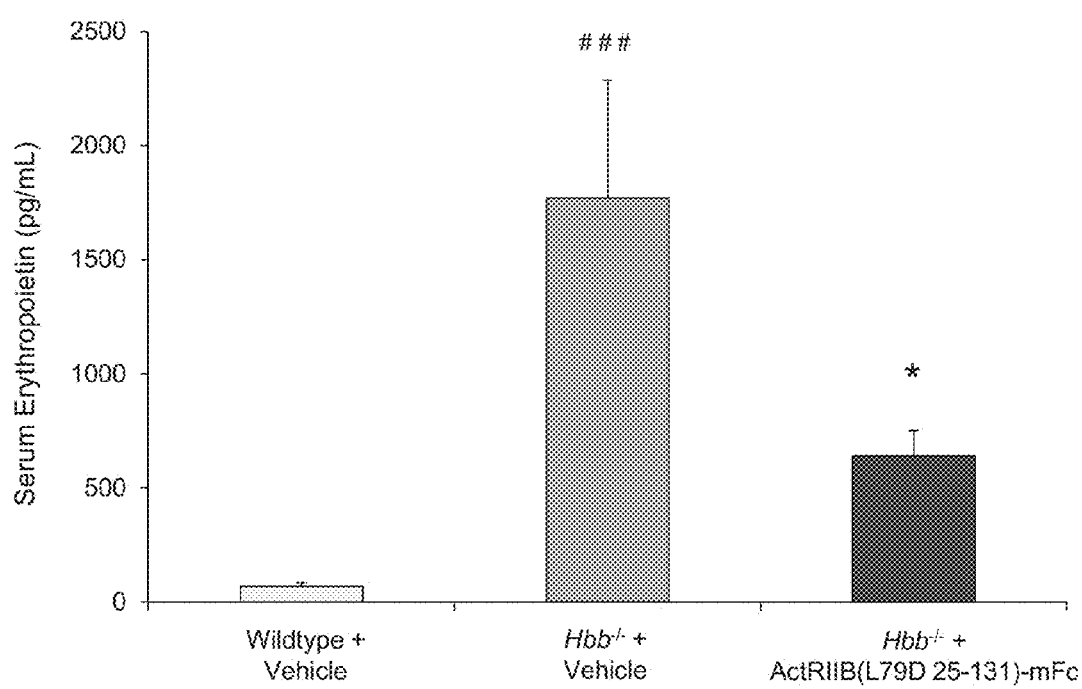

FIG. 37 shows the effect of ActRIIB(L79D 25-131)-mFc treatment for 2 months on serum EPO level in an $Hbb^{-/-}$ mouse model of β-thalassemia, with data from vehicle-dosed wildtype mice included for comparison. Data are means±SEM. # # #, $P<0.001$ vs. vehicle-treated wildtype mice; *, $P<0.05$ vs. vehicle-treated $Hbb^{-/-}$ mice. Treatment with ActRIIB(L79D 25-131)-mFc reduced mean circulating EPO levels by more than 60% in $Hbb^{-/-}$ mice.

Figure 38A:
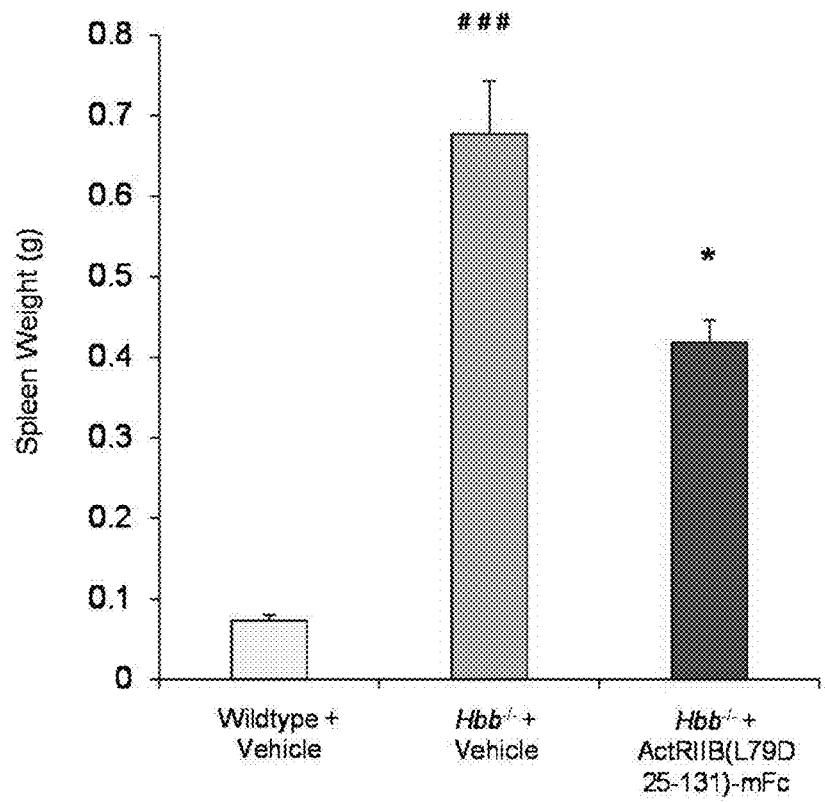
Figure 38B:
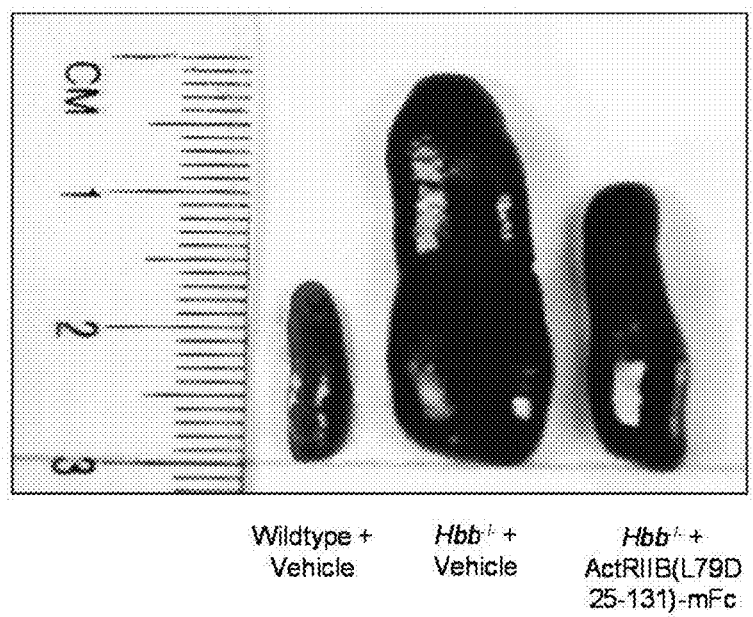

FIGS. 38A and 38B show the effect of ActRIIB(L79D 25-131)-mFc on splenomegaly in an $Hbb^{-/-}$ mouse model of β-thalassemia, with data from vehicle-dosed wildtype mice included for comparison. A. Means±SEM from mice starting at 3 months of age after treatment with 1 mg/kg twice weekly for 2 months. # # #, $P<0.001$ vs. vehicle-treated wildtype mice; *, $P<0.05$ vs. vehicle-treated $Hbb^{-/-}$ mice. B. Representative spleen sizes, as observed in a separate study in mice starting at 6-8 months of age after treatment with 1 mg/kg twice weekly for 3 months. Treatment with ActRIIB (L79D 25-131)-mFc reduced spleen weight significantly in $Hbb^{-/-}$ mice.

Figure 39:
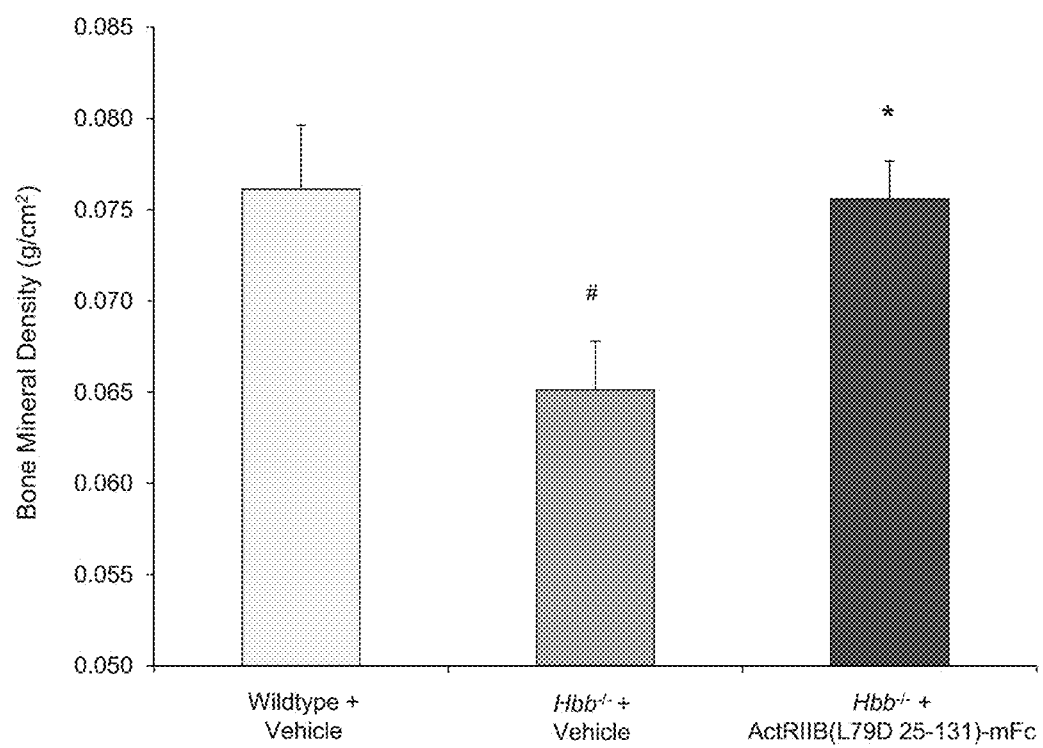

FIG. 39 shows the effect of ActRIIB(L79D 25-131)-mFc treatment for 2 months on bone mineral density in an $Hbb^{-/-}$ mouse model of β-thalassemia, with data from vehicle-dosed wildtype mice included for comparison. Means±SEM based on femur analysis. #, $P<0.05$ vs. vehicle-treated wildtype mice; *, $P<0.05$ vs. vehicle-treated $Hbb^{-/-}$ mice. Treatment with ActRIIB(L79D 25-131)-mFc normalized bone mineral density in $Hbb^{-/-}$ mice.

Figure 40A:
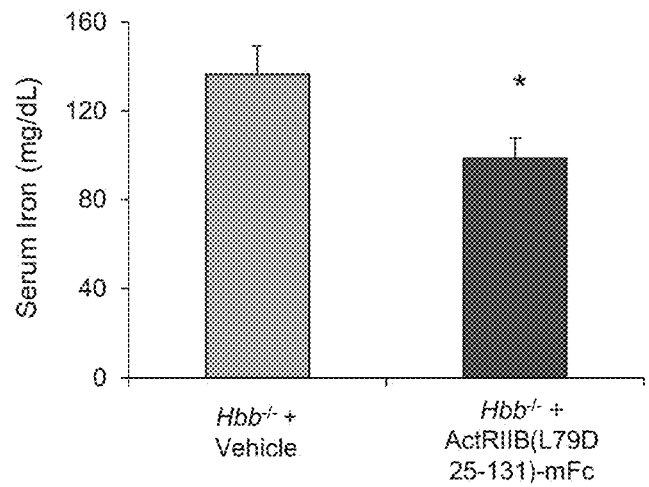
Figure 40B:
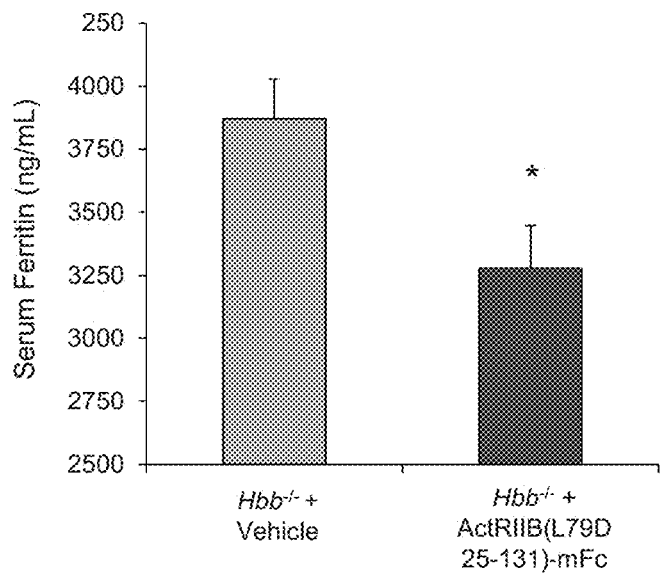
Figure 40C:
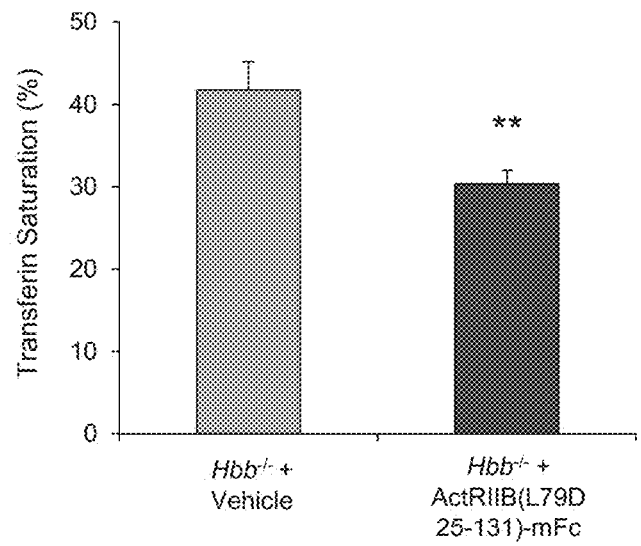

FIGS. 40A-C show the effect of ActRIIB(L79D 25-131)-mFc treatment for 2 months on parameters of iron homeostasis in an $Hbb^{-/-}$ mouse model of β-thalassemia. Means±SEM for serum iron (A), serum ferritin (B), and transferin saturation (C). *, $P<0.05$; **, $P<0.01$ vs. vehicle-treated $Hbb^{-/-}$ mice. Treatment with ActRIIB(L79D 25-131)-mFc reduced each measure of iron overload significantly in $Hbb^{-/-}$ mice.

Figure 41:
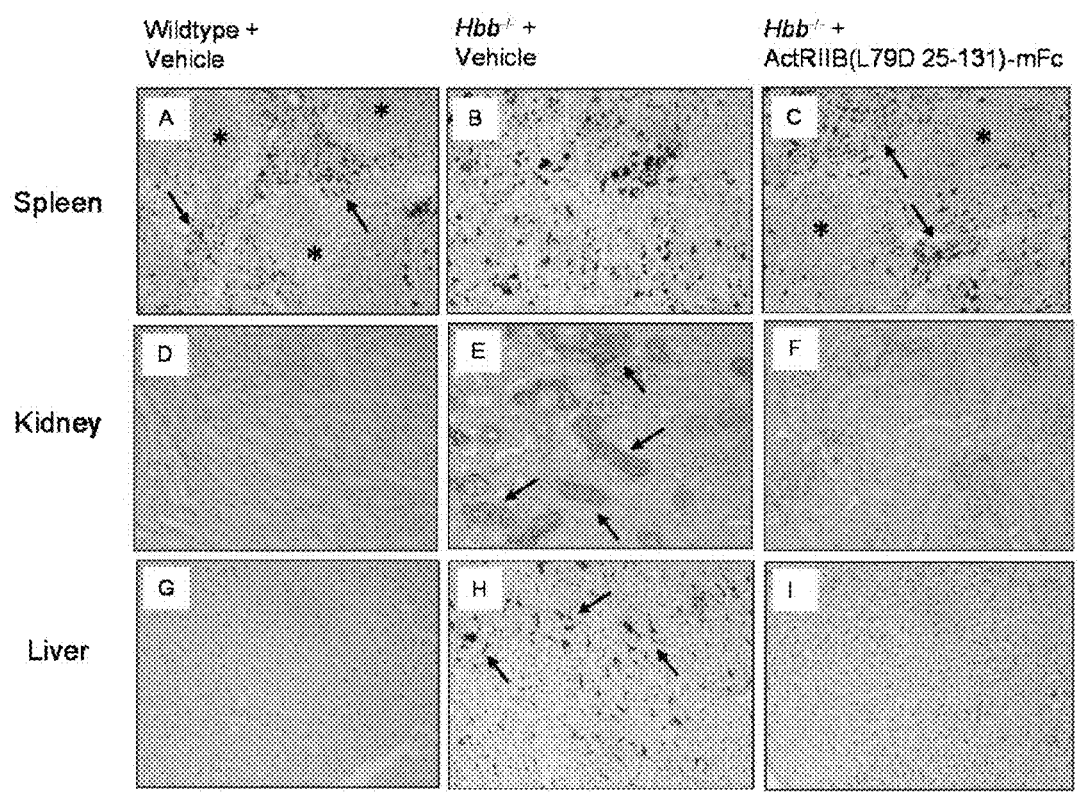

FIG. 41 shows the effect of ActRIIB(L79D 25-131)-mFc treatment for 2 months on tissue iron overload in an mouse model of β-thalassemia. Iron levels in tissue sections (200 μm) from spleen (A-C), liver (D-F), and kidney (G-I) were determined by staining with Perl's Prussian blue. Iron staining in wildtype spleen (A) was abundant in red pulp (arrows) but absent in white pulp (*). Increased iron staining in spleen of Hbb$^{-/-}$ mice (B) reflects expansion of red pulp regions due to extramedullary erythropoiesis. ActRIIB(L79D 25-131)-mFc in Hbb$^{-/-}$ mice decreased splenic erythropoiesis and restored the wildtype pattern of splenic iron staining (C) In addition, abnormal iron staining in hepatic Kupffer cells (H, arrows) and renal cortex (E, arrows) of Hbb$^{-/-}$ mice was normalized by ActRIIB(L79D 25-131)-mFc (F and I). Magnification, 200×.

Figure 42:
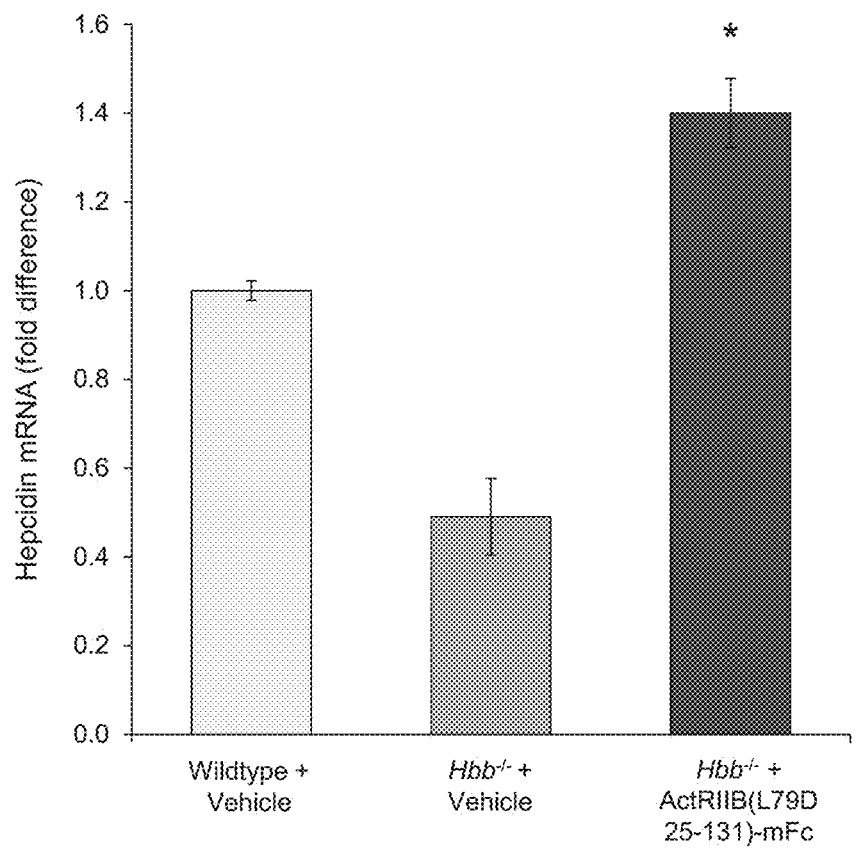

FIG. 42 shows the effect of ActRIIB(L79D 25-131)-mFc treatment for 2 months on hepatic levels of hepcidin mRNA in a Hbb$^{-/-}$ mouse model of β-thalassemia. Means±SEM; *, P<0.05 vs. vehicle-treated Hbb$^{-/-}$ mice. Treatment with ActRIIB(L79D 25-131)-mFc increased expression of hepcidin mRNA significantly in Hbb$^{-/-}$ mice.

Figure 43:
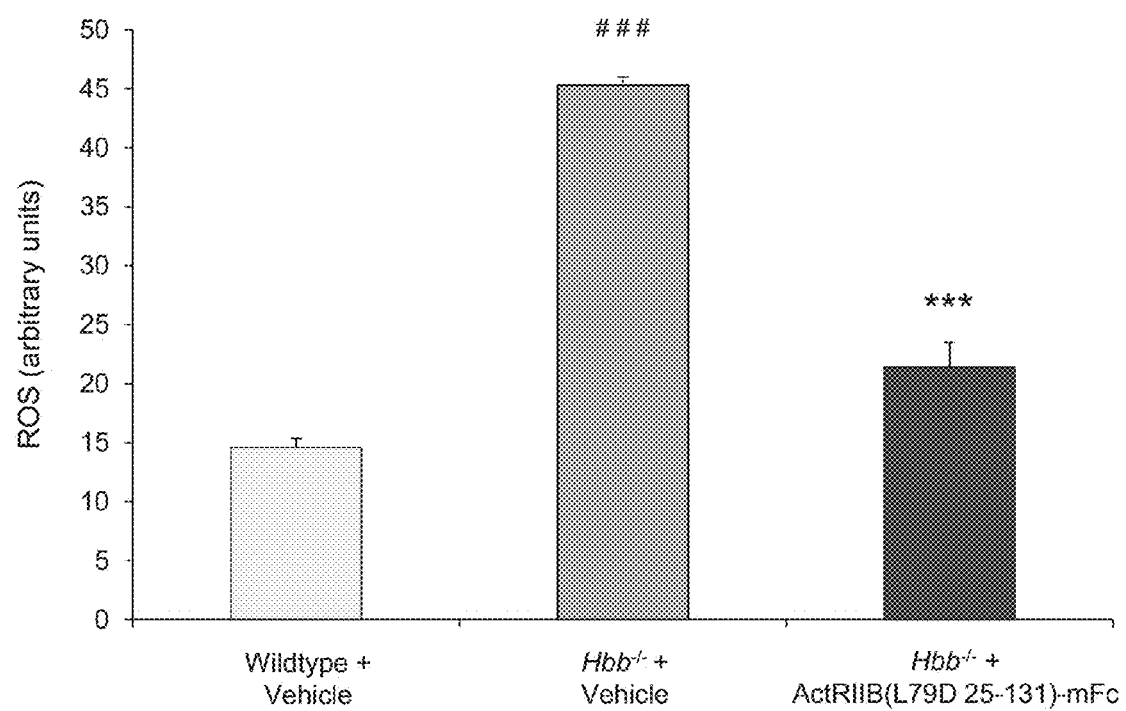

FIG. 43 shows the effect of ActRIIB(L79D 25-131)-mFc on circulating levels of reactive oxygen species (ROS) in an Hbb$^{-/-}$ mouse model of β-thalassemia, with data from vehicle-dosed wildtype mice included for comparison. Data are geometric means±SEM. # # #, P<0.001 vs. vehicle-treated wildtype mice; ***, P<0.001 vs. vehicle-treated Hbb$^{-/-}$ mice. Treatment with ActRIIB(L79D 25-131)-mFc reduced ROS significantly in Hbb$^{-/-}$ mice.

Figure 44:
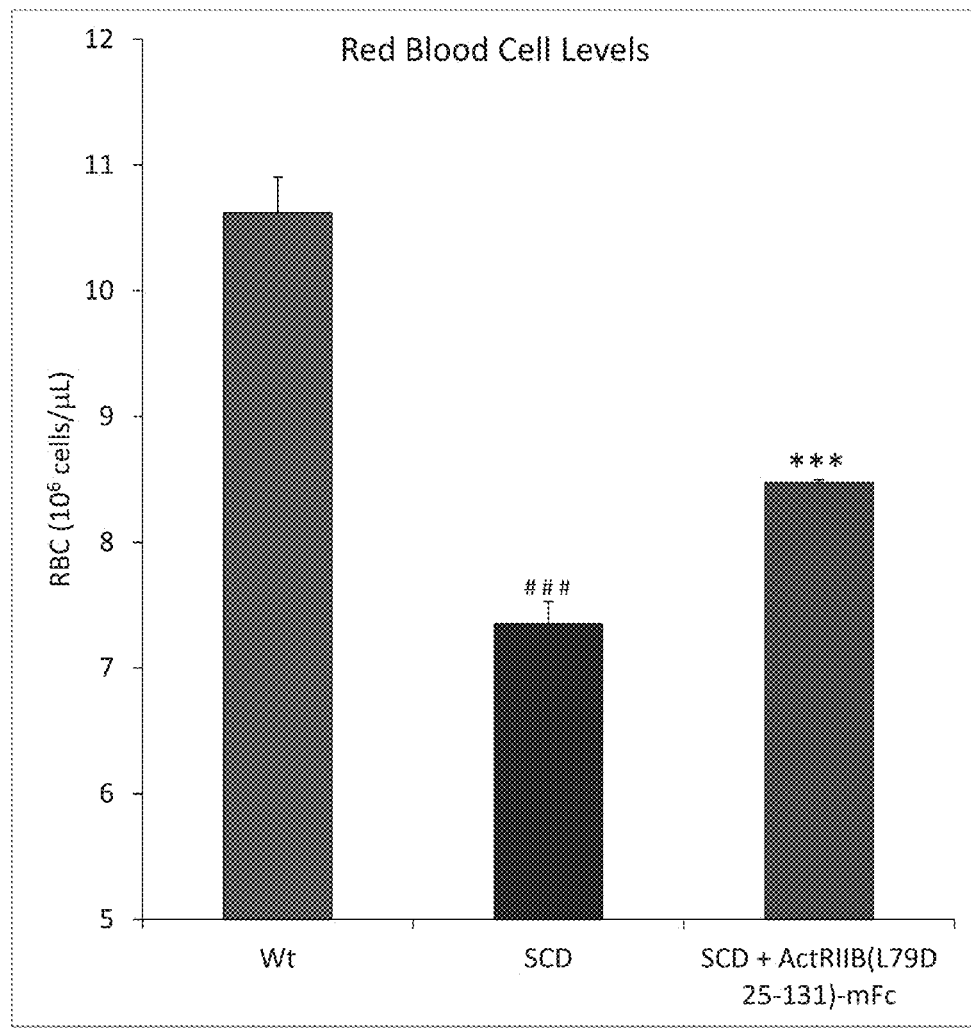

FIG. 44 shows the effect of ActRIIB(L79D 25-131)-mFc on the absolute change in red blood cell concentration in sickle-cell disease (SCD) mice. Data are means±SEM (n=5 per group). Wt=wild-type mice, which were non-symptomatic compound heterozygote (β/β$^S$) mice. ActRIIB(L79D 25-131)-mFc treatment resulted in a significant increase in red blood cell levels in sickle-cell mice (P<0.001) in comparison control mice (sickle-cell mice administered vehicle alone).

Figure 45:
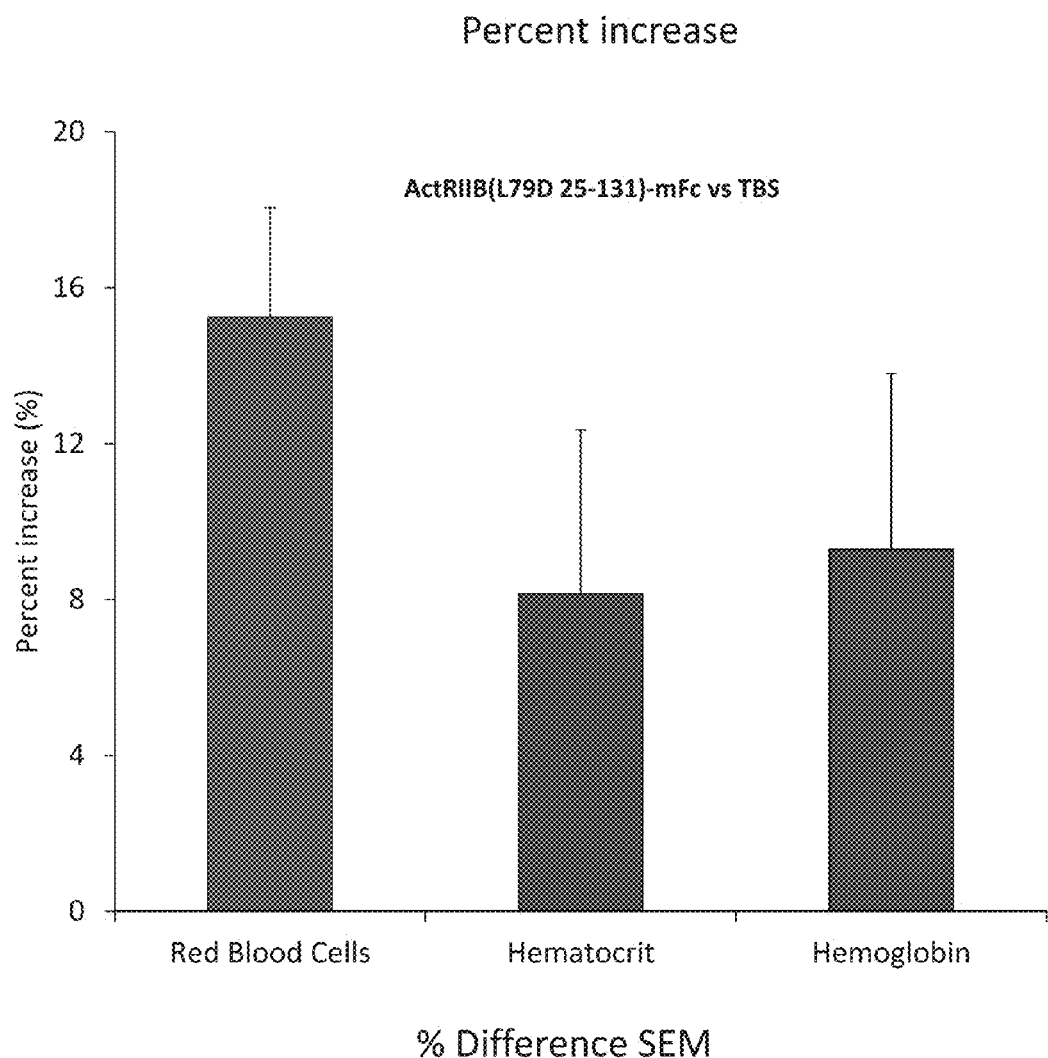

FIG. 45 shows the effect of ActRIIB(L79D 25-131)-mFc on red blood cell levels, hematocrit levels, and hemoglobin levels in sickle-cell mice. Data are mean changes from baseline over 4 weeks (±SEM) vs. sickle-cell control mice. ActRIIB(L79D 25-131)-mFc treatment resulted in a significant increase in red blood cell levels, hematocrit levels, and hemoglobin levels in sickle-cell mice in comparison to control mice.

Figure 46:
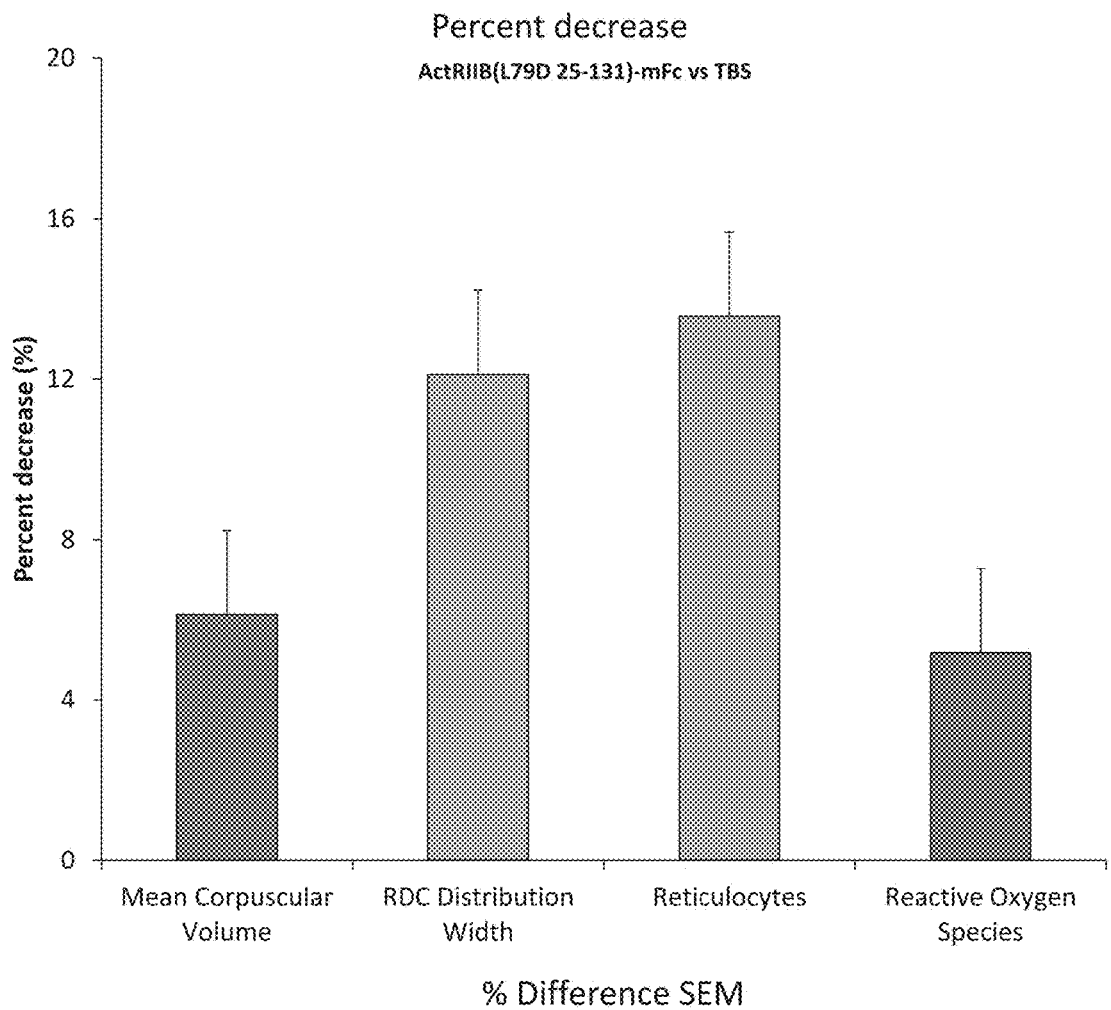

FIG. 46 shows the effect of ActRIIB(L79D 25-131)-mFc on various blood parameters (i.e., mean corpuscular volume, red blood cell (RDC) distribution width, reticulocytes, and reactive oxygen species in sickle-cell mice). Data are mean changes from baseline over 4 weeks (±SEM) vs. sickle-cell control mice. ActRIIB(L79D 25-131)-mFc treatment resulted in a significant increase in mean corpuscular volume, red blood cell (RDC) distribution width, reticulocytes, and reactive oxygen species in sickle-cell mice in comparison to control mice.

DETAIL DESCRIPTION OF THE INVENTION

1. Overview

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. See, e.g., Grobet et al. (1997) Nat Genet. 17(1):71-4. Furthermore, in humans, inactive alleles of GDF8 are associated with increased muscle mass and, reportedly, exceptional strength. See, e.g., Schuelke et al. (2004) N Engl J Med, 350:2682-8.

TGF-β signals are mediated by heteromeric complexes of type I and type II serine/threonine kinase receptors, which phosphorylate and activate downstream SMAD proteins (e.g., SMAD proteins 1, 2, 3, 5, and 8) upon ligand stimulation. See, e.g., Massagué (2000) Nat. Rev. Mol. Cell Biol. 1:169-178. These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling. Type II receptors are required for binding ligands and for expression of Type I receptors. Type I and II activin receptors form a stable complex after ligand binding, resulting in phosphorylation of Type I receptors by Type II receptors.

Two related Type II receptors (ActRII), ActRIIA and ActRIIB, have been identified as the Type II receptors for activins. See, e.g., Mathews and Vale (1991) Cell 65:973-982; and Attisano et al. (1992) Cell 68: 97-108. Besides activins, ActRIIA and ActRIIB can biochemically interact with several other TGF-β family proteins including, for example, BMP6, BMP7, Nodal, GDF8, and GDF11. See, e.g., Yamashita et al. (1995) J. Cell Biol. 130:217-226; Lee and McPherron (2001) Proc. Natl. Acad. Sci. 98:9306-9311; Yeo and Whitman (2001) Mol. Cell 7: 949-957; and Oh et al. (2002) Genes Dev. 16:2749-54. ALK4 is the primary type I receptor for activins, particularly for activin A, and ALK-7 may serve as a receptor for other activins as well, particularly for activin B. In certain embodiments, the present disclosure relates to antagonizing a ligand of an ActRII receptor (also referred to as an ActRII ligand) with one or more inhibitor agents disclosed herein, particularly inhibitor agents that can antagonize GDF11 and/or GDF8.

Activins are dimeric polypeptide growth factors that belong to the TGF-beta superfamily. There are three principal activin forms (A, B, and AB) that are homo/heterodimers of two closely related β subunits ($β_Aβ_A$, $β_Bβ_B$, and $β_Aβ_B$, respectively). The human genome also encodes an activin C and an activin E, which are primarily expressed in the liver, and heterodimeric forms containing $β_C$ or $β_E$ are also known.

In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos. DePaolo et al. (1991) Proc Soc Ep Biol Med. 198:500-512; Dyson et al. (1997) Curr Biol. 7:81-84; and Woodruff (1998) Biochem Pharmacol. 55:953-963. Moreover, erythroid differentiation factor (EDF) isolated from the stimulated human monocytic leukemic cells was found to be identical to activin A. Murata et al. (1988) PNAS, 85:2434. It has been suggested that activin A promotes erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follicle-related protein (FS), follistatin-related protein (FSRP, also known as FLRG or FSRL3), and $\alpha_2$-macroglobulin.

As described herein, agents that bind to "activin A" are agents that specifically bind to the $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the $\beta_A$ subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB" are agents that inhibit one or more activities as mediated by the $\beta_A$ subunit and one or more activities as mediated by the $\beta_B$ subunit.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as SMAD proteins. Studies support the idea that ActRIIA and ActRIIB serve as type II receptors for Nodal. See, e.g., Sakuma et al. (2002) Genes Cells. 2002, 7:401-12. It is suggested that Nodal ligands interact with their co-factors (e.g., cripto) to activate activin type I and type II receptors, which phosphorylate SMAD2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway SMADs, SMAD2 and SMAD3. Further evidence has shown that the extracellular cripto protein is required for Nodal signaling, making it distinct from activin or TGF-beta signaling.

Growth and Differentiation Factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle. McPherron et al., Nature (1997) 387:83-90. Similar increases in skeletal muscle mass are evident in naturally occurring mutations of GDF8 in cattle [see, e.g., Ashmore et al. (1974) Growth, 38:501-507; Swatland and Kieffer (1994) J. Anim. Sci. 38:752-757; McPherron and Lee (1997) Proc. Natl. Acad. Sci. USA 94:12457-12461; and Kambadur et al. (1997) Genome Res. 7:910-915] and, strikingly, in humans [see, e.g., Schuelke et al. (2004) N Engl J Med 350:2682-8]. Studies have also shown that muscle wasting associated with HIV-infection in humans is accompanied by increases in GDF8 protein expression. See, e.g., Gonzalez-Cadavid et al. (1998) PNAS 95:14938-43. In addition, GDF8 can modulate the production of muscle-specific enzymes (e.g., creatine kinase) and modulate myoblast cell proliferation. See, e.g. international patent application publication no. WO 00/43781. The GDF8 propeptide can noncovalently bind to the mature GDF8 domain dimer, inactivating its biological activity. See, e.g., Miyazono et al. (1988) J. Biol. Chem., 263: 6407-6415; Wakefield et al. (1988) J. Biol. Chem., 263: 7646-7654; and Brown et al. (1990) Growth Factors, 3: 35-43]. Other proteins which bind to GDF8 or structurally related proteins and inhibit their biological activity include follistatin, and potentially, follistatin-related proteins. See, e.g., Gamer et al. (1999) Dev. Biol., 208: 222-232.

Growth and Differentiation Factor-11 (GDF11), also known as BMP11, is a secreted protein. McPherron et al. (1999) Nat. Genet. 22: 260-264. GDF11 is expressed in the tail bud, limb bud, maxillary and mandibular arches, and dorsal root ganglia during mouse development. See, e.g., Nakashima et al. (1999) Mech. Dev. 80: 185-189. GDF11 plays a unique role in patterning both mesodermal and neural tissues. See, e.g., Gamer et al. (1999) Dev Biol., 208:222-32. GDF11 was shown to be a negative regulator of chondrogenesis and myogenesis in developing chick limb. See, e.g., Gamer et al. (2001) Dev Biol. 229:407-20. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium. See, e.g., Wu et al. (2003) Neuron. 37:197-207.

Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to Type II receptors, ActRIIA and ActRIIB. However, BMP7 and activin recruit distinct Type I receptors into heteromeric receptor complexes. The major BMP7 Type I receptor observed was ALK2, while activin bound exclusively to ALK4 (ActRIIB). BMP7 and activin elicited distinct biological responses and activated different SMAD pathways. See, e.g., Macias-Silva et al. (1998) J Biol Chem. 273:25628-36.

As demonstrated herein, ActRII polypeptides (e.g., ActRIIA and ActRIIB polypeptides) can be used to increase red blood cell levels in vivo. In certain examples, it is shown that a GDF Trap polypeptide (specifically a variant ActRIIB polypeptide) is characterized by unique biological properties in comparison to a corresponding sample of a wild-type (unmodified) ActRII polypeptide. This GDF Trap is characterized, in part, by substantial loss of binding affinity for activin A, and therefore significantly diminished capacity to antagonize activin A activity, but retains near wild-type levels of binding and inhibition of GDF11. In vivo, the GDF Trap is more effective at increasing red blood cell levels as compared to the wild-type ActRII polypeptide and has beneficial effects in patients with anemia including, e.g., patients with sickle-cell disease and patients with thalassemia. For example, it is shown herein that GDF Trap therapy results in increased hemoglobin levels in human patients that have thalassemia. In addition to improvements in red blood cell parameters, certain thalassemia patients were observed to have substantial resolution of a leg ulcer (which is a common cutaneous complication of anemia, particularly in hemolytic anemias such as thalassemia and sickle-cell disease) during the course of GDF Trap therapy. These data indicate a much broader use for ActRII antagonists in the treatment of various complications of anemic disorders beyond the positive effects on red blood cell parameters.

Accordingly, the methods of the present disclosure, in general, are directed to the use of one or more ActRII antagonist agents described herein, optionally in combination with one or more supportive therapies, to increase in red blood cell levels in a subject in need thereof, treat or prevent an anemia in a subject in need thereof, and/or to treat or prevent one or more complications of anemia including, for example, ulcers, particularly cutaneous ulcers.

Furthermore, the data of the present disclosure indicates that the observed biological activity of an ActRII polypeptide, with respect to red blood cell parameters and ulcers, is not dependent on activin A inhibition. However, it is to be noted that the unmodified ActRIIB polypeptide, which retains activin A binding, still demonstrates the capacity to increase red blood cells in vivo. Furthermore, an ActRIIB or ActRIIA polypeptide that retains activin A inhibition may be better suited in some applications, in comparison to a GDF Trap having diminished binding affinity for activin A, where more modest gains in red blood cell levels are desirable and/or where some level of off-target activity is acceptable (or even desirable).

It should be noted that hematopoiesis is a complex process, regulated by a variety of factors, including erythropoietin, G-CSF and iron homeostasis. The terms "increase red blood cell levels" and "promote red blood cell formation" refer to clinically observable metrics, such as hematocrit, red blood cell counts, and hemoglobin measurements, and are intended to be neutral as to the mechanism by which such changes occur.

EPO is a glycoprotein hormone involved in the growth and maturation of erythroid progenitor cells into erythrocytes. EPO is produced by the liver during fetal life and by the kidney in adults. Decreased production of EPO, which commonly occurs in adults as a consequence of renal failure, leads to anemia. EPO has been produced by genetic engineering techniques based on expression and secretion of the protein from a host cell transfected with the EPO gene. Administration of such recombinant EPO has been effective in the treatment of anemia. For example, Eschbach et al. (1987, N Engl J Med 316:73) describe the use of EPO to correct anemia caused by chronic renal failure.

Effects of EPO are mediated through its binding to, and activation of, a cell surface receptor belonging to the cytokine receptor superfamily and designated the EPO receptor. The human and murine EPO receptors have been cloned and expressed. See, e.g., D'Andrea et al. (1989) Cell 57:277; Jones et al. (1990) Blood 76:31; Winkelman et al. (1990) Blood 76:24; and U.S. Pat. No. 5,278,065. The human EPO receptor gene encodes a 483 amino acid transmembrane protein comprising an extracellular domain of approximately 224 amino acids and exhibits approximately 82% amino acid sequence identity with the murine EPO receptor. See, e.g., U.S. Pat. No. 6,319,499. The cloned, full-length EPO receptor expressed in mammalian cells (66-72 kDa) binds EPO with an affinity ($K_D$=100-300 nM) similar to that of the native receptor on erythroid progenitor cells. Thus, this form is thought to contain the main EPO binding determinant and is referred to as the EPO receptor. By analogy with other closely related cytokine receptors, the EPO receptor is thought to dimerize upon agonist binding. Nevertheless, the detailed structure of the EPO receptor, which may be a multimeric complex, and its specific mechanism of activation are not completely understood. See, e.g., U.S. Pat. No. 6,319,499.

Activation of the EPO receptor results in several biological effects. These include increased proliferation of immature erythroblasts, increased differentiation of immature erythroblasts, and decreased apoptosis in erythroid progenitor cells. See, e.g., Liboi et al. (1993) Proc Natl Acad Sci USA 90:11351-11355; Koury et al. (1990) Science 248:378-381. The EPO receptor signal transduction pathways mediating proliferation and differentiation appear to be distinct. See, e.g., Noguchi et al. (1988) Mol Cell Biol 8:2604; Patel et al. (1992) J Biol Chem, 267:21300; and Liboi et al. (1993) Proc Natl Acad Sci USA 90:11351-11355). Some results suggest that an accessory protein may be required for mediation of the differentiation signal. See, e.g., Chiba et al. (1993) Nature 362:646; and Chiba et al. (1993) Proc Natl Acad Sci USA 90:11593. However, there is controversy regarding the role of accessory proteins in differentiation since a constitutively activated form of the receptor can stimulate both proliferation and differentiation. See, e.g., Pharr et al. (1993) Proc Natl Acad Sci USA 90:938.

EPO receptor activators include small molecule erythropoiesis-stimulating agents (ESAs) as well as EPO-based compounds. An example of the former is a dimeric peptide-based agonist covalently linked to polyethylene glycol (proprietary name Hematide™ and Omontys®), which has shown erythropoiesis-stimulating properties in healthy volunteers and in patients with both chronic kidney disease and endogenous anti-EPO antibodies. See, e.g., Stead et al. (2006) Blood 108:1830-1834; and Macdougall et al. (2009) N Engl J Med 361:1848-1855. Other examples include nonpeptide-based ESAs. See, e.g., Qureshi et al. (1999) Proc Natl Acad Sci USA 96:12156-12161.

EPO receptor activators also include compounds that stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. Therefore, inhibitors of HIF prolyl hydroxylase enzymes are being investigated for EPO-inducing activity in vivo. Other indirect activators of EPO receptor include inhibitors of GATA-2 transcription factor [see, e.g., Nakano et al. (2004) Blood 104:4300-4307], which tonically inhibits EPO gene expression, and inhibitors of hemopoietic cell phosphatase (HCP or SHP-1), which functions as a negative regulator of EPO receptor signal transduction [see, e.g., Klingmuller et al. (1995) Cell 80:729-738.

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope or meaning of any use of a term will be apparent from the specific context in which they are used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

As used herein "does not substantially bind to X" is intended to mean that an agent has a $K_D$ that is greater than about $10^{-7}$, $10^{-6}$, $10^{-5}$, $10^{-4}$ or greater (e.g., no detectable binding by the assay used to determine the $K_D$) for "X".

2. ActRII Antagonist

The data presented herein demonstrates that antagonists (inhibitors) of ActRII (e.g., antagonist of ActRIIA and/or ActRIIB SMAD 2/3 and/or SMAD 1/5/8 signaling) can be used in increasing red blood cell levels in vivo. In particular, such ActRII antagonists are shown herein to be effective in treating various anemias as well as various complications (e.g., disorders/conditions) of anemia including, for example, cutaneous ulcers. Accordingly, the present disclosure provides, in part, various ActRII antagonist agents that can be used, alone or in combination with one or more erythropoiesis stimulating agents (e.g., EPO) or other supportive therapies [e.g., treatment with hydroxyurea, blood transfusion, iron chelation therapy, and/or pain management (e.g., treatment with one or more of opioid analgesic agents, non-steroidal anti-inflammatory drugs, and/or corticosteroids)], to treat or prevent an anemia in a subject in need thereof and/or to treat or prevent a cutaneous ulcer in a patient that has anemia.

In certain embodiments, the ActRII antagonists to be used in accordance with the methods disclosed herein are GDF-ActRII antagonists (e.g., antagonists of GDF-mediated ActRIIA and/or ActRIIB signaling transduction, such as SMAD 2/3 signaling), particularly GDF11- and/or GDF8-mediated ActRII signaling. In some embodiments, ActRII antagonists of the present disclosure are soluble ActRII polypeptides (e.g., soluble ActRIIA and ActRIIB polypeptides) and GDF Trap polypeptides, such as ActRIIA-Fc fusion proteins, ActRIIB-Fc fusion proteins, and GDF Trap-Fc fusion proteins.

Although soluble ActRII polypeptides and GDF Trap polypeptides of the disclosure may affect red blood cell levels and/or cutaneous ulcers through a mechanism other than GDF (e.g. GDF11 and/or GDF8) antagonism [e.g., GDF11 and/or GDF8 inhibition may be an indicator of the tendency of an agent to inhibit the activities of a spectrum of additional agents, including, perhaps, other members of the TGF-beta superfamily (e.g., activin B, activin C, activin E, BMP6, BMP7, and/or Nodal) and such collective inhibition may lead to the desired effect on, e.g., hematopoiesis], other types of GDF-ActRII antagonist are expected to be useful including, for example, anti-GDF11 antibodies; anti-GDF8 antibodies; anti-ActRIIA antibodies; anti-ActRIIB antibodies; antisense, RNAi, or ribozyme nucleic acids that inhibit the production of one or more of GDF11, GDF8, ActRIIA, and/or ActRIIB; and other inhibitors (e.g., small molecule inhibitors) of one or more of GDF11, GDF8, ActRIIA, and/or ActRIIB, particularly agents that disrupt GDF11- and/or GDF8-ActRIIA binding and/or GDF11- and/or GDF8-ActRIIB binding as well as agents that inhibit expression of one or more of GDF11, GDF8, ActRIIA, and/or ActRIIB. Optionally, GDF-ActRII antagonists of the present disclosure may bind to and/or inhibit the activity (or expression) of other ActRII ligands including, for example, activin A, activin AB, activin B, activin C, activin E, BMP6, BMP7, and/or Nodal. Optionally, a GDF-ActRII antagonist of the present disclosure may be used in combination with at least one additional ActRII antagonist agent that binds to and/or inhibits the activity (or expression) of one or more additional ActRII ligands including, for example, activin A, activin AB, activin B, activin C, activin E, BMP6, BMP7, and/or Nodal. In some embodiments, ActRII antagonists to be used in accordance with the methods disclosed herein do not substantially bind to and/or inhibit activin A (e.g., activin A-mediated activation of ActRIIA and/or ActRIIB signaling transduction, such as SMAD 2/3 signaling).

A. ActRII Polypeptides and GDF Traps

In certain aspects, the present disclosure relates to ActRII polypeptides. In particular, the disclosure provides methods of using ActRII polypeptides to, e.g., treat or prevent an anemia in a subject in need thereof and/or treat or prevent one or more complication of anemia including, for example, cutaneous ulcers. As used herein the term "ActRII" refers to the family of type II activin receptors. This family includes both the activin receptor type IIA and the activin receptor type IIB. In some embodiments, the disclosure provides methods of using ActRII polypeptides to treat an anemia in a subject in need thereof and/or treat one or more complications of anemia including, for example, cutaneous ulcers, in a subject having anemia. In some embodiments, the disclosure provides methods of using ActRII polypeptides to prevent an anemia in a subject in need thereof and/or prevent one or more complications of anemia including, for example, cutaneous ulcers in a subject having anemia. In some embodiments, the ActRII polypeptides are ActRIIA polypeptides. In some embodiments, the ActRII polypeptides are ActRIIB polypeptides.

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Optionally, ActRIIB polypeptides of the present disclosure can be used to increase red blood cell levels in a subject. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

The signal peptide is indicated with singleunderlined; the extracellular domain is indicated in bold font; and the potential, endogenous N-linked glycosylation sites are indicated with doubleunderline.

The processed soluble (extracellular) human ActRIIB polypeptide sequence is as follows:

```
                                                   (SEQ ID NO: 2)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT.
```

In some embodiments, the protein may be produced with an "SGR . . . " sequence at the N-terminus. The C-terminal "tail" of the extracellular domain is indicated by singleunderline. The sequence with the "tail" deleted (a Δ15 sequence) is as follows:

```
                                                   (SEQ ID NO: 3)
GRGEAETRECIYYNANWELERTNQSGLERCEGEQDKRLHCYASWRNSSGT

IELVKKGCWLDDFNCYDRQECVATEENPQVYFCCCEGNECNERFTHL

PEA.
```

A form of ActRIIB with an alanine at position 64 of SEQ ID NO: 1 (A64) is also reported in the literature. See, e.g., Hilden et al. (1994) Blood, 83(8): 2163-2170. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

```
                                                             (SEQ ID NO: 1)
  1 MTAPWVALAL LWGSLCAGSG RGEAETRECI YYNANWELER TNQSGLERCE

51 GEQDKRLHCY ASWRNSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

(SEQ ID NO: 4)
```
  1 MTAPWVALAL LWGSLCAGSG RGEAETRECI YYNANWELER TNQSGLERCE

51 GEQDKRLHCY ASWANSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI_.
```

The signal peptide is indicated by singleunderline and the extracellular domain is indicated by bold font.

The processed soluble (extracellular) ActRIIB polypeptide sequence of the alternative A64 form is as follows:

(SEQ ID NO: 5)
GRGEAETRECIYYNANWELERTNQSGLERCEGEQDKRLHCYASWANSSGT

IELVKKGCWLDDFNCYDRQECVATEENPQVYFCCCEGNFCNERFTHLPEA

GGPEVTYEPPPTAPT.

In some embodiments, the protein may be produced with an "SGR . . . " sequence at the N-terminus. The C-terminal "tail" of the extracellular domain is indicated by singleunderline. The sequence with the "tail" deleted (a Δ15 sequence) is as follows:

(SEQ ID NO: 6)
GRGEAETRECIYYNANWELERTNQSGLERCEGEQDKRLHCYASWANSSGT

IELVKKGCWLDDFNCYDRQECVATEENPQVYFCCCEGNFCNERFTHL

PEA.

The nucleic acid sequence encoding a human ActRIIB precursor protein is shown below (SEQ ID NO:7), consisting of nucleotides 25-1560 of Genbank Reference Sequence NM_001106.3, which encode amino acids 1-513 of the ActRIIB precursor. The sequence as shown provides an arginine at position 64 and may be modified to provide an alanine instead.

The signal sequence is underlined.

(SEQ ID NO: 7)
```
  1 ATGACGGCGC CCTGGGTGGC CCTCGCCCTC CTCTGGGGAT CGCTGTGCGC

51 CGGCTCTGGG CGTGGGGAGG CTGAGACACG GGAGTGCATC TACTACAACG

101 CCAACTGGGA GCTGGAGCGC ACCAACCAGA GCGGCCTGGA GCGCTGCGAA

151 GGCGAGCAGG ACAAGCGGCT GCACTGCTAC GCCTCCTGGC GCAACAGCTC

201 TGGCACCATC GAGCTCGTGA AGAAGGGCTG CTGGCTAGAT GACTTCAACT

251 GCTACGATAG GCAGGAGTGT GTGGCCACTG AGGAGAACCC CCAGGTGTAC

301 TTCTGCTGCT GTGAAGGCAA CTTCTGCAAC GAACGCTTCA CTCATTTGCC

351 AGAGGCTGGG GGCCCGGAAG TCACGTACGA GCCACCCCCG ACAGCCCCCA

401 CCCTGCTCAC GGTGCTGGCC TACTCACTGC TGCCCATCGG GGGCCTTTCC

451 CTCATCGTCC TGCTGGCCTT TTGGATGTAC CGGCATCGCA AGCCCCCCTA

501 CGGTCATGTG GACATCCATG AGGACCCTGG GCCTCCACCA CCATCCCCTC

551 TGGTGGGCCT GAAGCCACTG CAGCTGCTGG AGATCAAGGC TCGGGGGCGC

601 TTTGGCTGTG TCTGGAAGGC CCAGCTCATG AATGACTTTG TAGCTGTCAA

651 GATCTTCCCA CTCCAGGACA AGCAGTCGTG GCAGAGTGAA CGGGAGATCT

701 TCAGCACACC TGGCATGAAG CACGAGAACC TGCTACAGTT CATTGCTGCC

751 GAGAAGCGAG GCTCCAACCT CGAAGTAGAG CTGTGGCTCA TCACGGCCTT

801 CCATGACAAG GGCTCCCTCA CGGATTACCT CAAGGGGAAC ATCATCACAT
```

```
 851 GGAACGAACT GTGTCATGTA GCAGAGACGA TGTCACGAGG CCTCTCATAC

901 CTGCATGAGG ATGTGCCCTG GTGCCGTGGC GAGGGCCACA AGCCGTCTAT

951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA

1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG

1351 GCCCAGCTTT GTGTGACCAT CGAGGAGTGC TGGGACCATG ATGCAGAGGC

1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC.
```

A nucleic acid sequence encoding processed soluble (extracellular) human ActRIIB polypeptide is as follows (SEQ ID NO:8). The sequence as shown provides an arginine at position 64 and may be modified to provide an alanine instead.

```
                                             (SEQ ID NO: 8)
  1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT

251 GCTGTGAAGG CAACTTCTGC AACGAACGCT TCACTCATTT GCCAGAGGCT

301 GGGGGCCCGG AAGTCACGTA CGAGCCACCC CCGACAGCCC CCACC.
```

In certain embodiments, the present disclosure relates to ActRIIA polypeptides. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Optionally, ActRIIA polypeptides of the present disclosure can be used to increase red blood cell levels in a subject. Numbering of amino acids for all ActRIIA-related polypeptides described herein is based on the numbering of the human ActRIIA precursor protein sequence provided below (SEQ ID NO:9), unless specifically designated otherwise.

The human ActRIIA precursor protein sequence is as follows:

(SEQ ID NO: 9)
```
  1 MGAAAKLAFA VFLISCSSGA ILGRSETQEC LFFNANWEKD RTNQTGVEPC
 51 YGDKDKRRHC FATWKNISGS IEIVKQGCWL DDINCYDRTD CVEKKDSPEV
101 YFCCCEGNMC NEKFSYFPEM EVTQPTSNPV TPKPPYYNIL LYSLVPLMLI
151 AGIVICAFWV YRHHKMAYPP VLVPTQDPGP PPPSPLLGLK PLQLLEVKAR
201 GRFGCVWKAQ LLNEYVAVKI FPIQDKQSWQ NEYEVYSLPG MKHENILQFI
251 GAEKRGTSVD VDLWLITAFH EKGSLSDFLK ANVVSWNELC HIAETMARGL
301 AYLHEDIPGL KDGHKPAISH RDIKSKNVLL KNNLTACIAD FGLALKFEAG
351 KSAGDTHGQV GTRRYMAPEV LEGAINFQRD AFLRIDMYAM GLVLWELASR
401 CTAADGPVDE YMLPFEEEIG QHPSLEDMQE VVVHKKKRPV LRDYWQKHAG
451 MAMLCETIEE CWDHDAEARL SAGCVGERIT QMQRLTNIIT TEDIVTVVTM
501 VTNVDFPPKE SSL
```

The signal peptide is indicated by single underline; the extracellular domain is indicated in bold font; and the potential, endogenous N-linked glycosylation sites are indicated by double underline.

The processed soluble (extracellular) human ActRIIA polypeptide sequence is as follows:

(SEQ ID NO: 10)
ILGRSETQECLFFNANWEKDRTNQTGVEPCYGDKDKRRHCFATWKNISGS
IEIVKQGCWLDDINCYDRTDCVEKKDSPEVYFCCCEGNMCNEKFSYFPEM
EVTQPTSNPVTPKPP

The C-terminal "tail" of the extracellular domain is indicated by single underline. The sequence with the "tail" deleted (a Δ15 sequence) is as follows:

(SEQ ID NO: 11)
ILGRSETQECLFFNANWEKDRTNQTGVEPCYGDKDKRRHCFATWKNISGS
IEIVKQGCWLDDINCYDRTDCVEKKDSPEVYFCCCEGNMCNEKFSYFPEM

The nucleic acid sequence encoding human ActRIIA precursor protein is shown below (SEQ ID NO: 12), as follows nucleotides 159-1700 of Genbank Reference NM_001616.4. The signal sequence is underlined.

(SEQ ID NO: 12)
```
  1 atgggagctg ctgcaaagtt ggcgtttgcc gtcttcctta tctcctgttc
 51 ttcaggtgct atacttggta gatcagaaac tcaggagtgt cttttcttta
101 atgctaattg ggaaaaagac agaaccaatc aaactggtgt tgaaccgtgt
151 tatggtgaca agataaacg gcggcattgt tttgctacct ggaagaatat
201 ttctggttcc attgaaatag tgaaacaagg ttgttggctg gatgatatca
251 actgctatga caggactgat tgtgtagaaa aaaagacag ccctgaagta
301 tattttgtt gctgtgaggg caatatgtgt aatgaaaagt ttctctattt
351 tccggagatg gaagtcacac agcccacttc aaatccagtt acacctaagc
401 caccctatta caacatcctg ctctattcct tggtgccact tatgttaatt
451 gcggggattg tcatttgtgc attttgggtg tacaggcatc acaagatggc
501 ctaccctcct gtacttgttc caactcaaga cccaggacca cccccacctt
551 ctccattact aggtttgaaa ccactgcagt tattagaagt gaaagcaagg
601 ggaagatttg gttgtgtctg gaaagcccag ttgcttaacg aatatgtggc
651 tgtcaaaata tttccaatac aggacaaaca gtcatggcaa aatgaatacg
701 aagtctacag tttgcctgga atgaagcatg agaacatatt acagttcatt
751 ggtgcagaaa aacgaggcac cagtgttgat gtggatcttt ggctgatcac
801 agcatttcat gaaaagggtt cactatcaga ctttcttaag gctaatgtgg
851 tctcttgaa tgaactgtgt catattgcag aaaccatggc tagaggattg
901 gcatatttac atgaggatat acctggccta aaagatggcc acaaacctgc
```

```
 951 catatctcac agggacatca aaagtaaaaa tgtgctgttg aaaaacaacc 1001 tgacagcttg cattgctgac tttgggttgg ccttaaaatt tgaggctggc 1051 aagtctgcag gcgataccca tggacaggtt ggtacccgga ggtacatggc 1101 tccagaggta ttagagggtg ctataaactt ccaaagggat gcatttttga 1151 ggatagatat gtatgccatg ggattagtcc tatgggaact ggcttctcgc 1201 tgtactgctg cagatggacc tgtagatgaa tacatgttgc catttgagga 1251 ggaaattggc cagcatccat ctcttgaaga catgcaggaa gttgttgtgc 1301 ataaaaaaaa gaggcctgtt ttaagagatt attggcagaa acatgctgga 1351 atggcaatgc tctgtgaaac cattgaagaa tgttgggatc acgacgcaga 1401 agccaggtta tcagctggat gtgtaggtga aagaattacc cagatgcaga 1451 gactaacaaa tattattacc acagaggaca ttgtaacagt ggtcacaatg 1501 gtgacaaatg ttgactttcc tcccaaagaa tctagtcta
```

The nucleic acid sequence encoding processed soluble (extracellular human ActRIIA polypeptide is as follows:

(SEQ ID NO: 13)
```
  1 atacttggta gatcagaaac tcaggagtgt cttttcttta atgctaattg 51 ggaaaaagac agaaccaatc aaactggtgt tgaaccgtgt tatggtgaca 101 aagataaacg gcggcattgt tttgctacct ggaagaatat ttctggttcc 151 attgaaatag tgaaacaagg ttgttggctg gatgatatca actgctatga 201 caggactgat tgtgtagaaa aaaaagacag ccctgaagta tattttgtt 251 gctgtgaggg caatatgtgt aatgaaaagt tttcttattt tccggagatg 301 gaagtcacac agcccacttc aaatccagtt acacctaagc caccc.
```

Figure 2:
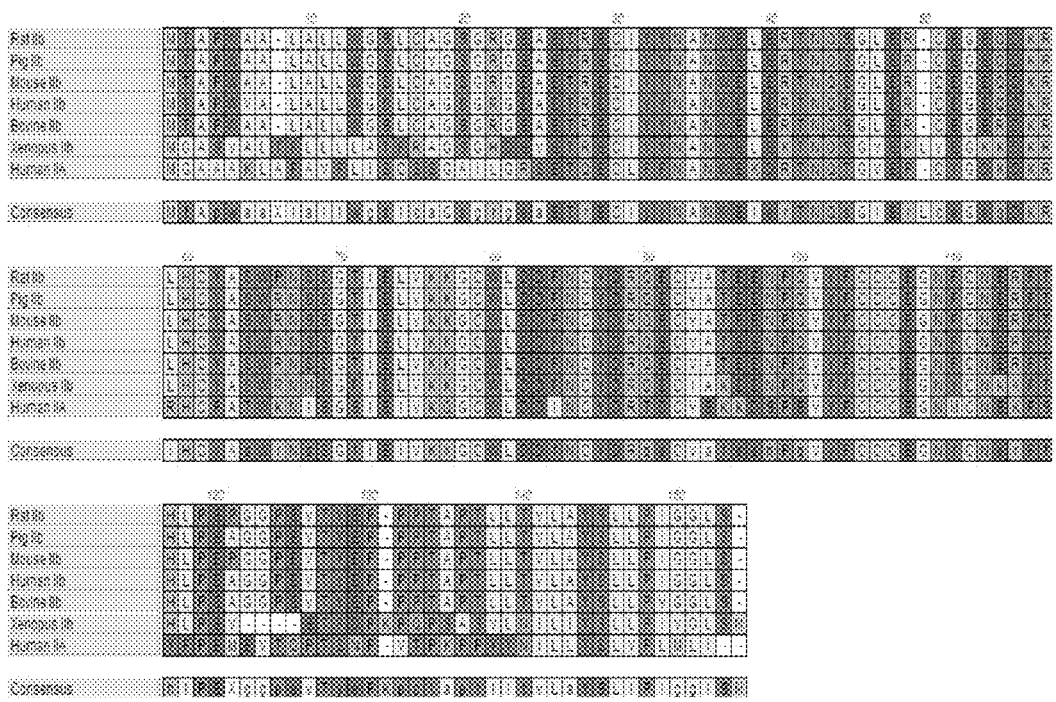
FIG. 2 shows a multiple sequence alignment of various vertebrate ActRIIB proteins and human ActRIIA (SEQ ID NOs: 57-63 and 69).

An alignment of the amino acid sequences of human ActRIIB soluble extracellular domain and human ActRIIA soluble extracellular domain are illustrated in FIG. 1. This alignment indicates amino acid residues within both receptors that are believed to directly contact ActRII ligands. FIG. 2 depicts a multiple sequence alignment of various vertebrate ActRIIB proteins and human ActRIIA. From these alignments is it possible to predict key amino acid positions within the ligand-binding domain that are important for normal ActRII-ligand binding activities as well as to predict amino acid positions that are likely to be tolerant to substitution without significantly altering normal ActRII-ligand binding activities.

In other aspects, the present disclosure relates to GDF Trap polypeptides (also referred to as "GDF Traps"). In particular, the disclosure provides methods of using GDF Trap polypeptides to, e.g., treat or prevent an anemia in a subject in need thereof, treat sickle cell disease in a subject in need thereof and/or treat or prevent one or more complications of anemia including, for example, cutaneous ulcers. In some embodiments, the disclosure provides methods of using GDF Trap polypeptides to treat an anemia in a subject in need thereof and/or treat one or more complications of anemia including, for example, cutaneous ulcers, in a subject having anemia. In some embodiments, the disclosure provides methods of using GDF Trap polypeptides to prevent an anemia in a subject in need thereof and/or prevent one or more complications of anemia including, for example, cutaneous ulcers, in a subject having anemia.

In some embodiments, GDF Traps of the present disclosure are soluble, variant ActRII polypeptides (e.g., ActRIIA and ActRIIB polypeptides) that comprise one or more mutations (e.g., amino acid additions, deletions, substitutions, and combinations thereof) in the extracellular domain (also referred to as the ligand-binding domain) of an ActRII polypeptide (e.g., a "wild-type" ActRII polypeptide) such that the variant ActRII polypeptide has one or more altered ligand-binding activities than the corresponding wild-type ActRII polypeptide. In some embodiments, GDF Trap polypeptides of the present disclosure retain at least one similar activity as a corresponding wild-type ActRII polypeptide (e.g., an ActRIIA or ActRIIB polypeptide). For example, a GDF Trap may bind to and/or inhibit (e.g. antagonize) the function of one or more ActRII ligands (e.g., inhibit ActRII ligand-mediated activation of the ActRIIA and/or ActRIIB signaling transduction, such as SMAD 2/3 and/or SMAD 1/5/8 signaling pathway). In some embodiments, GDF Traps of the present disclosure bind to and/or inhibit one or more of activin A, activin B, activin AB, activin C, activin E, Nodal, GDF8, GDF11, BMP6 and/or BMP7).

In certain embodiments, GDF Trap polypeptides of the disclosure have elevated binding affinity for one or more specific ActRII ligands (e.g., GDF8, GDF11, BMP6, Nodal, and/or BMP7). In other embodiments, GDF Trap polypeptides of the disclosure have decreased binding affinity for one or more specific ActRII ligands (e.g., activin A, activin B, activin AB, activin C, and/or activin E). In still other embodiments, GDF Trap polypeptides of the disclosure have elevated binding affinity for one or more specific ActRII ligands and decreased binding affinity for one or more different/other ActRII ligands. Accordingly, the present disclosure provides GDF Trap polypeptides that have an altered binding specificity for one or more ActRII ligands.

In certain embodiments, GDF Traps of the present disclosure are designed to preferentially bind to and antagonize GDF11 and/or GDF8 (also known as myostatin), e.g., in comparison to a wild-type ActRII polypeptide. Optionally, such GDF11 and/or GDF8-binding Traps may further bind to and/or antagonize one or more of Nodal, GDF8, GDF11, BMP6 and/or BMP7. Optionally, such GDF11 and/or GDF8-binding Traps may further bind to and/or antagonize one or more of activin B, activin C, activin E, Nodal, GDF8, GDF11, BMP6 and/or BMP7. Optionally, such GDF11 and/or GDF8-binding Traps may further bind to and/or antagonize one or more of activin A, activin A/B, activin B, activin C, activin E, Nodal, GDF8, GDF11, BMP6 and/or BMP7. In certain embodiments, GDF Traps of the present disclosure have diminished binding affinity for activins (e.g., activin A, activin A/B, activin B, activin C, activin E), e.g., in comparison to a wild-type ActRII polypeptide. In certain embodiments, a GDF Trap polypeptide of the present disclosure has diminished binding affinity for activin A.

For example, the disclosure provides GDF Trap polypeptides that preferentially bind to and/or antagonize GDF8/GDF11 relative to activin A. As demonstrated by the Examples of the disclosure, such GDF Trap polypeptides are more potent activators of erythropoiesis in vivo in comparison to ActRII polypeptides that retain high binding affinity for activin A. Furthermore, these non-activin A-binding GDF Traps polypeptides demonstrate decreased effects on other tissues. Therefore, such GDF Traps may be useful for increasing red blood cell levels in a subject while reducing potential off-target effects associated with binding/antagonizing activin A. However, such selective GDF Trap polypeptides may be less desirable in some applications wherein more modest gains in red blood cell levels may be needed for therapeutic effect and wherein some level of off-target effect is acceptable (or even desirable).

Amino acid residues of the ActRIIB proteins (e.g., E39, K55, Y60, K74, W78, L79, D80, and F101) are in the ActRIIB ligand-binding pocket and help mediate binding to its ligands including, for example, activin A, GDF11, and GDF8. Thus the present disclosure provides GDF Trap polypeptides comprising an altered-ligand binding domain (e.g., a GDF8/GDF11-binding domain) of an ActRIIB receptor which comprises one or more mutations at those amino acid residues.

Optionally, the altered ligand-binding domain can have increased selectivity for a ligand such as GDF11 and/or GDF8 relative to a wild-type ligand-binding domain of an ActRIIB receptor. To illustrate, one or more mutations may be selected that increase the selectivity of the altered ligand-binding domain for GDF11 and/or GDF8 over one or more activins (activin A, activin B, activin AB, activin C, and/or activin A), particularly activin A. Optionally, the altered ligand-binding domain has a ratio of $K_d$ for activin binding to $K_d$ for GDF11 and/or GDF8 binding that is at least 2-, 5-, 10-, 20-, 50-, 100- or even 1000-fold greater relative to the ratio for the wild-type ligand-binding domain. Optionally, the altered ligand-binding domain has a ratio of $IC_{50}$ for inhibiting activin to $IC_{50}$ for inhibiting GDF11 and/or GDF8 that is at least 2-, 5-, 10-, 20-, 50-, 100- or even 1000-fold greater relative to the wild-type ligand-binding domain. Optionally, the altered ligand-binding domain inhibits GDF11 and/or GDF8 with an $IC_{50}$ at least 2-, 5-, 10-, 20-, 50-, 100- or even 1000-times less than the $IC_{50}$ for inhibiting activin.

As a specific example, the positively-charged amino acid residue Asp (D80) of the ligand-binding domain of ActRIIB can be mutated to a different amino acid residue to produce a GDF Trap polypeptide that preferentially binds to GDF8, but not activin. Preferably, the D80 residue with respect to SEQ ID NO: 1 is changed to an amino acid residue selected from the group consisting of: an uncharged amino acid residue, a negative amino acid residue, and a hydrophobic amino acid residue. As a further specific example, the hydrophobic residue L79 of SEQ ID NO: 1 can be altered to confer altered activin-GDF11/GDF8 binding properties. For example, an L79P substitution reduces GDF11 binding to a greater extent than activin binding. In contrast, replacement of L79 with an acidic amino acid [an aspartic acid or glutamic acid; an L79D or an L79E substitution] greatly reduces activin A binding affinity while retaining GDF11 binding affinity. In exemplary embodiments, the methods described herein utilize a GDF Trap polypeptide which is a variant ActRIIB polypeptide comprising an acidic amino acid (e.g., D or E) at the position corresponding to position 79 of SEQ ID NO: 1, optionally in combination with one or more additional amino acid substitutions, additions, or deletions.

As will be recognized by one of skill in the art, most of the described mutations, variants or modifications described herein may be made at the nucleic acid level or, in some cases, by post-translational modification or chemical synthesis. Such techniques are well known in the art and some of which are described herein.

In certain embodiments, the present disclosure relates to ActRII polypeptides (ActRIIA and ActRIIB polypeptides) which are soluble ActRII polypeptides. As described herein, the term "soluble ActRII polypeptide" generally refers to polypeptides comprising an extracellular domain of an ActRII protein. The term "soluble ActRII polypeptide," as used herein, includes any naturally occurring extracellular domain of an ActRII protein as well as any variants thereof (including mutants, fragments, and peptidomimetic forms) that retain a useful activity (e.g., a GDF Trap polypeptide as described herein). Other examples of soluble ActRII polypeptides comprise a signal sequence in addition to the extracellular domain of an ActRII or GDF Trap protein. For example, the signal sequence can be a native signal sequence of an ActRIIA or ActRIIB protein, or a signal sequence from another protein including, for example, a tissue plasminogen activator (TPA) signal sequence or a honey bee melittin (HBM) signal sequence.

In part, the present disclosure identifies functionally-active portions and variants of ActRII polypeptides that can be used as guidance for generating and using ActRIIA polypeptides, ActRIIB polypeptides, and GDF Trap polypeptides within the scope of the methods described herein.

ActRII proteins have been characterized in the art in terms of structural and functional characteristics, particularly with respect to ligand-binding. See, e.g., Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; and U.S. Pat. Nos. 7,709,605, 7,612,041, and 7,842,663.

For example, Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO:1, "ActRIIB(20-119)-Fc", has reduced binding to GDF-11 and activin relative to an ActRIIB(20-134)-Fc, which includes the proline knot region and the complete juxtamembrane domain. See, e.g., U.S. Pat. No. 7,842,663. However, an ActRIIB(20-129)-Fc protein retains similar but somewhat reduced activity relative to the wild-type, even though the proline knot region is disrupted. Thus, ActRIIB extracellular domains that stop at amino acid 134, 133, 132, 131, 130 and 129 (with respect to present SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, mutations of P129 and P130 (with respect to SEQ ID NO:1) do not substantially decrease ligand binding. Therefore, an ActRIIB polypeptide or an ActRIIB-based GDF Trap polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO: 1) is poorly conserved and so is readily altered or truncated. ActRIIB polypeptides and ActRIIB-based GDF Traps ending at 128 (with respect to present SEQ ID NO: 1) or later should retain ligand binding activity. ActRIIB polypeptides and ActRIIB-based GDF Traps ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to present SEQ ID NO: 1) will retain ligand-binding activity. Amino acid 29 represents the initial cysteine. An alanine-to-asparagine mutation at position 24 (with respect to present SEQ ID NO: 1) introduces an N-linked glycosylation sequence without substantially affecting ligand-binding. See, e.g., U.S. Pat. No. 7,842,663. This confirms that mutations in the region between the signal cleavage peptide and the cysteine cross-linked region, corresponding to amino acids 20-29 are well tolerated. In particular, ActRIIB polypeptides and ActRIIB-based GDF Traps beginning at position 20, 21, 22, 23, and 24 (with respect to present SEQ ID NO: 1) should retain general ligand-biding activity, and ActRIIB polypeptides and ActRIIB-based GDF Traps beginning at positions 25, 26, 27, 28, and 29 (with respect to present SEQ ID NO:1) are also expected to retain ligand-biding activity. Data shown herein as well as in, e.g., U.S. Pat. No. 7,842,663 demonstrates that, surprisingly, an ActRIIB construct beginning at 22, 23, 24, or 25 will have the most activity.

Taken together, an active portion (e.g., ligand-binding activity) of ActRIIB comprises amino acids 29-109 of SEQ ID NO:1. Therefore ActRIIB polypeptides and ActRIIB-based GDF Traps of the present disclosure may, for example, comprise an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at amino acid 20, 21, 22, 23, 24, 25, 26, 27, 28, or 29) of SEQ ID NO: 1 and ending at a position corresponding to amino acids 109-134 (e.g., ending at amino acid 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In some embodiments, ActRIIB-based GDF Trap polypeptides of the present disclosure do not comprise or consist of amino acids 29-109 of SEQ ID NO:1. Other examples include polypeptides that begin at a position from 20-29 (e.g., position 20, 21, 22, 23, 24, 25, 26, 27, 28, or 29) or 21-29 (e.g., position 21, 22, 23, 24, 25, 26, 27, 28, or 29) and end at a position from 119-134 (e.g., 119, 120, 121, 122, 123, 124, 125, 126, 127, 128, 129, 130, 131, 132, 133, or 134), 119-133 (e.g., 119, 120, 121, 122, 123, 124, 125, 126, 127, 128, 129, 130, 131, 132, or 133), 129-134 (e.g., 129, 130, 131, 132, 133, or 134), or 129-133 (e.g., 129, 130, 131, 132, or 133) of SEQ ID NO: 1. Other examples include constructs that begin at a position from 20-24 (e.g., 20, 21, 22, 23, or 24), 21-24 (e.g., 21, 22, 23, or 24), or 22-25 (e.g., 22, 22, 23, or 25) and end at a position from 109-134 (e.g., 109, 110, 111, 112, 113, 114, 115, 116, 117, 118, 119, 120, 121, 122, 123, 124, 125, 126, 127, 128, 129, 130, 131, 132, 133, or 134), 119-134 (e.g., 119, 120, 121, 122, 123, 124, 125, 126, 127, 128, 129, 130, 131, 132, 133, or 134) or 129-134 (e.g., 129, 130, 131, 132, 133, or 134) of SEQ ID NO: 1. Variants within these ranges are also contemplated, particularly those having at least 80%, 81%, 82%, 83%, 84%, 85%, 86%, 87%, 88%, 89%, 90%, 91%, 92%, 93%, 94%, 95%, 96%, 97%, 98%, 99%, or 100% identity to the corresponding portion of SEQ ID NO: 1. In some embodiments, the ActRIIB polypeptides and ActRIIB-based GDF Traps comprise a polypeptide having an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to amino acid residues 25-131 of SEQ ID NO: 1. In certain embodiments, ActRIIB-based GDF Trap polypeptides do not comprise or consist of amino acids 25-131 of SEQ ID NO: 1.

The disclosure includes the results of an analysis of composite ActRIIB structures, shown in FIG. 1, demonstrating that the ligand-binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, a general formula for an ActRIIB polypeptide and ActRIIB-based GDF Trap polypeptide of the disclosure is one that comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to amino acids 29-109 of SEQ ID NO: 1, optionally beginning at a position ranging from 20-24 (e.g., 20, 21, 22, 23, or 24) or 22-25 (e.g., 22, 23, 24, or 25) and ending at a position ranging from 129-134 (e.g., 129, 130, 131, 132, 133, or 134), and comprising no more than 1, 2, 5, 10 or 15 conservative amino acid changes in the ligand-binding pocket, and zero, one or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO:1). An asparagine to alanine alteration at position 65 (N65A) actually improves ligand-binding in the A64 background, and is thus expected to have no detrimental effect on ligand-binding in the R64 background. See, e.g., U.S. Pat. No. 7,842,663. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64. See, e.g., U.S. Pat. No. 7,842,663.

ActRIIB is well-conserved across nearly all vertebrates, with large stretches of the extracellular domain conserved completely. Many of the ligands that bind to ActRIIB are also highly conserved. Accordingly, comparisons of ActRIIB sequences from various vertebrate organisms provide insights into residues that may be altered. Therefore, an active, human ActRIIB variant polypeptide and ActRIIB-based GDF Trap useful in accordance with the presently disclosed methods may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in *Xenopus* ActRIIB, and so this position may be altered, and optionally may be altered to another hydrophobic residue, such as V, I or F, or a non-polar residue such as A. E52 is a K in *Xenopus*, indicating that this site may be tolerant of a wide variety of changes, including polar residues, such as E, D, K, R, H, S, T, P, G, Y and probably A. T93 is a K in *Xenopus*, indicating that a wide structural variation is tolerated at this position, with polar residues favored, such as S, K, R, E, D, H, G, P, G and Y. F108 is a Y in *Xenopus*, and therefore Y or other hydrophobic group, such as I, V or L should be tolerated. E111 is K in *Xenopus*, indicating that charged residues will be tolerated at this position, including D, R, K and H, as well as Q and N. R112 is K in *Xenopus*, indicating that basic residues are tolerated at this position, including R and H. A at position 119 is relatively poorly conserved, and appears as P in rodents and V in *Xenopus*, thus essentially any amino acid should be tolerated at this position.

It has been previously demonstrated that the addition of a further N-linked glycosylation site (N-X-S/T) is well-tolerated relative to the ActRIIB(R64)-Fc form. See, e.g., U.S. Pat. No. 7,842,663. Therefore, N-X-S/T sequences may be generally introduced at positions outside the ligand binding pocket defined in FIG. 1 in ActRIIB polypeptide and ActRIIB-based GDF Traps of the present disclosure. Particularly suitable sites for the introduction of non-endogenous N-X-S/T sequences include amino acids 20-29, 20-24, 22-25, 109-134, 120-134 or 129-134 (with respect to SEQ ID NO: 1). N-X-S/T sequences may also be introduced into the linker between the ActRIIB sequence and an Fc domain or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E105N, R112N, G120N, E123N, P129N, A132N, R112S and R112T (with respect to SEQ ID NO: 1). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T (with respect to SEQ ID NO: 1) are contemplated. Likewise, in an A24N variant, an S26T alteration may be used. Accordingly, an ActRIIB polypeptide and ActRIIB-based GDF Trap polypeptide of the present disclosure may be a variant having one or more additional, non-endogenous N-linked glycosylation consensus sequences as described above.

The variations described herein may be combined in various ways. Additionally, the results of the mutagenesis program described herein indicate that there are amino acid positions in ActRIIB that are often beneficial to conserve. With respect to SEQ ID NO: 1, these include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, in the ActRIIB polypeptides and ActRIIB-based GDF Traps disclosed herein, the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

A general formula for an active (e.g., ligand binding) ActRIIA polypeptide is one that comprises a polypeptide that starts at amino acid 30 and ends at amino acid 110 of SEQ ID NO:9. Accordingly, ActRIIA polypeptides and ActRIIA-based GDF Traps of the present disclosure may comprise a polypeptide that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to amino acids 30-110 of SEQ ID NO:9. In some embodiments, ActRIIA-based GDF Traps of the present disclosure do not comprise or consist of amino acids 30-110 of SEQ ID NO:9. Optionally, ActRIIA polypeptides and ActRIIA-based GDF Trap polypeptides of the present disclosure comprise a polypeptide that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to amino acids amino acids 12-82 of SEQ ID NO:9 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115), respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO:9.

In certain embodiments, functionally active fragments of ActRII polypeptides (e.g. ActRIIA and ActRIIB polypeptides) and GDF Trap polypeptides of the present disclosure can be obtained by screening polypeptides recombinantly produced from the corresponding fragment of the nucleic acid encoding an ActRII polypeptide or GDF Trap polypeptide (e.g., SEQ ID NOs: 7, 8, 12, 13, 27, 32, 39, 40, 42, 46, and 48). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRII receptors and/or one or more ActRII ligands (e.g., GDF11, GDF8, activin A, activin B, activin AB, activin C, activin E, BMP6, BMP7, and/or Nodal).

In some embodiments, an ActRIIA polypeptide of the present disclosure is a polypeptide comprising an amino acid sequence that is at least 75% identical to an amino acid sequence selected from SEQ ID NOs: 9, 10, 11, 22, 26, and 28. In certain embodiments, the ActRIIA polypeptide comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 9, 10, 11, 22, 26, and 28. In certain embodiments, the ActRIIA polypeptide consists essentially of, or consists of, an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 9, 10, 11, 22, 26, and 28.

In some embodiments, an ActRIIB polypeptide of the present disclosure is a polypeptide comprising an amino acid sequence that is at least 75% identical to an amino acid sequence selected from SEQ ID NOs: 1, 2, 3, 4, 5, 6, 29, 31, and 49. In certain embodiments, the ActRIIB polypeptide comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 1, 2, 3, 4, 5, 6, 29, 31, and 49.

In certain embodiments, the ActRIIB polypeptide consists essentially of, or consists of, an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 1, 2, 3, 4, 5, 6, 29, 31, and 49.

In some embodiments, a GDF Trap polypeptide of the present disclosure is a variant ActRIIB polypeptide comprising an amino acid sequence that is at least 75% identical to an amino acid sequence selected from SEQ ID NOs: 1, 2, 3, 4, 5, 6, 29, 30, 31, 36, 37, 38, 41, 44, 45, 49, 50, and 51. In certain embodiments, the GDF Trap comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 1, 2, 3, 4, 5, 6, 29, 30, 31, 36, 37, 38, 41, 44, 45, 49, 50, and 51. In certain embodiments, the GDF Trap comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 1, 2, 3, 4, 5, 6, 29, 30, 31, 36, 37, 38, 41, 44, 45, 49, 50, and 51, wherein the position corresponding to L79 of SEQ ID NO: 1, 4, or 49 is an acidic amino acids (a D or E amino acid residue). In certain embodiments, the GDF Trap consists essentially of, or consists of, an amino acid sequence that at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 36, 37, 38, 41, 44, 45, 50, and 51. In certain embodiments, the GDF Trap does not comprise or consists of an amino acid sequence selected from SEQ ID NOs: 1, 2, 3, 4, 5, 6, 29, and 31.

In some embodiments, a GDF Trap polypeptide of the present disclosure is a variant ActRIIA polypeptide comprising an amino acid sequence that is at least 75% identical to an amino acid sequence selected from SEQ ID NOs: 9, 10, 11, 22, 26, 28, 29, and 31. In certain embodiments, the GDF Trap comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 9, 10, 11, 22, 26, 28, 29, and 31. In certain embodiments, the GDF Trap consists essentially of, or consists of, an amino acid sequence that at least 80%, 81%, 82%, 83%, 84%, 85%, 86%, 87%, 88%, 89%, 90%, 91%, 92%, 93%, 94%, 95%, 96%, 97%, 98%, 99%, or 100% identical to an amino acid sequence selected from SEQ ID NOs: 9, 10, 11, 22, 26, 28, 29, and 31. In certain embodiments, the GDF Trap does not comprise or consists of an amino acid sequence selected from SEQ ID NOs: 9, 10, 11, 22, 26, 28, 29, and 31.

In some embodiments, the present disclosure contemplates making functional variants by modifying the structure of an ActRII polypeptide (e.g. and ActRIIA or ActRIIB polypeptide) or a GDF Trap for such purposes as enhancing therapeutic efficacy, or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more ligands, such as GDF11, activin A, activin B, activin AB, activin C, activin E, GDF8, BMP6, and BMP7, as compared to the unmodified or a wild-type polypeptide.

In certain embodiments, the present disclosure contemplates specific mutations of ActRII polypeptides and GDF Trap polypeptides of the present disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, ActRII polypeptides and GDF Trap polypeptides of the present disclosure for use in humans may be expressed in a mammalian cell line that provides proper glycosylation, such as HEK293 or CHO cell lines, although other mammalian expression cell lines are expected to be useful as well.

This disclosure further contemplates a method of generating mutants, particularly sets of combinatorial mutants of ActRII polypeptides and GDF Trap polypeptides of the present disclosure, as well as truncation mutants. Pools of combinatorial mutants are especially useful for identifying ActRII and GDF Trap sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, ActRII polypeptides and GDF Trap polypeptides may be screened for ability to bind to an ActRII receptor, to prevent binding of an ActRII ligand (e.g., GDF11, GDF8, activin A, activin B, activin AB, activin C, activin E, BMP7, BMP6, and/or Nodal) to an ActRII polypeptide, or to interfere with signaling caused by an ActRII ligand.

The activity of an ActRII polypeptides or GDF Trap polypeptides may also be tested in a cell-based or in vivo assay. For example, the effect of an ActRII polypeptide or GDF Trap polypeptide on the expression of genes involved in hematopoiesis may be assessed. This may, as needed, be performed in the presence of one or more recombinant ActRII ligand proteins (e.g., GDF11, GDF8, activin A, activin B, activin AB, activin C, activin E, BMP7, BMP6, and/or Nodal), and cells may be transfected so as to produce an ActRII polypeptide or GDF Trap polypeptide, and optionally, an ActRII ligand. Likewise, an ActRII polypeptide or GDF Trap polypeptide may be administered to a mouse or other animal, and one or more blood count measurements (e.g., an RBC count, hemoglobin, or reticulocyte) or cutaneous ulcer parameters may be assessed using art recognized methods.

Combinatorial-derived variants can be generated which have a selective or generally increased potency relative to a reference ActRII polypeptide or GDF Trap polypeptide. Such variants, when expressed from recombinant DNA constructs, can be used in gene therapy protocols. Likewise, mutagenesis can give rise to variants which have intracellular half-lives dramatically different than the corresponding unmodified ActRII polypeptide or GDF Trap polypeptide. For example, the altered protein can be rendered either more stable or less stable to proteolytic degradation or other cellular processes which result in destruction of, or otherwise inactivation of an unmodified polypeptide. Such variants, and the genes which encode them, can be utilized to alter ActRII polypeptide or GDF Trap polypeptide levels by modulating the half-life of the polypeptide. For instance, a short half-life can give rise to more transient biological effects and, when part of an inducible expression system, can allow tighter control of recombinant ActRII polypeptide or GDF Trap polypeptide levels within the cell. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRII or GDF Trap sequences. For instance, a mixture of synthetic oligonucleotides can be enzymatically ligated into gene sequences such that the degenerate set of potential ActRII or GDF Trap polypeptide encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art. See, e.g., Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins. See, e.g., Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRII polypeptides or GDF Trap polypeptides of the present disclosure can be generated and isolated from a library by screening using, for example, alanine scanning mutagenesis [see, e.g., Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis (see, e.g., Gustin et al. (1993) Virology 193:653-660; and Brown et al. (1992) Mol. Cell Biol. 12:2644-2652; McKnight et al. (1982) Science 232:316), by saturation mutagenesis [see, e.g., Meyers et al., (1986) Science 232:613]; by PCR mutagenesis [see, e.g., Leung et al. (1989) Method Cell Mol Biol 1:11-19]; or by random mutagenesis, including chemical mutagenesis [see, e.g., Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of ActRII polypeptides.

A wide-range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRII polypeptides or GDF Trap polypeptides of the disclosure. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. In some embodiments, assays include ActRII ligand (e.g., GDF11, GDF8, activin A, activin B, activin AB, activin C, activin E, BMP7, BMP6, and/or Nodal) binding assays and/or ActRII ligand-mediated cell signaling assays.

In certain embodiments, ActRII polypeptides or GDF Trap polypeptides of the present disclosure may further comprise post-translational modifications in addition to any that are naturally present in the ActRII (e.g., an ActRIIA or ActRIIB polypeptide) or GDF Trap polypeptide. Such modifications include, but are not limited to, acetylation, carboxylation, glycosylation, phosphorylation, lipidation, and acylation. As a result, the ActRII polypeptide or GDF Trap polypeptide may contain non-amino acid elements, such as polyethylene glycols, lipids, polysaccharide- or mono-saccharide, and phosphates. Effects of such non-amino acid elements on the functionality of a ligand Trap polypeptide may be tested as described herein for other ActRII or GDF Trap variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the ActRII polypeptides or GDF Trap polypeptides.

In certain aspects, ActRII polypeptides or GDF Trap polypeptides of the present disclosure include fusion proteins having at least a portion (domain) of an ActRII polypeptide (e.g., an ActRIIA or ActRIIB polypeptide) or GDF Trap polypeptide and one or more heterologous portions (domains). Well known examples of such fusion domains include, but are not limited to, polyhistidine, Glu-Glu, glutathione S transferase (GST), thioredoxin, protein A, protein G, an immunoglobulin heavy chain Fc region, maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress system (Qiagen) useful with (HIS$_6$) (SEQ ID NO:66) fusion partners. As another example, a fusion domain may be selected so as to facilitate detection of the ligand Trap polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, an ActRII polypeptide or a GDF Trap polypeptide is fused with a domain that stabilizes the polypeptide in vivo (a "stabilizer" domain). By "stabilizing" is meant anything that increases serum half-life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

In certain embodiments, the present disclosure provides ActRII or GDF Trap fusion proteins comprising an immunoglobulin Fc domain. In some embodiments, the immunoglobulin Fc domain is a mammalian immunoglobulin domain. In some embodiments, the immunoglobulin Fc domain is a human immunoglobulin domain. In some embodiments, the immunoglobulin Fc domain is a mouse immunoglobulin domain. In certain embodiments, the immunoglobulin Fc domain is an IgA, IgD, IgE, IgG, or IgM Fc domain. In certain embodiments, the immunoglobulin Fc domain is an IgG$_1$, IgG$_2$, IgG$_3$, IgG$_4$, IgA$_1$, or IgA$_2$ Fc domain. In some embodiments, the immunoglobulin Fc domain is a human IgG1 Fc domain, or a human IgG2 Fc domain.

In certain embodiments, the present disclosure provides ActRII or GDF Trap fusion proteins comprising the following IgG1 Fc domain sequence:

```
                                                   (SEQ ID NO: 14)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPVPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK.
```

In other embodiments, the present disclosure provides ActRII or GDF Trap fusion proteins comprising the following variants of the IgG1 Fc domain:

```
                                                  (SEQ ID NO: 64)
  1THTCPPCPAP ELLGGPSVFL FPPKPKDTLM ISRTPEVTCV VVDVSHEDPE

51VKFNWYVDGV EVHNAKTKPR EEQYNSTYRV VSVLTVLHQD WLNGKEYKCK

101VSNKALPAPI EKTISKAKGQ PREPQVYTLP PSREEMTKNQ VSLTCLVKGF
```

```
151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 15)
  1 THTCPPCPAP ELLGGPSVFL FPPKPKDTLM ISRTPEVTCV VVD(A)VSHEDPE

51 VKFNWYVDGV EVHNAKTKPR EEQYNSTYRV VSVLTVLHQD WLNGKEYKCK(A)

101 VSNKALPVPI EKTISKAKGQ PREPQVYTLP PSREEMTKNQ VSLTCLVKGF

151 YPSDIAVEWE SNGQPENNYK TTPPVLDSDG PFFLYSKLTV DKSRWQQGNV

201 FSCSVMHEAL HN(A)HYTQKSLS LSPGK.
```

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MHC class I-related Fc-receptor (FcRN) relative to a wild-type IgG1 Fc domain.

In certain other embodiments, the present disclosure provides ActRII or GDF trap fusion proteins comprising variants of the IgG2 Fc domain, including the following:

```
                                                        (SEQ ID NO: 65)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF LYSKLTVDK SRWQQGNVFS

201 CSVMHEALHN HYTQKSLSLS PGK
```

It is understood that different elements of the fusion proteins may be arranged in any manner that is consistent with the desired functionality. For example, an ActRII polypeptide domain or GDF Trap polypeptide domain may be placed C-terminal to a heterologous domain, or alternatively, a heterologous domain may be placed C-terminal to an ActRII polypeptide domain or GDF Trap polypeptide domain. The ActRII polypeptide domain or GDF Trap polypeptide domain and the heterologous domain need not be adjacent in a fusion protein, and additional domains or amino acid sequences may be included C- or N-terminal to either domain or between the domains.

For example, an ActRII or GDF Trap fusion protein may comprises an amino acid sequence as set forth in the formula A-B-C. The B portion corresponds to an ActRII polypeptide domain or a GDF Trap polypeptide domain. The A and C portions may be independently zero, one or more than one amino acids, and both the A and C portions when present are heterologous to B. The A and/or C portions may be attached to the B portion via a linker sequence. Exemplary linkers are include short polypeptide linkers such as 2-10, 2-5, 2-4, 2-3 glycine residues (SEQ ID NO:67), such as, for example, a Gly-Gly-Gly linker. Other suitable linkers are described herein above [e.g., a TGGG linker (SEQ ID NO:53)]. In certain embodiments, an ActRII or GDF Trap fusion protein comprises an amino acid sequence as set forth in the formula A-B-C, wherein A is a leader (signal) sequence, B consists of an ActRII or GDF polypeptide domain, and C is a polypeptide portion that enhances one or more of in vivo stability, in vivo half-life, uptake/administration, tissue localization or distribution, formation of protein complexes, and/or purification. In certain embodiments, an ActRII or GDF Trap fusion protein comprises an amino acid sequence as set forth in the formula A-B-C, wherein A is a TPA leader sequence, B consists of an ActRII or GDF polypeptide domain, and C is an immunoglobulin Fc domain. In some embodiments, fusion proteins comprise the amino acid sequences set forth in any one of SEQ ID NOs: 22, 26, 29, 31, 36, 38, 41, 44, and 51.

In certain embodiments, ActRII polypeptides or GDF Trap polypeptides of the present disclosure contain one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ActRII polypeptide domain or a GDF Trap polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol.

In some embodiments, ActRII polypeptides and GDF Traps to be used in accordance with the methods described herein are isolated polypeptides. As used herein, an isolated protein or polypeptide is one which has been separated from a component of its natural environment. In some embodiments, a polypeptide of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art. See, e.g., Flatman et al., (2007) J. Chromatogr. B 848:79-87.

In certain embodiments, ActRII polypeptides and GDF Traps of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (see, e.g., Advanced ChemTech Model 396; Milligen/Biosearch 9600). Alternatively, the polypeptides of the disclosure, including fragments or variants thereof, may be recombinantly produced using various expression systems (e.g., E. coli, Chinese Hamster Ovary (CHO) cells, COS cells, baculovirus) as is well known in the art. In a further embodiment, the modified or unmodified polypeptides of the disclosure may be produced by digestion of recombinantly produced full-length ActRII or GDF Trap polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such polypeptides may be produced from recombinantly produced full-length ActRII or GDF Trap polypeptides using chemical cleavage (e.g., cyanogen bromide, hydroxylamine, etc.).

Any of the ActRII polypeptides disclosed herein (e.g., ActRIIA or ActRIIB polypeptides) can be combined with one or more additional ActRII antagonist agents of the disclosure to achieve the desired effect (e.g., treat or prevent an anemia, treat or prevent one or more complications of anemia such as cutaneous ulcers, etc.). In some embodiments, the desired effect is treating one or more complications of anemia such as cutaneous ulcers. In some embodiments, the desired effect is preventing one or more complications of anemia such as cutaneous ulcers. For example, an ActRII polypeptide disclosed herein can be used in combination with i) one or more additional ActRII polypeptides disclosed herein, ii) one or more GDF Traps disclosed herein; iii) one or more ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP7 antibody, an anti-ActRIIA antibody, and/or or an anti-ActRIIB antibody); iv) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); v) one or more of the polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

Similarly, any of the GDF Traps disclosed herein can be combined with one or more additional ActRII antagonist agents of the disclosure to achieve the desired effect (e.g., treat or prevent an anemia, treat or prevent one or more complications of anemia such as cutaneous ulcers, etc.). In some embodiments, the desired effect is treating one or more complications of anemia such as cutaneous ulcers. In some embodiments, the desired effect is preventing one or more complications of anemia such as cutaneous ulcers. For example, a GDF Trap disclosed herein can be used in combination with i) one or more additional GDF Traps disclosed herein, ii) one or more ActRII polypeptides disclosed herein (e.g., ActRIIA or ActRIIB polypeptides) disclosed herein; iii) one or more ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP7 antibody, an anti-ActRIIA antibody, and/or or an anti-ActRIIB antibody); iv) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); v) one or more of the polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

B. Nucleic Acids Encoding ActRII Polypeptides and GDF Traps

In certain embodiments, the present disclosure provides isolated and/or recombinant nucleic acids encoding the ActRII polypeptides and GDF Trap polypeptides (including fragments, functional variants, and fusion proteins thereof) disclosed herein. For example, SEQ ID NO: 12 encodes the naturally occurring human ActRIIA precursor polypeptide, while SEQ ID NO: 13 encodes the processed extracellular domain of ActRIIA. In addition, SEQ ID NO:7 encodes a naturally occurring human ActRIIB precursor polypeptide (the R64 variant described above), while SEQ ID NO:8 encodes the processed extracellular domain of ActRIIB (the R64 variant described above). The subject nucleic acids may be single-stranded or double stranded. Such nucleic acids may be DNA or RNA molecules. These nucleic acids may be used, for example, in methods for making ActRII-based ligand Trap polypeptides of the present disclosure.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ActRII polypeptides and GDF Traps of the present disclosure are understood to include nucleic acids that are variants of any one of SEQ ID NOs: 7, 8, 12, 13, 27, 32, 39, 40, 42, 43, 46, 47, and 48. Variant nucleotide sequences include sequences that differ by one or more nucleotide substitutions, additions, or deletions including allelic variants, and therefore, will including coding sequences that differ from the nucleotide sequence designated in any one of SEQ ID NOs: 7, 8, 12, 13, 27, 32, 39, 40, 42, 43, 46, 47, and 48.

In certain embodiments, ActRII polypeptides and GDF Traps of the present disclosure are encoded by isolated or recombinant nucleic acid sequences that are at least 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NOs: 7, 8, 12, 13, 27, 32, 39, 40, 42, 43, 46, 47, and 48 In some embodiments, GDF Traps of the present disclosure are not encoded by nucleic acid sequences that comprise or consist of any one of nucleotide sequences corresponding to any one of SEQ ID NOs: 7, 8, 12, 13, 27, and 32. One of ordinary skill in the art will appreciate that nucleic acid sequences that are at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequences complementary to SEQ ID NOs: 7, 8, 12, 13, 27, 32, 39, 42, 47, and 48, and variants thereof, are also within the scope of the present disclosure. In further embodiments, the nucleic acid sequences of the disclosure can be isolated, recombinant, and/or fused with a heterologous nucleotide sequence, or in a DNA library.

In other embodiments, nucleic acids of the present disclosure also include nucleotide sequences that hybridize under highly stringent conditions to the nucleotide sequence designated in SEQ ID NOs: 7, 8, 12, 13, 27, 32, 39, 40, 42, 43, 46, 47, and 48, complement sequence of SEQ ID NOs: 7, 8, 12, 13, 27, 32, 39, 40, 42, 43, 46, 47, and 48, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 27, 32, 39, 40, 42, 43, 46, 47, and 48 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects of the present disclosure, the subject nucleic acid is provided in an expression vector comprising a nucleotide sequence encoding an ActRII polypeptide or a GDF Trap and operably linked to at least one regulatory sequence. Regulatory sequences are art-recognized and are selected to direct expression of the ActRII or GDF Trap polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRII or GDF Trap polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ActRII or GDF Trap polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures. See, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the 8-gal containing pBlueBac III).

In some embodiments, a vector will be designed for production of the subject ActRII or GDF Trap polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRII polypeptides in cells propagated in culture, e.g., to produce proteins, including fusion proteins or variant proteins, for purification.

This disclosure also pertains to a host cell transfected with a recombinant gene including a coding sequence for one or more of the subject ActRII or GDF Trap polypeptides. The host cell may be any prokaryotic or eukaryotic cell. For example, an ActRII or GDF Trap polypeptide of the disclosure may be expressed in bacterial cells such as E. coli, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ActRII and GDF Trap polypeptides. For example, a host cell transfected with an expression vector encoding an ActRII or GDF Trap polypeptide can be cultured under appropriate conditions to allow expression of the ActRII or GDF Trap polypeptide to occur. The polypeptide may be secreted and isolated from a mixture of cells and medium containing the polypeptide. Alternatively, the ActRII or GDF Trap polypeptide may be retained cytoplasmically or in a membrane fraction and the cells harvested, lysed and the protein isolated. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRII or GDF Trap polypeptides and affinity purification with an agent that binds to a domain fused to the ActRII or GDF Trap polypeptide (e.g., a protein A column may be used to purify an ActRII-Fc or GDF Trap-Fc fusion protein). In some embodiments, the ActRII or GDF Trap polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ActRII-Fc or GDF Trap-Fc protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ActRII or GDF Trap polypeptide, can allow purification of the expressed fusion protein by affinity chromatography using a $Ni^{2+}$ metal resin. The purification leader sequence can then be subsequently removed by treatment with enterokinase to provide the purified ActRII or GDF Trap polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

C. Antibody Antagonist

In certain aspects, the present disclosure relates to an antibody, or combination of antibodies, that antagonize ActRII activity (e.g., inhibition of ActRIIA and/or ActRIIB signaling transduction, such as SMAD 2/3 and/or SMAD 1/5/8 signaling). In particular, the disclosure provides methods of using an antibody ActRII antagonist, or combination of antibody ActRII antagonists, to, e.g., treat or prevent an anemia in a subject in need thereof and/or treat or prevent one or more complication of anemia including, for example, cutaneous ulcers. In some embodiments, the disclosure provides methods of using an antibody ActRII antagonist, or combination of antibody ActRII antagonists, to treat an anemia in a subject in need thereof and/or treat one or more complications of anemia including, for example, cutaneous ulcers in a subject having anemia. In some embodiments, the disclosure provides methods of using an antibody ActRII antagonist, or combination of antibody ActRII antagonists, to prevent an anemia in a subject in need thereof and/or prevent one or more complications of anemia including, for example, cutaneous ulcers in a subject having anemia.

In certain embodiments, an antibody ActRII antagonist of the disclosure is an antibody, or combination of antibodies, that binds to and/or inhibits activity of at least GDF11 (e.g., GDF11-mediated activation of ActRIIA and/or ActRIIB signaling transduction, such as SMAD 2/3 signaling). Optionally, the antibody, or combination of antibodies, further binds to and/or inhibits activity of GDF8 (e.g., GDF8-mediated activation of ActRIIA and/or ActRIIB signaling transduction, such as SMAD 2/3 signaling), particularly in the case of a multi-specific antibody that has binding affinity for both GDF11 and GDF8 or in the context of a combination of one or more anti-GDF11 antibodies and one or more anti-GDF8 antibodies. Optionally, an antibody, or combination of antibodies, of the disclosure does not substantially bind to and/or inhibit activity of activin A (e.g., activin A-mediated activation of ActRIIA or ActRIIB signaling transduction, such as SMAD 2/3 signaling). In some embodiments, an antibody, or combination of antibodies, of the disclosure that binds to and/or inhibits the activity of GDF11 and/or GDF8 further binds to and/or inhibits activity of one of more of activin A, activin B, activin AB, activin C, activin E, BMP6, BMP7, and Nodal (e.g., activation of ActRIIA or ActRIIB SMAD 2/3 and/or SMAD 1/5/8 signaling), particularly in the case of a multi-specific antibody that has binding affinity for multiple ActRII ligands or in the context of a combination of multiple antibodies—each having binding affinity for a different ActRII ligand.

In certain aspects, an ActRII antagonist of the present disclosure is an antibody, or combination of antibodies, that binds to and/or inhibits activity of at least GDF8 (e.g., GDF8-mediated activation of ActRIIA and/or ActRIIB signaling transduction, such as SMAD 2/3 signaling). Optionally, the antibody, or combination of antibodies, further binds to and/or inhibits activity of GDF11 (e.g., GDF11-mediated activation of ActRIIA and/or ActRIIB signaling transduction, such as SMAD 2/3 signaling), particularly in the case of a multi-specific antibody that has binding affinity for both GDF8 and GDF11 or in the context of a combination of one or more anti-GDF8 antibodies and one or more anti-GDF11 antibodies. Optionally, an antibody, or combination of antibodies, of the disclosure does not substantially bind to and/or inhibit activity of activin A (e.g., activin A-mediated activation of ActRIIA or ActRIIB signaling transduction, such as SMAD 2/3 signaling). In some embodiments, an antibody, or combination of antibodies, of the disclosure that binds to and/or inhibits the activity of GDF8 and/or GDF11 further binds to and/or inhibits activity of one of more of activin A, activin B, activin AB, activin C, activin E, BMP6, BMP7, and Nodal (e.g., activation of ActRIIA or ActRIIB signaling transduction, such as SMAD 2/3 and/or SMAD 1/5/8 signaling), particularly in the case of a multi-specific antibody that has binding affinity for multiple ActRII ligands or in the context of a combination multiple antibodies—each having binding affinity for a different ActRII ligand.

In another aspect, an ActRII antagonist of the present disclosure is an antibody, or combination of antibodies, that binds to and/or inhibits activity of an ActRII receptor (e.g. an ActRIIA or ActRIIB receptor). In some embodiments, an anti-ActRII receptor antibody (e.g. an anti-ActRIIA or anti-ActRIIB receptor antibody), or combination of antibodies, of the disclosure binds to an ActRII receptor and prevents binding and/or activation of the ActRII receptor by at least GDF11 (e.g., GDF11-mediated activation of ActRIIA and/or ActRIIB signaling transduction, such as SMAD 2/3 signaling). Optionally, an anti-ActRII receptor antibody, or combination of antibodies, of the disclosure further prevents binding and/or activation of the ActRII receptor by GDF8. Optionally, an anti-ActRII receptor antibody, or combination of antibodies, of the disclosure does not substantially inhibit activin A from binding to and/or activating an ActRII receptor. In some embodiments, an anti-ActRII receptor antibody, or combination of antibodies, of the disclosure that binds to an ActRII receptor and prevents binding and/or activation of the ActRII receptor by GDF11 and/or GDF8 further prevents binding and/or activation of the ActRII receptor by one or more of activin A, activin B, activin AB, activin C, activin E, BMP6, BMP7, and Nodal.

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. See, e.g., Hudson et al. (2003) Nat. Med. 9:129-134; Plückthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894, 5,587,458, and 5,869,046. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In some embodiments, the antibodies of the present disclosure are isolated antibodies.

Diabodies are antibody fragments with two antigen-binding sites that may be bivalent or bispecific. See, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448. Triabodies and tetrabodies are also described in Hudson et al. (2003) Nat. Med. 9:129-134.

Single-domain antibodies are antibody fragments comprising all or a portion of the heavy chain variable domain or all or a portion of the light chain variable domain of an antibody. In certain embodiments, a single-domain antibody is a human single-domain antibody. See, e.g., U.S. Pat. No. 6,248,516.

Antibody fragments can be made by various techniques, including but not limited to proteolytic digestion of an intact antibody as well as production by recombinant host cells (e.g., *E. coli* or phage), as described herein.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, $IgG_1$, $IgG_2$, $IgG_3$, $IgG_4$, $IgA_1$, and $IgA_2$. The heavy chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, surface plasmon resonance (Biacore™ assay), radiolabeled antigen binding assay (RIA), and ELISA. In some embodiments, antibodies of the present disclosure bind to their target antigens (e.g. GDF11, GDF8, ActRIIA, ActRIIB, etc.) with at least a $K_D$ of $1\times10^{-7}$ or stronger, $1\times10^{8}$ or stronger, $1\times10^{-9}$ or stronger, $1\times10^{10}$ or stronger, $1\times10^{11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radio-labeled antigen (e.g., $^{125}$I-labeled) in the presence of a titration series of unlabeled antigen, then capturing bound antigen with an anti-Fab antibody-coated plate. See, e.g., Chen et al. (1999) J. Mol. Biol. 293:865-881. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (Biacore, Inc., Piscataway, N.J.) with immobilized antigen CM5 chips at about 10 response units (RU). Briefly, carboxymethylated dextran biosensor chips (CM5, Biacore Inc.) are activated with N-ethyl-N'-(3-dimethylaminopropyl)-carbodiimide hydrochloride (EDC) and N-hydroxysuccinimide (NHS) according to the supplier's instructions. For example, an antigen can be diluted with 10 mM sodium acetate, pH 4.8, to 5 µg/ml (about 0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., (1999) J. Mol. Biol. 293:865-881. If the on-rate exceeds, for example, $10^6$ M$^{-1}$ s$^{-1}$ by the surface plasmon resonance assay above, then the on-rate can be determined by using a fluorescence quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophometer (Aviv Instruments) or a 8000-series SLM-AMINCO® spectrophotometer (ThermoSpectronic) with a stirred cuvette.

As used herein, anti-GDF11 antibody generally refers to an antibody that is capable of binding to GDF11 with sufficient affinity such that the antibody is useful as a diagnostic and/or therapeutic agent in targeting GDF11. In certain embodiments, the extent of binding of an anti-GDF11 antibody to an unrelated, non-GDF11 protein is less than about 10%, 9%, 8%, 7%, 6%, 5%, 4%, 3%, 2%, or less than 1% of the binding of the antibody to GDF11 as measured, for example, by a radioimmunoassay (RIA). In certain embodiments, an anti-GDF11 antibody binds to an epitope of GDF11 that is conserved among GDF11 from different species. In certain some embodiments, an anti-GDF11 antibody of the present disclosure is an antagonist antibody that can inhibit GDF11 activity. For example, an anti-GDF11 antibody of the disclosure may inhibit GDF11 from binding to a cognate receptor (e.g., ActRIIA or ActRIIB receptor) and/or inhibit GDF11-mediated signal transduction (activation) of a cognate receptor, such as SMAD2/3 signaling by ActRIIA and/or ActRIIB receptors. In some embodiments, anti-GDF11 antibodies of the present disclosure do not substantially bind to and/or inhibit activity of activin A. It should be noted that GDF11 has high sequence homology to GDF8 and therefore antibodies that bind and/or to GDF11, in some cases, may also bind to and/or inhibit GDF8.

An anti-GDF8 antibody refers to an antibody that is capable of binding to GDF8 with sufficient affinity such that the antibody is useful as a diagnostic and/or therapeutic agent in targeting GDF8. In certain embodiments, the extent of binding of an anti-GDF8 antibody to an unrelated, non-GDF8 protein is less than about 10%, 9%, 8%, 7%, 6%, 5%, 4%, 3%, 2%, or less than 1% of the binding of the antibody to GDF8 as measured, for example, by a radioimmunoassay (RIA). In certain embodiments, an anti-GDF8 antibody binds to an epitope of GDF8 that is conserved among GDF8 from different species. In some embodiments, an anti-GDF8 antibody of the present disclosure is an antagonist antibody that can inhibit GDF8 activity. For example, an anti-GDF8 antibody of the disclosure may inhibit GDF8 from binding to a cognate receptor (e.g., ActRIIA or ActRIIB receptor) and/or inhibit GDF8-mediated signal transduction (activation) of a cognate receptor, such as SMAD2/3 signaling by ActRIIA and/or ActRIIB receptors. In some embodiments, anti-GDF8 antibodies of the present disclosure do not substantially bind to and/or inhibit activity of activin A. It should be noted that GDF8 has high sequence homology to GDF11 and therefore antibodies that bind and/or to GDF8, in many cases, may also bind to and/or inhibit GDF11.

An anti-ActRIIA antibody refers to an antibody that is capable of binding to ActRIIA with sufficient affinity such that the antibody is useful as a diagnostic and/or therapeutic agent in targeting ActRIIA. In certain embodiments, the extent of binding of an anti-ActRIIA antibody to an unrelated, non-ActRIIA protein is less than about 10%, 9%, 8%, 7%, 6%, 5%, 4%, 3%, 2%, or less than 1% of the binding of the antibody to ActRIIA as measured, for example, by a radioimmunoassay (RIA). In certain embodiments, an anti-ActRIIA antibody binds to an epitope of ActRIIA that is conserved among ActRIIA from different species. In some embodiments, an anti-ActRIIA antibody of the present disclosure is an antagonist antibody that can inhibit ActRIIA activity. For example, an anti-ActRIIA antibody of the present disclosure may inhibit one or more ActRIIA ligands selected from activin A, activin B, activin AB, activin C, activin E, GDF11, GDF8, activin A, BMP6, and BMP7 from binding to the ActRIIA receptor and/or inhibit one of these ligands from activating ActRIIA signaling (e.g., SMAD2/3 and/or SMAD 1/5/8 ActRIIA signaling). In some embodiments, anti-ActRIIA antibodies of the present disclosure inhibit GDF11 from binding to the ActRIIA receptor and/or inhibit GDF11 from activating ActRIIA signaling. Optionally, anti-ActRIIA antibodies of the disclosure further inhibit GDF8 from binding to the ActRIIA receptor and/or inhibit GDF8 from activating ActRIIA signaling. Optionally, anti-ActRIIA antibodies of the present disclosure do not substantially inhibit activin A from binding to the ActRIIA receptor and/or do not substantially inhibit activin A-mediated activation of ActRIIA signaling. In some embodiments, an anti-ActRIIA antibody of the disclosure that inhibits GDF11 and/or GDF8 from binding to and/or activating an ActRIIA receptor further inhibits one or more of activin A, activin B, activin AB, activin C, activin E, activin A, GDF8, BMP6, and BMP7 from binding to and/or activating the ActRIIA receptor.

An anti-ActRIIB antibody refers to an antibody that is capable of binding to ActRIIB with sufficient affinity such that the antibody is useful as a diagnostic and/or therapeutic agent in targeting ActRIIB. In certain embodiments, the extent of binding of an anti-ActRIIB antibody to an unrelated, non-ActRIIB protein is less than about 10%, 9%, 8%, 7%, 6%, 5%, 4%, 3%, 2%, or less than 1% of the binding of the antibody to ActRIIB as measured, for example, by a radioimmunoassay (RIA). In certain embodiments, an anti-ActRIIB antibody binds to an epitope of ActRIIB that is conserved among ActRIIB from different species. In some embodiments, an anti-ActRIIB antibody of the present disclosure is an antagonist antibody that can inhibit ActRIIB activity. For example, an anti-ActRIIB antibody of the present disclosure may inhibit one or more ActRIIB ligands selected from activin A, activin B, activin AB, activin C, activin E, GDF11, GDF8, activin A, BMP6, and BMP7 from binding to the ActRIIB receptor and/or inhibit one of these ligands from activating ActRIIB signaling (e.g., SMAD2/3 and/or SMAD 1/5/8 ActRIIB signaling). In some embodiments, anti-ActRIIB antibodies of the present disclosure inhibit GDF11 from binding to the ActRIIB receptor and/or inhibit GDF11 from activating ActRIIB signaling. Optionally, anti-ActRIIB antibodies of the disclosure further inhibit GDF8 from binding to the ActRIIB receptor and/or inhibit GDF8 from activating ActRIIB signaling. Optionally, anti-ActRIIB antibodies of the present disclosure do not substantially inhibit activin A from binding to the ActRIIB receptor and/or do not substantially inhibit activin A-mediated activation of ActRIIB signaling. In some embodiments, an anti-ActRIIB antibody of the disclosure that inhibits GDF11 and/or GDF8 from binding to and/or activating an ActRIIB receptor further inhibits one or more of activin A, activin B, activin AB, activin C, activin E, activin A, GDF8, BMP6, and BMP7 from binding to and/or activating the ActRIIB receptor.

The nucleic acid and amino acid sequences of human GDF11, GDF8, activin A, activin B, activin AB, activin C, activin E, GDF8, BMP6, BMP7, ActRIIB, and ActRIIA or are well known in the art and thus antibody antagonists for use in accordance with this disclosure may be routinely made by the skilled artisan based on the knowledge in the art and teachings provided herein.

In certain embodiments, an antibody provided herein (e.g., an anti-GDF11 antibody, an anti-GDF8 antibody, an anti-ActRIIA antibody, or an anti-ActRIIB antibody) is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein (e.g., an anti-GDF11 antibody, an anti-GDF8 antibody, an anti-ActRIIA antibody, or an anti-ActRIIB antibody) is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337, 7,527,791, 6,982,321, and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling).

Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light-chain or heavy-chain variable regions [see, e.g., Carter et al. (1992) Proc. Natl. Acad. Sci. USA, 89:4285; and Presta et al. (1993) J. Immunol., 151: 2623]; human mature (somatically mutated) framework regions or human germline framework regions [see, e.g., Almagro and Fransson (2008) Front. Biosci. 13:1619-1633]; and framework regions derived from screening FR libraries (see, e.g., Baca et cd., (1997) J. Biol. Chem. 272:10678-10684; and Rosok et cd., (1996) J. Biol. Chem. 271:22611-22618).

In certain embodiments, an antibody provided herein (e.g., an anti-GDF11 antibody, an anti-GDF8 antibody, an anti-ActRIIA antibody, or an anti-ActRIIB antibody) is a human antibody. Human antibodies can be produced using various techniques known in the art. Human antibodies are described generally in van Dijk and van de Winkel (2001) Curr. Opin. Pharmacol. 5: 368-74 and Lonberg (2008), Curr. Opin. Immunol. 20:450-459.

Human antibodies may be prepared by administering an immunogen (e.g., a GDF11 polypeptide, GDF8 polypeptide, an ActRIIA polypeptide, or an ActRIIB polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals see, for example, Lonberg (2005) Nat. Biotechnol. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE(technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described. See, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91.

Human antibodies provided herein (e.g., an anti-GDF11 antibody, an anti-activin B antibody, an anti-ActRIIA antibody, or an anti-ActRIIB antibody) may also be generated by isolating Fv clone variable domain sequences selected from human-derived phage display libraries. Such variable domain sequences may then be combined with a desired human constant domain. Techniques for selecting human antibodies from antibody libraries are described herein.

For example, antibodies of the present disclosure may be isolated by screening combinatorial libraries for antibodies with the desired activity or activities. A variety of methods are known in the art for generating phage display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., GDF11, activin B, ActRIIA, or ActRIIB) without the requirement of constructing hybridomas. Alternatively, the naive repertoire can be cloned (e.g., from human) to provide a single source of antibodies directed against a wide range of non-self and also self-antigens without any immunization as described by Griffiths et al. (1993) EMBO J, 12: 725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multi-specific antibody, for example, a bispecific antibody. Multi-specific antibodies (typically monoclonal antibodies) have binding specificities for at least two different epitopes (e.g., two, three, four, five, or six or more) on one or more (e.g., two, three, four, five, six or more) antigens.

In certain embodiments, a multi-specific antibody of the present disclosure comprises two or more binding specificities, with at least one of the binding specificities being for a GDF11 epitope, and optionally one or more additional binding specificities being for an epitope on a different ActRII ligand (e.g., GDF8, activin A, activin B, activin AB, activin C, activin E, BMP6 BMP7 and/or Nodal) and/or an ActRII receptor (e.g., an ActRIIA and/or ActRIIB receptor). In certain embodiments, multi-specific antibodies may bind to two or more different epitopes of GDF11. Preferably a multi-specific antibody of the disclosure that has binding affinity, in part, for an GDF11 epitope can be used to inhibit a GDF11 activity (e.g., the ability to bind to and/or activate an ActRIIA and/or ActRIIB receptor), and optionally inhibit the activity of one or more different ActRII ligands (e.g., GDF8, activin A, activin B, activin AB, activin C, activin E, BMP6, BMP7 and/or Nodal) and/or an ActRII receptor (e.g., an ActRIIA or ActRIIB receptor).

In certain embodiments, multi-specific antibodies of the present disclosure that bind to and/or inhibit GDF11 further bind to and/or inhibit at least GDF8. Optionally, multi-specific antibodies of the disclosure that bind to and/or inhibit GDF11 do not substantially bind to and/or substantially inhibit activin A. In some embodiments, multi-specific antibodies of the disclosure that bind to and/or inhibit GDF11 and GDD8 further bind to and/or inhibit one or more of activin A, activin B, activin AB, activin C, activin E, BMP6, BMP7 and/or Nodal.

In certain embodiments, a multi-specific antibody of the present disclosure comprises two or more binding specificities, with at least one of the binding specificities being for a GDF8 epitope, and optionally one or more additional binding specificities being for an epitope on a different ActRII ligand (e.g., GDF11, activin A, activin B, activin AB, activin C, activin E, BMP6, BMP7 and/or Nodal) and/or an ActRII receptor (e.g., an ActRIIA and/or ActRIIB receptor). In certain embodiments, multi-specific antibodies may bind to two or more different epitopes of GDF8. Preferably a multi-specific antibody of the disclosure that has binding affinity, in part, for an GDF8 epitope can be used to inhibit an GDF8 activity (e.g., the ability to bind to and/or activate an ActRIIA and/or ActRIIB receptor), and optionally inhibit the activity of one or more different ActRII ligands (e.g., GDF11, activin A, activin B, activin AB, activin C, activin E, BMP6, BMP7 and/or Nodal) and/or an ActRII receptor (e.g., an ActRIIA or ActRIIB receptor). In certain embodiments, multi-specific antibodies of the present disclosure that bind to and/or inhibit GDF8 further bind to and/or inhibit at least GDF11. Optionally, multi-specific antibodies of the disclosure that bind to and/or inhibit GDF8 do not substantially bind to and/or substantially inhibit activin A. In some embodiments, multi-specific antibodies of the disclosure that bind to and/or inhibit GDF8 and GDF11 further bind to and/or inhibit one or more of activin A, activin B, activin AB, activin C, activin E, BMP6, BMP7 and/or Nodal.

Engineered antibodies with three or more functional antigen binding sites, including "Octopus antibodies," are also included herein. See, e.g., US 2006/0025576A1.

In certain embodiments, the antibodies disclosed herein (e.g., an anti-GDF11 antibody, an anti-activin B antibody, an anti-ActRIIA antibody, or an anti-ActRIIB antibody) are monoclonal antibodies. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from GDF11 or GDF8, anti-protein/anti-peptide antisera or monoclonal antibodies can be made by standard protocols. See, e.g., Antibodies: A Laboratory Manual (1988) ed. by Harlow and Lane, Cold Spring Harbor Press: 1988. A mammal, such as a mouse, a hamster, or rabbit can be immunized with an immunogenic form of the GDF11 or GDF8 polypeptide, an antigenic fragment which is capable of eliciting an antibody response, or a fusion protein. Techniques for conferring immunogenicity on a protein or peptide include conjugation to carriers or other techniques well known in the art. An immunogenic portion of a GDF11 or GDF8 polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of GDF11 or GDF8, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a GDF11 or GDF8 polypeptide, and monoclonal antibodies isolated from a culture comprising such hybridoma cells.

In certain embodiments, one or more amino acid modifications may be introduced into the Fc region of an antibody provided herein (e.g., an anti-GDF11 antibody, an anti-activin B antibody, an anti-ActRIIA antibody, or an anti-ActRIIB antibody), thereby generating an Fc region variant. The Fc region variant may comprise a human Fc region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet for which certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Nat'l Acad. Sci. USA 83:7059-7063]; Hellstrom, I et al. (1985) Proc. Nat'l Acad. Sci. USA 82:1499-1502; U.S. Pat. No. 5,821,337; and Bruggemann, M. et al. (1987) J. Exp. Med. 166:1351-1361. Alternatively, non-radioactive assays methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed. See, e.g., Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743. FcRn binding and in vivo clearance/half-life determinations can also be performed using methods known in the art. See, e.g., Petkova, S. B. et al. (2006) Int'l. Immunol. 18(12):1759-1769.

Antibodies of the present disclosure (e.g., an anti-GDF11 antibody, an anti-activin B antibody, an anti-ActRIIA antibody, or an anti-ActRIIB antibody) with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into, and/or substitutions of residues within the amino acid sequences of the antibody and/or binding polypeptide. Any combination of deletion, insertion, and substitution can be made to arrive at the final construct, provided that the final construct possesses the desired characteristics, e.g., target-binding (GDF11, GDF8, ActRIIA, and/or ActRIIB binding).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury (2008) Methods Mol. Biol. 207:179-196 (2008)), and/or SDRs (a-CDRs), with the resulting variant VH or VL being tested for binding affinity. Affinity maturation by constructing and reselecting from secondary libraries has been described in the art. See, e.g., Hoogenboom et al., in Methods in Molecular Biology 178:1-37, O'Brien et al., ed., Human Press, Totowa, N.J., (2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two, or three amino acid substitutions.

A useful method for identification of residues or regions of the antibody and/or the binding polypeptide that may be targeted for mutagenesis is called "alanine scanning mutagenesis" as described by Cunningham and Wells (1989) Science, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional non-proteinaceous moieties that are known in the art and readily available. The moieties suitable for derivatization of the antibody and/or binding polypeptide include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

Any of the ActRII antagonist antibodies disclosed herein (e.g., an anti-activin A antibody, an anti-activin B antibody, an anti-activin C antibody, an anti-activin E antibody, an anti-GDF11 antibody, an anti-GDF8 antibody, an anti-BMP6 antibody, an anti-BMP7 antibody, an anti-ActRIIA antibody, and/or or an anti-ActRIIB antibody) can be combined with one or more additional ActRII antagonist agents of the disclosure to achieve the desired effect (e.g., treat or prevent an anemia in a subject in need thereof and/or treat or prevent one or more complications of anemia including, for example, cutaneous ulcers). For example, an ActRII antagonist antibody disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody) can be used in combination with i) one or more additional ActRII antagonist antibodies disclosed herein, ii) one or more ActRII polypeptides disclosed herein (e.g., ActRIIA and/or ActRIIB polypeptides), iii) one or more GDF Traps disclosed herein; iv) one or more small molecule ActRII antagonist disclosed herein (e.g., a small molecule antagonist of one or more of GDF11, GDF8, activin A, activin B, activin AB, activin C, activin E, BMP6, BMP7, Nodal, ActRIIA, and/or ActRIIB); v) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

D. Small Molecule Antagonists

In another aspect, the present disclosure relates to a small molecule, or combination of small molecules, that antagonizes ActRII activity (e.g., inhibition of ActRIIA and/or ActRIIB signaling transduction, such as SMAD 2/3 and/or SMAD 1/5/8 signaling). In particular, the disclosure provides methods of using a small molecule antagonist, or combination of small molecule antagonists, of ActRII to, e.g., treat or prevent an anemia in a subject in need thereof and/or treat or prevent one or more complications of anemia including, for example, cutaneous ulcers. In some embodiments, the disclosure provides methods of using a small molecule antagonist, or combination of small molecule antagonists of ActRII, to treat an anemia in a subject in need thereof and/or treat one or more complications of anemia including, for example, cutaneous ulcers, in a subject having anemia. In some embodiments, the disclosure provides methods of using a small molecule antagonist, or combination of small molecule antagonists of ActRII, to prevent an anemia in a subject in need thereof and/or prevent one or more complications of anemia including, for example, cutaneous ulcers in a subject having anemia.

In some embodiments, an ActRII antagonist of the present disclosure is a small molecule antagonist, or combination of small molecule antagonists, that direct or indirect inhibits at least GDF11 activity. Optionally, such a small molecule antagonist, or combination of small molecule antagonists, may further inhibit, either directly or indirectly, GDF8. Optionally, a small molecule antagonist, or combination of small molecule antagonists, of the present disclosure does not substantially inhibit activin A activity. In some embodiments, a small molecule antagonist, or combination of small molecule antagonists, of the present disclosure that inhibits, either directly or indirectly, GDF11 and/or GDF8 activity further inhibits, either directly or indirectly, activity of one or more of activin A, activin B, activin AB, activin C, activin E, BMP6, BMP7, Nodal, ActRIIA, and ActRIIB.

In certain embodiments, a small molecule antagonist, or combination of small molecule antagonists, of the present disclosure is an indirect inhibitor of one or more of GDF11, GDF8, activin A, activin B, activin AB, activin C, activin E, BMP6, Nodal, ActRIIA, and ActRIIB. For example, a small molecule antagonist, or combination of small molecule antagonists, of the present disclosure may inhibit the expression (e.g., transcription, translation, cellular secretion, or combinations thereof) of at least GDF11. Optionally, such a small molecule antagonist, or combination of small molecule antagonists, may further inhibit expression of GDF8. Optionally, a small molecule antagonist, or combinations of small molecule antagonists, of the disclosure does not substantially inhibit the expression of activin A. In some embodiments, a small molecule antagonist, or combination of small molecule antagonists, of the disclosure that inhibits expression of GDF11 and/or GDF8 may further inhibit the expression of one or more of activin A, activin B, activin AB, activin C, activin E, BMP6, BMP7, Nodal, ActRIIA, and ActRIIB.

In other embodiments, a small molecule antagonist, or combination of small molecule antagonists, of the present disclosure is direct inhibitor of one or more of GDF11, GDF8, activin A, activin B, activin AB, activin C, activin E, BMP6, BMP7, Nodal, ActRIIA, and ActRIIB. For example, a small molecule antagonist, or combination of small molecule antagonists, of the present disclosure directly binds to and inhibits at least GDF11 activity (e.g. inhibits the ability GDF11 to bind to an ActRIIA and/or ActRIIB receptor; inhibit GDF11-mediated activation of the ActRIIA and/or ActRIIB signaling transduction, such as SMAD 2/3 signaling). Optionally, a small molecule antagonist, or combinations of small molecule antagonists, of the disclosure may further bind to and inhibit GDF8 activity (e.g. inhibit the ability of GDF8 to bind to an ActRIIA and/or ActRIIB receptor; inhibit GDF8-mediated activation of the ActRIIA and/or ActRIIB signaling transduction, such as SMAD 2/3 signaling). Optionally, a small molecule antagonist, or combinations of small molecule antagonists, of the disclosure does not substantially bind to or inhibit activin A activity (e.g. the ability of activin A to bind to an ActRIIA and/or ActRIIB receptor; activin A-mediated activation of the ActRIIA and/or ActRIIB signaling transduction, such as SMAD 2/3 signaling pathway). In some embodiments, a small molecule antagonist, or combinations of small molecule antagonists, of the disclosure that binds to and inhibits the activity of GDF11 and/or GDF8 further binds to and inhibits the activity of one or more of activin A, activin B, activin AB, activin C, activin E, BMP6, BMP7, Nodal, ActRIIA, and ActRIIB.

In some embodiments, a small molecule antagonist, or combination of small molecule antagonists, of the present disclosure directly binds to and inhibits at least GDF8 activity (e.g. inhibits the ability GDF8 to bind to an ActRIIA and/or ActRIIB receptor; inhibits GDF8-mediated activation of the ActRIIA and/or ActRIIB signaling transduction, such as SMAD 2/3 signaling). Optionally, a small molecule antagonist, or combinations of small molecule antagonists, of the disclosure may further bind to and inhibit GDF11 activity (e.g. inhibit the ability of GDF11 to bind to an ActRIIA and/or ActRIIB receptor; inhibit GDF11-mediated activation of the ActRIIA and/or ActRIIB signaling transduction, such as SMAD 2/3 signaling). Optionally, a small molecule antagonist, or combinations of small molecule antagonists, of the disclosure does not substantially bind to or inhibit activin A activity (e.g. the ability of activin A to bind to an ActRIIA and/or ActRIIB receptor; activin A-mediated activation of the ActRIIA and/or ActRIIB signaling transduction, SMAD 2/3 signaling). In some embodiments, a small molecule antagonist, or combinations of small molecule antagonists, of the disclosure that binds to and inhibits the activity of GDF8 and/or GDF11 further binds to and inhibits the activity of one or more of activin A, activin B, activin AB, activin C, activin E, BMP6, BMP7, Nodal, ActRIIA, and ActRIIB.

In some embodiments, a small molecule antagonist, or combination of small molecule antagonists, of the present disclosure directly binds to and inhibits at least ActRIIA activity (e.g. ActRII ligand-mediated activation of ActRIIA signaling transduction, such as SMAD 2/3 signaling). For example, a small molecule antagonist, or combination of small molecule antagonists, of the disclosure binds to an ActRIIA receptor and inhibits at least GDF11 from binding to and/or activating the ActRIIA receptor. Optionally, such a small molecule antagonist, or combination of small molecule antagonists, may further inhibit GDF8 from binding to and/or activating the ActRIIA receptor. Optionally, a small molecule antagonist, or combination of small molecule antagonists, of the disclosure does not substantially inhibit activin A from binding to and/or activating an ActRIIA receptor. In some embodiments, a small molecule antagonist, or combination of small molecule antagonists, of the disclosure that inhibits GDF11 and/or GDF8 from binding to and/or activating the ActRIIA receptor further inhibits one or more of activin A, activin B, activin AB, activin C, activin E, BMP6, BMP7, and Nodal from binding to/and or activating the ActRIIA receptor.

In some embodiments, a small molecule antagonist, or combination of small molecule antagonists, of the present disclosure directly binds to and inhibits at least ActRIIB activity (e.g. ActRII ligand-mediated activation of ActRIIB signaling transduction, such as SMAD 2/3 signaling). For example, a small molecule antagonist, or combination of small molecule antagonists, of the disclosure binds to an ActRIIB receptor and inhibits at least GDF11 from binding to and/or activating the ActRIIB receptor. Optionally, such a small molecule antagonist, or combination of small molecule antagonists, may further inhibit GDF8 from binding to and/or activating the ActRIIB receptor. Optionally, a small molecule antagonist, or combination of small molecule antagonists, of the disclosure does not substantially inhibit activin A from binding to and/or activating an ActRIIB receptor. In some embodiments, a small molecule antagonist, or combination of small molecule antagonists, of the disclosure that inhibits GDF11 and/or GDF8 from binding to and/or activating the ActRIIB receptor further inhibits one or more of activin A, activin B, activin AB, activin C, activin E, BMP6, BMP7, and Nodal from binding to/and or activating the ActRIIB receptor.

Binding organic small molecule antagonists of the present disclosure may be identified and chemically synthesized using known methodology (see, e.g., PCT Publication Nos. WO 00/00823 and WO 00/39585). In general, small molecules antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein (e.g., GDF11, GDF8, ActRIIA, and ActRIIB).

Such small molecule antagonists may be identified without undue experimentation using well known techniques. In this regard, it is noted that techniques for screening organic small molecule libraries for molecules that are capable of binding to a polypeptide target are well known in the art. See, e.g., international patent publication Nos. WO00/00823 and WO00/39585.

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

Any of the small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB) can be combined with one or more additional ActRII antagonist agents of the disclosure to achieve the desired effect (e.g., increase red blood cell levels and/or hemoglobin in a subject in need thereof, treat or prevent an anemia, treat sickle-cell disease, treat or prevent one or more complications of sickle-cell disease). For example, an small molecule ActRII antagonist disclosed herein (e.g., a small molecule antagonist of one or more of GDF11, GDF8, activin A, activin B, activin AB, activin C, activin E, BMP6, BMP7, Nodal, ActRIIA, and/or ActRIIB) can be used in combination with i) one or more additional small molecule ActRII antagonists disclosed herein, ii) one or more ActRII polypeptides disclosed herein (e.g., ActRIIA and/or ActRIIB polypeptides), iii) one or more GDF Traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an anti-BMP7 antibody, an anti-ActRIIA antibody, or an anti-ActRIIB antibody); v) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

E. Antagonist Polynucleotides

In another aspect, the present disclosure relates to a polynucleotide, or combination of polynucleotides, that antagonizes ActRII activity (e.g., inhibition of ActRIIA and/or ActRIIB signaling transduction, such as SMAD 2/3 and/or SMAD 1/5/8 signaling). In particular, the disclosure provides methods of using a polynucleotide ActRII antagonist, or combination of polynucleotide ActRII antagonists, to, e.g., treat or prevent an anemia in a subject in need thereof and/or treat or prevent one or more complication of anemia including, for example, cutaneous ulcers. In some embodiments, the disclosure provides methods of using a polynucleotide ActRII antagonist, or combination of polynucleotide ActRII antagonists, to treat an anemia in a subject in need thereof and/or treat one or more complications of anemia including, for example, cutaneous ulcers, in a subject having anemia. In some embodiments, the disclosure provides methods of using a polynucleotide ActRII antagonist, or combination of polynucleotide ActRII antagonists, to prevent an anemia in a subject in need thereof and/or prevent one or more complications of anemia including, for example, cutaneous ulcers in a subject having anemia.

In some embodiments, a polynucleotide ActRII antagonist, or combination of polynucleotide ActRII antagonist, of the present disclosure can be used to inhibit the activity and/or expression of one or more of GDF11, GDF8, activin A, activin B, activin AB, activin C, activin C, activin E, BMP6, BMP7, Nodal, ActRIIA, and/or ActRIIB. In certain embodiments, a polynucleotide ActRII antagonist, or combination of polynucleotide ActRII antagonist, of the disclosure is a GDF-ActRII antagonist.

In some embodiments, a polynucleotide antagonist, or combination of polynucleotide antagonists, of the disclosure inhibits the activity and/or expression (e.g., transcription, translation, secretion, or combinations thereof) of at least GDF11. Optionally, such a polynucleotide antagonist, or combination of polynucleotide antagonists, may further inhibit the activity and/or expression of GDF8. Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of GDF11 and/or GDF8 may further inhibit the activity and or expression of one or more of activin A, activin B, activin AB, activin C, activin E, BMP6, BMP7, Nodal, ActRIIA, and/or ActRIIB.

In some embodiments, a polynucleotide antagonist, or combination of polynucleotide antagonists, of the disclosure inhibits the activity and/or expression (e.g., transcription, translation, secretion, or combinations thereof) of at least GDF8. Optionally, such polynucleotide antagonist, or combination of polynucleotide antagonists, may further inhibit the activity and/or expression of GDF11. Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of GDF8 and/or GDF11 may further inhibit the activity and or expression of one or more of activin A, activin B, activin AB, activin C, activin E, BMP6, BMP7, Nodal, ActRIIA, and/or ActRIIB.

In some embodiments, a polynucleotide antagonist, or combination of polynucleotide antagonists, of the disclosure inhibits the activity and/or expression (e.g., transcription, translation, secretion, or combinations thereof) of at least ActRIIA. Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of ActRIIA may further inhibit the activity and or expression of one or more of activin A, activin B, activin AB, activin C, activin E, BMP6, BMP7, Nodal, and/or ActRIIB.

In some embodiments, a polynucleotide antagonist, or combination of polynucleotide antagonists, of the disclosure inhibits the activity and/or expression (e.g., transcription, translation, secretion, or combinations thereof) of at least ActRIIB. Optionally, a polynucleotide antagonist, or combination of polynucleotide antagonists, of the disclosure does not substantially inhibit the activity and/or expression of activin A. In some embodiments, a polynucleotide antagonist, or combination of polynucleotide antagonists, of the disclosure that inhibits the activity and/or expression of ActRIIB may further inhibit the activity and or expression of one or more of activin A, activin B, activin AB, activin C, activin E, BMP6, BMP7, Nodal, and/or ActRIIA.

The polynucleotide antagonists of the present disclosure may be an antisense nucleic acid, an RNAi molecule (e.g., small interfering RNA (siRNA), small-hairpin RNA (shRNA), microRNA (miRNA)), an aptamer and/or a ribozyme. The nucleic acid and amino acid sequences of human GDF11, GDF8, activin A, activin B, activin C, activin E, BMP6, BMP7, Nodal, ActRIIA, and ActRIIB are known in the art and thus polynucleotide antagonists for use in accordance with methods of the present disclosure may be routinely made by the skilled artisan based on the knowledge in the art and teachings provided herein.

For example, antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple helix formation is discussed in, for instance, Cooney et al. (1988) Science 241:456; and Dervan et al., (1991) Science 251: 1300. The methods are based on binding of a polynucleotide to a complementary DNA or RNA. In some embodiments, the antisense nucleic acids comprise a single-stranded RNA or DNA sequence that is complementary to at least a portion of an RNA transcript of a gene disclosed herein (e.g., GDF11, GDF8, activin A, activin B, activin C, activin C, activin E, BMP6, BMP7, Nodal, ActRIIA, and ActRIIB). However, absolute complementarity, is not required.

A sequence "complementary to at least a portion of an RNA," referred to herein, means a sequence having sufficient complementarity to be able to hybridize with the RNA, forming a stable duplex; in the case of double stranded antisense nucleic acids of a gene disclosed herein (e.g., GDF11, GDF8, activin A, activin B, activin C, activin E, BMP6, BMP7, Nodal, ActRIIA, and ActRIIB), a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See, e.g., Wagner, R., (1994) Nature 372:333-335. Thus, oligonucleotides complementary to either the 5'- or 3'-untranslated, non-coding regions of a gene of the disclosure (e.g., GDF11, GDF8, activin A, activin B, activin C, activin E, BMP6, BMP7, Nodal, ActRIIA, and ActRIIB), could be used in an antisense approach to inhibit translation of an endogenous mRNA.

Polynucleotides complementary to the 5' untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-untranslated, 3'-untranslated or coding region of an mRNA of the disclosure (e.g., an GDF11, GDF8, activin A, activin B, activin C, activin E, BMP6, BMP7, Nodal, ActRIIA, and ActRIIB mRNA), antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

In one embodiment, the antisense nucleic acid of the present disclosure (e.g., a GDF11, GDF8, activin A, activin B, activin C, activin E, BMP6, BMP7, Nodal, ActRIIA, or ActRIIB antisense nucleic acid) is produced intracellularly by transcription from an exogenous sequence. For example, a vector or a portion thereof, is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 29:304-310], the promoter contained in the 3' long terminal repeat of Rous sarcoma virus (see, e.g., Yamamoto et al. (1980) Cell 22:787-797, the herpes thymidine promoter [see, e.g., Wagner et al. (1981) Proc. Natl. Acad. Sci. U.S.A. 78:1441-1445], and the regulatory sequences of the metallothionein gene (see, e.g., Brinster, et al. (1982) Nature 296:39-42.

In some embodiments, the polynucleotide antagonists are interfering RNA or RNAi molecules that target the expression of one or more of: GDF11, GDF8, activin A, activin B, activin C, activin E, BMP6, BMP7, Nodal, ActRIIA, and ActRIIB. RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short hairpin RNA (shRNA); also short interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to effect RNAi. Accordingly, such short hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double stranded RNA (dsRNA) products of the DICER RNase and, in any event, have the same capacity for inhibiting expression of a specific gene. The shRNA can be expressed from a lentiviral vector. An miRNA is a single stranded RNA of about 10 to 70 nucleotides in length that are initially transcribed as pre-miRNA characterized by a "stem-loop" structure and which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as *E. coli* RNase III (Yang et al., Proc Natl Acad Sci USA 99:9942-9947, 2002).

According to another aspect, the disclosure provides polynucleotide antagonists including but not limited to, a decoy DNA, a double stranded DNA, a single-stranded DNA, a complexed DNA, an encapsulated DNA, a viral DNA, a plasmid DNA, a naked RNA, an encapsulated RNA, a viral RNA, a double stranded RNA, a molecule capable of generating RNA interference, or combinations thereof.

In some embodiments, the polynucleotide antagonists of the disclosure are aptamers. Aptamers are nucleic acid molecules, including double stranded DNA and single stranded RNA molecules, which bind to and form tertiary structures that specifically bind to a target molecule, such as a GDF11, GDF8, activin A, activin B, activin C, activin E, BMP6, BMP7, Nodal, ActRIIA, and ActRIIB polypeptide. The generation and therapeutic use of aptamers are well established in the art. See, e.g., U.S. Pat. No. 5,475,096. Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567,588, 5,707,796, 5,763,177, 6,011,577, and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo. See, e.g., Oligodeoxynucleotides as Antisense Inhibitors of Gene Expression, CRC Press, Boca Raton, Fla. (1988).

Any of the polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB) can be combined with one or more additional ActRII antagonist agents of the disclosure to achieve the desired effect (e.g., treat or prevent an anemia in a subject in need thereof and/or treat or prevent one or more complications of anemia including, for example, cutaneous ulcers). For example, an polynucleotide ActRII antagonist disclosed herein (e.g., a polynucleotide antagonist of one or more of GDF11, GDF8, activin A, activin B, activin AB, activin C, activin E, BMP6, BMP7, Nodal, ActRIIA, and/or ActRIIB) can be used in combination with i) one or more additional polynucleotide ActRII antagonists disclosed herein, ii) one or more ActRII polypeptides disclosed herein (e.g., ActRIIA and/or ActRIIB polypeptides), iii) one or more GDF Traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); v) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); vi) one or more follistatin polypeptides disclosed herein; and/or vii) one or more FLRG polypeptides disclosed herein.

F. Other Antagonists

In other aspects, an agent for use in accordance with the methods disclosed herein (e.g., methods of treating or preventing an anemia in an subject in need thereof and/or methods of treating or preventing one or more complications of anemia including, for example, cutaneous ulcers) is a follistatin polypeptide. The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. In certain embodiments, follistatin polypeptides of the disclosure bind to and/or inhibit activin activity, particularly activin A (e.g., activin-mediated activation of ActRIIA and/or ActRIIB SMAD 2/3 signaling). Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 18-20, the follistatin N-terminal domain ("FSND" SEQ ID NO: 18), FSD2 (SEQ ID NO: 20), and to a lesser extent FSD1 (SEQ ID NO: 19) represent exemplary domains within follistatin that are important for activin binding. In addition, methods for making and testing libraries of polypeptides are described above in the context of ActRII polypeptides and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity.

Examples of follistatin polypeptides include the mature follistatin polypeptide or shorter isoforms or other variants of the human follistatin precursor polypeptide (SEQ ID NO: 16) as described, for example, in WO2005/025601.

The human follistatin precursor polypeptide isoform FST344 is as follows:

```
                                  (SEQ ID NO: 16; NCBI Reference No. NP_037541.1
                                                       follistatin isoform FST344)
  1 mvrarhqpgg lclllllcq fmedrsaqag ncwlrqakng rcqvlyktel 51 skeeccstgr lstswteedv ndntlfkwmi fnggapncip cketcenvdc 101 gpgkkcrmnk knkprcvcap dcsnitwkgp vcgldgktyr necallkarc 151 keqpelevqy qgrckktcrd vfcpgsstcv vdqtnnaycv tcnricpepa 201 sseqylcgnd gvtyssachl rkatcllgrs iglayegkci kakscediqc
```

```
251 tggkkclwdf kvgrgrcslc delcpdsksd epvcasdnat yasecamkea 301 acssgvllev khsgscnsis edteeeeede dqdysfpiss ilew
```

The signal peptide is underlined; also underlined above are the last 27 residues in which represent the C-terminal extension distinguishing this follistatin isoform from the shorter follistatin isoform FST317 shown below.

The human follistatin precursor polypeptide isoform FST317 is as follows:

```
                 (SEQ ID NO: 17; NCBI Reference No. NP_006341.1)
  1 MVRARHQPGG LCLLLLLLCQ FMEDRSAQAG NCWLRQAKNG RCQVLYKTEL

51 SKEECCSTGR LSTSWTEEDV NDNTLFKWMI FNGGAPNCIP CKETCENVDC

101 GPGKKCRMNK KNKPRCVCAP DCSNITWKGP VCGLDGKTYR NECALLKARC

151 KEQPELEVQY QGRCKKTCRD VFCPGSSTCV VDQTNNAYCV TCNRICPEPA

201 SSEQYLCGND GVTYSSACHL RKATCLLGRS IGLAYEGKCI KAKSCEDIQC

251 TGGKKCLWDF KVGRGRCSLC DELCPDSKSD EPVCASDNAT YASECAMKEA

301 ACSSGVLLEV KHSGSCN
```

The signal peptide is underlined.

The follistatin N-terminus domain (FSND) sequence is as follows:

```
                                              (SEQ ID NO: 18; FSND)
GNCWLRQAKNGRCQVLYKTELSKEECCSTGRLSTSWTEEDVNDNTLFKW

MIFNGGAPNCIPCK
```

The FSD1 and FSD2 sequences are as follows:

```
                                (SEQ ID NO: 19; FSD1)
ETCENVDCGPGKKCRMNKKNKPRCV (SEQ ID NO: 20; FSD2)
KTCRDVFCPGSSTCVVDQTNNAYCVT
```

In other aspects, an agent for use in accordance with the methods disclosed herein (e.g., methods of treating or preventing an anemia in an subject in need thereof and/or methods of treating or preventing a complication of anemia including, for example, cutaneous ulcers) is a follistatin-like related gene (FLRG), also known as follistatin-related protein 3 (FSTL3). In some embodiments, the agent is used to treat a complication of anemia including, for example, cutaneous ulcers. In some embodiments, the agent is used to prevent a complication of anemia including, for example, cutaneous ulcers. The term "FLRG polypeptide" includes polypeptides comprising any naturally occurring polypeptide of FLRG as well as any variants thereof (including mutants, fragments, fusions, and peptidomimetic forms) that retain a useful activity.

In certain embodiments, FLRG polypeptides of the disclosure bind to and/or inhibit activin activity, particularly activin A (e.g., activin-mediated activation of ActRIIA and/or ActRIIB SMAD 2/3 signaling). Variants of FLRG polypeptides that retain activin binding properties can be identified using routine methods to assay FLRG and activin interactions. See, e.g., U.S. Pat. No. 6,537,966. In addition, methods for making and testing libraries of polypeptides are described above in the context of ActRII polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG (follistatin-related protein 3 precursor) polypeptide is as follows:

```
                 (SEQ ID NO: 21; NCBI Reference No. NP_005851.1)
  1 MRPGAPGPLW PLPWGALAWA VGFVSSMGSG NPAPGGVCWL QQGQEATCSL

51 VLQTDVTRAE CCASGNIDTA WSNLTHPGNK INLLGFLGLV HCLPCKDSCD

101 GVECGPGKAC RMLGGRPRCE CAPDCSGLPA RLQVCGSDGA TYRDECELRA

151 ARCRGHPDLS VMYRGRCRKS CEHVVCPRPQ SCVVDQTGSA HCVVCRAAPC

201 PVPSSPGQEL CGNNNVTYIS SCHMRQATCF LGRSIGVRHA GSCAGTPEEP

251 PGGESAEEEE NFV
```

The signal peptide is underlined.

In certain embodiments, functional variants or modified forms of the follistatin polypeptides and FLRG polypeptides include fusion proteins having at least a portion of the follistatin polypeptides or FLRG polypeptides and one or more fusion domains, such as, for example, domains that facilitate isolation, detection, stabilization or multimerization of the polypeptide. Suitable fusion domains are discussed in detail above with reference to the ActRII polypeptides. In some embodiment, an antagonist agent of the disclosure is a fusion protein comprising an activin-binding portion of a follistatin polypeptide fused to an Fc domain. In another embodiment, an antagonist agent of the disclosure is a fusion protein comprising an activin binding portion of an FLRG polypeptide fused to an Fc domain.

Any of the follistatin polypeptides disclosed herein may be combined with one or more additional ActRII antagonist agents of the disclosure to achieve the desired effect (e.g., treat or prevent an anemia in a subject in need thereof and/or treat or prevent one or more complications of anemia including, for example, cutaneous ulcers). For example, a follistatin polypeptide disclosed herein can be used in combination with i) one or more additional follistatin polypeptides disclosed herein, ii) one or more ActRII polypeptides disclosed herein (e.g., ActRIIA and/or ActRIIB polypeptides), iii) one or more GDF Traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); v) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); vi) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); and/or one or more FLRG polypeptides disclosed herein.

Similarly, any of the FLRG polypeptides disclosed herein may be combined with one or more additional ActRII antagonist agents of the disclosure to achieve the desired effect (e.g., treat or prevent an anemia in a subject in need thereof and/or treat or prevent one or more complications of anemia including, for example, cutaneous ulcers). For example, a FLRG polypeptide disclosed herein can be used in combination with i) one or more additional FLRG polypeptides disclosed herein, ii) one or more ActRII polypeptides disclosed herein (e.g., ActRIIA and/or ActRIIB polypeptides), iii) one or more GDF Traps disclosed herein; iv) one or more ActRII antagonist antibodies disclosed herein (e.g., an anti-GDF11 antibody, an anti-activin B antibody, an anti-activin C antibody, an anti-activin E antibody, an anti-GDF11 antibody, an anti-GDF8 antibody, an anti-BMP6 antibody, an-anti-BMP7 antibody, an anti-ActRIIA antibody, or an anti-ActRIIB antibody); v) one or more small molecule ActRII antagonists disclosed herein (e.g., a small molecule antagonist of one or more of GDF11, GDF8, activin A, activin B, activin AB, activin C, activin E, BMP6, BMP7, Nodal, ActRIIA, and/or ActRIIB); vi) one or more polynucleotide ActRII antagonists disclosed herein (e.g., a polynucleotide antagonist of one or more of GDF11, GDF8, activin A, activin B, activin AB, activin C, activin E, BMP6, BMP7, Nodal, ActRIIA, and/or ActRIIB); and/or one or more follistatin polypeptides disclosed herein.

4. Screening Assays

In certain aspects, the present disclosure relates to the use of the subject ActRII polypeptides (e.g., ActRIIA and ActRIIB polypeptides) and GDF Trap polypeptides to identify compounds (agents) which are agonist or antagonists of ActRIIB polypeptides. Compounds identified through this screening can be tested to assess their ability to modulate red blood cell, hemoglobin, and/or reticulocyte levels as well as effect cutaneous ulcers. These compounds can be tested, for example, in animal models.

There are numerous approaches to screening for therapeutic agents for increasing red blood cell or hemoglobin levels by targeting ActRII signaling (e.g., ActRIIA and/or ActRIIB SMAD 2/3 and/or SMAD 1/5/8 signaling). In certain embodiments, high-throughput screening of compounds can be carried out to identify agents that perturb ActRII-mediated effects on a selected cell line. In certain embodiments, the assay is carried out to screen and identify compounds that specifically inhibit or reduce binding of an ActRII polypeptide or GDF Trap polypeptide to its binding partner, such as an ActRII ligand (e.g., activin A, activin B, activin AB, activin C, Nodal, GDF8, GDF11 or BMP7). Alternatively, the assay can be used to identify compounds that enhance binding of an ActRII polypeptide or GDF Trap polypeptide to its binding partner such as an ActRII ligand. In a further embodiment, the compounds can be identified by their ability to interact with an ActRII polypeptide or GDF Trap polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRII polypeptide or a GDF Trap polypeptide and its binding partner (e.g., an ActRII ligand).

Merely to illustrate, in an exemplary screening assay of the present disclosure, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added to a composition containing an ActRIIB ligand (e.g., GDF11). Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between an ActRII polypeptide or GDF Trap polypeptide and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRII polypeptide or GDF Trap polypeptide and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between an ActRII polypeptide of GDF Trap polypeptide and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two hybrid assay," for identifying agents that disrupt or potentiate interaction between an ActRII polypeptide or GDF Trap polypeptide and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two hybrid systems to identify compounds (e.g., small molecules or peptides) that dissociate interactions between an ActRII polypeptide or GDF Trap and its binding protein. See, e.g., Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRII polypeptide or GDF Trap polypeptide. The interaction between the compound and the ActRII polypeptide or GDF Trap polypeptide may be covalent or non-covalent. For example, such interaction can be identified at the protein level using in vitro biochemical methods, including photo-crosslinking, radiolabeled ligand binding, and affinity chromatography. See, e.g., Jakoby W B et al. (1974) Methods in Enzymology 46:1. In certain cases, the compounds may be screened in a mechanism based assay, such as an assay to detect compounds which bind to an ActRII polypeptide of GDF Trap polypeptide. This may include a solid phase or fluid phase binding event. Alternatively, the gene encoding an ActRII polypeptide or GDF Trap polypeptide can be transfected with a reporter system (e.g., P-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

5. Exemplary Therapeutic Uses

In certain aspects, an ActRII antagonist agent, or combination of ActRII antagonist agents, of the present disclosure can be used to increase red blood cell levels in a subject (e.g., a patient) in need thereof, particularly mammals such as rodents, primates, and humans. In some embodiments, an ActRII antagonist agent, or combination of ActRII antagonist agents, of the present disclosure can be used to treat or prevent an anemia in a subject (e.g., a patient) in need thereof and/or one or more complications of anemia including, for example, an ulcer, particularly a cutaneous ulcer. In some embodiments, an ActRII antagonist agent, or combination of ActRII antagonist agents, of the present disclosure can be used to treat an anemia in a subject (e.g., a patient) in need thereof and/or one or more complications of anemia including, for example, an ulcer, particularly a cutaneous ulcer. In some embodiments, an ActRII antagonist agent, or combination of ActRII antagonist agents, of the present disclosure can be used to prevent an anemia in a subject (patient) in need thereof and/or one or more complications of anemia including, for example, an ulcer, particularly a cutaneous ulcer. In some embodiments, an ActRII antagonist agent, or combination of ActRII antagonist agents, of the present disclosure can be used to treat or prevent an ulcer in a subject (e.g., a patient) having anemia, particularly mammals such as rodents, primates, and humans. In some embodiments, an ActRII antagonist agent, or combination of ActRII antagonist agents, of the present disclosure can be used to treat or prevent an ulcer that is associated with anemia in a subject (e.g., a patient) in need thereof, particularly mammals such as rodents, primates, and humans. In some embodiments, an ActRII antagonist agent, or combination of ActRII antagonist agents, of the present disclosure can be used to treat or prevent a cutaneous (e.g., skin) ulcer in a subject (e.g., a patient) having anemia, particularly mammals such as rodents, primates, and humans. In some embodiments, an ActRII antagonist agent, or combination of ActRII antagonist agents, of the present disclosure can be used to treat or prevent a cutaneous ulcer associated with anemia in a subject (e.g., patient) in need thereof, particularly mammals such as rodents, primates, and humans. In some embodiments, an ActRII antagonist agent, or combination of ActRII antagonist agents, of the present disclosure can be used to treat or prevent an ulcer (e.g., a cutaneous ulcer) in a subject (e.g., patient) having a hemolytic anemia, particularly mammals such as rodents, primates, and humans. In some embodiments, an ActRII antagonist agent, or combination of ActRII antagonist agents, of the present disclosure can be used to treat or prevent an ulcer (e.g., a cutaneous ulcer) in a subject (e.g., patient) having a hemoglobinopathy anemia, particularly mammals such as rodents, primates, and humans. In some embodiments, an ActRII antagonist agent, or combination of ActRII antagonist agents, of the present disclosure can be used to treat or prevent an ulcer (e.g., a cutaneous ulcer) in a subject (patient) having a thalassemia syndrome (e.g., β-thalassemia syndrome, β-thalassemia intermedia, etc.), particularly mammals such as rodents, primates, and humans. In some embodiments, an ActRII antagonist agent, or combination of ActRII antagonist agents, of the present disclosure can be used to treat or prevent an ulcer (e.g., a cutaneous ulcer) in a subject (patient) having sickle-cell disease, particularly mammals such as rodents, primates, and humans. In some of the foregoing embodiments, the ActRII antagonist agent, or combination of ActRII antagonist agents, of the present disclosure are used to treat an ulcer (e.g., a cutaneous ulcer) in a subject (e.g., patient) having anemia (e.g., hemolytic anemia, hemoglobinopathy anemia, a thalassemia syndrome (e.g., β-thalassemia syndrome, β-thalassemia intermedia, etc.), sickle-cell disease, etc.). In some of the foregoing embodiments, the ActRII antagonist agent, or combination of ActRII antagonist agents, of the present disclosure are used to prevent an ulcer (e.g., a cutaneous ulcer) in a subject (e.g., patient) having anemia (e.g., hemolytic anemia, hemoglobinopathy anemia, a thalassemia syndrome (e.g., β-thalassemia syndrome, β-thalassemia intermedia, etc.), sickle-cell disease, etc.). In some embodiments, the subject having anemia has sickle cell disease. In some embodiments, the subject having anemia has a thalassemia syndrome (e.g., β-thalassemia syndrome, β-thalassemia intermedia, etc.). In some embodiments, the subject having anemia has a cutaneous ulcer. In some embodiments, the cutaneous ulcer is a skin ulcer. In some embodiments, the ulcer occurs on legs or ankes.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. For example, using an ActRII antagonist of the disclosure to prevent an ulcer (e.g., cutaneous ulcer) in a subject having anemia refers to reducing the occurrence of ulcer in the subject or delays the onset or reduces the severity of ulcer in the subject relative to a subject having anemia who is not receiving an ActRII antagonist.

The term "treating" as used herein includes amelioration or elimination of the condition once it has been established. In either case, prevention or treatment may be discerned in the diagnosis provided by a physician or other health care provider and the intended result of administration of the therapeutic agent. In some embodiments, treating an ulcer refers to promoting wound healing of ulcer tissues.

In general, treatment or prevention of a disease or condition as described in the present disclosure is achieved by administering one or more of the ActRII antagonists (e.g., an ActRIIA and/or ActRIIB antagonist) of the present disclosure in an effective amount. An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

Ulcers and Anemia

An ulcer is a sore on the skin or mucous membrane which is accompanied by the disintegration of tissue. Cutaneous (skin) ulcers can result in complete loss of epidermis and often portions of the dermis and even subcutaneous fat. Cutaneous ulcers are most common on the skin of the lower extremities but do occur on other areas of the body. Typically, ulcers appear as open craters, often round, with layers of skin that have eroded, and such lesions are highly susceptible to infection. The skin around the ulcer may be red, swollen, and/or tender. In general, ulcers tend to heal more slowly that other types of skin injuries and are resistant to treatment.

Ulcers develop in stages. In stage 1, the skin is red with soft underlying tissue. In the second stage, the redness of the skin becomes more pronounced, swelling appears, and there may be some blisters and loss of outer skin layers. During the next stage, the skin may become necrotic down through the deep layer of the skin, and the fat beneath may become exposed. In the last two stages, the sore may cause a deeper loss of fat and necrosis of muscle—in serve cases, it can extend to destruction of the bone and cause sepsis. In view of staged progression of ulcer pathology, physicians have adopted grading systems to classify ulcers. The Wagner Grading System classifies ulcers into 5 categories: i) a superficial ulcer is designated as Grade 1; ii) a ulcer deeper into subcutaneous tissue exposing soft tissue (but no abscess or osteomyelitis) is designated as Grade 2; iii) an ulcer with abscess formation and/or osteomyelitis is designated as Grade 3; iv) an ulcer having associated gangrene on part of a tissue or limb is designated as Grade 4; and v) an ulcer having extensive gangrene to a large area or entire limb is designated as Grade 5.

Ulcers, particularly cutaneous ulcers, occur as a complication of many anemias. In most patients, these ulcers occur in the legs or ankles, but may occur on other parts of the body. The relationship between anemia and ulcer formation is multifactorial, but it is generally expected that elevated hemolysis, oxidative stress, poor tissue oxygenation and vascular congestion may all contribute to the formation of ulcers. Elevated hemolysis causes the release of free hemoglobin into the serum, which causes oxidative damage and consumes nitric oxide that is needed to maintain proper vascular tone. Ulcers are associated with many hereditary and acquired anemias, including hereditary spherocytosis, hereditary elliptocytosis, hereditary stomacytosis, glucose6-phosphate dehydrogenase deficiency, sickle cell disease, thalassemia (both alpha and beta), paroxysmal nocturnal hemoglobinuria. Sickle cell disease and the thalassemias are particularly noted for causing ulcers, probably because all of the risk factors are present in these diseases. Ulcers are associated with many hemolytic anemias, which describes an anemic condition that results from excessive destruction of red blood cells. Hemolytic anemias may result from infections, such as hepatitis, cytomegalovirus (CMV), Epstein-Barr virus (EBV), typhoid fever, *E. coli* (*escherichia coli*), mycoplasma pneumonia, or streptococcus, medications, such as penicillin, antimalaria medications, sulfa medications, or acetaminophen, cancers such as leukemia or lymphoma and solid tumors of various types, autoimmune disorders, such as systemic lupus erythematous (SLE, or lupus), rheumatoid arthritis, Wiskott-Aldrich syndrome, or ulcerative colitis, hypersplenism, and autoimmune hemolytic anemia, in which the body's immune system creates an antibody against its own blood cells. Microangiopathic hemolytic anemia and thrombotic thrombocytopenic purpura are also associated with anemia and ulcer formation.

In some embodiments, an ActRII antagonist agent, or combination of ActRII antagonist agents, of the present disclosure can be used to treat or prevent an ulcer (e.g., a cutaneous ulcer) in a subject (patient) having an anemia selected from: including hereditary spherocytosis, hereditary elliptocytosis, hereditary stomacytosis, glucose6-phosphate dehydrogenase deficiency, a hemolytic anemia, a hemoglobinopathy anemia, sickle-cell disease, thalassemia (both alpha and beta), a β-thalassemia syndrome, β-thalassemia intermedia, paroxysmal nocturnal hemoglobinuria, microangiopathic hemolytic anemia, thrombotic thrombocytopenic purpra, an anemia associated with an infection (e.g., hepatitis, cytomegalovirus (CMV), Epstein-Barr virus (EBV), typhoid fever, E. coli (escherichia coli), mycoplasma pneumonia, or streptococcus), an anemia associated with administration of a medication (e.g., penicillin, antimalaria medications, sulfa medications, or acetaminophen), anemia associated with a cancer (e.g., leukemia, lymphoma, and solid tumors of various types), and anemia associated with an autoimmune disorder (e.g., systemic lupus erythematous (SLE, or lupus), rheumatoid arthritis, Wiskott-Aldrich syndrome, or ulcerative colitis, hypersplenism, and autoimmune hemolytic anemia, in which the body's immune system creates an antibody against its own blood cells). In some embodiments, an ActRII antagonist agent, or combination of ActRII antagonist agents, of the present disclosure can be used to treat or prevent an ulcer (e.g., a cutaneous ulcer) in a subject (patient) having a hemolytic anemia. In some embodiments, an ActRII antagonist agent, or combination of ActRII antagonist agents, of the present disclosure can be used to treat or prevent an ulcer (e.g., a cutaneous ulcer) in a subject (patient) having a hemoglobinopathy anemia. In some embodiments, an ActRII antagonist agent, or combination of ActRII antagonist agents, of the present disclosure can be used to treat or prevent an ulcer (e.g., a cutaneous ulcer) in a subject (patient) having a thalassemia syndrome. In some embodiments, an ActRII antagonist agent, or combination of ActRII antagonist agents, of the present disclosure can be used to treat or prevent an ulcer (e.g., a cutaneous ulcer) in a subject (patient) having a β-thalassemia syndrome. In some embodiments, an ActRII antagonist agent, or combination of ActRII antagonist agents, of the present disclosure can be used to treat or prevent an ulcer (e.g., a cutaneous ulcer) in a subject (patient) having β-thalassemia intermedia. In some embodiments, an ActRII antagonist agent, or combination of ActRII antagonist agents, of the present disclosure can be used to improve the Grade classification (e.g., the Wager Grading System) of the ulcer (e.g., a cutaneous ulcer) by at least one Grade (e.g., by at least one, two, three, four, or five Grades).

In certain embodiments, one or more ActRII antagonist agents of the disclosure (e.g., a GDF-ActRII antagonist, an ActRIIA polypeptide, an ActRIIB polypeptide, a GDF Trap, etc.) may be used in combination with supportive therapies for ulcers. Conventional care of cutaneous ulcers involves debridement and cleansing of the wound followed by application of occlusive dressing. See, e.g., Marti-Carvajal et al (2012) The Cochrane Collaboration, Published by Wiley & Sons, Ltd. Additional interventions can generally be classified into two major treatment groups: pharmaceutical interventions (systemic and topical agents) and non-pharmaceutical interventions. Systemic pharmaceutical interventions include, for example, vascular drugs (e.g., pentoxifylline, isoxsuprine hydrochloride, and xanthinol nicotinate), antioxidant agents (e.g., L-carnitine), EPO and EPO-stimulating agents, growth factors (e.g., Bosentan), minerals (e.g., zinc sulphate), agonists of HbF synthesis (e.g., arginine butyrate), and antibiotics. Topical pharmaceutical interventions include, for example, antibiotics, antiseptics, growth factors (e.g., GM-CSF, RGD peptide matrix, Solcoseryl®), steroids (e.g., cortisone), and pain relievers (e.g., opioids). Non-pharmaceutical interventions include, for example, reconstructive surgery, cell therapy, laser therapy, and hyperbaric oxygen.

Ulcers and Sickle Cell Disease

Numerous genes contribute to classical sickle-cell disease (SCD; drepanocytosis; sickle cell anemia). Primarily, SCD is an inherited disorder caused by a mutation in the β-globin gene (a mutation of a glutamate to a valine at codon 6). See, e.g., Kassim et al. (2013) Annu Rev Med, 64: 451-466. Sickle-cell anemia refers to the most common form of SCD, with a homozygous mutation in the $β^S$ allele (HbSS), affecting 60 to 70% of people with SCD.

Because of the mutation in the β-globin gene, abnormal hemoglobin molecules are produced with a hydrophobic motif that is exposed when it is in a deoxygenated state. See, e.g., Eaton et al. (1990) Adv Protein Chem, 40: 63-279; Steinberg, M H (1999) N Engl J Med 340(13): 1021-1030; and Ballas et al. (1992) Blood, 79(8) 2154-63. Once exposed, the chains of the separate hemoglobin molecules polymerize, which results in damage to the red blood cell membrane and cellular dehydration. The membrane damage is manifested, in part, by a redistribution of membrane lipids leading to the expression of phosphatidylserine on the outer leaflet of the erythrocyte membrane. See, e.g., (2002) Blood 99(5): 1564-1571. Externalized phosphatidylserine promotes adhesion to both macrophages and activated endothelial cells, which contributes to vascular (vaso) occlusion. Thus, at low oxygen states, the red cell's hemoglobin precipitates into long crystals that cause it to elongate, morphologically switching into a "sickled" red blood cell. Both genotype and the extent and degree of deoxygenation contribute to the severity of hemoglobin polymerization. It has been demonstrated that the presence of fetal hemoglobin proportionally reduces the amount of pathological hemoglobin polymers and is protective from vaso-occlusive crises.

Most sickle-cell disease patients experience painful episodes call pain crises. A sickle-cell pain crisis refers to acute sickling-related pain that lasts for at least 1 hour (e.g., at least 1, 2, 3, 4, 5, 6, or 10 hours) and optionally requires pain management therapy such as, e.g., administration of one or more narcotic and/or non-steroid anti-inflammatory agent. A pain crisis typically results in patient admission to a medical facility for pain management therapy. Acute pain in patients with SCD is generally ischemic in nature and can result from the occlusion of microvascular beds. Clinical data indicate that some patients with SCD have from three to ten episodes of pain crisis per year. In many patients a pain crisis episode will typically be resolved in about a week. In some cases, severe episodes may persist for several weeks or even months. SCD pain management often requires administration of one or more opioid analgesics (e.g. hydromorphone, meperidine, etc.), non-steroidal anti-inflammatory drugs (e.g., ketorolac tromethamine), and corticosteroids. In some embodiments, one or more ActRII antagonist agents of the disclosure, optionally in combination with one or more agents and/or supportive therapies for treating SCD, may be used to treat or prevent pain crisis in a patient with SCD. In some embodiments, one or more ActRII antagonist agents of the disclosure, optionally in combination with one or more agents and/or supportive therapies for treating SCD, may be used to reduce the frequency of pain management (e.g., treatment with one or more narcotics, non-steroid anti-inflammatory drugs, and/or corticosteroids) in a SCD patient. In some embodiments, one or more ActRII antagonist agents of the disclosure, optionally in combination with one or more agents and/or supportive therapies for treating SCD, may be used to reduce the dosage amount of one or more pain management agents (e.g., narcotics, non-steroid anti-inflammatory drugs, and/or corticosteroids) in a SCD patient.

Vaso-occlusive crises are one of the clinical hallmarks of SCD. See, e.g., Rees et al. (2010) Lancet, 376: 2018-2031. Hypoxia, acidosis, inflammatory stress, and endothelial cell activation promote the entrapment of rigid, polymerized sickled erythrocytes and leukocytes within small vessels. Sickled red blood cells obstruct capillaries and restrict blood flow to the organ, leading to ischemia, pain, tissue necrosis, and damage to various organs. This can cause vascular obstruction, leading to tissue ischemia. Although polymerization and early membrane damage are initially reversible, repeated sickling episodes lead to irreversibly sickled erythrocytes, which can impact a variety of organ systems and lead to death. In some embodiments, one or more ActRII antagonist agents of the disclosure, optionally in combination with one or more agents and/or supportive therapies for treating SCD, may be used to treat or prevent vaso-occlusive crisis in a SCD patient. In some embodiments, one or more ActRII antagonist agents of the disclosure, optionally in combination with one or more agents and/or supportive therapies for treating SCD, may be used to treat or prevent vaso-occlusion in a SCD patient. In some embodiments, one or more ActRII antagonist agents of the disclosure, optionally in combination with one or more agents and/or supportive therapies for treating SCD, may be used to treat or prevent a complication of vaso-occlusion in a SCD patient. In some embodiments, one or more ActRII antagonist agents of the disclosure, optionally in combination with one or more agents and/or supportive therapies for treating SCD, may be used to treat or prevent vaso-occlusion pain in a SCD patient.

Like vaso-occlusive complications, hemolytic anemia leads to significant morbidity in SCD patients. See, e.g., Pakbaz et al. (2014) Hematol Oncol Clin N Am 28: 355-374; Kassim et al. (2013) Annu Rev Med 64: 451-466. Multiple factors contribute to chronic anemia in SCD. As erythrocytes become deformed, antibodies are created to exposed antigens, which leads to increased destruction of erythrocytes, with an average lifespan of 17 days instead of 110 to 120 days. The release of hemoglobin during hemolysis inhibits nitric oxide signaling, leading to endothelial cell dysfunction and contributing to a hypercoagulable state. Chronic hemolysis contributes to anemia along with an impaired erythrocyte compensatory mechanism caused by hormone and vitamin deficiencies. Progressive renal disease is common in SCD, leading to decreased erythropoietin and thus impaired stimulation erythropoiesis. Folate and iron deficiency are common because of higher demand from erythrocyte production and increased urinary iron losses. All of these factors contribute to chronic anemia in SCD patients. In some embodiments, one or more ActRII antagonist agents of the disclosure, optionally in combination with one or more agents and/or supportive therapies for treating SCD, may be used to treat or prevent anemia in a SCD patient. In some embodiments, one or more ActRII antagonist agents of the disclosure, optionally in combination with one or more agents and/or supportive therapies for treating sickle cell disease, may be used to treat or prevent a complication of anemia in a SCD patient. In some embodiments, one or more ActRII antagonist agents of the disclosure, optionally in combination with one or more agents and/or supportive therapies for treating SCD, may be used to treat anemia in a SCD patient. In some embodiments, one or more ActRII antagonist agents of the disclosure, optionally in combination with one or more agents and/or supportive therapies for treating SCD, may be used to treat a complication of anemia in a SCD patient. In some embodiments, one or more ActRII antagonist agents of the disclosure, optionally in combination with one or more agents and/or supportive therapies for treating SCD, may be used to prevent anemia in a SCD patient. In some embodiments, one or more ActRII antagonist agents of the disclosure, optionally in combination with one or more agents and/or supportive therapies for treating SCD, may be used to prevent a complication of anemia in a SCD patient.

Acute anemia, which can be severe and potentially fatal, is associated with a 10% to 15% mortality rate, in SCD patients. In general, severe episodes are precipitated by three main causes: splenic sequestration crises, aplastic crises, or hyperhemolytic crises. See, e.g., Ballas et al. (2010) Am J Hematol, 85: 6-13.

Splenic sequestration crises occur as a result of erythrocyte vaso-occlusion within the spleen, where a pooling of erythrocytes causes its rapid enlargement. As such, there is a decrease in circulating hemoglobin (e.g., decreasing by 2 g/dL) and effective circulating volume, which may lead to hypovolemic shock. In some embodiments, one or more ActRII antagonist agents of the disclosure, optionally in combination with one or more agents and/or supportive therapies for treating SCD, may be used to treat or prevent splenic sequestration crises in a SCD patient. In some embodiments, one or more ActRII antagonist agents of the disclosure, optionally in combination with one or more agents and/or supportive therapies for treating SCD, may be used to treat or prevent splenic sequestration of red blood cells in a SCD patient. In some embodiments, one or more ActRII antagonist agents of the disclosure, optionally in combination with one or more agents and/or supportive therapies for treating SCD, may be used to treat or prevent splenomegaly in a SCD patient. In some embodiments, one or more ActRII antagonist agents of the disclosure, optionally in combination with one or more agents and/or supportive therapies for treating SCD, may be used to treat splenomegaly in a SCD patient. In some embodiments, one or more ActRII antagonist agents of the disclosure, optionally in combination with one or more agents and/or supportive therapies for treating SCD, may be used to prevent splenomegaly in a SCD patient.

Aplastic crises arise when erythropoiesis is impaired. Because of the constant overproduction of erythrocytes, an aplastic crisis can rapidly result in severe anemia. Infections, such as parvovirus B 19, streptococci, salmonella, and Epstein-Barr virus, are common causes for the transient arrest of erythropoiesis. Circulating erythrocytes and reticulocytes are both decreased during aplastic crises. In some embodiments, one or more ActRII antagonist agents of the disclosure, optionally in combination with one or more agents and/or supportive therapies for treating SCD, may be used to treat or prevent aplastic crises in a SCD patient. In some embodiments, one or more ActRII antagonist agents of the disclosure, optionally in combination with one or more agents and/or supportive therapies for treating SCD, may be used to treat or prevent aplastic anemia in a SCD patient. In some embodiments, one or more ActRII antagonist agents of the disclosure, optionally in combination with one or more agents and/or supportive therapies for treating SCD, may be used to treat aplastic crises in a SCD patient. In some embodiments, one or more ActRII antagonist agents of the disclosure, optionally in combination with one or more agents and/or supportive therapies for treating SCD, may be used to prevent aplastic crises in a SCD patient. In some embodiments, one or more ActRII antagonist agents of the disclosure, optionally in combination with one or more agents and/or supportive therapies for treating SCD, may be used to treat aplastic anemia in a SCD patient. In some embodiments, one or more ActRII antagonist agents of the disclosure, optionally in combination with one or more agents and/or supportive therapies for treating SCD, may be used to prevent aplastic anemia in a SCD patient.

Hyperhemolysis occurs when there is a sudden exacerbation of anemia with reticulocytosis, without evidence of splenic sequestration. Hyperhemolysis crises have been documented in patients with multiple transfusions or in patients receiving intravenous immunoglobulin therapy. In some embodiments, one or more ActRII antagonist agents of the disclosure, optionally in combination with one or more agents and/or supportive therapies for treating SCD, may be used to treat or prevent hyperhemolytic crises in a SCD patient. In some embodiments, one or more ActRII antagonist agents of the disclosure, optionally in combination with one or more agents and/or supportive therapies for treating SCD, may be used to treat or prevent hyperhemolytic anemia in a SCD patient. In some embodiments, one or more ActRII antagonist agents of the disclosure, optionally in combination with one or more agents and/or supportive therapies for treating SCD, may be used to treat hyperhemolytic crises in a SCD patient. In some embodiments, one or more ActRII antagonist agents of the disclosure, optionally in combination with one or more agents and/or supportive therapies for treating SCD, may be used to prevent hyperhemolytic crises in a SCD patient. In some embodiments, one or more ActRII antagonist agents of the disclosure, optionally in combination with one or more agents and/or supportive therapies for treating SCD, may be used to treat hyperhemolytic anemia in a SCD patient. In some embodiments, one or more ActRII antagonist agents of the disclosure, optionally in combination with one or more agents and/or supportive therapies for treating SCD, may be used to prevent hyperhemolytic anemia in a SCD patient.

In certain aspects, ActRII antagonist agents of the disclosure, optionally in combination with one or more agents and/or supportive therapies for treating SCD, may be used to treat or prevent a cardiac complication of SCD. Typically, chronic anemia in SCD causes a compensatory increased cardiac output. This, in turn, leads to cardiomegaly and left ventricular hypertrophy with left ventricular dysfunction. See, e.g., Adebayo et al. (2002) Niger J Med, 11: 145-152; Sachdev et al. (2007) J Am Coll Cardiol, 49: 472-279; and Zilberman et al. (2007) Am J Hematol 82: 433-438. Acute myocardial infarction can occur, even without coronary artery disease, and is thus underdiagnosed in SCD. See, e.g., Pannu et al. (2008) Crit Pathw Cardio, 7: 133-138. Cardiac arrhythmias and congestive heart failure have also been linked to premature death in SCD patients. See, e.g., Fitzhugh et al. (2010) Am J Hematol 85: 36-40. In some embodiments, ActRII antagonist agents of the disclosure, optionally in combination with one or more agents and/or supportive therapies for treating SCD, may be used to treat or prevent one or more cardiac complications of SCD including, e.g., increased cardiac output, cardiomegaly, cardiomyopathy, left ventricular hypertrophy, acute myocardial infarction, arrhythmia, and congestive heart failure. In some embodiments, ActRII antagonist agents of the disclosure, optionally in combination with one or more agents and/or supportive therapies for treating SCD, may be used to treat one or more cardiac complications of SCD. In some embodiments, ActRII antagonist agents of the disclosure, optionally in combination with one or more agents and/or supportive therapies for treating SCD, may be used to prevent one or more cardiac complications of SCD.

In certain aspects, ActRII antagonist agents of the disclosure, optionally in combination with one or more agents and/or supportive therapies for treating SCD, may be used to treat or prevent a pulmonary complication of SCD. SCD frequently results in both acute and chronic pulmonary complications. See, e.g., Rucknagel, D L (2001) Pediatr Pathol MOl Med, 20: 137-154; Haynes et al. (1986) Am J Med 80: 833-840. Acute complications may include infection, pulmonary emboli from thrombi, bone marrow infarction, and fat emboli. Pulmonary dysfunction may occur because of local pain from rib and sternal infarctions, leading to hypoventilation and atelectasis with hypoxemia. Chronic complications include sickle cell chronic lung disease and pulmonary hypertension. Acute chest syndrome (ACS) is unique to people with sickle disease and is defined by a new pulmonary infiltrate involving at least 1 complete lung segment, chest pain, and temperature above 38.5° C. along with tachypnea, wheeze, or cough. See, e.g., Vichinsky et al. (2000) N Engl J Med, 342: 1855-1865. Development of pulmonary infarction, fat embolism, and infections may all contribute to ACS. Infection is a major cause of morbidity and mortality in ACS patients.

Pulmonary hypertension is currently a major cause of morbidity and mortality in SCD. See, e.g., De Castro et al. (2008) Am J Hematol, 83: 19-25; Gladwin et al. (2004) N Engl J Med 350: 886-895. Pulmonary hypertension has been documented in 32% of adults with SCD and is related to vaso-occlusive crises and hemolysis. See, e.g., Machado et al. (2010) Chest, 137(6 supple): 30S-38S. Cell-free hemoglobin from hemolysis is thought to decrease nitric oxide, a pulmonary vasodilator, contributing to vaso-occlusion. See, e.g., Wood et al. (2008) Free Radic Biol Med 44: 1506-1528. In some embodiments, ActRII antagonist agents of the disclosure, optionally in combination with one or more agents and/or supportive therapies for treating SCD, may be used to treat or prevent one or more pulmonary complications of SCD including, e.g., fat or bone marrow emboli, pulmonary edema, sickle-cell lung disease, pulmonary hypertension, thromboemboli, and Acute chest syndrome. In some embodiments, ActRII antagonist agents of the disclosure, optionally in combination with one or more agents and/or supportive therapies for treating SCD, may be used to treat one or more pulmonary complications of SCD. In some embodiments, ActRII antagonist agents of the disclosure, optionally in combination with one or more agents and/or supportive therapies for treating SCD, may be used to prevent one or more pulmonary complications of SCD.

In certain aspects, ActRII antagonist agents of the disclosure, optionally in combination with one or more agents and/or supportive therapies for treating SCD, may be used to treat or prevent a hepatic complication of SCD. Liver pathology is common in SCD, with hepatomegaly being observed in ~90% of autopsy cases. See, e.g., Bauer et al. (1980) Am J med 69: 833-837; Mills et al. (1988) Arch Pathol Lab Med 112: 290-294. The effects of sickle cell anemia on the liver include intrasinusoidal sickling with proximal sinusoidal dilation, Kupffer cell hyperplasia with erythrophagocytosis, and hemosiderosis. Focal necrosis, regenerative nodules, and cirrhosis have also been described in postmortem examinations. Vaso-occlusion can lead to sinusoidal obstruction and ischemia, resulting in acute sickle hepatic crises. Similar to splenic sequestration, erythrocytes can be sequestered within the liver, leading to acute anemia. See, e.g., Lee et al. (1996) Postgrad Med J 72: 487-488. Hepatic sequestration can also lead to intrahepatic cholestasis. See, e.g., Shao et al. (1995) Am J Gastroenterol 90: 2045-2050. Ischemia within hepatocytes from sickling episodes also leads to ballooning of erythrocytes and intracanalicular cholestasis. Some therapies used for treating SCD also contribute to liver pathology. For example, frequent transfusions lead to increased iron deposition within Kupffer cells (which may lead to iron overload) and increase the risk of infection with blood-borne disease such as viral hepatitis. In some embodiments, ActRII antagonist agents of the disclosure, optionally in combination with one or more agents and/or supportive therapies for treating SCD, may be used to treat or prevent one or more hepatic complications of SCD including, e.g., hepatic failure, hepatomegaly, hepatic sequestration, intrahepatic cholestasis, cholelithiasis, and iron overload.

In certain aspects, ActRII antagonist agents of the disclosure, optionally in combination with one or more agents and/or supportive therapies for treating SCD, may be used to treat or prevent a splenic complication of SCD. Splenic sequestration, as previously discussed, occurs as a result of vaso-occlusion of erythrocytes within the spleen. Acute exacerbations result in splenomegaly and occasionally splenic infarction. More commonly, subclinical splenic sequestration may lead to the gradual loss of splenic function, leading to functional hyposplenia and asplenia. This, in turn, can lead to an increased susceptibility to sepsis as a result of encapsulated bacteria. In some embodiments, ActRII antagonist agents of the disclosure, optionally in combination with one or more agents and/or supportive therapies for treating SCD, may be used to treat or prevent one or more splenic complications of SCD including, e.g., acute or chronic splenic sequestration, splenomegaly, hyposplenia, asplenia, and splenic infarction. In some embodiments, ActRII antagonist agents of the disclosure, optionally in combination with one or more agents and/or supportive therapies for treating SCD, may be used to treat one or more splenic complications of SCD. In some embodiments, ActRII antagonist agents of the disclosure, optionally in combination with one or more agents and/or supportive therapies for treating SCD, may be used to prevent one or more splenic complications of SCD.

In certain aspects, ActRII antagonist agents of the disclosure, optionally in combination with one or more agents and/or supportive therapies for treating SCD, may be used to treat or prevent a renal complication of SCD. Approximately twelve percent of people with SCD develop renal failure. See, e.g., Powars et al. (2205) Medicine 84: 363-376; Scheinman, J I (2009) Nat Clin Pract Nephrol 5: 78-88. Vaso-occlusion within the vasa recta capillaries leads to microthrombotic infarction and extravasation of erythrocytes into the renal medulla. Blood becomes more viscous in the renal medulla because of low oxygen tension, low pH, and high osmolality and, if severe, can contribute to ischemia, infarction, and papillary necrosis. Repeated glomerular ischemia leads to glomerulosclerosis. Clinical consequences of ischemic damage include hematuria, proteinuria, decreased concentrating ability, renal tubular acidosis, abnormal proximal tubular function, acute and chronic renal failure, and urinary tract infections. In some embodiments, ActRII antagonist agents of the disclosure, optionally in combination with one or more agents and/or supportive therapies for treating SCD, may be used to treat or prevent one or more renal complications of SCD including, e.g., acute and/or chronic renal failure, pyelonephritis, and renal medullary carcinoma. In some embodiments, ActRII antagonist agents of the disclosure, optionally in combination with one or more agents and/or supportive therapies for treating SCD, may be used to treat one or more renal complications of SCD. In some embodiments, ActRII antagonist agents of the disclosure, optionally in combination with one or more agents and/or supportive therapies for treating SCD, may be used to prevent one or more renal complications of SCD.

In certain aspects, ActRII antagonist agents of the disclosure, optionally in combination with one or more agents and/or supportive therapies for treating SCD, may be used to treat or prevent a bone and/or joint complication of SCD. Bone and joint complications are a common complication in SCD patients. See, e.g., Hernigou et al. (1991) J Bone Join Surg Am, 73: 81-92. Pain from the small bones in the hands and feet, dactylitis, occurs frequently in infants with SCD. Long-term consequences of vaso-occlusion within bone marrow include infarcts, necrosis, and ultimately degenerative changes. Because of hyposplenia, bacterial infections are more common in SCD. Infarcted bone and bone marrow are common sites of infection, leading to osteomyelitis and septic arthritis. Osteonecrosis, or avascular necrosis, occurs after infarction with bone and bone marrow. Infarctions are most common within long bones such as the humerus, tibia, and femur. Chronic weight bearing causes stress on abnormal femoral heads and leads to progressive joint destruction and arthritis. In some embodiments, ActRII antagonist agents of the disclosure, optionally in combination with one or more agents and/or supportive therapies for treating SCD, may be used to treat or prevent one or more bone and/or joint complications of SCD including, e.g., infarction, necrosis, osteomyelitis, septic arthritis, osteonecrosis, and osteopenia. In some embodiments, ActRII antagonist agents of the disclosure, optionally in combination with one or more agents and/or supportive therapies for treating SCD, may be used to treat one or more bone and/or joint complications of SCD. In some embodiments, ActRII antagonist agents of the disclosure, optionally in combination with one or more agents and/or supportive therapies for treating SCD, may be used to prevent one or more bone and/or joint complications of SCD.

In certain aspects, ActRII antagonist agents of the disclosure, optionally in combination with one or more agents and/or supportive therapies for treating SCD, may be used to treat or prevent a neurological complication of SCD. Approximately 25 percent of individuals with SCD are affected by neurological injury. See, e.g., Ohene-Frempong et al. (1998) Blood, 91: 288-294; Verduzco et al. (2009) Blood 114: 5117-5125. The injuries may be acute or chronic. Cerebrovascular accidents are most common in adults, but depend on the genotype. A person with HbSS has the highest cerebrovascular risk, with a 24 percent likelihood of having a clinical stroke by the age of 45. Ischemic strokes are more common in children under 9 years of age, whereas hemorrhagic strokes are more common in adults. Ischemic strokes occur because of the occlusion of large intracranial arteries, leading to ischemia. The ischemia is secondary to occlusion of smaller vessels by rigid erythrocytes, exacerbated by chronic anemia, a hypercoagulable state, and flow-related hemodynamic injury to the arterial endothelium, further increasing the likelihood of erythrocyte adhesion. In contrast, hemorrhagic strokes may occur in intraventricular, intraparenchymal, and subarachnoid spaces. See, e.g., Anson, et al. (1991) J Neurosurg, 75: 552-558. Intraventricular hemorrhage may be associated with rupture of anterior cerebral artery aneurysms or direct extension of intraparenchymal hemorrhage into the lateral or third ventricle. In some embodiments, ActRII antagonist agents of the disclosure, optionally in combination with one or more agents and/or supportive therapies for treating SCD, may be used to treat or prevent one or more neurological complications of SCD including, e.g., aneurysm, ischemic stroke, intraparenchymal hemorrhage, subarachnoid hemorrhage, and intraventricular hemorrhage. In some embodiments, ActRII antagonist agents of the disclosure, optionally in combination with one or more agents and/or supportive therapies for treating SCD, may be used to treat one or more neurological complications of SCD. In some embodiments, ActRII antagonist agents of the disclosure, optionally in combination with one or more agents and/or supportive therapies for treating SCD, may be used to prevent one or more neurological complications of SCD.

In certain aspects, ActRII antagonist agents of the disclosure, optionally in combination with one or more agents and/or supportive therapies for treating SCD, may be used to treat or prevent an ophthalmic complication of SCD. Eye complications in SCD mainly affect the retina. See, e.g., Downes et al. (2005) Opthalmology, 112: 1869-1875; Fadugbagbe et al. (2010) Ann Trop Paediatr 30: 19-26. As a result of vaso-occlusive crises, peripheral retinal ischemia occurs. New blood vessels (sea fan formations) form mostly near arteriovenous crossings and are known as proliferative sickle retinopathy. These new vessels can bleed easily, causing traction retinal detachments and ultimately blindness. Non-proliferative retinal changes are also more common in SCD. In some embodiments, ActRII antagonist agents of the disclosure, optionally in combination with one or more agents and/or supportive therapies for treating SCD, may be used to treat or prevent one or more ophthalmic complications of SCD including, e.g., peripheral retinal ischemia, proliferative sickle retinopathy, vitreous hemorrhage, retinal detachment, and non-proliferative retinal changes. In some embodiments, ActRII antagonist agents of the disclosure, optionally in combination with one or more agents and/or supportive therapies for treating SCD, may be used to treat one or more ophthalmic complications of SCD. In some embodiments, ActRII antagonist agents of the disclosure, optionally in combination with one or more agents and/or supportive therapies for treating SCD, may be used to prevent one or more ophthalmic complications of SCD.

In certain aspects, ActRII antagonist agents of the disclosure, optionally in combination with one or more agents and/or supportive therapies for treating SCD, may be used to treat or prevent a cutaneous (skin) complication of SCD. One of the common cutaneous complications of SCD is the manifestation of ulcers. See, e.g., Keast et al. (2004) Ostomy Wound Manage., 50(10): 64-70; Trent et al. (2004) Adv Skin Wound Care, 17(8): 410-416; J. R. Eckman (1996) Hematol Oncol Clin North Am., 10(6): 1333-1344; and Chung et al. (1996) Advances in Wound Care, 9(5): 46-50. While the mechanism for ulcer development in SCD patients has not been fully elucidated, it is believed to be a multifactorial process that is influenced by various aspects of SCD including, for example, vascular obstruction, increased venous and capillary pressure, abnormal blood rheology, tissue hypoxia, and increased susceptibility to bacterial invasion caused by venous stasis, increased venous pressure, or both. The rate of ulcer healing has been found to be three to 16 times slower that the rate in patients with SCD. Ulcers may persist for months to years and there is a high incidence of reoccurrence in SCD patients. In some embodiments, ActRII antagonist agents of the disclosure, optionally in combination with one or more agents and/or supportive therapies for treating SCD, may be used to treat or prevent one or more cutaneous complication of SCD including, e.g., ulcers. In some embodiments, ActRII antagonist agents of the disclosure, optionally in combination with one or more agents and/or supportive therapies for treating SCD, may be used to treat one or more cutaneous complications complications of SCD, e.g., ulcers. In some embodiments, ActRII antagonist agents of the disclosure, optionally in combination with one or more agents and/or supportive therapies for treating SCD, may be used to prevent one or more cutaneous complications of SCD, e.g., ulcers.

In certain aspects, ActRII antagonist agents of the disclosure may be administered to a subject in need thereof in combination with one or more additional agents (e.g., hydroxyurea, an EPO antagonist, EPO, an opioid analgesic, a non-steroidal anti-inflammatory drug, a corticosteroids, an iron-chelating agent) or supportive therapies (e.g., red blood cell transfusion) for treating sickle-cell disease or one or more complications of sickle-cell disease (e.g., cutaneous complications such as cutaneous ulcers).

The mainstay of treatment for the majority of SCD patients is supportive. Current treatment options for patients with sickle cell disease include antibiotics, pain management, intravenous fluids, blood transfusion, surgery, and compounds such as hydroxyurea.

Hydroxyurea (e.g. Droxia®) is an approved drug for treating Sickle Cell Disease. Hydroxyurea is an S-phase cytotoxic drug and is used for long-term therapy. It is believed to increase the levels of hemoglobin F which prevents formation of S-polymers and red cell sickling. It is also believed to increase NO production. A multi-center trial of hydroxyurea in adults with Sickle Cell Disease showed that hydroxyurea reduced the incidence of painful episodes by nearly half. However, presently hydroxyurea is used only in patients who suffer severe complications of SCD and who are capable of following the daily dosage regimes. The general belief is that hydroxyurea therapy is effective only if given in a structured environment with a high potential for compliance. Unfortunately, many SCD patients are refractory to hydroxyurea. In some embodiments, the methods of the present disclosure relate to treating sickle-cell disease in a subject in need thereof by administering a combination of an ActRII antagonist of the disclosure and hydroxyurea. In some embodiments, the methods of the present disclosure relate to treating or preventing one or more complications (e.g., cutaneous complications such as cutaneous ulcers) of sickle-cell disease in a subject in need thereof by administering a combination of an ActRII antagonist of the disclosure and hydroxyurea.

Regular red blood cell transfusions are also a common therapy for SCD patients. However, several issues make them unsuitable for long-term use. Although regular transfusions have been shown to prevent stroke, ACS, and vaso-occlusive pain crises, they do not prevent the development of silent infarcts or the progression of moyamoya disease, a disorder of the cerebral circulation in which certain arteries are constricted and the compensatory collateral vessels are prone to hemorrhage. See, e.g., Bishop et al. (2011) Blood Cells, Molecules & Disease, 47: 125-128; DeBaun et al. (2012) Blood, 119: 4787-4596. Furthermore, SCD patients may develop iron overload as a consequence of red blood cell transfusion, which is associated with its own morbidity. Regular red blood cell transfusion requires exposure to various donor units of blood and hence a higher risk of alloimmunization. Difficulties with vascular access, availability of and compliance with iron chelation, and the high cost are some of the reasons why regular transfusions are not an optimal option for universal therapy. Wayne et al. (2000) Blood, 96: 2369-2372. In some embodiments, the methods of the present disclosure relate to treating sickle-cell disease in a subject in need thereof by administering a combination of an ActRII antagonist of the disclosure and one or more blood cell transfusions. In some embodiments, the methods of the present disclosure relate to treating or preventing one or more complication of sickle-cell disease in a subject in need thereof by administering a combination of an ActRII antagonist of the disclosure and one or more red blood cell transfusions. In some embodiments, treatment with one or more ActRII antagonists of the disclosure is effective at decreasing the transfusion requirement in a SCD patient, e.g., reduces the frequency and/or amount of blood transfusion required to effectively treat SCD or one or more complications of SCD.

In certain embodiments, one or more ActRII antagonist agents of the disclosure (e.g., a GDF-ActRII antagonist, an ActRIIA polypeptide, an ActRIIB polypeptide, a GDF Trap, etc.) may be used in combination with supportive therapies for SCD. Such therapies include transfusion with either red blood cells or whole blood to treat anemia. In SCD patients, normal mechanisms for iron homeostasis are overwhelmed by repeated transfusions, eventually leading to toxic and potentially fatal accumulation of iron in vital tissues such as heart, liver, and endocrine glands. Thus, supportive therapies for SCD patients also include treatment with one or more iron-chelating molecules to promote iron excretion in the urine and/or stool and thereby prevent, or reverse, tissue iron overload. Effective iron-chelating agents should be able to selectively bind and neutralize ferric iron, the oxidized form of non-transferrin bound iron which likely accounts for most iron toxicity through catalytic production of hydroxyl radicals and oxidation products. See, e.g., Esposito et al. (2003) Blood 102:2670-2677. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate). Kalinowski et al. (2005) Pharmacol Rev 57:547-583. In general, effective iron-chelating agents also are relatively low molecular weight (e.g., less than 700 daltons), with solubility in both water and lipids to enable access to affected tissues. Specific examples of iron-chelating molecules include deferoxamine (also known as desferrioxamine B, desferoxamine B, DFO-B, DFOA, DFB, or Desferal®), a hexadentate agent of bacterial origin requiring daily parenteral administration, and the orally active synthetic agents deferiprone (also known as Ferriprox®) (bidentate) and deferasirox (also known as bis-hydroxyphenyl-triazole, ICL670, or Exjade®) (tridentate). Combination therapy consisting of same-day administration of two iron-chelating agents shows promise in patients unresponsive to chelation monotherapy and also in overcoming issues of poor patient compliance with dereroxamine alone. Cao et al. (2011) Pediatr Rep 3(2):e17; and Galanello et al. (2010) Ann NY Acad Sci 1202:79-86.

Ineffective Erythropoiesis and Ulcers

In certain aspects, ActRII antagonist agents of the disclosure, optionally in combination with one or more agents and/or supportive therapies, may be used to treat or prevent an ineffective erythropoiesis in a subject in need thereof.

Originally distinguished from aplastic anemia, hemorrhage, or peripheral hemolysis on the basis of ferrokinetic studies (Ricketts et al., 1978, Clin Nucl Med 3:159-164), ineffective erythropoiesis describes a diverse group of anemias in which production of mature RBCs is less than would be expected given the number of erythroid precursors (erythroblasts) present in the bone marrow (Tanno et al., 2010, Adv Hematol 2010:358283). In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis (Aizawa et al, 2003, Am J Hematol 74:68-72), erythroblast-induced bone pathology (Di Matteo et al., 2008, J Biol Regul Homeost Agents 22:211-216), and tissue iron overload, even in the absence of therapeutic RBC transfusions (Pippard et al., 1979, Lancet 2:819-821). Thus, by boosting erythropoietic effectiveness, an ActRII antagonist of the disclosure may break the aforementioned cycle and may alleviate not only the underlying anemia but also the associated complications of elevated erythropoietin levels, splenomegaly, bone pathology, and tissue iron overload. ActRII antagonists can treat ineffective erythropoiesis, including anemia and elevated EPO levels, as well as complications such as splenomegaly, erythroblast-induced bone pathology, and iron overload, cutaneous ulcers, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors (Musallam et al., 2012, Cold Spring Harb Perspect Med 2:a013482). With erythroblast-induced bone pathology, attendant pathologies include low bone mineral density, osteoporosis, and bone pain (Haidar i., 2011, Bone 48:425-432). With iron overload, attendant pathologies include hepcidin suppression and hyperabsorption of dietary iron (Musallam et al., 2012, Blood Rev 26(Suppl 1):S16-S19), multiple endocrinopathies and liver fibrosis/cirrhosis (Galanello et al., 2010, Orphanet J Rare Dis 5:11), and iron-overload cardiomyopathy (Lekawanvijit et al., 2009, Can J Cardiol 25:213-218).

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation (Schrier, 2002, Curr Opin Hematol 9:123-126). Thalassemias are collectively among the most frequent genetic disorders worldwide, with changing epidemiologic patterns predicted to contribute to a growing public health problem in both the U.S. and globally (Vichinsky, 2005, Ann NY Acad Sci 1054:18-24). Thalassemia syndromes are named according to their severity. Thus, a-thalassemias include a-thalassemia minor (also known as a-thalassemia trait; two affected a-globin genes), hemoglobin H disease (three affected a-globin genes), and α-thalassemia major (also known as hydrops fetalis; four affected a-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia (Rund et al, 2005, N Engl J Med 353:1135-1146). As demonstrated herein with a mouse model of β-thalassemia, an ActRIIa antagonist, optionally combined with an EPO receptor activator, can be used to treat thalassemia syndromes. Furthermore, data disclosed herein demonstrates that a GDF Trap polypeptide can be used to promote positive effects on red blood cell parameters (e.g., increased levels of serum hemoglobin) as well as treat complications of thalassemia (e.g., cutaneous ulcers) in human thalassemia patients.

In certain aspects, ActRII antagonist agents of the disclosure, optionally in combination with one or more agents and/or supportive therapies for treating an ineffective erythropoiesis disorder, such as a thalassemia syndrome, may be used to treat or prevent a cutaneous (skin) complication of ineffective erythropoiesis. A common cutaneous complication of ineffective erythropoiesis, particularly thalassemia, is the manifestation of ulcers. While the mechanism for ulcer development in thalassemia patients has not been fully elucidated, it is believed to be a multifactorial process that is influenced by various aspects of thalassemia including, for example, and tissue hypoxia. In some embodiments, ActRII antagonist agents of the disclosure, optionally in combination with one or more agents and/or supportive therapies for treating ineffective erythropoiesis (e.g., thalassemia), may be used to treat or prevent one or more cutaneous complication of ineffective erythropoiesis (e.g., thalassemia) including, e.g., ulcers. In some embodiments, ActRII antagonist agents of the disclosure, optionally in combination with one or more agents and/or supportive therapies for treating ineffective erythropoiesis (e.g., thalassemia), may be used to treat one or more cutaneous complications of ineffective erythropoiesis (e.g., thalassemia) including, e.g., ulcers. In some embodiments, ActRII antagonist agents of the disclosure, optionally in combination with one or more agents and/or supportive therapies for treating ineffective erythropoiesis (e.g., thalassemia), may be used to prevent one or more cutaneous complications of ineffective erythropoiesis (e.g., thalassemia) including, e.g., ulcers. In some embodiments, ActRII antagonist agents of the disclosure, optionally in combination with one or more agents and/or supportive therapies for treating β-thalassemia (e.g., β-thalassemia intermedia), may be used to treat one or more cutaneous complications of β-thalassemia (e.g., β-thalassemia intermedia) including, e.g., ulcers. In some embodiments, ActRII antagonist agents of the disclosure, optionally in combination with one or more agents and/or supportive therapies for treating β-thalassemia (e.g., β-thalassemia intermedia), may be used to prevent one or more cutaneous complications of β-thalassemia (e.g., β-thalassemia intermedia) including, e.g., ulcers.

Other Anemia Indications

ActRII antagonist of the disclosure, optionally combined with one or more supportive therapies, can be used for treating disorders of ineffective erythropoiesis besides thalassemia syndromes. Such disorders include sideroblastic anemia (inherited or acquired); dyserythropoietic anemia (Types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anema, refractory megaloblastic anemia, or erythroleukemia); myelophthisic anemias, including myelofibrosis (myeloid metaplasia) and myelophthisis; congenital erythropoietic porphyria; and lead poisoning.

As shown herein, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator and one or more additional supportive therapies, may be used to increase red blood cell, hemoglobin, or reticulocyte levels in healthy individuals and selected patient populations. Examples of appropriate patient populations include those with undesirably low red blood cell or hemoglobin levels, such as patients having an anemia, sickle-cell patients, and those that are at risk for developing undesirably low red blood cell or hemoglobin levels, such as those patients that are about to undergo major surgery or other procedures that may result in substantial blood loss. In some embodiments, a patient with adequate red blood cell levels is treated with one or more ActRII antagonist agents to increase red blood cell levels, and then blood is drawn and stored for later use in transfusions.

One or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator and/or other one or more additional supportive therapies, may be used to increase red blood cell levels, hemoglobin levels, and/or hematocrit levels in a patient having an anemia (e.g., a sickle-cell patient, a thalassemia patient, etc.). When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in health adults, although, in terms of therapy, a lower target level may cause fewer cardiovascular side effects. See, e.g., Jacobs et al. (2000) Nephrol Dial Transplant 15, 15-19. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

Anemia is frequently observed in patients having a tissue injury, an infection, and/or a chronic disease, particularly cancer. In some subjects, anemia is distinguished by low erythropoietin levels and/or an inadequate response to erythropoietin in the bone marrow. See, e.g., Adamson, 2008, Harrison's Principles of Internal Medicine, 17th ed.; McGraw Hill, N.Y., pp 628-634. Potential causes of anemia include, for example, blood-loss, nutritional deficits (e.g. reduced dietary intake of protein), medication reaction, various problems associated with the bone marrow, and many diseases. More particularly, anemia has been associated with a variety of disorders and conditions that include, for example, bone marrow transplantation; solid tumors (e.g., breast cancer, lung cancer, and colon cancer); tumors of the lymphatic system (e.g., chronic lymphocyte leukemia, non-Hodgkin's lymphoma, and Hodgkin's lymphoma); tumors of the hematopoietic system (e.g., leukemia, a myelodysplastic syndrome and multiple myeloma); radiation therapy; chemotherapy (e.g., platinum containing regimens); inflammatory and autoimmune diseases, including, but not limited to, rheumatoid arthritis, other inflammatory arthritides, systemic lupus erythematosis (SLE), acute or chronic skin diseases (e.g., psoriasis), inflammatory bowel disease (e.g., Crohn's disease and ulcerative colitis); acute or chronic renal disease or failure, including idiopathic or congenital conditions; acute or chronic liver disease; acute or chronic bleeding; situations where transfusion of red blood cells is not possible due to patient allo- or auto-antibodies and/or for religious reasons (e.g., some Jehovah's Witnesses); infections (e.g., malaria and osteomyelitis); hemoglobinopathies including, for example, sickle cell disease (anemia), a thalassemias; drug use or abuse (e.g., alcohol misuse); pediatric patients with anemia from any cause to avoid transfusion; and elderly patients or patients with underlying cardiopulmonary disease with anemia who cannot receive transfusions due to concerns about circulatory overload. See, e.g., Adamson (2008) Harrison's Principles of Internal Medicine, 17th ed.; McGraw Hill, N.Y., pp 628-634. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat or prevent anemia associated with one or more of the disorders or conditions disclosed herein. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat anemia associated with one or more of the disorders or conditions disclosed herein. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to prevent anemia associated with one or more of the disorders or conditions disclosed herein.

Many factors can contribute to cancer-related anemia. Some are associated with the disease process itself and the generation of inflammatory cytokines such as interleukin-1, interferon-gamma, and tumor necrosis factor. Bron et al. (2001) Semin Oncol 28(Suppl 8): 1-6. Among its effects, inflammation induces the key iron-regulatory peptide hepcidin, thereby inhibiting iron export from macrophages and generally limiting iron availability for erythropoiesis. See, e.g., Ganz (2007) J Am Soc Nephrol 18:394-400. Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat a cancer-related anemia. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to prevent a cancer-related anemia.

A hypoproliferative anemia can result from primary dysfunction or failure of the bone marrow. Hypoproliferative anemias include: anemia of chronic disease, anemia of kidney disease, anemia associated with hypometabolic states, and anemia associated with cancer. In each of these types, endogenous erythropoietin levels are inappropriately low for the degree of anemia observed. Other hypoproliferative anemias include: early-stage iron-deficient anemia, and anemia caused by damage to the bone marrow. In these types, endogenous erythropoietin levels are appropriately elevated for the degree of anemia observed. Prominent examples would be myelosuppression caused by cancer and/or chemotherapeutic drugs or cancer radiation therapy. A broad review of clinical trials found that mild anemia can occur in 100% of patients after chemotherapy, while more severe anemia can occur in up to 80% of such patients. See, e.g., Groopman et al. (1999) J Natl Cancer Inst 91:1616-1634. Myelosuppressive drugs include, for example: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and *vinca* alkaloids (e.g., vinorelbine); 6) monoclonal antibodies (e.g., rituximab); and 7) topoisomerase inhibitors (e.g., topotecan and etoposide). In addition, conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat or prevent a hyperproliferative anemia.

Chronic kidney disease is sometimes associated with hypoproliferative anemia, and the degree of the anemia varies in severity with the level of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function. See, e.g., Levin et al. (1999) Am J Kidney Dis 27:347-354; Nissenson (1992) Am J Kidney Dis 20(Suppl 1):21-24; Revicki et al. (1995) Am J Kidney Dis 25:548-554; Gafter et al., (1994) Kidney Int 45:224-231. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat or prevent anemia associated with acute or chronic renal disease or failure. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat anemia associated with acute or chronic renal disease or failure. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to prevent anemia associated with acute or chronic renal disease or failure.

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. In some embodiments, one or more ActRII antagonist agents of the disclosure (e.g., a GDF-ActRII antagonist, an ActRIIA polypeptide, an ActRIIB polypeptide, a GDF Trap, etc.), may be used to treat anemia resulting from acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs. See, e.g., Adamson (2008) Harrison's Principles of Internal Medicine, 17th ed.; McGraw Hill, N.Y., pp 628-634. Appropriate therapy for iron-deficiency anemia depends on its cause and severity, with oral iron preparations, parenteral iron formulations, and RBC transfusion as major conventional options. In some embodiments, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat a chronic iron-deficiency.

Myelodysplastic syndrome (MDS) is a diverse collection of hematological conditions characterized by ineffective production of myeloid blood cells and risk of transformation to acute mylogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effect due to frequency of such therapies. For example, patients who receive frequent red blood cell transfusion can have tissue and organ damage from the buildup of extra iron. Accordingly, one or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, may be used to treat patients having MDS. In certain embodiments, patients suffering from MDS may be treated using one or more ActRII antagonist agents of the disclosure (e.g., a GDF-ActRII antagonist, an ActRIIA polypeptide, an ActRIIB polypeptide, a GDF Trap, etc.), optionally in combination with an EPO receptor activator. In other embodiments, patient suffering from MDS may be treated using a combination of one or more ActRII antagonist agents of the disclosure (e.g., a GDF-ActRII antagonist, an ActRIIA polypeptide, an ActRIIB polypeptide, a GDF Trap, etc.) and one or more additional therapeutic agents for treating MDS including, for example, thalidomide, lenalidomide, azacitadine, decitabine, erythropoietins, deferoxamine, antithymocyte globulin, and filgrastrim (G-CSF).

As used herein, "in combination with" or "conjoint administration" refers to any form of administration such that the second therapy is still effective in the body (e.g., the two agents or compounds are simultaneously effective in the patient, which may include synergistic effects of the two agents or compounds). Effectiveness may not correlate to measurable concentration of the agent in blood, serum, or plasma. For example, the different therapeutic agents or compounds can be administered either in the same formulation or in separate formulations, either concomitantly or sequentially, and on different schedules. Thus, an individual who receives such treatment can benefit from a combined effect of different therapies. One or more GDF11 and/or activin B antagonist agents (optionally further antagonists of one or more of GDF8, activin A, activin C, activin E, and BMP6) of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, one or more ActRII antagonist agents of the disclosure (e.g., a GDF-ActRII antagonist, an ActRIIA polypeptide, an ActRIIB polypeptide, a GDF Trap, etc.) may be used in combination with hepcidin or a hepcidin agonist for treating sickle-cell disease, particularly sickle-cell disease complications associated with iron overload. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of sickle-cell disease, particularly sickle-cell disease complications associated with iron overload.

One or more ActRII antagonist agents of the disclosure (e.g., a GDF-ActRII antagonist, an ActRIIA polypeptide, an ActRIIB polypeptide, a GDF Trap, etc.), optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

In certain embodiments, the present disclosure provides methods of treating or preventing anemia in an individual in need thereof by administering to the individual a therapeutically effective amount of one or more ActRII antagonist agents of the disclosure (e.g., a GDF-ActRII antagonist, an ActRIIA polypeptide, an ActRIIB polypeptide, a GDF Trap, etc.) and a EPO receptor activator. In certain embodiments, one or more ActRII antagonist agents of the disclosure (e.g., a GDF-ActRII antagonist, an ActRIIA polypeptide, an ActRIIB polypeptide, a GDF Trap, etc.) may be used in combination with EPO receptor activators to reduce the required dose of these activators in patients that are susceptible to adverse effects of EPO. These methods may be used for therapeutic and prophylactic treatments of a patient.

One or more ActRII antagonist agents of the disclosure (e.g., a GDF-ActRII antagonist, an ActRIIA polypeptide, an ActRIIB polypeptide, a GDF Trap, etc.) of the disclosure may be used in combination with EPO receptor activators to achieve an increase in red blood cells, particularly at lower dose ranges. This may be beneficial in reducing the known off-target effects and risks associated with high doses of EPO receptor activators. The primary adverse effects of EPO include, for example, an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that antagonists of the present disclosure act by a different mechanism that EPO, these antagonists may be useful for increasing red blood cell and hemoglobin levels in patients that do not respond well to EPO. For example, an ActRII antagonist of the present disclosure may be beneficial for a patient in which administration of a normal to increased (>300 IU/kg/week) dose of EPO does not result in the increase of hemoglobin level up to the target level. Patients with an inadequate EPO response are found for all types of anemia, but higher numbers of non-responders have been observed particularly frequently in patients with cancers and patients with end-stage renal disease. An inadequate response to EPO can be either constitutive (observed upon the first treatment with EPO) or acquired (observed upon repeated treatment with EPO).

In certain embodiments, the present disclosure provides methods for managing a patient that has been treated with, or is a candidate to be treated with, one or more one or more ActRII antagonist agents of the disclosure (e.g., a GDF-ActRII antagonist, an ActRIIA polypeptide, an ActRIIB polypeptide, a GDF Trap, etc.) by measuring one or more hematologic parameters in the patient. The hematologic parameters may be used to evaluate appropriate dosing for a patient who is a candidate to be treated with the antagonist of the present disclosure to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more ActRII antagonist agents of the disclosure (e.g., a GDF-ActRII antagonist, an ActRIIA polypeptide, an ActRIIB polypeptide, a GDF Trap, etc.) may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more ActRII antagonist agents of the disclosure (e.g., a GDF-ActRII antagonist, an ActRIIA polypeptide, an ActRIIB polypeptide, a GDF Trap, etc.), then onset of administration of the one or more antagonists of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more antagonists of the disclosure may be delayed until the levels have returned to a normal or acceptable level.

In certain embodiments, if one or more hematologic parameters are outside the normal range or on the high side of normal in a patient who is a candidate to be treated with one or more ActRII antagonist agents of the disclosure (e.g., a GDF-ActRII antagonist, an ActRIIA polypeptide, an ActRIIB polypeptide, a GDF Trap, etc.), then the onset of administration may not be delayed. However, the dosage amount or frequency of dosing of the one or more antagonists of the disclosure may be set at an amount that would reduce the risk of an unacceptable increase in the hematologic parameters arising upon administration of the one or more antagonists of the disclosure. Alternatively, a therapeutic regimen may be developed for the patient that combines one or more ActRII antagonist agents of the disclosure (e.g., a GDF-ActRII antagonist, an ActRIIA polypeptide, an ActRIIB polypeptide, a GDF Trap, etc.) with a therapeutic agent that addresses the undesirable level of the hematologic parameter. For example, if the patient has elevated blood pressure, then a therapeutic regimen may be designed involving administration of one or more ActRII antagonist agents of the disclosure (e.g., a GDF-ActRII antagonist, an ActRIIA polypeptide, an ActRIIB polypeptide, a GDF Trap, etc.) and a blood pressure lowering agent. For a patient having lower than desired iron stores, a therapeutic regimen may be developed involving one or more ActRII antagonist agents of the disclosure (e.g., a GDF-ActRII antagonist, an ActRIIA polypeptide, an ActRIIB polypeptide, a GDF Trap, etc.) and iron supplementation.

In one embodiment, baseline parameter(s) for one or more hematologic parameters may be established for a patient who is a candidate to be treated with one or more ActRII antagonist agents of the disclosure (e.g., a GDF-ActRII antagonist, an ActRIIA polypeptide, an ActRIIB polypeptide, a GDF Trap, etc.) and an appropriate dosing regimen established for that patient based on the baseline value(s). Alternatively, established baseline parameters based on a patient's medical history could be used to inform an appropriate antagonist dosing regimen for a patient. For example, if a healthy patient has an established baseline blood pressure reading that is above the defined normal range it may not be necessary to bring the patient's blood pressure into the range that is considered normal for the general population prior to treatment with the one or more antagonist of the disclosure. A patient's baseline values for one or more hematologic parameters prior to treatment with one or more ActRII antagonist agents of the disclosure (e.g., a GDF-ActRII antagonist, an ActRIIA polypeptide, an ActRIIB polypeptide, a GDF Trap, etc.) may also be used as the relevant comparative values for monitoring any changes to the hematologic parameters during treatment with the one or more antagonists of the disclosure.

In certain embodiments, one or more hematologic parameters are measured in patients who are being treated with one or more ActRII antagonist agents of the disclosure (e.g., a GDF-ActRII antagonist, an ActRIIA polypeptide, an ActRIIB polypeptide, a GDF Trap, etc.). The hematologic parameters may be used to monitor the patient during treatment and permit adjustment or termination of the dosing with the one or more antagonist of the disclosure or additional dosing with another therapeutic agent. For example, if administration of one or more ActRII antagonist agents of the disclosure (e.g., a GDF-ActRII antagonist, an ActRIIA polypeptide, an ActRIIB polypeptide, a GDF Trap, etc.) results in an increase in blood pressure, red blood cell level, or hemoglobin level, or a reduction in iron stores, then the dose of the one or more antagonist of the disclosure may be reduced in amount or frequency in order to decrease the effects of the one or more antagonist of the disclosure on the one or more hematologic parameters. If administration of one or more ActRII antagonist agents of the disclosure (e.g., a GDF-ActRII antagonist, an ActRIIA polypeptide, an ActRIIB polypeptide, a GDF Trap, etc.) results in a change in one or more hematologic parameters that is adverse to the patient, then the dosing of the one or more antagonist of the disclosure may be terminated either temporarily, until the hematologic parameter(s) return to an acceptable level, or permanently. Similarly, if one or more hematologic parameters are not brought within an acceptable range after reducing the dose or frequency of administration of the one or more antagonist of the disclosure, then the dosing may be terminated. As an alternative, or in addition to, reducing or terminating the dosing with the one or more antagonist of the disclosure, the patient may be dosed with an additional therapeutic agent that addresses the undesirable level in the hematologic parameter(s), such as, for example, a blood pressure lowering agent or an iron supplement. For example, if a patient being treated with one or more ActRII antagonist agents of the disclosure (e.g., a GDF-ActRII antagonist, an ActRIIA polypeptide, an ActRIIB polypeptide, a GDF Trap, etc.)e has elevated blood pressure, then dosing with the one or more antagonist of the disclosure may continue at the same level and a blood pressure lowering agent is added to the treatment regimen, dosing with the one or more antagonist of the disclosure may be reduce (e.g., in amount and/or frequency) and a blood pressure lowering agent is added to the treatment regimen, or dosing with the one or more antagonist of the disclosure may be terminated and the patient may be treated with a blood pressure lowering agent.

6. Pharmaceutical Compositions

In certain aspects, one or more ActRII antagonist agents of the disclosure (e.g., a GDF-ActRII antagonist, an ActRIIA polypeptide, an ActRIIB polypeptide, a GDF Trap, etc.) can be administered alone or as a component of a pharmaceutical formulation (also referred to as a therapeutic composition or pharmaceutical composition). A pharmaceutical formation refers to a preparation which is in such form as to permit the biological activity of an active ingredient (e.g., an agent of the present disclosure) contained therein to be effective and which contains no additional components which are unacceptably toxic to a subject to which the formulation would be administered. The subject ActRII antagonist agents may be formulated for administration in any convenient way for use in human or veterinary medicine. For example, one or more ActRII antagonist agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In general, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject ActRII antagonist agents in the methods of the present disclosure.

In certain aspects, the disclosure provides a method of using a pharmaceutical compostion comprising an ActRII antagonist and a pharmacetucally acceptable carrier to treat or prevent treat or prevent an anemia in a subject in need thereof and/or treat or prevent one or more complication of anemia including, for example, cutaneous ulcers. In some embodiments, the disclosure provides methods of using a pharmaceutical composition comprising an ActRII antagonist, or combination of ActRII antagonists, and a pharmaceutically acceptable carrier to treat an anemia in a subject in need thereof and/or treat one or more complications of anemia including, for example, cutaneous ulcers in a subject having anemia. In some embodiments, the disclosure provides methods of using a pharmaceutical composition comprising an ActRII antagonist, or combination of ActRII antagonists, and a pharmaceutically acceptable carrier to prevent an anemia in a subject in need thereof and/or prevent one or more complications of anemia including, for example, cutaneous ulcers in a subject having anemia. In some of the foregoing embodiments, the pharmaceutical compositions comprising an ActRII antagonist, or combination of ActRII antagonists, and a pharmaceutically acceptable carrier of the present disclosure are used to treat an ulcer (e.g., a cutaneous ulcer) in a subject (e.g., patient) having anemia (e.g., hemolytic anemia, hemoglobinopathy anemia, a thalassemia syndrome (e.g., β-thalassemia syndrome, β-thalassemia intermedia, etc.), sickle-cell disease, etc.). In some of the foregoing embodiments, the pharmaceutical compositions comprising an ActRII antagonist, or combination of ActRII antagonists, and a pharmaceutically acceptable carrier of the present disclosure are used to prevent an ulcer (e.g., a cutaneous ulcer) in a subject (e.g., patient) having anemia (e.g., hemolytic anemia, hemoglobinopathy anemia, a thalassemia syndrome (e.g., β-thalassemia syndrome, β-thalassemia intermedia, etc.), sickle-cell disease, etc.). In some embodiments, the subject having anemia has sickle cell disease. In some embodiments, the subject having anemia has a thalassemia syndrome (e.g., β-thalassemia syndrome, β-thalassemia intermedia, etc.). In some embodiments, the subject having anemia has a cutaneous ulcer. In some embodiments, the cutaneous ulcer is a skin ulcer. In some embodiments, the ulcer occurs on legs or ankes.

In certain embodiments, the ActRII antagonist agents or the pharmaceutical compositions of the disclosure will be administered parenterally [e.g., by intravenous (I.V.) injection, intraarterial injection, intraosseous injection, intramuscular injection, intrathecal injection, subcutaneous injection, or intradermal injection]. Pharmaceutical compositions suitable for parenteral administration may comprise one or more ActRII antagonist agents of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants. In certain embodiments, the ActRII antagonist agents or the pharmaceutical compositions of the disclosure will be administered subcutaneously (e.g., subcutaneous injection). In certain embodiments, the ActRII antagonist agents or the pharmaceutical compositions of the disclosure will be administered topically.

In some embodiments, a therapeutic method of the present disclosure includes administering the pharmaceutical composition of the present disclosure systemically, or locally, from an implant or device. Further, the pharmaceutical composition of the present disclosure may be encapsulated or injected in a form for delivery to a target tissue site (e.g., bone marrow or muscle). In certain embodiments, the pharmaceutical compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined including, for example, bone or dermal collagen. Further matrices are comprised of pure proteins or extracellular matrix components. Other potential matrices are non-biodegradable and chemically defined including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, the pharmaceutical compositions of the present disclosure can be administered topically. "Topical application" or "topically" means contact of the pharmaceutical composition with body surfaces including, for example, the skin, wound sites, ulcer sites, and mucous membranes. The topical pharmaceutical compositions can have various application forms and typically comprise a drug-containing layer, which is adapted to be placed near to or in direct contact with the tissue upon topically administering the composition. Pharmaceutical compositions suitable for topical administration may comprise one or more ActRII antagonist agents of the disclosure (e.g., a GDF-ActRII antagonist, an ActRIIA polypeptide, an ActRIIB polypeptide, a GDF Trap, etc.) formulated as a liquid, a gel, a cream, a lotion, an ointment, a foam, a paste, a putty, a semi-solid, or a solid. Pharmaceutical compositions in the liquid, gel, cream, lotion, ointment, foam, paste, or putty form can be applied by spreading, spraying, smearing, dabbing or rolling the composition on the target tissue. The pharmaceutical compositions also may be impregnated into sterile dressings, transdermal patches, plasters, and bandages. Pharmaceutical compositions of the putty, semi-solid or solid forms may be deformable. They may be elastic or non-elastic (e.g., flexible or rigid). In certain aspects, the pharmaceutical composition forms part of a composite and can include fibers, particulates, or multiple layers with the same or different compositions.

Topical compositions in the liquid form may include pharmaceutically acceptable solutions, emulsions, microemulsions, and suspensions. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof].

Topical gel, cream, lotion, ointment, semi-solid or solid compositions may include one or more thickening agents, such as a polysaccharide, synthetic polymer or protein-based polymer. In one embodiment of the invention, the gelling agent herein is one that is suitably nontoxic and gives the desired viscosity. The thickening agents may include polymers, copolymers, and monomers of: vinylpyrrolidones, methacrylamides, acrylamides N-vinylimidazoles, carboxy vinyls, vinyl esters, vinyl ethers, silicones, polyethyleneoxides, polyethyleneglycols, vinylalcohols, sodium acrylates, acrylates, maleic acids, NN-dimethylacrylamides, diacetone acrylamides, acrylamides, acryloyl morpholine, pluronic, collagens, polyacrylamides, polyacrylates, polyvinyl alcohols, polyvinylenes, polyvinyl silicates, polyacrylates substituted with a sugar (e.g., sucrose, glucose, glucosamines, galactose, trehalose, mannose, or lactose), acylamidopropane sulfonic acids, tetramethoxyorthosilicates, methyltrimethoxyorthosilicates, tetraalkoxyorthosilicates, trialkoxyorthosilicates, glycols, propylene glycol, glycerine, polysaccharides, alginates, dextrans, cyclodextrin, celluloses, modified celluloses, oxidized celluloses, chitosans, chitins, guars, carrageenans, hyaluronic acids, inulin, starches, modified starches, agarose, methylcelluloses, plant gums, hylaronans, hydrogels, gelatins, glycosaminoglycans, carboxymethyl celluloses, hydroxyethyl celluloses, hydroxy propyl methyl celluloses, pectins, low-methoxy pectins, cross-linked dextrans, starch-acrylonitrile graft copolymers, starch sodium polyacrylate, hydroxyethyl methacrylates, hydroxyl ethyl acrylates, polyvinylene, polyethylvinylethers, polymethyl methacrylates, polystyrenes, polyurethanes, polyalkanoates, polylactic acids, polylactates, poly (3-hydroxybutyrate), sulfonated hydrogels, AMPS (2-acrylamido-2-methyl-1-propanesulfonic acid), SEM (sulfoethylmethacrylate), SPM (sulfopropyl methacrylate), SPA (sulfopropyl acrylate), N,N-dimethyl-N-methacryloxyethyl-N-(3-sulfopropyl)ammonium betaine, methacryllic acid amidopropyl-dimethyl ammonium sulfobetaine, SPI (itaconic acid-bis(1-propyl sulfonizacid-3) ester di-potassium salt), itaconic acids, AMBC (3-acrylamido-3-methylbutanoic acid), beta-carboxyethyl acrylate (acrylic acid dimers), and maleic anhydride-methylvinyl ether polymers, derivatives thereof, salts thereof, acids thereof, and combinations thereof. In certain embodiments, pharmaceutical compositions of present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of an ActRII antagonist agent of the present disclosure and optionally one or more other active ingredients. An ActRII antagonist agent of the present disclosure and optionally one or more other active ingredients may also be administered as a bolus, electuary, or paste.

In solid dosage forms for oral administration (e.g., capsules, tablets, pills, dragees, powders, and granules), one or more ActRII antagonist agents of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition of the disclosure may include pharmaceutically acceptable emulsions, microemulsions, solutions, suspensions, syrups, and elixirs. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active ActRII antagonist agents, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the pharmaceutical compositions. In addition, prolonged absorption of an injectable pharmaceutical form may be brought about by the inclusion of an agent that delay absorption including, for example, aluminum monostearate and gelatin.

It is understood that the dosage regimen will be determined by the attending physician considering various factors which modify the action of the one or more of the agents of the present disclosure. The various factors include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the ActRII antagonist agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. In some embodiments, therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. In some embodiments, targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form. See, e.g., Fraley, et al. (1981) Trends Biochem. Sci., 6:77. Methods for efficient gene transfer using a liposome vehicle are known in the art. See, e.g., Mannino, et al. (1988) Biotechniques, 6:682, 1988.

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used including, for example a phosphatidyl compound (e.g., phosphatidylglycerol, phosphatidylcholine, phosphatidylserine, phosphatidylethanolamine, a sphingolipid, a cerebroside, and a ganglioside), egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1: ActRIIa-Fc Fusion Proteins

Applicant constructed a soluble ActRIIA fusion protein that has the extracellular domain of human ActRIIa fused to a human or mouse Fc domain with a minimal linker in between. The constructs are referred to as ActRIIA-hFc and ActRIIA-mFc, respectively.

ActRIIA-hFc is shown below as purified from CHO cell lines (Fc portion underlined) (SEQ ID NO:22):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP<u>TGGGTHTCPPCPAPELLGGPSVFLFPPKPKDTLMI</u>

<u>SRTPEVTCVVVDVSHEDPEVKFNWYVDGVEVHNAKTKPREEQYNSTYRVV</u>

<u>SVLTVLHQDWLNGKEYKCKVSNKALPVPIEKTISKAKGQPREPQVYTLPP</u>

<u>SREEMTKNQVSLTCLVKGFYPSDIAVEWESNGQPENNYKTTPPVLDSDGS</u>

<u>FFLYSKLTVDKSRWQQGNVFSCSVMHEALHNHYTQKSLSLSPGK</u>

The ActRIIA-hFc and ActRIIA-mFc proteins were expressed in CHO cell lines. Three different leader sequences were considered:

(i) Honey bee mellitin (HBML):
(SEQ ID NO: 23)
MKFLVNVALVFMVVYISYIYA (ii) Tissue plasminogen activator (TPA):
(SEQ ID NO: 24)
MDAMKRGLCCVLLLCGAVFVSP (iii) Native:
(SEQ ID NO: 25)
MGAAAKLAFAVFLISCSSGA.

The selected form employs the TPA leader and has the following unprocessed amino acid sequence:

(SEQ ID NO: 26)
MDAMKRGLCCVLLLCGAVFVSPGAAILGRSETQECLFFNANWEKDRTNQT

GVEPCYGDKDKRRHCFATWKNISGSIEIVKQGCWLDDINCYDRTDCVEKK

DSPEVYFCCCEGNMCNEKFSYFPEMEVTQPTSNPVTPKPPTGGGTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PVPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVM

HEALHNHYTQKSLSLSPGK

This polypeptide is encoded by the following nucleic acid sequence:

(SEQ ID NO: 27)
ATGGATGCAATGAAGAGAGGGCTCTGCTGTGTGCTGCTGCTGTGTGGAGC

AGTCTTCGTTTCGCCCGGCGCCGCTATACTTGGTAGATCAGAAACTCAGG

AGTGTCTTTTTTTAATGCTAATTGGGAAAAAGACAGAACCAATCAAACTG

GTGTTGAACCGTGTTATGGTGACAAAGATAAACGGCGGCATTGTTTTGCT

ACCTGGAAGAATATTTCTGGTTCCATTGAATAGTGAAACAAGGTTGTTGG

CTGGATGATATCAACTGCTATGACAGGACTGATTGTGTAGAAAAAAAAGA

CAGCCCTGAAGTATATTTCTGTTGCTGTGAGGGCAATATGTGTAATGAAA

AGTTTTCTTATTTTCCGGAGATGGAAGTCACACAGCCCACTTCAAATCCA

GTTACACCTAAGCCACCCACCGGTGGTGGAACTCACACATGCCCACCGTG

CCCAGCACCTGAACTCCTGGGGGGACCGTCAGTCTTCCTCTTCCCCCCAA

AACCCAAGGACACCCTCATGATCTCCCGGACCCCTGAGGTCACATGCGTG

-continued
```
GTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGT

ACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCC

AGTCCCCATCGAGAAAACCATCTCCAAAGCCAAAGGGCAGCCCCGAGAAC

CACAGGTGTACACCCTGCCCCCATCCCGGGAGGAGATGACCAAGAACCAG

GTCAGCCTGACCTGCCTGGTCAAAGGCTTCTATCCCAGCGACATCGCCGT

GGAGTGGGAGAGCAATGGGCAGCCGGAGAACAACTACAAGACCACGCCTC

CCGTGCTGGACTCCGACGGCTCCTTCTTCCTCTATAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGAATTC
```

Both ActRIIA-hFc and ActRIIA-mFc were remarkably amenable to recombinant expression. As shown in FIGS. 3A and 3B, the protein was purified as a single, well-defined peak of protein. N-terminal sequencing revealed a single sequence of ILGRSETQE (SEQ ID NO:34). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIA-hFc protein was purified to a purity of >98% as determined by size exclusion chromatography and >95% as determined by SDS PAGE.

Figure 4A:
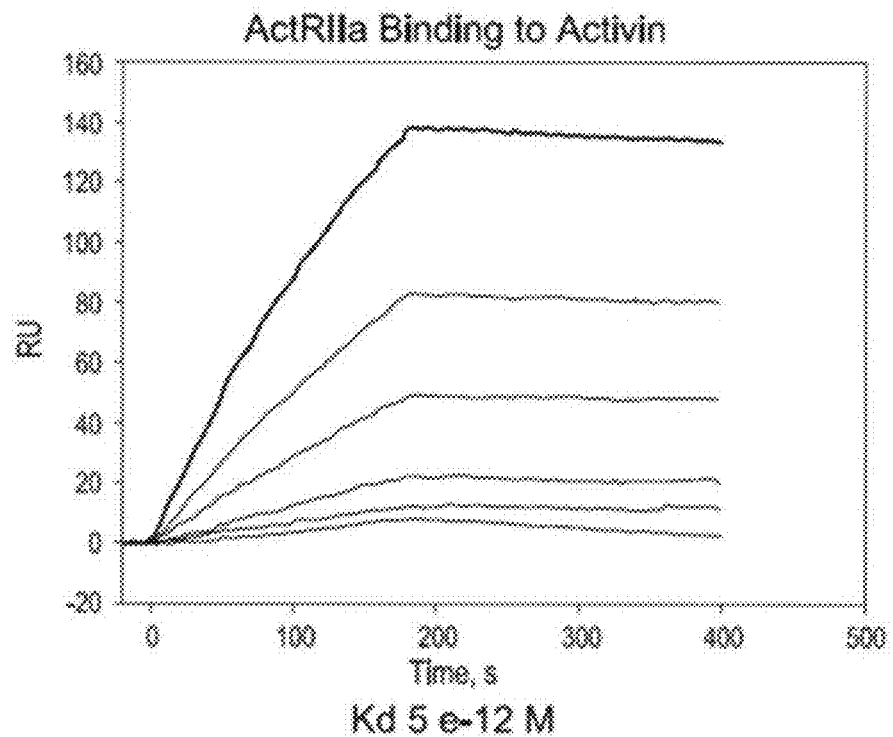
FIGS. 4A and 4B shows the binding of ActRIIA-hFc to activin and GDF-11, as measured by Biacore™ assay.
Figure 4B:
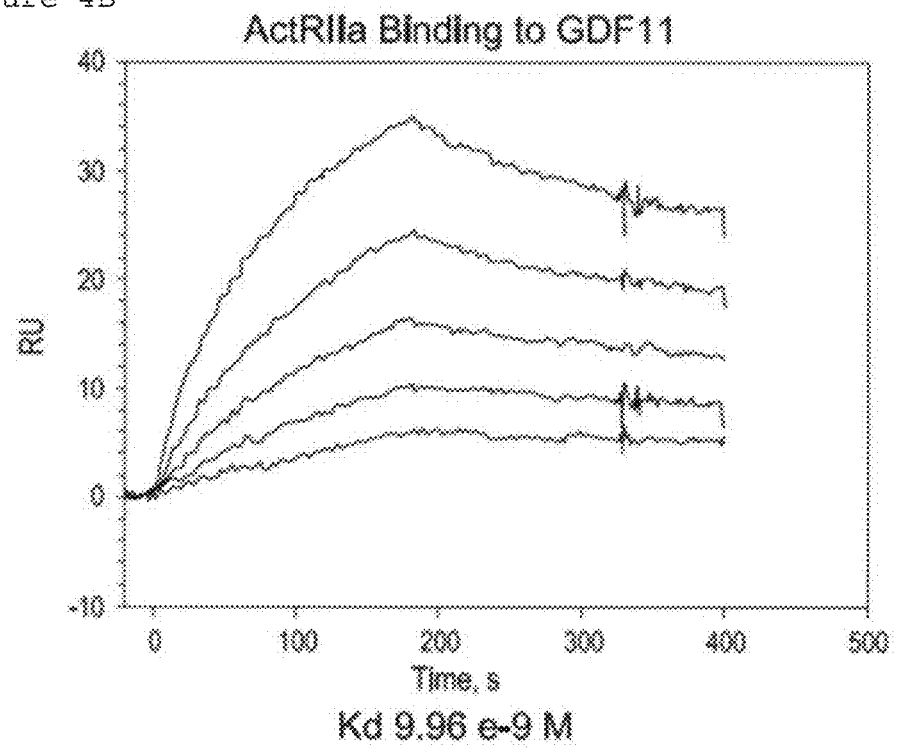
Figure 5A:
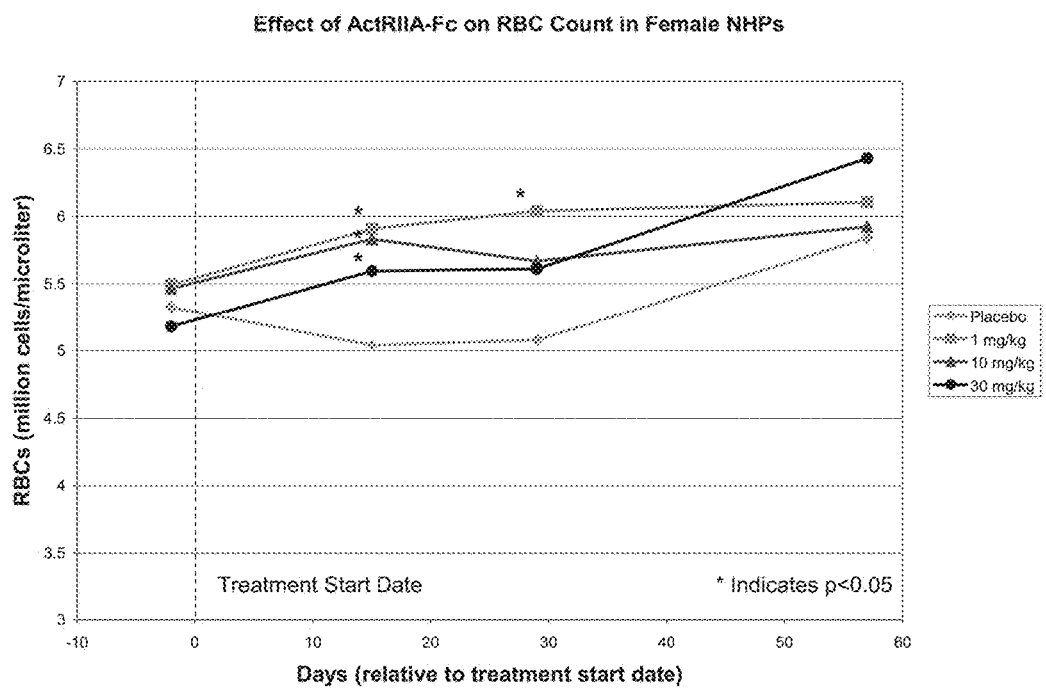
FIGS. 5A and 5B show the effects of ActRIIA-hFc on red blood cell counts in female non-human primates (NHPs). Female cynomolgus monkeys (four groups of five monkeys each) were treated with placebo or 1 mg/kg, 10 mg/kg or 30 mg/kg of ActRIIA-hFc on day 0, day 7, day 14 and day 21.
Figure 5B:
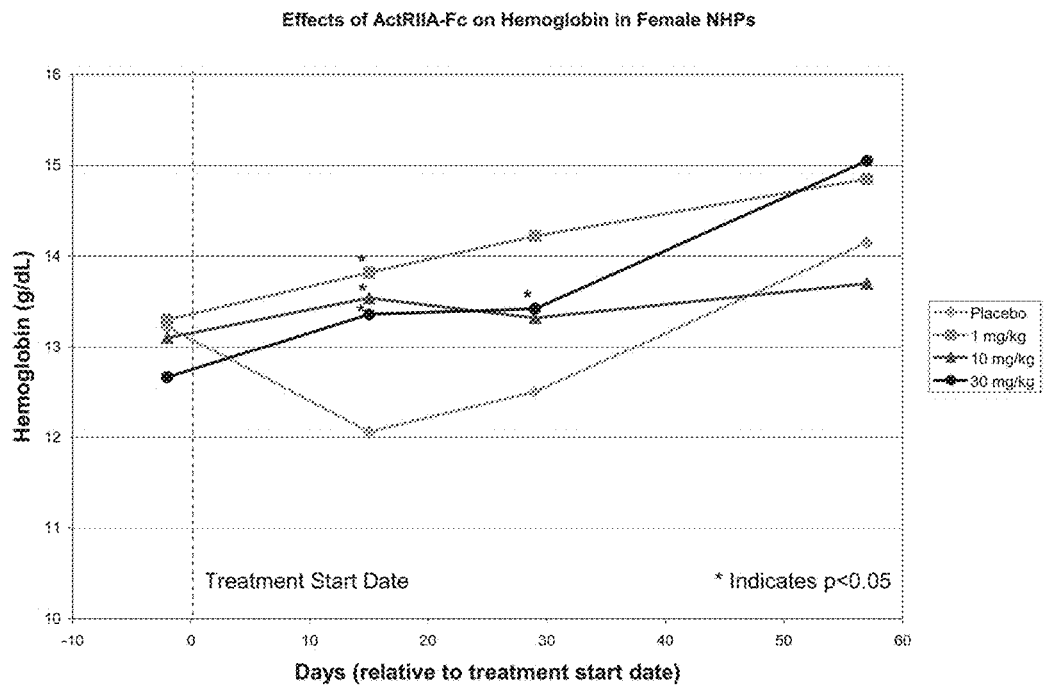
Figure 6A:
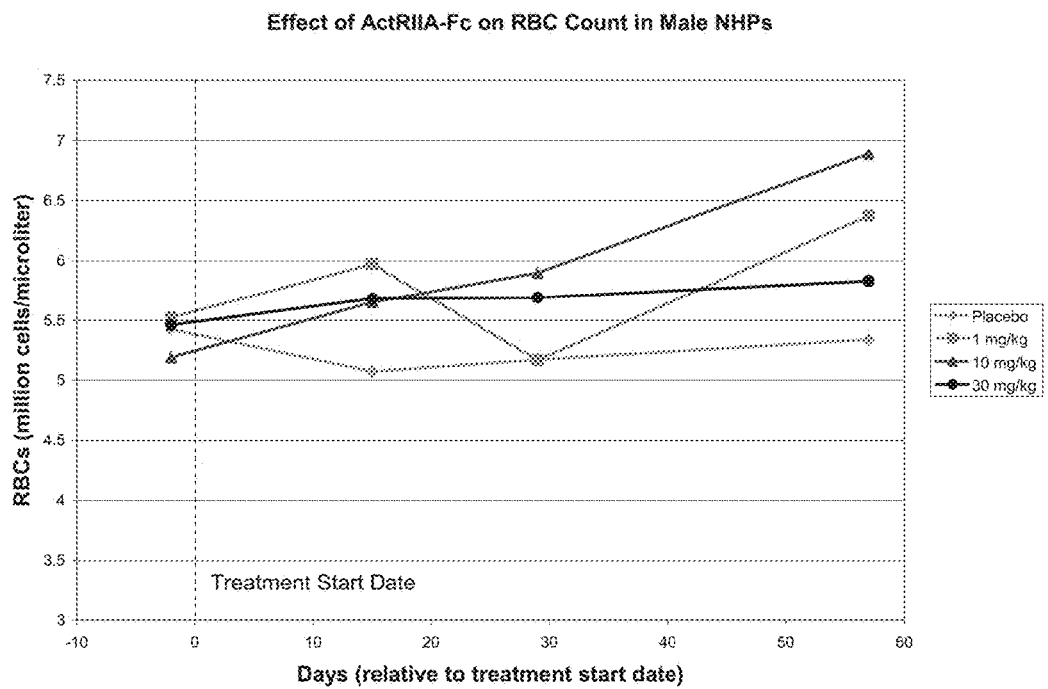
FIGS. 6A and 6B shows the effects of ActRIIA-hFc on red blood cell counts in male non-human primates. Male cynomolgus monkeys (four groups of five monkeys each) were treated with placebo or 1 mg/kg, 10 mg/kg, or 30 mg/kg of ActRIIA-hFc on day 0, day 7, day 14, and day 21.
Figure 6B:
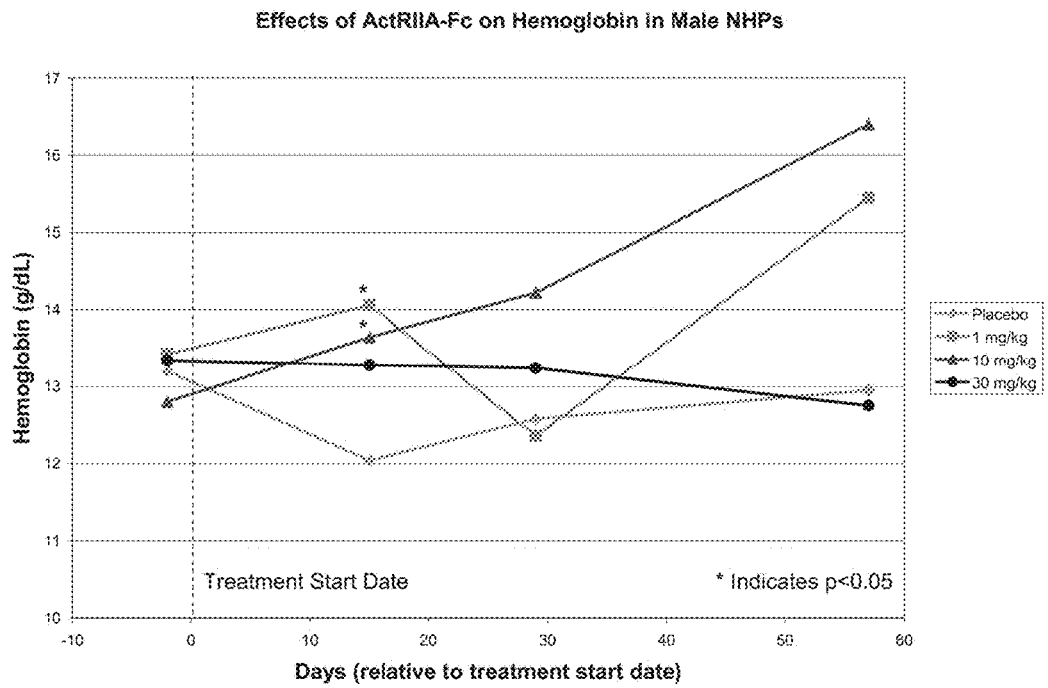
Figure 7A:
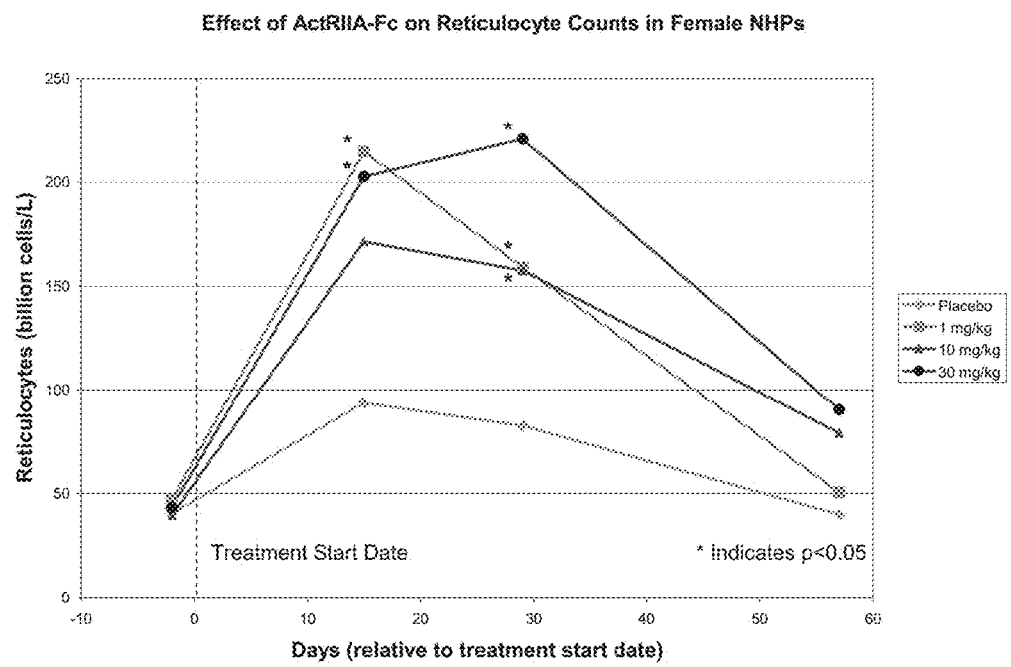
FIGS. 7A and 7B shows the effects of ActRIIA-hFc on reticulocyte counts in female non-human primates. Cynomolgus monkeys (four groups of five monkeys each) were treated with placebo or 1 mg/kg, 10 mg/kg, or 30 mg/kg of ActRIIA-hFc on day 0, day 7, day 14 and day 21.
Figure 7B:
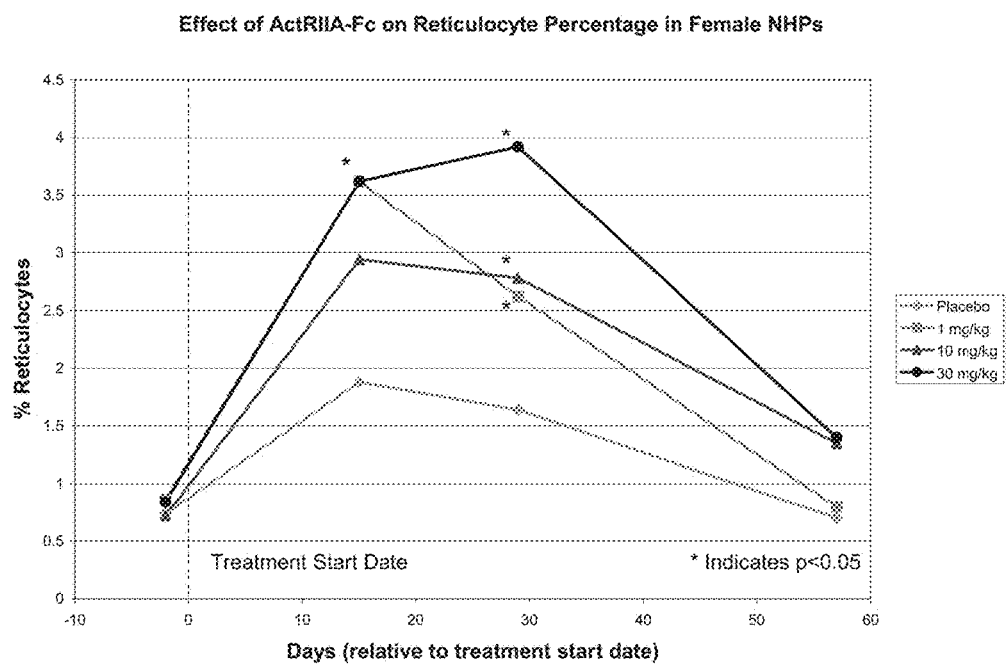
Figure 8A:
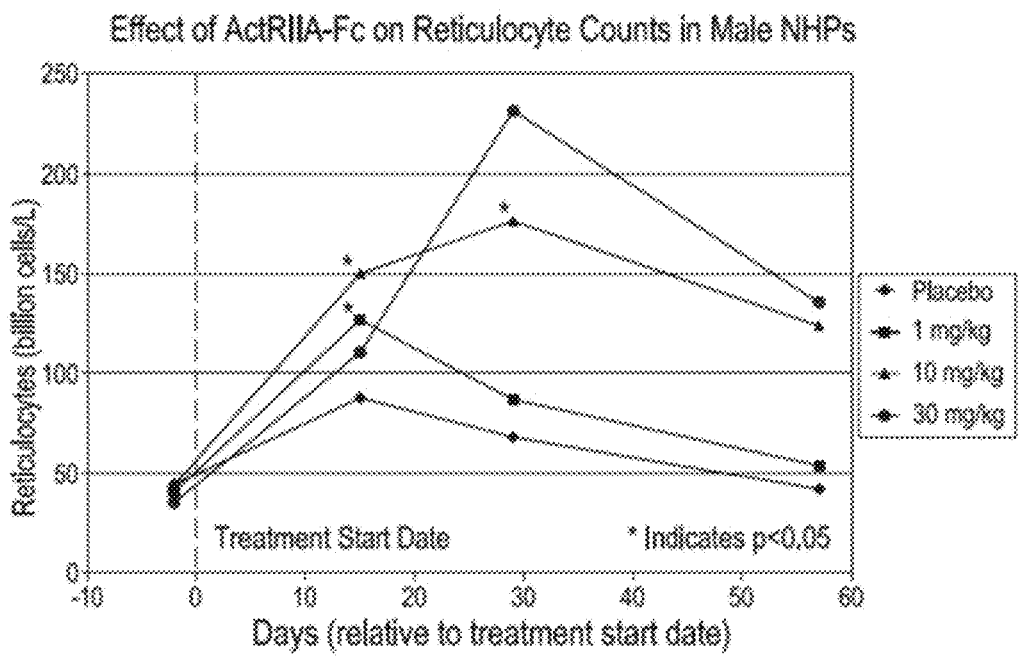
FIGS. 8A and 8B shows the effects of ActRIIA-hFc on reticulocyte counts in male non-human primates. Cynomolgus monkeys (four groups of five monkeys each) were treated with placebo or 1 mg/kg, 10 mg/kg or 30 mg/kg of ActRIIA-hFc on day 0, day 7, day 14 and day 21.
Figure 8B:
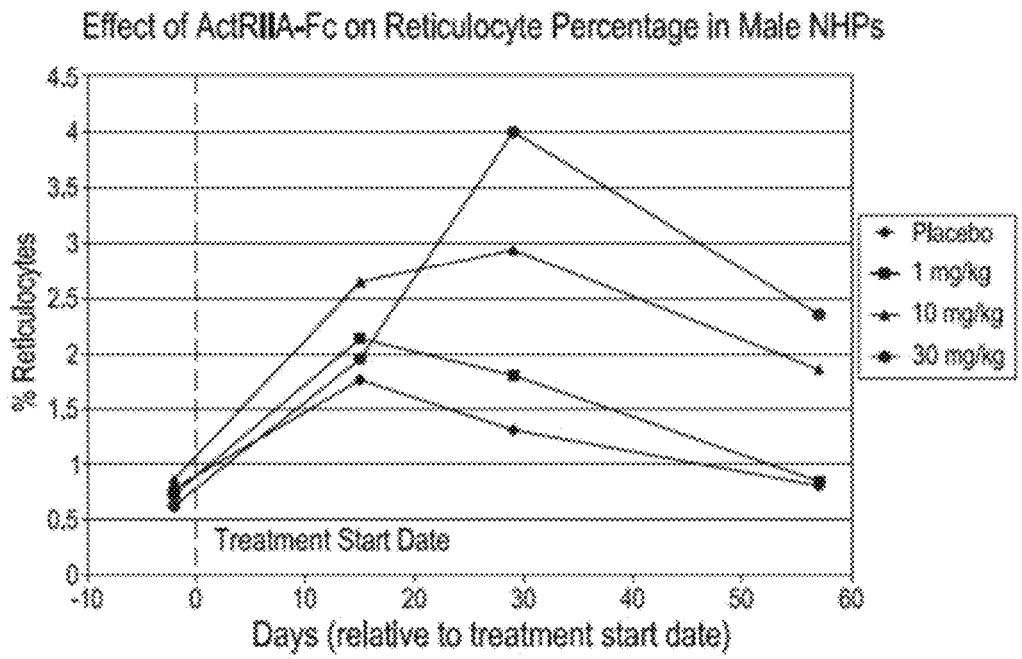

ActRIIA-hFc and ActRIIA-mFc showed a high affinity for ligands, particularly activin A. GDF-11 or activin A were immobilized on a Biacore™ CM5 chip using standard amine coupling procedure. ActRIIA-hFc and ActRIIA-mFc proteins were loaded onto the system, and binding was measured. ActRIIA-hFc bound to activin with a dissociation constant ($K_D$) of $5 \times 10^{-12}$, and bound to GDF11 with a $K_D$ of $9.96 \times 10^{-9}$. See FIGS. 4A and 4B. ActRIIA-mFc behaved similarly.

The ActRIIA-hFc was very stable in pharmacokinetic studies. Rats were dosed with 1 mg/kg, 3 mg/kg or 10 mg/kg of ActRIIA-hFc protein and plasma levels of the protein were measured at 24, 48, 72, 144 and 168 hours. In a separate study, rats were dosed at 1 mg/kg, 10 mg/kg or 30 mg/kg. In rats, ActRIIA-hFc had an 11-14 day serum half-life and circulating levels of the drug were quite high after two weeks (11 μg/ml, 110 μg/ml or 304 μg/ml for initial administrations of 1 mg/kg, 10 mg/kg or 30 mg/kg, respectively.) In cynomolgus monkeys, the plasma half-life was substantially greater than 14 days and circulating levels of the drug were 25 μg/ml, 304 μg/ml or 1440 μg/ml for initial administrations of 1 mg/kg, 10 mg/kg or 30 mg/kg, respectively.

Example 2: Characterization of an ActRIIA-hFc Protein

ActRIIA-hFc fusion protein was expressed in stably transfected CHO-DUKX B11 cells from a pAID4 vector (SV40 ori/enhancer, CMV promoter), using a tissue plasminogen leader sequence of SEQ ID NO:24. The protein, purified as described above in Example 1, had a sequence of SEQ ID NO:22. The Fc portion is a human IgG1 Fc sequence, as shown in SEQ ID NO:22. Protein analysis reveals that the ActRIIA-hFc fusion protein is formed as a homodimer with disulfide bonding.

Example 3. ActRIIA-hFc Increases Red Blood Cell Levels in Non-Human Primates

The study employed four groups of five male and five female cynomolgus monkeys each, with three per sex per group scheduled for termination on Day 29, and two per sex per group scheduled for termination on Day 57. Each animal was administered the vehicle (Group I) or ActRIIA-Fc at doses of 1, 10, or 30 mg/kg (Groups 2, 3 and 4, respectively) via intravenous (IV) injection on Days 1, 8, 15 and 22. The dose volume was maintained at 3 mL/kg. Various measures of red blood cell levels were assessed two days prior to the first administration and at days 15, 29 and 57 (for the remaining two animals) after the first administration.

The ActRIIA-hFc caused statistically significant increases in mean red blood cell parameters [red blood cell count (RBC, hemoglobin (HGB), and hematocrit (HCT)] for males and females, at all dose levels and time points throughout the study, with accompanying elevations in absolute and relative reticulocyte counts (ARTC; RTC). See FIGS. 5-8.

Statistical significance was calculated for each treatment group relative to the mean for the treatment group at baseline.

Notably, the increases in red blood cell counts and hemoglobin levels are roughly equivalent in magnitude to effects reported with erythropoietin. The onset of these effects is more rapid with ActRIIA-Fc than with erythropoietin.

Similar results were observed with rats and mice.

Example 4: ActRIIA-hFc Increases Red Blood Cell Levels and Markers of Bone Formation in Human Patients The ActRIIA-hFc fusion protein described in Example 1 was administered to human patients in a randomized, double-blind, placebo-controlled study that was conducted to evaluate, primarily, the safety of the protein in healthy, postmenopausal women. Forty-eight subjects were randomized in cohorts of 6 to receive either a single dose of ActRIIA-hFc or placebo (5 active: 1 placebo). Dose levels ranged from 0.01 to 3.0 mg/kg intravenously (IV) and 0.03 to 0.1 mg/kg subcutaneously (SC). All subjects were followed for 120 days. In addition to pharmacokinetic (PK) analyses, the biologic activity of ActRIIA-hFc was also assessed by measurement of biochemical markers of bone formation and resorption as well as FSH levels.

To look for potential changes, hemoglobin and RBC numbers were examined in detail for all subjects over the course of the study and compared to the baseline levels. Platelet counts were compared over the same time as the control. There were no clinically significant changes from the baseline values over time for the platelet counts.

Figure 9:
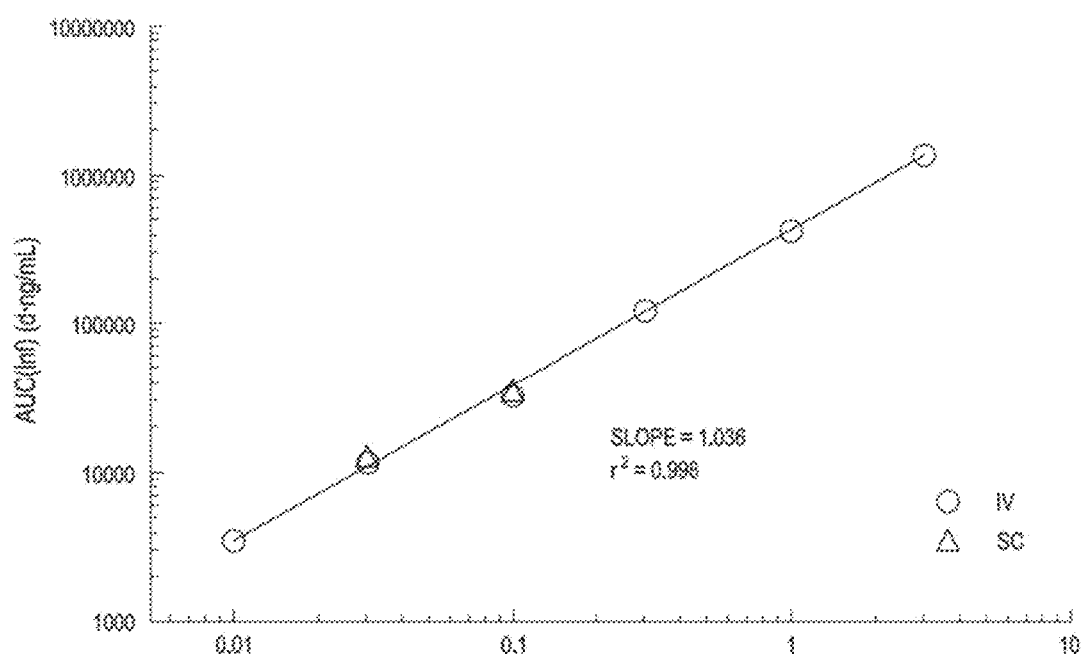
FIG. 9 shows results from the human clinical trial described in Example 5, where the area-under-curve (AUC) and administered dose of ActRIIA-hFc have a linear correlation, regardless of whether ActRIIA-hFc was administered intravenously (IV) or subcutaneously (SC).
Figure 10:
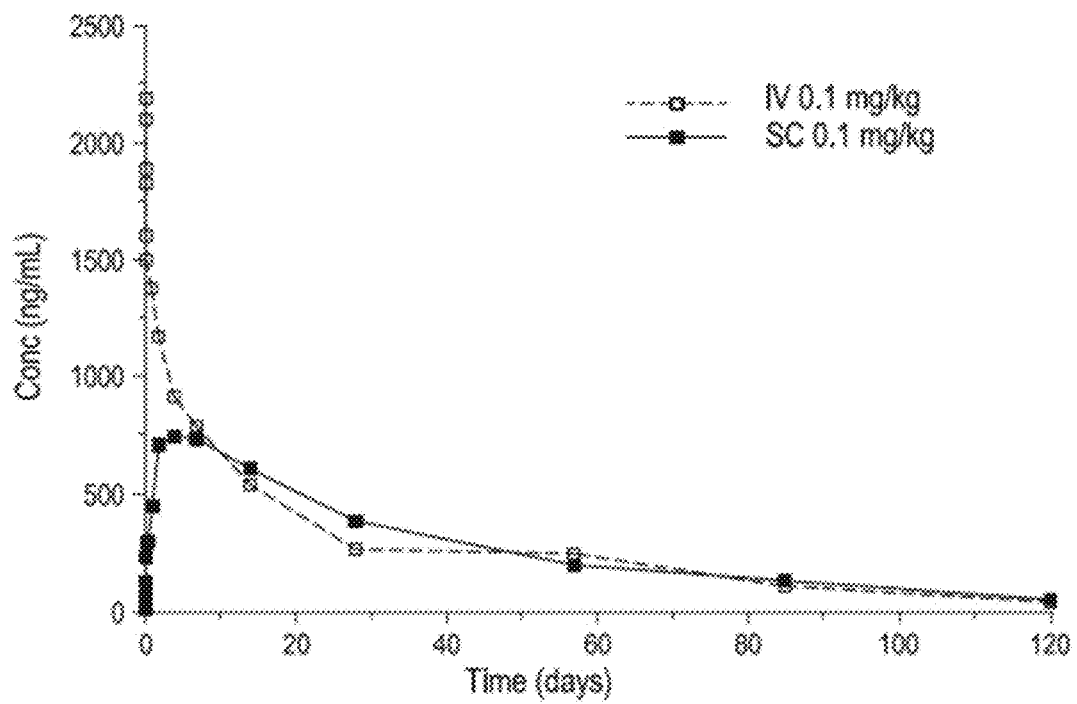
FIG. 10 shows a comparison of serum levels of ActRIIA-hFc in patients administered IV or SC.
Figure 11:
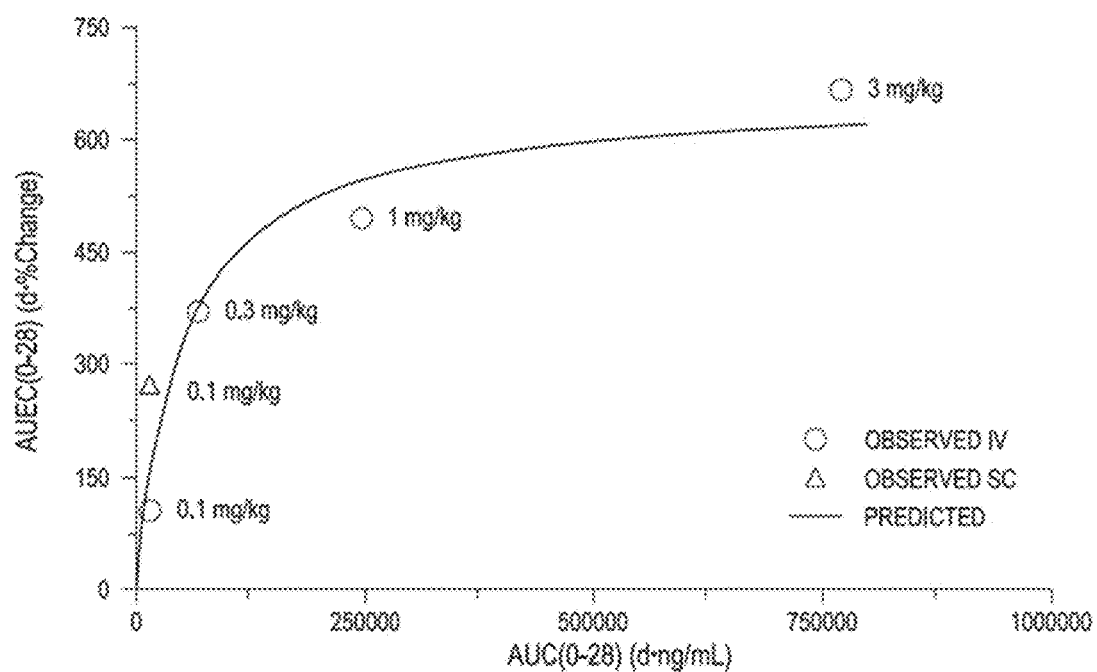
FIG. 11 shows bone alkaline phosphatase (BAP) levels in response to different dose levels of ActRIIA-hFc. BAP is a marker for anabolic bone growth.
Figure 12:
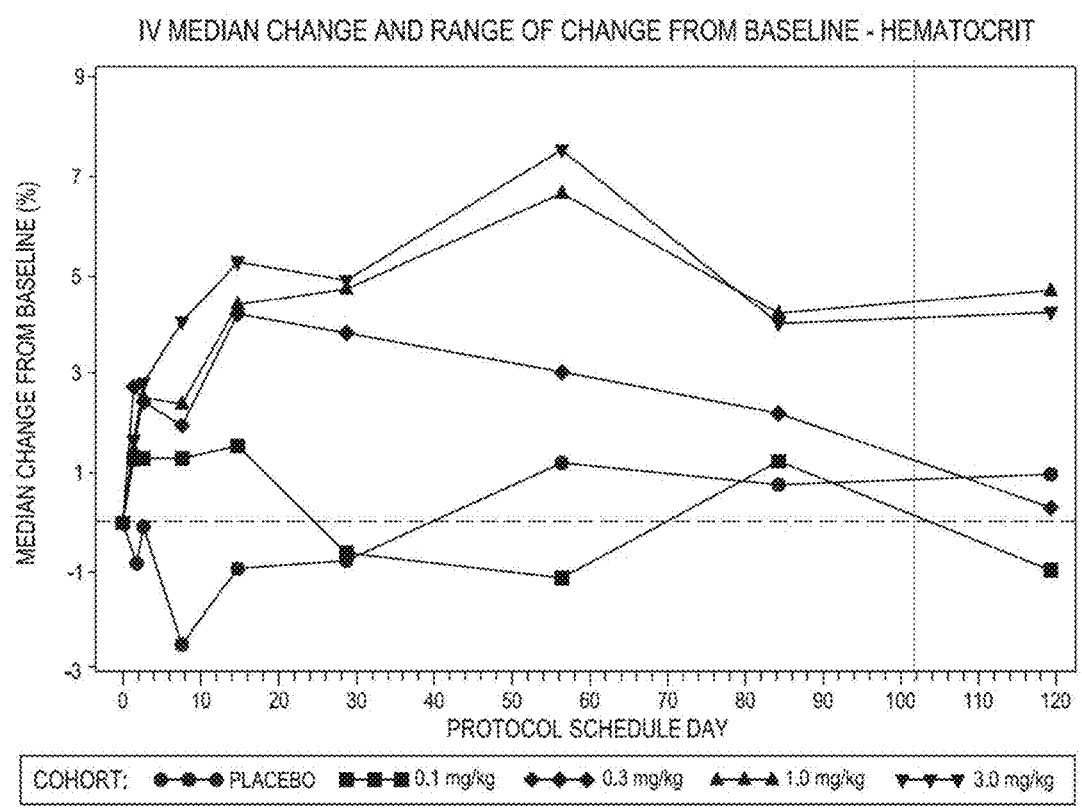
FIG. 12 depicts the median change from baseline of hematocrit levels from the human clinical trial described in Example 5. ActRIIA-hFc was administered intravenously (IV) at the indicated dosage.
Figure 13:
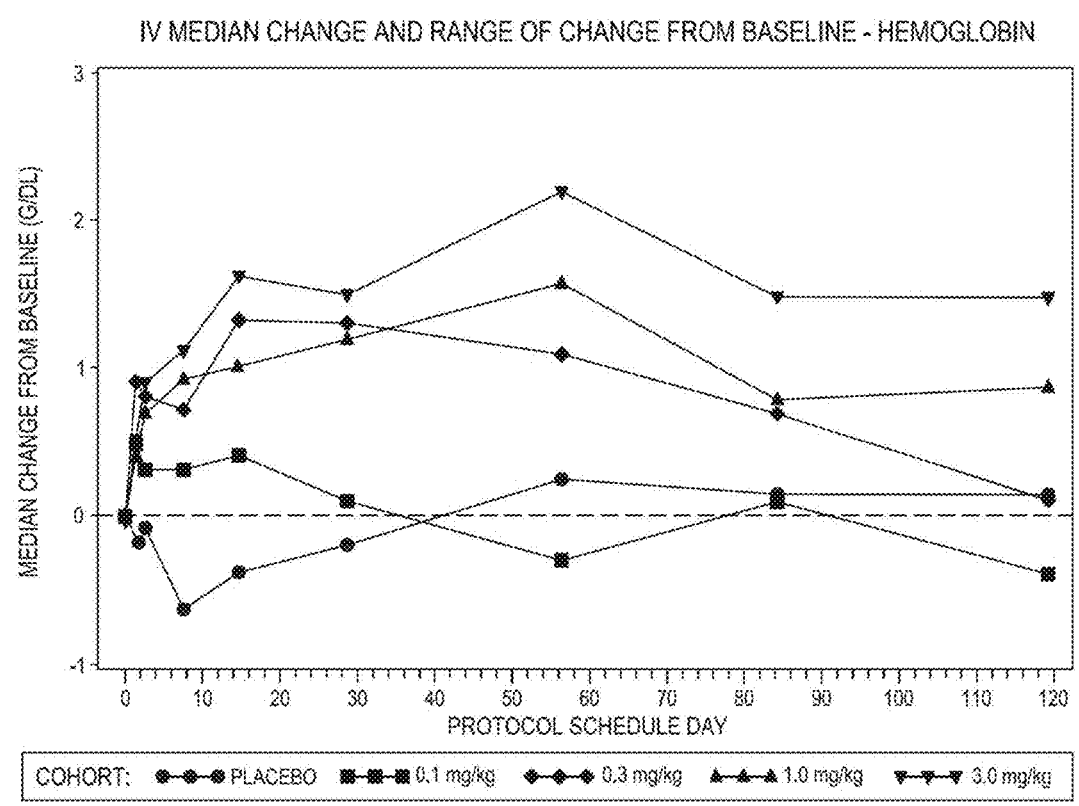
FIG. 13 depicts the median change from baseline of hemoglobin levels from the human clinical trial described in Example 5. ActRIIA-hFc was administered intravenously (IV) at the indicated dosage.
Figure 14:
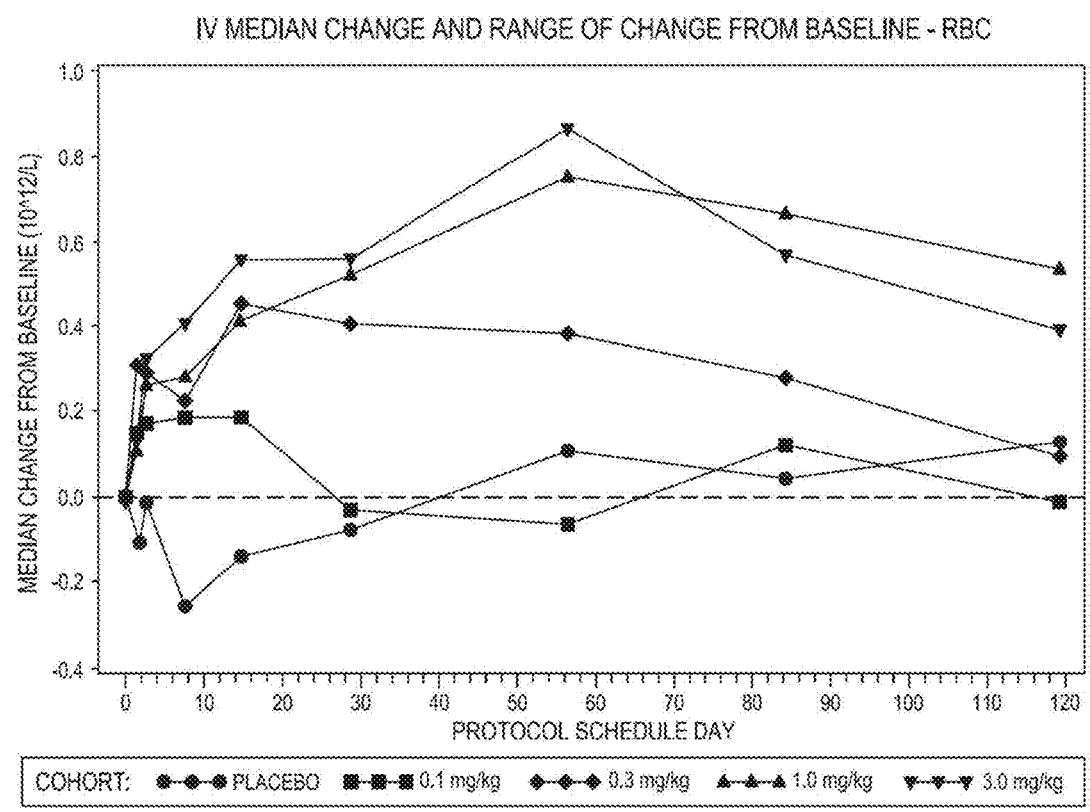
FIG. 14 depicts the median change from baseline of RBC (red blood cell) count from the human clinical trial described in Example 5. ActRIIA-hFc was administered intravenously (IV) at the indicated dosage.
Figure 15:
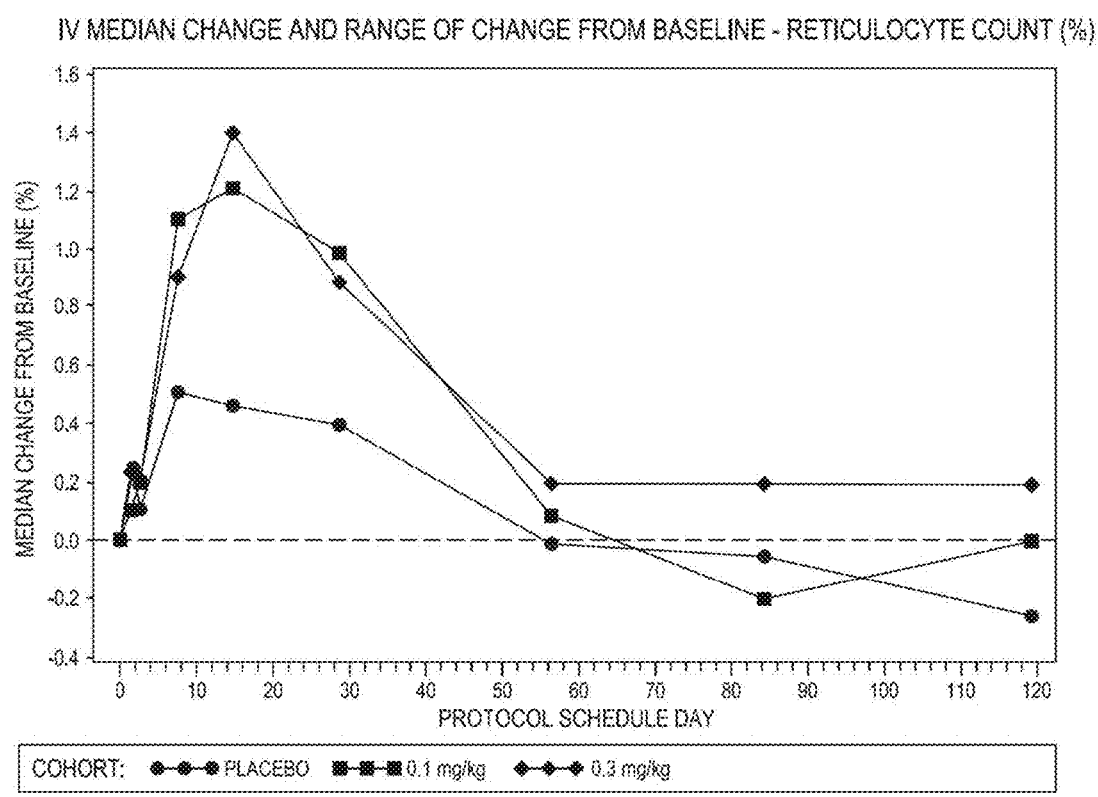
FIG. 15 depicts the median change from baseline of reticulocyte count from the human clinical trial described in Example 5. ActRIIA-hFc was administered intravenously (IV) at the indicated dosage.

PK analysis of ActRIIA-hFc revealed a linear profile with dose, and a mean half-life of approximately 25-32 days. The area-under-curve (AUC) for ActRIIA-hFc was linearly related to dose, and the absorption after SC dosing was essentially complete. See FIGS. 9 and 10. These data indicate that SC is a desirable approach to dosing because it provides equivalent bioavailability and serum-half life for drug while avoiding the spike in serum concentrations of drug associated with the first few days of IV dosing. See FIG. 10. ActRIIA-hFc caused a rapid, sustained dose-dependent increase in serum levels of bone-specific alkaline phosphatase (BAP), which is a marker for anabolic bone growth, and a dose-dependent decrease in C-terminal type 1 collagen telopeptide and tartrate-resistant acid phosphatase 5b levels, which are markers for bone resorption. Other markers, such as P1NP showed inconclusive results. BAP levels showed near saturating effects at the highest dosage of drug, indicating that half-maximal effects on this anabolic bone biomarker could be achieved at a dosage of 0.3 mg/kg, with increases ranging up to 3 mg/kg. Calculated as a relationship of pharmacodynamic effect to AUC for drug, the EC50 was 51,465 (day*ng/ml). See FIG. 11. These bone biomarker changes were sustained for approximately 120 days at the highest dose levels tested. There was also a dose-dependent decrease in serum FSH levels consistent with inhibition of activin.

Overall, there was a very small non-drug related reduction in hemoglobin over the first week of the study probably related to study phlebotomy in the 0.01 and 0.03 mg/kg groups whether given IV or SC. The 0.1 mg/kg SC and IV hemoglobin results were stable or showed modest increases by Day 8-15. At the 0.3 mg/kg IV dose level there was a clear increase in HGB levels seen as early as Day 2 and often peaking at Day 15-29 that was not seen in the placebo-treated subjects. At the 1.0 mg/kg IV dose and the 3.0 mg/kg IV dose, mean increases in hemoglobin of greater than 1 g/dl were observed in response to the single dose, with corresponding increases in RBC counts and hematocrit. These hematologic parameters peaked at about 60 days after the dose and substantial decrease by day 120. This indicates that dosing for the purpose of increasing red blood cell levels may be more effective if done at intervals less than 120 days (i.e., prior to return to baseline), with dosing intervals of 90 days or less or 60 days or less may be desirable. For a summary of hematological changes, see FIGS. 12-15.

Overall, ActRIIA-hFc showed a dose-dependent effect on red blood cell counts and reticulocyte counts.

Example 5: Treatment of an Anemic Patient with ActRIIA-hFc

A clinical study was designed to treat patients with multiple doses of ActRIIA-hFc, at 30 dose levels of 0.1 mg/kg, 0.3 mg/kg, and 1.0 mg/kg, with dosing to occur every thirty days. Normal healthy patients in the trial exhibited an increase in hemoglobin and hematocrit that is consistent with the increases seen in the Phase I clinical trial reported in Example 4, except that in some instances, the hemoglobin (Hg) and hematocrit (Hct) are elevated beyond the normal range. An anemic patient with hemoglobin levels of approximately 7.5 g/dL also received two doses at the 1 mg/kg level, resulting in a hemoglobin level of approximately 10.5 g/dL after two months. The patient's anemia was a microcytic anemia, thought to be caused by chronic iron deficiency.

ActRIIA-Fc fusion proteins have been further demonstrated to be effective in increasing red blood cell levels in various models of anemia including, for example, chemotherapy-induced anemia and anemia associated with chronic kidney disease. See, e.g., U.S. Patent Application Publication No. 2010/0028331.

Example 6: Alternative ActRIIA-Fc Proteins

A variety of ActRIIA variants that may be used according to the methods described herein are described in the International Patent Application published as WO2006/012627 (see e.g., pp. 59-60), incorporated herein by reference in its entirety. An alternative construct may have a deletion of the C-terminal tail (the final 15 amino acids of the extracellular domain of ActRIIA. The sequence for such a construct is presented below (Fc portion underlined) (SEQ ID NO:28):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

<u>TGGGTHTCPPCPAPELLGGPSVFLFPPKPKDTLMISRTPEVTCVVVDVSH</u>

<u>EDPEVKFNWYVDGVEVHNAKTKPREEQYNSTYRVVSVLTVLHQDWLNGKE</u>

<u>YKCKVSNKALPVPIEKTISKAKGQPREPQVYTLPPSREEMTKNQVSLTCL</u>

<u>VKGFYPSDIAVEWESNGQPENNYKTTPPVLDSDGSFFLYSKLTVDKSRWQ</u>

<u>QGNVFSCSVMHEALHNHYTQKSLSLSPGK</u>

Example 7: Generation of ActRIIB-Fc Fusion Proteins

Applicant constructed a soluble ActRIIB fusion protein that has the extracellular domain of human ActRIIB fused to a human or mouse Fc domain with a minimal linker (three glycine amino acids) in between. The constructs are referred to as ActRIIB-hFc and ActRIIB-mFc, respectively.

ActRIIB-hFc is shown below as purified from CHO cell lines (SEQ ID NO:29)

GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT<u>GGGTHTCPPCPAPELLGGPSVFLFPPKPKDTLMIS</u>

<u>RTPEVTCVVVDVSHEDPEVKFNWYVDGVEVHNAKTKPREEQYNSTYRVVS</u>

<u>VLTVLHQDWLNGKEYKCKVSNKALPVPIEKTISKAKGQPREPQVYTLPPS</u>

<u>REEMTKNQVSLTCLVKGFYPSDIAVEWESNGQPENNYKTTPPVLDSDGSF</u>

<u>FLYSKLTVDKSRWQQGNVFSCSVMHEALHNHYTQKSLSLSPGK</u>

The ActRIIB-hFc and ActRIIB-mFc proteins were expressed in CHO cell lines. Three different leader sequences were considered:

```
(i) Honey bee mellitin (HBML):
                                   (SEQ ID NO: 23)
MKFLVNVALVFMVVYISYIYA (ii) Tissue plasminogen activator (TPA):
                                   (SEQ ID NO: 24)
MDAMKRGLCCVLLLCGAVFVSP (iii) Native:
                                   (SEQ ID NO: 30)
MTAPWVALALLWGSLCAGS.
```

The selected form employs the TPA leader and has the following unprocessed amino acid sequence (SEQ ID NO: 31):

<u>MDAMKRGLCCVLLLCGAVFVSP</u>GASGRGEAETRECIYYNANWELERTNQS

GLERCEGEQDKRLHCYASWRNSSGTIELVKKGCWLDDFNCYDRQECVATE

ENPQVYFCCCEGNFCNERFTHLPEAGGPEVTYEPPPTAPT<u>GGGTHTCPPC</u>

<u>PAPELLGGPSVFLFPPKPKDTLMISRTPEVTCVVVDVSHEDPEVKFNWYV</u>

-continued

DGVEVHNAKTKPREEQYNSTYRVVSVLTVLHQDWLNGKEYKCKVSNKALP

VPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMH

EALHNHYTQKSLSLSPGK

This polypeptide is encoded by the following nucleic acid sequence (SEQ ID NO:32):

```
A TGGATGCAAT GAAGAGAGGG CTCTGCTGTG TGCTGCTGCT
GTGTGGAGCA GTCTTCGTTT CGCCCGGCGC CTCTGGGCGT
GGGGAGGCTG AGACACGGGA GTGCATCTAC TACAACGCCA
ACTGGGAGCT GGAGCGCACC AACCAGAGCG GCCTGGAGCG
CTGCGAAGGC GAGCAGGACA AGCGGCTGCA CTGCTACGCC
TCCTGGCGCA ACAGCTCTGG CACCATCGAG CTCGTGAAGA
AGGGCTGCTG GCTAGATGAC TTCAACTGCT ACGATAGGCA
GGAGTGTGTG GCCACTGAGG AGAACCCCCA GGTGTACTTC
TGCTGCTGTG AAGGCAACTT CTGCAACGAG CGCTTCACTC
ATTTGCCAGA GGCTGGGGGC CCGGAAGTCA CGTACGAGCC
ACCCCCGACA GCCCCCACCG GTGGTGGAAC TCACACATGC
CCACCGTGCC CAGCACCTGA ACTCCTGGGG GGACCGTCAG
TCTTCCTCTT CCCCCCAAAA CCCAAGGACA CCCTCATGAT
CTCCCGGACC CCTGAGGTCA CATGCGTGGT GGTGGACGTG
AGCCACGAAG ACCCTGAGGT CAAGTTCAAC TGGTACGTGG
ACGGCGTGGA GGTGCATAAT GCCAAGACAA AGCCGCGGGA
GGAGCAGTAC AACAGCACGT ACCGTGTGGT CAGCGTCCTC
ACCGTCCTGC ACCAGGACTG GCTGAATGGC AAGGAGTACA
AGTGCAAGGT CTCCAACAAA GCCCTCCCAG TCCCCATCGA
GAAAACCATC TCCAAAGCCA AAGGGCAGCC CCGAGAACCA
CAGGTGTACA CCCTGCCCCC ATCCCGGGAG GAGATGACCA
AGAACCAGGT CAGCCTGACC TGCCTGGTCA AAGGCTTCTA
TCCCAGCGAC ATCGCCGTGG AGTGGGAGAG CAATGGGCAG
CCGGAGAACA ACTACAAGAC CACGCCTCCC GTGCTGGACT
CCGACGGCTC CTTCTTCCTC TATAGCAAGC TCACCGTGGA
CAAGAGCAGG TGGCAGCAGG GGAACGTCTT CTCATGCTCC
GTGATGCATG AGGCTCTGCA CAACCACTAC ACGCAGAAGA
GCCTCTCCCT GTCTCCGGGT AAATGA
```

N-terminal sequencing of the CHO-cell produced material revealed a major polypeptide sequence of -GRGEAE (SEQ ID NO:33). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

ActRIIB-Fc fusion proteins were also expressed in HEK293 cells and COS cells. Although material from all cell lines and reasonable culture conditions provided protein with muscle-building activity in vivo, variability in potency was observed perhaps relating to cell line selection and/or culture conditions.

Applicant generated a series of mutations in the extracellular domain of ActRIIB and produced these mutant proteins as soluble fusion proteins between extracellular ActRIIB and an Fc domain. The background ActRIIB-Fc fusion has the sequence of SEQ ID NO:29.

Various mutations, including N- and C-terminal truncations, were introduced into the background ActRIIB-Fc protein. Based on the data presented in Example 1, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into E. coli DH5 alpha, colonies were picked and DNAs were isolated. For murine constructs (mFc), a murine IgG2a was substituted for the human IgG1. Sequences of all mutants were verified. All of the mutants were produced in HEK293T cells by transient transfection. In summary, in a 500 ml spinner, HEK293T cells were set up at $6 \times 10^5$ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, a protein A column and eluted with low pH (3.0) glycine buffer. After neutralization, these were dialyzed against PBS.

Mutants were also produced in CHO cells by similar methodology.

Mutants were tested in binding assays and/or bioassays described in WO 2008/097541 and WO 2006/012627 incorporated by reference herein. In some instances, assays were performed with conditioned medium rather than purified proteins. Additional variations of ActRIIB are described in U.S. Pat. No. 7,842,663.

Example 8: ActRIIB-Fc Stimulates Erythropoiesis in Non-Human Primates

Cynomolgus monkeys were allocated into seven groups (6/sex/group) and administered ActRIIB(20-134)-hFc as a subcutaneous injection at dosages of 0.6, 3, or 15 mg/kg every 2 weeks or every 4 weeks over a 9 month period. The control group (6/sex/group) received the vehicle at the same dose volume (0.5 ml/kg/dose) as ActRIIB(20-134)-hFc-treated animals. Animals were monitored for changes in general clinical pathology parameters (e.g., hematology, clinical chemistry, coagulation, and urinalysis). Hematology, coagulation, and clinical chemistry parameters (including iron parameters, lipase, and amylase) were evaluated twice prior to initiation of dosing and on Days 59, 143, 199, 227, and on Days 267 (for groups dosed every 4 weeks) or 281 (for groups dosed every 2 weeks). The evaluations on Days 267/281 occurred 2 weeks after the final dose was administered.

Administration of ActRIIB(20-134)-hFc resulted in non-adverse, dose-related changes to hematology parameters in male and female monkeys. These changes included increased red blood cell count, reticulocyte count and red cell distribution width and decreased mean corpuscular volume, mean corpuscular hemoglobin, and platelet count. In males, RBC count was increased at all dose levels and the magnitude of increase was generally comparable whether ActRIIB(20-134)-hFc was administered every 2 weeks or every 4 weeks. Mean RBC count was increased at all time points between Days 59 and 267/281 (except RBC count was not increased in Group 2 males [0.6 mg/kg every 2 weeks] on Day 281). In females, RBC count was increased at ≥3 mg/kg every 2 weeks and the changes occurred between Days 143 and 281; at 15 mg/kg every 4 weeks mean RBC count was increased between Days 59 and 267.

These effects are consistent with a positive effect of ActRIIB(20-134)-hFc on stimulating erythropoiesis.

Example 9: Generation of a GDF Trap

Applicant constructed a GDF Trap as follows. A polypeptide having a modified extracellular domain of ActRIIB (amino acids 20-134 of SEQ ID NO: 1 with an L79D substitution) with greatly reduced activin A binding relative to GDF11 and/or myostatin (as a consequence of a leucine-to-aspartate substitution at position 79 in SEQ ID NO: 1) was fused to a human or mouse Fc domain with a minimal linker (three glycine amino acids) in between. The constructs are referred to as ActRIIB(L79D 20-134)-hFc and ActRIIB(L79D 20-134)-mFc, respectively. Alternative forms with a glutamate rather than an aspartate at position 79 performed similarly (L79E). Alternative forms with an alanine rather than a valine at position 226 with respect to SEQ ID NO:36, below were also generated and performed equivalently in all respects tested. The aspartate at position 79 (relative to SEQ ID NO: 1, or position 60 relative to SEQ ID NO:36) is indicated with doubleunderlining below. The valine at position 226 relative to SEQ ID NO:36 is also indicated by doubleunderlining below.

The GDF Trap ActRIIB(L79D 20-134)-hFc is shown below as purified from CHO cell lines (SEQ ID NO:36).

GRGEAETRECIYYNANWELERTNQSGLERCEGEQDKRLHCYASWRNSSGT

IELVKKGCW<u>D</u>DDFNCYDRQECVATEENPQVYFCCCEGNFCNERFTHLPEA

GGPEVTYEPPPTAPT<u>GGGTHTCPPCPAPELLGGPSVFLFPPKPKDTLMIS</u>

<u>RTPEVTCVVVDVSHEDPEVKFNWYVDGVEVHNAKTKPREEQYNSTYRVVS</u>

<u>VLTVLHQDWLNGKEYKCKVSNKALP<u>V</u>PIEKTISKAKGQPREPQVYTLPPS</u>

<u>REEMTKNQVSLTCLVKGFYPSDIAVEWESNGQPENNYKTTPPVLDSDGSF</u>

<u>FLYSKLTVDKSRWQQGNVFSCSVMHEALHNHYTQKSLSLSPGK</u>

The ActRIIB-derived portion of the GDF Trap has an amino acid sequence set forth below (SEQ ID NO: 37), and that portion could be used as a monomer or as a non-Fc fusion protein as a monomer, dimer or greater order complex.

(SEQ ID NO: 37)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEVTYEPPPTAPT

The GDF Trap protein was expressed in CHO cell lines. Three different leader sequences were considered:

(i) Honey bee melittin (HBML):
(SEQ ID NO: 23)
MKFLVNVALVFMVVYISYIYA (ii) Tissue plasminogen activator (TPA):
(SEQ ID NO: 24)
MDAMKRGLCCVLLLCGAVFVSP (iii) Native:
(SEQ ID NO: 30)
MTAPWVALALLWGSLCAGS.

The selected form employs the TPA leader and has the following unprocessed amino acid sequence:

(SEQ ID NO: 38)
<u>MDAMKRGLCCVLLLCGAVFVSPGAS</u>GRGEAETRECIYYNANWELERTNQS

GLERCEGEQDKRLHCYASWRNSSGTIELVKKGCWDDDFNCYDRQECVATE

ENPQVYFCCCEGNFCNERFTHLPEAGGPEVTYEPPPTAPT<u>GGGTHTCPPC</u>

<u>PAPELLGGPSVFLFPPKPKDTLMISRTPEVTCVVVDVSHEDPEAKFNWYV</u>

<u>DGVEVHNAKTKPREEQYNSTYRVVSVLTVLHQDWLNGKEYKCKVSNKALP</u>

<u>VPIEKTISKAKGQPREPQVYTLPPSREEMTKNQVSLTCLVKGFYPSDIAV</u>

<u>EWESNGQPENNYKTTPPVLDSDGSFFLYSKLTVDKSRWQQGNVFSCSVMH</u>

<u>EALHNHYTQKSLSLSPGK</u>

This polypeptide is encoded by the following nucleic acid sequence (SEQ ID NO:681139M:

```
A TGGATGCAAT GAAGAGAGGG CTCTGCTGTG TGCTGCTGCT
  GTGTGGAGCA GTCTTCGTTT CGCCCGGCGC CTCTGGGCGT
  GGGGAGGCTG AGACACGGGA GTGCATCTAC TACAACGCCA
  ACTGGGAGCT GGAGCGCACC AACCAGAGCG GCCTGGAGCG
  CTGCGAAGGC GAGCAGGACA AGCGGCTGCA CTGCTACGCC
  TCCTGGCGCA ACAGCTCTGG CACCATCGAG CTCGTGAAGA
  AGGGCTGCTG GGACGATGAC TTCAACTGCT ACGATAGGCA
  GGAGTGTGTG GCCACTGAGG AGAACCCCCA GGTGTACTTC
  TGCTGCTGTG AAGGCAACTT CTGCAACGAG CGCTTCACTC
  ATTTGCCAGA GGCTGGGGGC CCGGAAGTCA CGTACGAGCC
  ACCCCCGACA GCCCCCACCG GTGGTGGAAC TCACACATGC
  CCACCGTGCC CAGCACCTGA ACTCCTGGGG GGACCGTCAG
  TCTTCCTCTT CCCCCCAAAA CCCAAGGACA CCCTCATGAT
  CTCCCGGACC CCTGAGGTCA CATGCGTGGT GGTGGACGTG
  AGCCACGAAG ACCCTGAGGT CAAGTTCAAC TGGTACGTGG
  ACGGCGTGGA GGTGCATAAT GCCAAGACAA AGCCGCGGGA
```

-continued

```
GGAGCAGTAC AACAGCACGT ACCGTGTGGT CAGCGTCCTC

ACCGTCCTGC ACCAGGACTG GCTGAATGGC AAGGAGTACA

AGTGCAAGGT CTCCAACAAA GCCCTCCCAG TCCCCATCGA

GAAAACCATC TCCAAAGCCA AAGGGCAGCC CCGAGAACCA

CAGGTGTACA CCCTGCCCCC ATCCCGGGAG GAGATGACCA

AGAACCAGGT CAGCCTGACC TGCCTGGTCA AAGGCTTCTA

TCCCAGCGAC ATCGCCGTGG AGTGGGAGAG CAATGGGCAG

CCGGAGAACA ACTACAAGAC CACGCCTCCC GTGCTGGACT

CCGACGGCTC CTTCTTCCTC TATAGCAAGC TCACCGTGGA

CAAGAGCAGG TGGCAGCAGG GGAACGTCTT CTCATGCTCC

GTGATGCATG AGGCTCTGCA CAACCACTAC ACGCAGAAGA

GCCTCTCCCT GTCTCCGGGT AAATGA
```

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. In an example of a purification scheme, the cell culture medium is passed over a protein A column, washed in 150 mM Tris/NaCl (pH 8.0), then washed in 50 mM Tris/NaCl (pH 8.0) and eluted with 0.1 M glycine, pH 3.0. The low pH eluate is kept at room temperature for 30 minutes as a viral clearance step. The eluate is then neutralized and passed over a Q sepharose ion exchange column and washed in 50 mM Tris pH 8.0, 50 mM NaCl, and eluted in 50 mM Tris pH 8.0, with an NaCl concentration between 150 mM and 300 mM. The eluate is then changed into 50 mM Tris pH 8.0, 1.1 M ammonium sulfate and passed over a phenyl sepharose column, washed, and eluted in 50 mM Tris pH 8.0 with ammonium sulfate between 150 and 300 mM. The eluate is dialyzed and filtered for use.

Additional GDF Traps (ActRIIB-Fc fusion proteins modified so as to reduce the ratio of activin A binding relative to myostatin or GDF11 binding) are described in WO 2008/097541 and WO 2006/012627, incorporated by reference herein.

Example 10: Bioassay for GDF-11 and Activin-Mediated Signaling

An A-204 reporter gene assay was used to evaluate the effects of ActRIIB-Fc proteins and GDF Traps on signaling by GDF-11 and activin A. Cell line: human rhabdomyosarcoma (derived from muscle). Reporter vector: pGL3 (CAGA)12 (described in Dennler et al, 1998, EMBO 17: 3091-3100). The CAGA12 motif is present in TGF-Beta responsive genes (e.g., PAI-1 gene), so this vector is of general use for factors signaling through SMAD2 and 3.

Day 1: Split A-204 cells into 48-well plate.

Day 2: A-204 cells transfected with 10 ug pGL3(CAGA)12 or pGL3(CAGA)12(10 ug)+pRLCMV (1 pg) and Fugene.

Day 3: Add factors (diluted into medium+0.1% BSA). Inhibitors need to be preincubated with factors for 1 hr before adding to cells. Six hrs later, cells were rinsed with PBS, and lysed.

This is followed by a luciferase assay. In the absence of any inhibitors, Activin A showed 10-fold stimulation of reporter gene expression and an ED50~2 ng/ml. GDF-11: 16 fold stimulation, ED50:~1.5 ng/ml.

ActRIIB(20-134) is a potent inhibitor of activin A, GDF-8, and GDF-11 activity in this assay. As described below ActRIIB variants were also tested in this assay.

Example 11: ActRIIB-Fc Variants, Cell-Based Activity

Activity of ActRIIB-Fc proteins and GDF Traps was tested in a cell based assay, as described above. Results are summarized in the table below. Some variants were tested in different C-terminal truncation constructs. As discussed above, truncations of five or fifteen amino acids caused reduction in activity. The GDF Traps (L79D and L79E variants) showed substantial loss of activin A inhibition while retaining almost wild-type inhibition of GDF-11.

Soluble ActRIIB-Fc Binding to GDF11 and Activin A:

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64 | 20-134 | +++ (approx. $10^{-8}$ M $K_I$) | +++ (approx. $10^{-8}$ M $K_I$) |
| A64 | 20-134 | + (approx. $10^{-6}$ M $K_I$) | + (approx. $10^{-6}$ M $K_I$) |
| R64 | 20-129 | +++ | +++ |
| R64 K74A | 20-134 | ++++ | ++++ |
| R64 A24N | 20-134 | +++ | +++ |
| R64 A24N | 20-119 | ++ | ++ |
| R64 A24N K74A | 20-119 | + | + |
| R64 L79P | 20-134 | + | + |
| R64 L79P K74A | 20-134 | + | + |
| R64 L79D | 20-134 | +++ | + |
| R64 L79E | 20-134 | +++ | + |
| R64K | 20-134 | +++ | +++ |
| R64K | 20-129 | +++ | +++ |

-continued

| ActRIIB-Fc Variations | Portion of ActRIIB (corresponds to amino acids of SEQ ID NO: 1) | GDF11 Inhibition Activity | Activin Inhibition Activity |
|---|---|---|---|
| R64 P129S P130A | 20-134 | +++ | +++ |
| R64N | 20-134 | + | + |

+ Poor activity (roughly $1 \times 10^{-6}$ $K_D$)
++ Moderate activity (roughly $1 \times 10^{-7}$ $K_D$)
+++ Good (wild-type) activity (roughly $1 \times 10^{-8}$ $K_D$)
++++ Greater than wild-type activity Several variants have been assessed for serum half-life in rats. ActRIIB(20-134)-Fc has a serum half-life of approximately 70 hours. ActRIIB(A24N 20-134)-Fc has a serum half-life of approximately 100-150 hours. The A24N variant has activity in the cell-based assay (above) and in vivo assays (below) that is equivalent to the wild-type molecule. Coupled with the longer half-life, this means that over time an A24N variant will give greater effect per unit of protein than the wild-type molecule. The A24N variant, and any of the other variants tested above, may be combined with the GDF Trap molecules, such as the L79D or L79E variants.

Example 12: GDF-11 and Activin A Binding

Binding of certain ActRIIB-Fc proteins and GDF Traps to ligands was tested in a Biacore™ assay.

The ActRIIB-Fc variants or wild-type protein were captured onto the system using an anti-hFc antibody. Ligands were injected and flowed over the captured receptor proteins. Results are summarized in the tables, below.

Ligand-Binding Specificity IIB Variants.

| Protein | Kon (1/Ms) | Koff (1/s) | KD (M) |
|---|---|---|---|
| | | GDF11 | |
| ActRIIB(20-134)-hFc | 1.34e−6 | 1.13e−4 | 8.42e−11 |
| ActRIIB(A24N 20-134)-hFc | 1.21e−6 | 6.35e−5 | 5.19e−11 |
| ActRIIB(L79D 20-134)-hFc | 6.7e−5 | 4.39e−4 | 6.55e−10 |
| ActRIIB(L79E 20-134)-hFc | 3.8e−5 | 2.74e−4 | 7.16e−10 |
| ActRIIB(R64K 20-134)-hFc | 6.77e−5 | 2.41e−5 | 3.56e−11 |
| | | GDF8 | |
| ActRIIB(20-134)-hFc | 3.69e−5 | 3.45e−5 | 9.35e−11 |
| ActRIIB(A24N 20-134)-hFc | | | |
| ActRIIB(L79D 20-134)-hFc | 3.85e−5 | 8.3e−4 | 2.15e−9 |
| ActRIIB(L79E 20-134)-hFc | 3.74e−5 | 9e−4 | 2.41e−9 |
| ActRIIB(R64K 20-134)-hFc | 2.25e−5 | 4.71e−5 | 2.1e−10 |
| ActRIIB(R64K 20-129)-hFc | 9.74e−4 | 2.09e−4 | 2.15e−9 |
| ActRIIB(P129S, P130R 20-134)-hFc | 1.08e−5 | 1.8e−4 | 1.67e−9 |
| ActRIIB(K74A 20-134)-hFc | 2.8e−5 | 2.03e−5 | 7.18e−11 |
| | | Activin A | |
| ActRIIB(20-134)-hFc | 5.94e6 | 1.59e−4 | 2.68e−11 |
| ActRIIB(A24N 20-134)-hFc | 3.34e6 | 3.46e−4 | 1.04e−10 |
| ActRIIB(L79D 20-134)-hFc | | | Low binding |
| ActRIIB(L79E 20-134)-hFc | | | Low binding |
| ActRIIB(R64K 20-134)-hFc | 6.82e6 | 3.25e−4 | 4.76e−11 |
| ActRIIB(R64K 20-129)-hFc | 7.46e6 | 6.28e−4 | 8.41e−11 |
| ActRIIB(P129S, P130R 20-134)-hFc | 5.02e6 | 4.17e−4 | 8.31e−11 |

These data obtained from a cell-free assay confirm the cell based assay data, demonstrating that the A24N variant retains ligand-binding activity that is similar to that of the ActRIIB(20-134)-hFc molecule, and that the L79D or L79E molecule retains myostatin and GDF11 binding but shows markedly decreased (non-quantifiable) binding to activin A.

Other variants have been generated and tested, as reported in WO2006/012627 (incorporated herein by reference in its entirety) See, e.g., pp. 59-60, using ligands coupled to the device and flowing receptor over the coupled ligands. Notably, K74Y, K74F, K74I (and presumably other hydrophobic substitutions at K74, such as K74L), and D80I, cause a decrease in the ratio of activin A (ActA) binding to GDF11 binding, relative to the wild-type K74 molecule. A table of data with respect to these variants is reproduced below:

Soluble ActRIIB-Fc Variants Binding to GDF11 and Activin a (BiaCore Assay)

| ActRIIB | ActA | GDF11 |
|---|---|---|
| WT (64A) | KD = 1.8e−7M (+) | KD = 2.6e−7M (+) |
| WT (64R) | na | KD = 8.6e−8M (+++) |
| +15tail | KD ~2.6e−8M (+++) | KD = 1.9e−8M (++++) |
| E37A | * | * |
| R40A | − | − |
| D54A | − | * |
| K55A | ++ | * |
| R56A | * | * |
| K74A | KD = 4.35e−9M (+++++) | KD = 5.3e−9M (+++++) |
| K74Y | * | −− |
| K74F | * | −− |
| K74I | * | −− |
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | −− |
| F82A | ++ | − |

* No observed binding
−− <1/5 WT binding
− ~1/2 WT binding
+ WT
++ <2x increased binding
+++ ~5x increased binding
++++ ~10x increased binding
+++++ ~40x increased binding Example 13: A GDF Trap Increases Red Blood Cell Levels In Vivo Twelve-week-old male C57BL/6NTac mice were assigned to one of two treatment groups (N=10). Mice were dosed with either vehicle or with a variant ActRIIB polypeptide ("GDF Trap") [ActRIIB(L79D 20-134)-hFc] by subcutaneous injection (SC) at 10 mg/kg twice per week for 4 weeks. At study termination, whole blood was collected by cardiac puncture into EDTA containing tubes and analyzed for cell distribution using an HM2 hematology analyzer (Abaxis, Inc).

Group Designation

| Group | N | Mice | Injection | Dose (mg/kg) | Route | Frequency |
|---|---|---|---|---|---|---|
| 1 | 10 | C57BL/6 | PBS | 0 | SC | Twice/week |
| 2 | 10 | C57BL/6 | GDF Trap [ActRIIB(L79D20-134)-hFc] | 10 | SC | Twice/week |

Treatment with the GDF Trap did not have a statistically significant effect on the number of white blood cells (WBC) compared to the vehicle controls. Red blood cell (RBC) numbers were increased in the treated group relative to the controls (see table below). Both the hemoglobin content (HGB) and hematocrit (HCT) were also increased due to the additional red blood cells. The average width of the red blood cells (RDWc) was higher in the treated animals, indicating an increase in the pool of immature red blood cells. Therefore, treatment with the GDF Trap leads to increases in red blood cells, with no distinguishable effects on white blood cell populations.

Hematology Results

|  | RBC $10^{12}$/L | HGB (g/dL) | HCT (%) | RDWc (%) |
|---|---|---|---|---|
| PBS | 10.7 ± 0.1 | 14.8 ± 0.6 | 44.8 ± 0.4 | 17.0 ± 0.1 |
| GDF Trap | 12.4 ± 0.4** | 17.0 ± 0.7* | 48.8 ± 1.8* | 18.4 ± 0.2** |

*= $p < 0.05$,
**= $p < 0.01$

Example 14: A GDF Trap is Superior to ActRIIB-Fc for Increasing Red Blood Cell Levels In Vivo Nineteen-week-old male C57BL/6NTac mice were randomly assigned to one of three groups. Mice were dosed with vehicle (10 mM Tris Buffered Saline, TBS), wild-type ActRIIB(20-134)-mFc, or GDF trap ActRIIB(L79D 20-134)-hFc by subcutaneous injection twice per week for three weeks. Blood was collected cheek bleed at baseline and after three weeks of dosing and analyzed for cell distribution using a hematology analyzer (HM2, Abaxis, Inc.)

Treatment with ActRIIB-Fc or the GDF trap did not have a significant effect on white blood cell (WBC) numbers compared to vehicle controls. The red blood cell count (RBC), hematocrit (HCT), and hemoglobin levels were all elevated in mice treated with GDF Trap compared to either the controls or the wild-type construct (see table below). Therefore, in a direct comparison, the GDF trap promotes increases in red blood cells to a significantly greater extent than a wild-type ActRIIB-Fc protein. In fact, in this experiment, the wild-type ActRIIB-Fc protein did not cause a statistically significant increase in red blood cells, suggesting that longer or higher dosing would be needed to reveal this effect.

Hematology Results after Three Weeks of Dosing

|  | RBC ($10^{12}$/ml) | HCT % | HGB g/dL |
|---|---|---|---|
| TBS | 11.06 ± 0.46 | 46.78 ± 1.9 | 15.7 ± 0.7 |
| ActRIIB-mFc | 11.64 ± 0.09 | 49.03 ± 0.3 | 16.5 ± 1.5 |
| GDF Trap | 13.19 ± 0.2** | 53.04 ± 0.8** | 18.4 ± 0.3** |

**= $p < 0.01$

Example 15: Generation of a GDF Trap with Truncated ActRIIB Extracellular Domain As described in Example 9, a GDF Trap referred to as ActRIIB(L79D 20-134)-hFc was generated by N-terminal fusion of TPA leader to the ActRIIB extracellular domain (residues 20-134 in SEQ ID NO: 1) containing a leucine-to-aspartate substitution (at residue 79 in SEQ ID NO: 1) and C-terminal fusion of human Fc domain with minimal linker (three glycine residues) (FIG. 16). A nucleotide sequence corresponding to this fusion protein is shown in FIGS. 17A and 17B.

A GDF Trap with truncated ActRIIB extracellular domain, referred to as ActRIIB(L79D 25-131)-hFc, was generated by N-terminal fusion of TPA leader to truncated extracellular domain (residues 25-131 in SEQ ID NO: 1) containing a leucine-to-aspartate substitution (at residue 79 in SEQ ID NO:1) and C-terminal fusion of human Fc domain with minimal linker (three glycine residues) (FIG. 18). A nucleotide sequence corresponding to this fusion protein is shown in FIGS. 19A and 19B.

Example 16: Selective Ligand Binding by GDF Trap with Double-Truncated ActRIIB Extracelluar Domain The affinity of GDF Traps and other ActRIIB-hFc proteins for several ligands was evaluated in vitro with a Biacore™ instrument. Results are summarized in the table below. Kd values were obtained by steady-state affinity fit due to the very rapid association and dissociation of the complex, which prevented accurate determination of $k_{on}$ and $k_{off}$.

Ligand Selectivity of ActRIIB-hFc Variants:

| Fusion Construct | Activin A (Kd e–11) | Activin B (Kd e–11) | GDF11 (Kd e–11) |
|---|---|---|---|
| ActRIIB(L79 20-134)-hFc | 1.6 | 1.2 | 3.6 |
| ActRIIB(L79D 20-134)-hFc | 1350.0 | 78.8 | 12.3 |
| ActRIIB(L79 25-131)-hFc | 1.8 | 1.2 | 3.1 |
| ActRIIB(L79D 25-131)-hFc | 2290.0 | 62.1 | 7.4 |

The GDF Trap with a truncated extracellular domain, ActRIIB(L79D 25-131)-hFc, equaled or surpassed the ligand selectivity displayed by the longer variant, ActRIIB (L79D 20-134)-hFc, with pronounced loss of activin A binding, partial loss of activin B binding, and nearly full retention of GDF11 binding compared to ActRIIB-hFc counterparts lacking the L79D substitution. Note that truncation alone (without L79D substitution) did not alter selectivity among the ligands displayed here [compare ActRIIB (L79 25-131)-hFc with ActRIIB(L79 20-134)-hFc].

Example 17: Generation of ActRIIB(L79D 25-131)-hFc with Alternative Nucleotide Sequences To generate ActRIIB(L79D 25-131)-hFc, the human ActRIIB extracellular domain with an aspartate substitution at native position 79 (SEQ ID NO: 1) and with N-terminal and C-terminal truncations (residues 25-131 in SEQ ID NO: 1) was fused N-terminally with a TPA leader sequence instead of the native ActRIIB leader and C-terminally with a human Fc domain via a minimal linker (three glycine residues) (FIG. 18). One nucleotide sequence encoding this fusion protein is shown in FIG. 19 (SEQ ID NO: 42), and an alternative nucleotide sequence encoding exactly the same fusion protein is shown in FIGS. 22A and 22B (SEQ ID NO: 46). This protein was expressed and purified using the methodology described in Example 9.

Example 18: GDF Trap with a Truncated ActRIIB Extracellular Domain Increases Proliferation of Erythroid Progenitors in Mice ActRIIB(L79D 25-131)-hFc was evaluated to determine its effect on proliferation of erythroid progenitors. Male C57BL/6 mice (8 weeks old) were treated with ActRIIB (L79D 25-131)-hFc (10 mg/kg, s.c.; n=6) or vehicle (TBS; n=6) on Days 1 and 4, then euthanized on Day 8 for collection of spleens, tibias, femurs, and blood. Cells of the spleen and bone marrow were isolated, diluted in Iscove's modified Dulbecco's medium containing 5% fetal bovine serum, suspended in specialized methylcellulose-based medium, and cultured for either 2 or 12 days to assess levels of clonogenic progenitors at the colony-forming unit-erythroid (CFU-E) and burst forming unit-erythroid (BFU-E) stages, respectively. Methylcellulose-based medium for BFU-E determination (MethoCult M3434, Stem Cell Technologies) included recombinant murine stem cell factor, interleukin-3, and interleukin-6, which were not present in methylcellulose medium for CFU-E determination (MethoCult M3334, Stem Cell Technologies), while both media contained erythropoietin, among other constituents. For both BFU-E and CFU-E, the number of colonies were determined in duplicate culture plates derived from each tissue sample, and statistical analysis of the results was based on the number of mice per treatment group.

Spleen-derived cultures from mice treated with ActRIIB (L79D 25-131)-hFc had twice the number of CFU-E colonies as did corresponding cultures from control mice (P<0.05), whereas the number of BFU-E colonies did not differ significantly with treatment in vivo. The number of CFU-E or BFU-E colonies from bone marrow cultures also did not differ significantly with treatment. As expected, increased numbers of CFU-E colonies in spleen-derived cultures were accompanied by highly significant (P<0.001) changes in red blood cell level (11.6% increase), hemoglobin concentration (12% increase), and hematocrit level (11.6% increase) at euthanasia in mice treated with ActRIIB (L79D 25-131)-hFc compared to controls. These results indicate that in vivo administration of a GDF Trap with truncated ActRIIB extracellular domain can stimulate proliferation of erythroid progenitors as part of its overall effect to increase red blood cell levels.

GDF Trap fusion proteins have been further demonstrated to be effective in increasing red blood cell levels in various models of anemia including, for example, chemotherapy-induced anemia, nephrectomy-induced anemia, and in a blood loss anemia. See, e.g., International Patent Application Publication No. WO 2010/019261.

Example 19: GDF Trap with Truncated ActRIIB Extracellular Domain Increases Levels of Red Blood Cells in Non-Human Primates Two GDF Traps, ActRIIB(L79D 20-134)-hFc and ActRIIB(L79D 25-131)-hFc, were evaluated for their ability to stimulate red blood cell production in cynomolgus monkey. Monkeys were treated subcutaneously with GDF Trap (10 mg/kg; n=4 males/4 females), or vehicle (n=2 males/2 females) on Days 1 and 8. Blood samples were collected on Days 1 (pretreatment baseline), 3, 8, 15, 29, and 44, and were analyzed for red blood cell levels (FIG. 24), hematocrit (FIG. 25), hemoglobin levels (FIG. 26), and reticulocyte levels (FIG. 27). Vehicle-treated monkeys exhibited decreased levels of red blood cells, hematocrit, and hemoglobin at all post-treatment time points, an expected effect of repeated blood sampling. In contrast, treatment with ActRIIB(L79D 20-134)-hFc or ActRIIB(L79D 25-131)-hFc increased these parameters by the first post-treatment time point (Day 3) and maintained them at substantially elevated levels for the duration of the study (FIGS. 24-26). Importantly, reticulocyte levels in monkeys treated with ActRIIB (L79D 20-134)-hFc or ActRIIB(L79D 25-131)-hFc were substantially increased at Days 8, 15, and 29 compared to vehicle (FIG. 27). This result demonstrates that GDF Trap treatment increased production of red blood cell precursors, resulting in elevated red blood cell levels.

Taken together, these data demonstrate that truncated GDF Traps, as well as a full-length variants, can be used as selective antagonists of GDF11 and potentially related ligands to increase red blood cell formation in vivo.

Example 20: GDF Trap Derived from ActRIIB5

Others have reported an alternate, soluble form of ActRIIB (designated ActRIIB5), in which exon 4, including the ActRIIB transmembrane domain, has been replaced by a different C-terminal sequence. See, e.g., WO 2007/053775.

The sequence of native human ActRIIB5 without its leader is as follows:

(SEQ ID NO: 49)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEGPWASTTIPSGGPEATAAAGDQGSGALWLCLEGPAHE

An leucine-to-aspartate substitution, or other acidic substitutions, may be performed at native position 79 (underlined) as described to construct the variant ActRIIB5(L79D), which has the following sequence:

(SEQ ID NO: 50)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHE

This variant may be connected to human Fc ( doubleunderline) with a TGGG linker (SEQ ID NO:53) ( singleunderline) to generate a human ActRIIB5(L79D)-hFc fusion protein with the following sequence:

(SEQ ID NO: 51)
GRGEAETRECIYYNANWELERTNQSGLERCEGEQDKRLHCYASWRNSSGT

IELVKKGCWDDDFNCYDRQECVATEENPQVYFCCCEGNFCNERFTHLPEA

GGPEGPWASTTIPSGGPEATAAAGDQGSGALWLCLEGPAHE<u>TGGG</u><u>THTCP</u>

<u>PCPAPELLGGPSVFLFPPKPKDTLMISRTPEVTCVVVDVSHEDPEVKFNW</u>

```
-continued
YVDGVEVHNAKTKPREEQYNSTYRVVSVLTVLHQDWLNGKEYKCKVSNKA

LPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSV

MHEALHNHYTQKSLSLSPGK.
```

This construct may be expressed in CHO cells.

Example 21: Effects in Mice of Combined Treatment with EPO and a GDF Trap with a Truncated ActRIIB Extracellular Domain EPO induces formation of red blood cells by increasing the proliferation of erythroid precursors, whereas GDF Traps could potentially affect formation of red blood cells in ways that complement or enhance EPO's effects. Therefore, Applicants investigated the effect of combined treatment with EPO and ActRIIB(L79D 25-131)-hFc on erythropoietic parameters. Male C57BL/6 mice (9 weeks old) were given a single i.p. injection of recombinant human EPO alone (epoetin alfa, 1800 units/kg), ActRIIB(L79D 25-131)-hFc alone (10 mg/kg), both EPO and ActRIIB(L79D 25-131)-hFc, or vehicle (Tris-buffered saline). Mice were euthanized 72 h after dosing for collection of blood, spleens, and femurs.

Spleens and femurs were processed to obtain erythroid precursor cells for flow cytometric analysis. After removal, the spleen was minced in Iscove's modified Dulbecco's medium containing 5% fetal bovine serum and mechanically dissociated by pushing through a 70-μm cell strainer with the plunger from a sterile 1-mL syringe. Femurs were cleaned of any residual muscle or connective tissue and ends were trimmed to permit collection of marrow by flushing the remaining shaft with Iscove's modified Dulbecco's medium containing 5% fetal bovine serum through a 21-gauge needle connected to a 3-mL syringe. Cell suspensions were centrifuged (2000 rpm for 10 min) and the cell pellets resuspended in PBS containing 5% fetal bovine serum. Cells ($10^6$) from each tissue were incubated with anti-mouse IgG to block nonspecific binding, then incubated with fluorescently labeled antibodies against mouse cell-surface markers CD71 (transferrin receptor) and Ter119 (an antigen associated with cell-surface glycophorin A), washed, and analyzed by flow cytometry. Dead cells in the samples were excluded from analysis by counterstaining with propidium iodide. Erythroid differentiation in spleen or bone marrow was assessed by the degree of CD71 labeling, which decreases over the course of differentiation, and Ter119 labeling, which is increased during terminal erythroid differentiation beginning with the proerythroblast stage (Socolovsky et al., 2001, Blood 98:3261-3273; Ying et al., 2006, Blood 108:123-133). Thus, flow cytometry was used to determine the number of proerythroblasts ($CD71^{high}Ter119^{low}$), basophilic erythroblasts ($CD71^{high}Ter119^{high}$), polychromatophilic+orthochromatophilic erythroblasts ($CD71^{med}Ter119^{high}$), and late orthochromatophilic erythroblasts+reticulocytes ($CD71^{low}Ter119^{high}$), as described.

Combined treatment with EPO and ActRIIB(L79D 25-131)-hFc led to a surprisingly vigorous increase in red blood cells. In the 72-h time frame of this experiment, neither EPO nor ActRIIB(L79D 25-131)-hFc alone increased hematocrit significantly compared to vehicle, whereas combined treatment with the two agents led to a nearly 25% increase in hematocrit that was unexpectedly synergistic, i.e., greater than the sum of their separate effects (FIG. 28). Synergy of this type is generally considered evidence that individual agents are acting through different cellular mechanisms. Similar results were also observed for hemoglobin concentrations (FIG. 29) and red blood cell concentrations (FIG. 30), each of which was also increased synergistically by combined treatment.

Analysis of erythroid precursor levels revealed a more complex pattern. In the mouse, the spleen is considered the primary organ responsible for inducible ("stress") erythropoiesis. Flow cytometric analysis of splenic tissue at 72 h revealed that EPO markedly altered the erythropoietic precursor profile compared to vehicle, increasing the number of basophilic erythroblasts by more than 170% at the expense of late precursors (late orthochromatophilic erythroblasts+reticulocytes), which decreased by more than one third (FIG. 31). Importantly, combined treatment increased basophilic erythroblasts significantly compared to vehicle, but to a lesser extent than EPO alone, while supporting undiminished maturation of late-stage precursors (FIG. 31). Thus, combined treatment with EPO and ActRIIB(L79D 25-131)-hFc increased erythropoiesis through a balanced enhancement of precursor proliferation and maturation. In contrast to spleen, the precursor cell profile in bone marrow after combined treatment did not differ appreciably from that after EPO alone. Applicants predict from the splenic precursor profile that combined treatment would lead to increased reticulocyte levels and would be accompanied by sustained elevation of mature red blood cell levels, if the experiment were extended beyond 72 h.

Taken together, these findings demonstrate that a GDF Trap with a truncated ActRIIB extracellular domain can be administered in combination with EPO to synergistically increase red blood cell formation in vivo. Acting through a complementary but undefined mechanism, a GDF trap can moderate the strong proliferative effect of an EPO receptor activator alone and still permit target levels of red blood cells to be attained with lower doses of an EPO receptor activator, thereby avoiding potential adverse effects or other problems associated with higher levels of EPO receptor activation.

Example 22: Effect of GDF Trap with a Truncated ActRIIB Extracellular Domain on RBC Levels and Morphology in a Mouse Model of β-Thalassemia In thalassemia syndromes, which represent the most common causes of ineffective erythropoiesis, imbalances in the expression of α- and β-globin chains result in anemia due to increased apoptosis during erythroblast maturation. RBC transfusion is currently a key maintenance therapy in thalassemia but over time causes potentially lethal iron accumulation in certain tissues (Tanno et al, 2010, Adv Hematol 2010:358283). For example, heart disease associated with iron overload can account for 50% of mortality in patients with thalassemia major (Borgna-Pignatti et al, 2005, Ann NY Acad Sci 1054:40-47). Importantly, endogenous EPO levels are typically elevated and contribute to disease etiology in thalassemia syndromes as well as other disorders of ineffective erythropoiesis; therefore, therapeutic use of recombinant EPO may be inappropriate. Thus, there is the need for alternative therapies for thalassemia and other disorders of ineffective erythropoiesis that would increase RBC levels without the iron overload that accompanies chronic transfusions.

Applicants investigated the effect of ActRIIB(L79D 25-131)-mFc on RBC formation in a mouse model of β-thalassemia intermedia in which the entire coding region of the 3-maj or globin coding gene has been deleted. Mice homozygous for this Hbb$^{th-1}$ allele exhibit a hypochromic, micocytic anemia with inclusion bodies in a high proportion of circulating RBCs (Skow et al, 1983, Cell 1043:1043-1052). In a preliminary experiment, Hbb$^{-/-}$ β-thalassemic mice (C57BL/6J-Hbb$^{d3th}$/J) at 2-5 months of age were randomly assigned to receive ActRIIB(L79D 25-131)-mFc (10 mg/kg) or vehicle (Tris-buffered saline) by subcutaneous injection twice-weekly. Wildtype littermates dosed with vehicle served as additional controls. Blood samples (100 µl) were collected by cheek bleed before the onset of dosing and at regular intervals thereafter for CBC analysis. Characterization of hematologic parameters at baseline confirmed that Hbb$^{-/-}$ 3-thalassemic mice were severely anemic (FIGS. 32A-C), and treatment of Hbb$^{-/-}$ mice with ActRIIB (L79D 25-131)-mFc for 4 weeks increased RBC number markedly compared with vehicle-treated Hbb$^{-/-}$ mice, thereby reducing the anemia observed in this model by half (FIG. 33). Treatment-associated increases in hematocrit and hemoglobin concentration were also seen. Importantly, treatment of Hbb$^{-/-}$ mice with ActRIIB(L79D 25-131)-mFc also resulted in improved RBC morphology and reduced hemolysis and erythrocytic debris compared to vehicle-treated Hbb$^{-/-}$ mice (FIG. 34), thus indicating a fundamental improvement in erythropoiesis. Hence, a GDF Trap polypeptide with truncated ActRIIB extracellular domain can provide therapeutic benefit for anemia in a murine model of β-thalassemia by increasing both RBC number and morphology. By promoting erythroblast maturation while reducing anemia, GDF Trap polypeptides can treat ineffective erythropoiesis. Unlike transfusions, which are inherently a source of exogenous iron, a GDF Trap polypeptide can raise RBC levels by promoting use of endogenous iron stores via erythropoiesis, thereby avoiding iron overloading and its negative consequences.

Example 23: Effect of a GDF Trap with Truncated ActRIIB Extracellular Domain on EPO Levels, Splenomegaly, Bone Density, and Iron Overload in a Mouse Model of 3-Thalassemia Hypoxia associated with ineffective erythropoiesis causes elevated EPO levels that can drive massive expansion of erythroblasts both within and outside the bone marrow, leading to splenomegaly (spleen enlargement), erythroblast-induced bone pathology, and tissue iron overload, even in the absence of therapeutic RBC transfusions. Untreated iron overload leads to tissue iron deposition, multiple organ dysfunction, and premature mortality (Borgna-Pignatti et al., 2005, Ann NY Acad Sci 1054:40-47; Borgna-Pignatti et al., 2011, Expert Rev Hematol 4:353-366), most often due to cardiomyopathy in severe forms of thalassemia (Lekawan-vijit et al., 2009, Can J Cardiol 25:213-218). By increasing erythropoietic effectiveness, a GDF Trap polypeptide may alleviate not only the underlying anemia and elevated EPO levels but also the associated complications of splenomegaly, bone pathology, and iron overload.

Applicants investigated effects of a GDF Trap polypeptide on these parameters in the same mouse model of β-thalassemia intermedia studied in Example 21. Hbb$^{-/-}$ β-thalassemic mice (C57BL/6J-Hbb$^{d3th}$/J) at 3 months of age were randomly assigned to receive ActRIIB(L79D 25-131)-mFc (1 mg/kg, n=7) or vehicle (Tris-buffered saline, n=7) by subcutaneous injection twice weekly for 2 months. Wildtype littermates dosed with vehicle (n=13) served as additional controls. Blood samples (100 µl) were collected at study termination for CBC analysis. At study termination, bone mineral density was determined by dual energy x-ray absorptiometry (DEXA), serum EPO levels were determined by ELISA, reactive oxygen species (ROS) were quantitated with 2',7'-dichlorodihydrofluorescein diacetate and flow cytometry (Suragani et al., 2012, Blood 119:5276-5284), and hepcidin mRNA levels were determined by quantitative polymerase chain reaction.

This GDF Trap polypeptide exerted multiple hematologic effects consistent with alleviation of ineffective erythropoiesis. Treatment of Hbb$^{-/-}$ mice with ActRIIB(L79D 25-131)-mFc for 2 months increased RBC counts by 25% compared with vehicle-dosed Hbb$^{-/-}$ mice (FIG. 35). In Hbb$^{-/-}$ mice, ActRIIB(L79D 25-131)-mFc treatment also increased hemoglobin concentration and hematocrit significantly at 2 months compared to vehicle controls. These changes were accompanied by reduced levels of circulating reticulocytes (31.3±2.3% vs. 44.8±5.0% for Hbb$^{-/-}$ mice treated with ActRIIB(L79D 25-131)-mFc or vehicle, respectively), which is consistent with alleviation of anemia. As in Example 21, treatment of Hbb$^{-/-}$ mice with ActRIIB(L79D 25-131)-mFc resulted in improved RBC morphology and reduced erythrocytic debris compared to vehicle-dosed Hbb$^{-/-}$ mice. Compared to healthy individuals, patients with thalassemia exhibit an increased rate of RBC destruction and elevated serum levels of bilirubin, which is a product of heme catabolism and marker of hemolysis (Orten, 1971, Ann Clin Lab Sci 1:113-124). In Hbb$^{-/-}$ mice, treatment with ActRIIB(L79D 25-131)-mFc reduced serum bilirubin levels at 2 months by nearly half compared to vehicle (FIG. 36), thereby providing evidence that ActRIIB(L79D 25-131)-mFc can unexpectedly improve the structural/functional integrity of mature RBCs as it promotes RBC formation. Importantly, treatment of Hbb$^{-/-}$ mice with ActRIIB (L79D 25-131)-mFc reduced serum EPO levels at 2 months by more than 60% compared to vehicle in the same model (FIG. 37). Since elevated EPO levels are a hallmark of ineffective erythropoiesis in β-thalassemia, the reduction of such levels here is strong evidence that ActRIIB(L79D 25-131)-mFc alleviates ineffective erythropoiesis itself, not just the anemia it causes, in this murine model of thalassemia.

This GDF Trap polypeptide also produced beneficial changes in endpoints representing major complications of ineffective erythropoiesis. In thalassemia patients, both splenomegaly and bone deterioration are caused by EPO-stimulated erythroid hyperplasia and extramedullary erythropoiesis. In Hbb$^{-/-}$ mice, treatment with ActRIIB(L79D 25-131)-mFc for 2 months reduced spleen weight significantly compared to vehicle (FIGS. 38A and 38B) and fully restored bone mineral density to wildtype values (FIG. 39). Iron homeostasis was also improved significantly by treatment with this GDF Trap polypeptide. Serum iron consists of both unbound (free) iron and iron bound to apotransferin (forming transferin), a specialized protein for transporting elemental iron in the circulation. Serum iron constitutes a relatively small and labile component of total body iron, whereas serum levels of ferritin, another form of iron storage found mainly intracellularly, represent a larger and less labile component. A third measure of iron load is transferin saturation, the degree to which the iron binding capacity of transferin is occupied. In Hbb$^{-/-}$ mice, ActRIIB(L79D 25-131)-mFc treatment for 2 months reduced each of these indicators of iron overload significantly compared to vehicle (FIGS. 40A-C). In addition to its effects on these diverse parameters of iron homeostasis, ActRIIB(L79D 25-131)-mFc normalized tissue iron overload in Hbb$^{-/-}$ mice as determined by histochemical analysis in spleen, liver, and kidney (FIG. 41). Moreover, this GDF Trap polypeptide exerted a beneficial effect on expression of hepcidin, a hepatic protein considered to be the master regulator of iron homeostasis (Gantz, 2011, Blood 117:4425-4433), whose levels vary inversely with dietary iron uptake. Treatment with ActRIIB(L79D 25-131)-mFc reversed the abnormally low expression of hepcidin in liver of Hbb$^{-/-}$ mice (FIG. 42). Finally, another study with similar design was performed to determine the effect of this GDF Trap on reactive oxygen species (ROS), which are thought to mediate many of the toxic effects of iron overload (Rund et al., 2005, N Engl J Med 353:1135-1146). In 3-month-old Hbb$^{-/-}$ mice, treatment with ActRIIB(L79D 25-131)-mFc at 1 mg/kg twice weekly for 2 months nearly normalized ROS levels (FIG. 43) and would therefore be predicted to greatly reduce the tissue damage mediated by ROS in thalassemia and other diseases characterized by ineffective erythropoiesis.

Together, the above findings demonstrate that GDF Trap polypeptides can treat ineffective erythropoiesis, including anemia and elevated EPO levels, as well as complications such as splenomegaly, erythroblast-induced bone pathology, and iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors (Musallam et al., 2012, Cold Spring Harb Perspect Med 2:a013482). With erythroblast-induced bone pathology, attendant pathologies include low bone mineral density, osteoporosis, and bone pain (Haidar et al., 2011, Bone 48:425-432). With iron overload, attendant pathologies include hepcidin suppression and hyperabsorption of dietary iron (Musallam et al., 2012, Blood Rev 26(Suppl 1):S16-S19), multiple endocrinopathies and liver fibrosis/cirrhosis (Galanello et al., 2010, Orphanet J Rare Dis 5:11), and iron-overload cardiomyopathy (Lekawanvijit et al., 2009, Can J Cardiol 25:213-218). In contrast to existing therapies for ineffective erythropoiesis, GDF Trap polypeptides such as ActRIIB(L79D 25-131)-mFc are able to reduce iron overloading in murine models while concurrently increasing RBC levels. This novel capability distinguishes GDF Trap polypeptides from blood transfusions, which inherently burden the body with exogenous iron in the course of treating anemia and do so without alleviating the underlying condition of ineffective erythropoiesis.

Example 24: GDF Trap Increases Hemoglobin Levels and Substantially Resolves a Cutaneous Ulcer in a Thalassemia Patient A clinical study was designed to treat thalassemia patients (P3-thalassemia intermedia and major patients) with multiple does of ActRIIB(L79D 25-131)-hFc. The study comprised both non-transfusion dependent patients (<4 units/8 weeks, hemoglobin <10 g/dL) and transfusion (blood) dependent patients (≥4 units/8 weeks confirmed over 6 months). Patients were divided into one of four treatment groups: i) administration of 0.2 mg/kg ActRIIB(L79D 25-131)-hFc by subcutaneous injection every three weeks; ii) administration of 0.4 mg/kg ActRIIB(L79D 25-131)-hFc by subcutaneous injection every three weeks; iii) administration of 0.6 mg/kg ActRIIB(L79D 25-131)-hFc by subcutaneous injection every three weeks; and iv) administration of 0.8 mg/kg ActRIIB(L79D 25-131)-hFc by subcutaneous injection every three weeks. Over the course of three months of treatment, patients were observed to have significant, dose-dependent increases in hemoglobin levels. Furthermore, ActRIIB(L79D 25-131)-hFc treatment was effective at decreasing transfusion dependency, i.e., all transfusion dependent patients experienced a >50% reduction in transfusion burden during the course of the study.

One patient with a baseline hemoglobin level of approximately 9.2 g/dL received 4 doses of ActRIIB(L79D 25-131)-hFc at the 0.4 mg/kg level, resulting in a hemoglobin level of approximately 10.6 g/dL after three months of treatment. The patient's thalassemia was β-thalassemia intermedia, and the patient was non-transfusion dependent. For approximately three years prior to this study, this patient had been afflicted with recurrent skin ulcers in the lower limbs. Such ulcers are common cutaneous complications of thalassemia. See, e.g., Rassi et al. (2008) Pediatric Annals 37(5): 322-328. Prior to ActRIIB(L79D 25-131)-hFc treatment, this patient was diagnosed with a leg ulcer. Ulcer healing was observed two weeks after administration of the first ActRIIB (L79D 25-131)-hFc dose. After six weeks of ActRIIB(L79D 25-131)-hFc treatment, the leg ulcer was determined to be substantially resolved. A second non-transfusion dependent patient began the study with a leg ulcer. The leg ulcer was substantially resolved after treatment with several doses of ActRIIB(L79D 25-131)-hFc at 1.25 mg/kg. In addition, a transfusion-dependent patient began the study with an ulcer on the left ankle. After five doses of ActRIIB(L79D 25-131)-hFc at 1.0 mg/kg the ulcer was substantially resolved and remained so for the duration of the study. Accordingly, ActRIIB(L79D 25-131)-hFc can be used to effectively treat ulcers that manifest in non-transfusion and transfusion dependent thalassemia patients.

Accordingly, these data demonstrate that ActRIIB(L79D 25-131)-hFc treatment is effective in increasing hemoglobin levels and can be used to reduced transfusion dependency in human thalassemia patients. In addition to the positive effects on the anemia aspects of the disease, the significant improvement in healing of the leg ulcers indicates that ActRIIB(L79D 25-131)-hFc can be used to effectively treat other non-anemia complications of thalassemia, which is consistent with the data from the mouse model of 3-thalassemia described above.

Example 25: GDF Trap Increases Red Blood Cell Levels and Improves Red Blood Cell Morphology in Sickle-Cell Disease Model Applicants investigated the effect of ActRIIB(L79D 25-131)-mFc on red blood cell (RBC) formation in a mouse model of sickle-cell disease (SCD) in which the mouse hemoglobin genes ($\alpha/\alpha$ and $\beta/\beta$) have been replaced with the human sickle hemoglobin genes ($\alpha/\alpha$, $\gamma/\gamma$, and $\beta^S/\beta^S$) Mice homozygous for the human ($\beta^S$ allele exhibit the major features (e.g., sever hemolytic anemia, irreversibly sickled red cells, vascular (vaso) occlusion, and multi-organ pathology) found in humans with SCD. See, e.g., Wu et al., (2006) Blood, 108(4): 1183-1188; Ryan et al. (1997) Science 278: 873-876.

SCD mice ($\beta^S/(\beta^S)$) at 3 months of age were randomly assigned to receive ActRIIB(L79D 25-131)-mFc (1 mg/kg) or vehicle [Tris-buffered saline (TBS)] by subcutaneous injections twice weekly. Non-symptomatic compound heterozygote ($\beta/\beta^S$) littermates dosed with vehicle served as additional controls (Wt animals). At baseline, SCD mice had reduced RBC levels (−28%, P<0.01) and hemoglobin levels (−14.5%, P<0.05) and increased reticulocyte levels (+50%, P<0.001) compared to the compound heterozygote mice, demonstrating that the SCD mice were severely anemic.

Following one month of treatment, subjects were assessed for changes in various red blood cell parameters. Treatment of SCD mice with ActRIIB(L79D 25-131)-mFc for 4 weeks increased RBC levels markedly (+15.2%, p<0.01) compared to vehicle-treated SCD mice, thereby reducing the anemia observed in this model (FIGS. 44 and 45). ActRIIB(L79D 25-131)-mFc treatment-associated increases in hematocrit and hemoglobin concentrations were also observed (FIG. 45) as well as significant decreases in mean corpuscular volume, RDC distribution width, reticulocyte numbers, and reactive oxygen species (FIG. 46), which is all consistent with improved red blood cell half-life. Surprisingly, treatment of SCD mice with ActRIIB(L79D 25-131)-mFc for 6 weeks resulted in a substantial decrease in phosphatidylserine (PS) exposure in peripheral blood cells (−14%, P=0.08), as determined by scramblase enzyme assay and annexin-V assay, indicating a trend toward improved membrane phospholipid asymmetry compared to vehicle-treated subjects.

Following three months of treatment, subjects were observed to have improvements in additional blood chemistry parameters. In particular, treatment of SCD mice with ActRIIB(L79D 25-131)-mFc for 12 weeks significantly decreased bilirubin (total) levels (−17.0%, p<0.05), blood urea nitrogen levels (−19.2%, p<0.05), and cell free hemoglobin (−30.7%, p=0.06) compared to vehicle-treated SCD mice. These data indicate that GDF Trap-treated subjects have decreased levels of red blood cell hemolysis in comparison to vehicle-treated subjects, which is consistent with the observed increase of red blood cell levels observed as early as one month following the start of ActRIIB(L79D 25-131)-mFc therapy. Annexin-V assays demonstrated a significant decrease in phosphatidylserine (PS) exposure in peripheral blood cells (−13.4%, p=0.06) after three months of therapy in comparison to vehicle-treated subjects. Moreover, blood smears performed after three months of treatment showed fewer irreversibly sickle-formed red blood cells in ActRIIB(L79D 25-131)-mFc-treated mice (−66.5%, p<0.0001; enumerated from approximately 2000 cells per group) in comparison to mice treated with vehicle alone. These data indicate a qualitative improvement in red blood cell morphology following ActRIIB(L79D 25-131)-mFc treatment, which is consistent with the scramblase enzyme assay and annexin-V assay data obtained after one and three months of ActRIIB(L79D 25-131)-mFc treatment. Furthermore, treatment of SCD mice with the GDF Trap for three months also resulted in a significant decrease in spleen weight (−20.5%, p<0.05) in comparison to vehicle-treated SCD mice. These data indicate that ActRIIB(L79D 25-131)-mFc may be useful in the treatment of other complications associated with SCD including, for example, splenic sequestration of red blood cells, which can result in splenic sequestration crisis and/or splenomegaly.

Together, these data indicate that a GDF Trap comprising a truncated ActRIIB extracellular domain can provide various therapeutic benefits in a murine model of SCD. In addition to increasing RBC levels and improving various blood parameters, the data demonstrate improvement in RBC morphology. This observed improvement in RBC morphology indicates that GDF Trap treatment may be used to treat or prevent various other complications of SCD (e.g., complications arising from vaso-occlusion) in addition to anemia. This is further supported by the observed decrease in spleen size in ActRIIB(L79D 25-131)-mFc-treated subjects.

Accordingly, the data presented herein suggest that GDF Trap polypeptides can be used to treat a variety of complications of sickle-cell disease. Unlike red blood cell transfusions, which are inherently a source of exogenous iron, a GDF Trap polypeptide can raise RBC levels by promoting use of endogenous iron stores via erythropoiesis and thus avoid iron overloading and its negative consequences.

As observed in thalassemia patients, skin ulcers are one of the most common cutaneous complications of sickle-cell disease. See, e.g., Keast et al. (2004) Ostomy Wound Manage., 50(10): 64-70; Trent et al. (2004) Adv Skin Wound Care, 17(8): 410-416; and J. R. Eckman (1996) Hematol Oncol Clin North Am., 10(6): 1333-1344. The underlying mechanism for ulcer formation in anemic patients has not been completely defined. However, it is believed that multiple complications of anemia contribute to ulcer development including, for example, ischemia, decreased nitric oxide bioavailability, vascular obstruction (particularly in the case of sickle-cell anemia and thalassemia), thrombosis, high levels of circulating reticulocytes, and hypoxia. Id. As discussed above, the instant disclosure demonstrates that ActRIIB(L79D 25-131)-Fc treatment alleviates many of these sickle-cell disease associated conditions. Accordingly, the data disclosed herein suggests that, as was observed in thalassemia patients described above, ActRII antagonists may be used in the treatment and prevention of ulcers in patients that have sickle-cell disease.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

I claim:

1. A method for treating a cutaneous ulcer in a subject that has a hemoglobinopathy anemia, comprising administering to the subject an ActRIIB polypeptide; wherein the polypeptide comprises an amino acid sequence that is at least 85% identical to the sequence of amino acids 29-109 of SEQ ID NO: 1.

2. The method of claim 1, wherein the polypeptide comprises an amino acid sequence that is at least 90% identical to the sequence of amino acids 29-109 of SEQ ID NO: 1, wherein the polypeptide comprises an acidic amino acid at the position corresponding to position 79 of SEQ ID NO: 1.

3. The method of claim 1, wherein the polypeptide is a fusion protein further comprising an immunoglobulin Fc domain.

4. The method of claim 3, wherein the fusion protein further comprises a linker domain positioned between the polypeptide and the immunoglobulin Fc domain.

5. The method of claim 1, wherein the polypeptide comprises one or more amino acid modifications selected from: a glycosylated amino acid, a PEGylated amino acid, a farnesylated amino acid, an acetylated amino acid, a biotinylated amino acid, and an amino acid conjugated to a lipid moiety.

6. The method of claim 1, wherein the polypeptide comprises an amino acid sequence that is 95% identical to amino acids 29-109 of SEQ ID NO: 1, and wherein the polypeptide comprises an acidic amino acid at the position corresponding to position 79 of SEQ ID NO: 1.

7. The method of claim 1, wherein the polypeptide comprises amino acids 29-109 of SEQ ID NO: 1, but wherein the polypeptide comprises an acidic amino acid at the position corresponding to position 79 of SEQ ID NO: 1.

8. The method of claim 1, wherein the polypeptide comprises an amino acid sequence that is at least 85% identical to the sequence of amino acids 25-131 of SEQ ID NO: 1, and wherein the polypeptide comprises an acidic amino acid at the position corresponding to position 79 of SEQ ID NO: 1.

9. The method of claim 1, wherein the polypeptide comprises an amino acid sequence that is at least 90% identical to the sequence of amino acids 25-131 of SEQ ID NO: 1, and wherein the polypeptide comprises an acidic amino acid at the position corresponding to position 79 of SEQ ID NO: 1.

10. The method of claim 1, wherein the polypeptide comprises an amino acid sequence that is at least 95% identical to the sequence of amino acids 25-131 of SEQ ID NO: 1, and wherein the polypeptide comprises an acidic amino acid at the position corresponding to position 79 of SEQ ID NO: 1.

11. The method of claim 1, wherein the polypeptide comprises amino acids 25-131 of SEQ ID NO: 1, but wherein the polypeptide comprises an acidic amino acid at the position corresponding to position 79 of SEQ ID NO: 1.

12. The method of claim 1, wherein the polypeptide comprises an amino acid sequence that is at least 85% identical to SEQ ID NO: 44, and wherein the polypeptide comprises an acidic amino acid at the position corresponding to position 79 of SEQ ID NO: 1.

13. The method of claim 1, wherein the polypeptide comprises an amino acid sequence that is at least 90% identical to SEQ ID NO: 44, and wherein the polypeptide comprises an acidic amino acid at the position corresponding to position 79 of SEQ ID NO: 1.

14. The method of claim 1, wherein the polypeptide comprises an amino acid sequence that is at least 95% identical to SEQ ID NO: 44, and wherein the polypeptide comprises an acidic amino acid at the position corresponding to position 79 of SEQ ID NO: 1.

15. The method of claim 1, wherein the polypeptide comprises the amino acid sequence of SEQ ID NO: 44, but wherein the polypeptide comprises an acidic amino acid at the position corresponding to position 79 of SEQ ID NO: 1.

16. The method of claim 1, wherein the polypeptide inhibits signaling by GDF8 in a cell-based assay.

17. The method of claim 1, wherein the polypeptide inhibits signaling by GDF11 in a cell-based assay.

18. The method of claim 1, wherein the amino acid at the position corresponding to position 79 of SEQ ID NO: 1 is an aspartic acid.

19. The method of claim 1, wherein the amino acid at the position corresponding to position 79 of SEQ ID NO: 1 is a glutamic acid.

20. The method of claim 1, wherein the polypeptide binds GDF8.

21. The method of claim 1, wherein the polypeptide binds GDF11.

* * * * *

SEQUENCE LISTING

```
<160> NUMBER OF SEQ ID NOS: 69

<210> SEQ ID NO 1
<211> LENGTH: 512
<212> TYPE: PRT
<213> ORGANISM: Homo sapiens

<400> SEQUENCE: 1

Met Thr Ala Pro Trp Val Ala Leu Ala Leu Leu Trp Gly Ser Leu Cys
1               5                   10                  15
```

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Glu Gly Asn Phe Cys Asn Glu Arg
            100                 105                 110

Phe Thr His Leu Pro Glu Ala Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Gly Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 3
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

```
<210> SEQ ID NO 4
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

```
Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 5
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 6
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30
```

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
            50                  55                  60

Cys Tyr Asp Arg Gln Glu Cys Val Ala Thr Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
        100

<210> SEQ ID NO 7
<211> LENGTH: 1536
<212> TYPE: DNA
<213> ORGANISM: Homo sapiens

<400> SEQUENCE: 7

| | | | | | |
|---|---|---|---|---|---|
| atgacggcgc | cctgggtggc | cctcgccctc | tctctgggat | cgctgtgcgc | cggctctggg | 60 |
| cgtggggagg | ctgagacacg | ggagtgcatc | tactacaacg | ccaactggga | gctggagcgc | 120 |
| accaaccaga | gcggcctgga | gcgctgcgaa | ggcgagcagg | acaagcggct | gcactgctac | 180 |
| gcctcctggc | gcaacagctc | tggcaccatc | gagctcgtga | agaagggctg | ctggctagat | 240 |
| gacttcaact | gctacgatag | gcaggagtgt | gtggccactg | aggagaaccc | ccaggtgtac | 300 |
| ttctgctgct | gtgaaggcaa | cttctgcaac | gaacgcttca | ctcatttgcc | agaggctggg | 360 |
| ggcccggaag | tcacgtacga | gccaccccg | acagccccca | ccctgctcac | ggtgctggcc | 420 |
| tactcactgc | tgcccatcgg | gggccttttcc | ctcatcgtcc | tgctggcctt | ttggatgtac | 480 |
| cggcatcgca | agccccccta | cggtcatgtg | gacatccatg | aggaccctgg | gcctccacca | 540 |
| ccatcccctc | tggtgggcct | gaagccactg | cagctgctgg | agatcaaggc | tcggggcgc | 600 |
| tttggctgtg | tctggaaggc | ccagctcatg | aatgactttg | tagctgtcaa | gatcttccca | 660 |
| ctccaggaca | agcagtcgtg | gcagagtgaa | cgggagatct | tcagcacacc | tggcatgaag | 720 |
| cacgagaacc | tgctacagtt | cattgctgcc | gagaagcgag | gctccaacct | cgaagtagag | 780 |
| ctgtggctca | tcacggcctt | ccatgacaag | ggctcctca | cggattacct | caagggggaac | 840 |
| atcatcacat | ggaacgaact | gtgtcatgta | gcagagacga | tgtcacgagg | cctctcatac | 900 |
| ctgcatgagg | atgtgccctg | gtgccgtggc | gagggccaca | agccgtctat | tgcccacagg | 960 |
| gactttaaaa | gtaagaatgt | attgctgaag | agcgacctca | cagccgtgct | ggctgacttt | 1020 |
| ggcttggctg | ttcgatttga | gccagggaaa | cctccagggg | acacccacgg | acaggtaggc | 1080 |
| acgagacggt | acatggctcc | tgaggtgctc | gagggagcca | tcaacttcca | gagagatgcc | 1140 |
| ttcctgcgca | ttgacatgta | tgccatgggg | ttggtgctgt | gggagcttgt | gtctcgctgc | 1200 |
| aaggctgcag | acggacccgt | ggatgagtac | atgctgccct | ttgaggaaga | gattggccag | 1260 |
| caccttcgt | tggaggagct | gcaggaggtg | gtggtgcaca | agaagatgag | gcccaccatt | 1320 |
| aaagatcact | ggttgaaaca | cccgggcctg | gcccagcttt | gtgtgaccat | cgaggagtgc | 1380 |
| tgggaccatg | atgcagaggc | tcgcttgtcc | gcgggctgtg | tggaggagcg | ggtgtccctg | 1440 |
| attcggaggt | cggtcaacgg | cactacctcg | gactgtctcg | tttccctggt | gacctctgtc | 1500 |
| accaatgtgg | acctgccccc | taaagagtca | agcatc | | | 1536 |

<210> SEQ ID NO 8
<211> LENGTH: 345

```
<212> TYPE: DNA
<213> ORGANISM: Homo sapiens

<400> SEQUENCE: 8
gggcgtgggg aggctgagac acgggagtgc atctactaca acgccaactg ggagctggag      60
cgcaccaacc agagcggcct ggagcgctgc gaaggcgagc aggacaagcg gctgcactgc     120
tacgcctcct ggcgcaacag ctctggcacc atcgagctcg tgaagaaggg ctgctggcta     180
gatgacttca actgctacga taggcaggag tgtgtggcca ctgaggagaa ccccaggtg     240 tacttctgct gctgtgaagg caacttctgc aacgaacgct tcactcattt gccagaggct     300
gggggcccgg aagtcacgta cgagccaccc ccgacagccc ccacc                     345

<210> SEQ ID NO 9
<211> LENGTH: 513
<212> TYPE: PRT
<213> ORGANISM: Homo sapiens

<400> SEQUENCE: 9

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285
```

-continued

Leu Cys His Ile Ala Glu Thr Met Ala Arg Gly Leu Ala Tyr Leu His
290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
                340                 345                 350

Ala Gly Asp Thr His Gly Gln Val Gly Thr Arg Arg Tyr Met Ala Pro
                355                 360                 365

Glu Val Leu Glu Gly Ala Ile Asn Phe Gln Arg Asp Ala Phe Leu Arg
370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
                420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
        450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 10
<211> LENGTH: 115
<212> TYPE: PRT
<213> ORGANISM: Homo sapiens

<400> SEQUENCE: 10

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
                35                  40                  45

Gly Ser Ile Glu Ile Val Lys Gln Gly Cys Trp Leu Asp Asp Ile Asn
50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 11
<211> LENGTH: 100

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ile Leu Gly Arg Ser Glu Thr Gln Glu Cys Leu Phe Phe Asn Ala Asn
1               5                  10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met
            100

<210> SEQ ID NO 12
<211> LENGTH: 1539
<212> TYPE: DNA
<213> ORGANISM: Homo sapiens

<400> SEQUENCE: 12
```

| | |
|---|---|
| atgggagctg ctgcaaagtt ggcgtttgcc gtctttctta tctcctgttc ttcaggtgct | 60 |
| atacttggta gatcagaaac tcaggagtgt cttttcttta tgctaattg ggaaaaagac | 120 |
| agaaccaatc aaactggtgt tgaaccgtgt tatggtgaca agataaacg gcggcattgt | 180 |
| tttgctacct ggaagaatat ttctggttcc attgaaatag tgaaacaagg ttgttggctg | 240 |
| gatgatatca actgctatga caggactgat tgtgtagaaa aaaagacag ccctgaagta | 300 |
| tatttttgtt gctgtgaggg caatatgtgt aatgaaaagt tttcttattt tccggagatg | 360 |
| gaagtcacac agcccacttc aaatccagtt acacctaagc caccctatta caacatcctg | 420 |
| ctctattcct tggtgccact tatgttaatt gcggggattg tcatttgtgc attttgggtg | 480 |
| tacaggcatc acaagatggc ctaccctcct gtacttgttc aactcaaga cccaggacca | 540 |
| cccccacctt ctccattact aggttttgaaa ccactgcagt tattagaagt gaaagcaagg | 600 |
| ggaagatttg gttgtgtctg gaaagcccag ttgcttaacg aatatgtggc tgtcaaaata | 660 |
| tttccaatac aggacaaaca gtcatggcaa atgaatacg aagtctacag tttgcctgga | 720 |
| atgaagcatg agaacatatt acagttcatt ggtgcagaaa aacgaggcac cagtgttgat | 780 |
| gtggatcttt ggctgatcac agcatttcat gaaagggtt cactatcaga ctttcttaag | 840 |
| gctaatgtgg tctcttggaa tgaactgtgt catattgcag aaaccatggc tagaggattg | 900 |
| gcatatttac atgaggatat acctggccta aaagatggcc acaaacctgc catatctcac | 960 |
| agggacatca aagtaaaaa tgtgctgttg aaaaacaacc tgacagcttg cattgctgac | 1020 |
| tttgggttgg ccttaaaatt tgaggctggc aagtctgcag cgatacccca tggacaggtt | 1080 |
| ggtacccgga ggtacatggc tccagagta ttagagggtg ctataaactt ccaaagggat | 1140 |
| gcattttga ggtagatat gtatgccatg ggattagtcc tatgggaact ggcttctcgc | 1200 |
| tgtactgctg cagatggacc tgtagatgaa tacatgttgc catttgagga ggaaattggc | 1260 |

```
cagcatccat ctcttgaaga catgcaggaa gttgttgtgc ataaaaaaaa gaggcctgtt    1320
ttaagagatt attggcagaa acatgctgga atggcaatgc tctgtgaaac cattgaagaa    1380
tgttgggatc acgacgcaga agccaggtta tcagctggat gtgtaggtga agaattacc    1440 cagatgcaga gactaacaaa tattattacc acagaggaca ttgtaacagt ggtcacaatg    1500
gtgacaaatg ttgactttcc tcccaaagaa tctagtcta                           1539

<210> SEQ ID NO 13
<211> LENGTH: 345
<212> TYPE: DNA
<213> ORGANISM: Homo sapiens

<400> SEQUENCE: 13
atacttggta gatcagaaac tcaggagtgt cttttcttta atgctaattg ggaaaaagac     60
agaaccaatc aaactggtgt tgaaccgtgt tatggtgaca aagataaacg gcggcattgt    120
tttgctacct ggaagaatat ttctggttcc attgaaatag tgaaacaagg ttgttggctg    180
gatgatatca actgctatga caggactgat tgtgtagaaa aaaagacag ccctgaagta     240 tatttttgtt gctgtgaggg caatatgtgt aatgaaaagt tttcttattt tccggagatg    300
gaagtcacac agcccacttc aaatccagtt acacctaagc caccc                    345

<210> SEQ ID NO 14
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Thr His Thr Cys Pro Pro Cys Pro Ala Pro Glu Leu Leu Gly Gly Pro
 1               5                  10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205
```

```
Ala Leu His Asn His Tyr Thr Gln Lys Ser Leu Ser Leu Ser Pro Gly
    210                 215                 220

Lys
225

<210> SEQ ID NO 15
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 15

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 16
<211> LENGTH: 344
<212> TYPE: PRT
```

<213> ORGANISM: Homo sapiens

<400> SEQUENCE: 16

```
Met Val Arg Ala Arg His Gln Pro Gly Gly Leu Cys Leu Leu Leu Leu
1               5                   10                  15
Leu Leu Cys Gln Phe Met Glu Asp Arg Ser Ala Gln Ala Gly Asn Cys
            20                  25                  30
Trp Leu Arg Gln Ala Lys Asn Gly Arg Cys Gln Val Leu Tyr Lys Thr
        35                  40                  45
Glu Leu Ser Lys Glu Cys Cys Ser Thr Gly Arg Leu Ser Thr Ser
    50                  55                  60
Trp Thr Glu Glu Asp Val Asn Asp Asn Thr Leu Phe Lys Trp Met Ile
65                  70                  75                  80
Phe Asn Gly Gly Ala Pro Asn Cys Ile Pro Cys Lys Glu Thr Cys Glu
                85                  90                  95
Asn Val Asp Cys Gly Pro Gly Lys Lys Cys Arg Met Asn Lys Lys Asn
                100                 105                 110
Lys Pro Arg Cys Val Cys Ala Pro Asp Cys Ser Asn Ile Thr Trp Lys
            115                 120                 125
Gly Pro Val Cys Gly Leu Asp Gly Lys Thr Tyr Arg Asn Glu Cys Ala
    130                 135                 140
Leu Leu Lys Ala Arg Cys Lys Glu Gln Pro Glu Leu Glu Val Gln Tyr
145                 150                 155                 160
Gln Gly Arg Cys Lys Lys Thr Cys Arg Asp Val Phe Cys Pro Gly Ser
                165                 170                 175
Ser Thr Cys Val Val Asp Gln Thr Asn Asn Ala Tyr Cys Val Thr Cys
                180                 185                 190
Asn Arg Ile Cys Pro Glu Pro Ala Ser Ser Glu Gln Tyr Leu Cys Gly
            195                 200                 205
Asn Asp Gly Val Thr Tyr Ser Ser Ala Cys His Leu Arg Lys Ala Thr
    210                 215                 220
Cys Leu Leu Gly Arg Ser Ile Gly Leu Ala Tyr Glu Gly Lys Cys Ile
225                 230                 235                 240
Lys Ala Lys Ser Cys Glu Asp Ile Gln Cys Thr Gly Gly Lys Lys Cys
                245                 250                 255
Leu Trp Asp Phe Lys Val Gly Arg Gly Arg Cys Ser Leu Cys Asp Glu
                260                 265                 270
Leu Cys Pro Asp Ser Lys Ser Asp Glu Pro Val Cys Ala Ser Asp Asn
            275                 280                 285
Ala Thr Tyr Ala Ser Glu Cys Ala Met Lys Glu Ala Ala Cys Ser Ser
    290                 295                 300
Gly Val Leu Leu Glu Val Lys His Ser Gly Ser Cys Asn Ser Ile Ser
305                 310                 315                 320
Glu Asp Thr Glu Glu Glu Glu Asp Glu Asp Gln Asp Tyr Ser Phe
                325                 330                 335
Pro Ile Ser Ser Ile Leu Glu Trp
            340
```

<210> SEQ ID NO 17
<211> LENGTH: 317
<212> TYPE: PRT
<213> ORGANISM: Homo sapiens

<400> SEQUENCE: 17

Met Val Arg Ala Arg His Gln Pro Gly Gly Leu Cys Leu Leu Leu Leu

```
                1               5                  10                 15
Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
                35                  40                  45

Glu Leu Ser Lys Glu Glu Cys Cys Ser Thr Gly Arg Leu Ser Thr Ser
                50                  55                  60

Trp Thr Glu Glu Asp Val Asn Asp Asn Thr Leu Phe Lys Trp Met Ile
 65                 70                  75                  80

Phe Asn Gly Gly Ala Pro Asn Cys Ile Pro Cys Lys Glu Thr Cys Glu
                    85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
                115                 120                 125

Gly Pro Val Cys Gly Leu Asp Gly Lys Thr Tyr Arg Asn Glu Cys Ala
                130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                    165                 170                 175

Ser Thr Cys Val Val Asp Gln Thr Asn Asn Ala Tyr Cys Val Thr Cys
                180                 185                 190

Asn Arg Ile Cys Pro Glu Pro Ala Ser Ser Glu Gln Tyr Leu Cys Gly
                195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                    245                 250                 255

Leu Trp Asp Phe Lys Val Gly Arg Gly Arg Cys Ser Leu Cys Asp Glu
                260                 265                 270

Leu Cys Pro Asp Ser Lys Ser Asp Glu Pro Val Cys Ala Ser Asp Asn
                275                 280                 285

Ala Thr Tyr Ala Ser Glu Cys Ala Met Lys Glu Ala Ala Cys Ser Ser
                290                 295                 300

Gly Val Leu Leu Glu Val Lys His Ser Gly Ser Cys Asn
305                 310                 315

<210> SEQ ID NO 18
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
                35                  40                  45
```

```
Trp Met Ile Phe Asn Gly Gly Ala Pro Asn Cys Ile Pro Cys Lys
         50                  55                  60

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Thr Cys Glu Asn Val Asp Cys Gly Pro Gly Lys Lys Cys Arg Met
1               5                   10                  15

Asn Lys Lys Asn Lys Pro Arg Cys Val
            20                  25

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Thr Cys Arg Asp Val Phe Cys Pro Gly Ser Ser Thr Cys Val Val
1               5                   10                  15

Asp Gln Thr Asn Asn Ala Tyr Cys Val Thr
            20                  25

<210> SEQ ID NO 21
<211> LENGTH: 263
<212> TYPE: PRT
<213> ORGANISM: Homo sapiens

<400> SEQUENCE: 21

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
```

```
                180                 185                 190
Val Val Cys Arg Ala Ala Pro Cys Pro Val Pro Ser Ser Pro Gly Gln
            195                 200                 205

Glu Leu Cys Gly Asn Asn Val Thr Tyr Ile Ser Ser Cys His Met
    210                 215                 220

Arg Gln Ala Thr Cys Phe Leu Gly Arg Ser Ile Gly Val Arg His Ala
225                 230                 235                 240

Gly Ser Cys Ala Gly Thr Pro Glu Glu Pro Pro Gly Gly Glu Ser Ala
            245                 250                 255

Glu Glu Glu Glu Asn Phe Val
            260

<210> SEQ ID NO 22
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270
```

```
Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr
        290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Lys Phe Leu Val Asn Val Ala Leu Val Phe Met Val Val Tyr Ile
1               5                   10                  15

Ser Tyr Ile Tyr Ala
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Asp Ala Met Lys Arg Gly Leu Cys Cys Val Leu Leu Leu Cys Gly
1               5                   10                  15

Ala Val Phe Val Ser Pro
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Gly Ala Ala Ala Lys Leu Ala Phe Ala Val Phe Leu Ile Ser Cys
1               5                   10                  15

Ser Ser Gly Ala
            20

<210> SEQ ID NO 26
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Ala Met Lys Arg Gly Leu Cys Cys Val Leu Leu Leu Cys Gly
1               5                   10                  15
```

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
         35                  40                  45

Gln Thr Gly Val Glu Pro Cys Tyr Gly Asp Lys Asp Lys Arg Arg His
     50                  55                  60

Cys Phe Ala Thr Trp Lys Asn Ile Ser Gly Ser Ile Glu Ile Val Lys
 65                  70                  75                  80

Gln Gly Cys Trp Leu Asp Asp Ile Asn Cys Tyr Asp Arg Thr Asp Cys
                 85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 27
<211> LENGTH: 1114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta     120
attgggaaaa agacagaacc aatcaaactg tgttgaacc gtgttatggt gacaaagata      180
aacggcggca ttgttttgct acctggaaga atatttctgg ttccattgaa tagtgaaaca     240
aggttgttgg ctggatgata tcaactgcta tgacaggact gattgtgtag aaaaaaaaga     300
cagccctgaa gtatatttct gttgctgtga gggcaatatg tgtaatgaaa agttttctta     360
ttttccggag atggaagtca cacagcccac ttcaaatcca gttacaccta agccacccac     420
cggtggtgga actcacacat gcccaccgtg cccagcacct gaactcctgg ggggaccgtc     480
agtcttcctc ttccccccaa acccaaggac acccctcatg atctcccgga cccctgaggt     540
cacatgcgtg gtggtggacg tgagccacga agaccctgag gtcaagttca actggtacgt     600
ggacggcgtg gaggtgcata atgccaagac aaagccgcgg gaggagcagt acaacagcac     660
gtaccgtgtg gtcagcgtcc tcaccgtcct gcaccaggac tggctgaatg caaggagta     720
caagtgcaag gtctccaaca aagccctccc agtccccatc gagaaaacca tctccaaagc     780
caaagggcag ccccgagaac cacaggtgta caccctgccc ccatcccggg aggagatgac     840
caagaaccag gtcagcctga cctgcctggt caaaggcttc tatcccagcg acatcgccgt     900
ggagtgggag agcaatgggc agccggagaa caactacaag accacgcctc ccgtgctgga     960
ctccgacggc tccttcttcc tctatagcaa gctcaccgtg gacaagagca ggtggcagca    1020
ggggaacgtc ttctcatgct ccgtgatgca tgaggctctg cacaaccact acacgcagaa    1080
gagcctctcc ctgtctccgg gtaaatgaga attc                                1114
```

<210> SEQ ID NO 28
<211> LENGTH: 329
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 28

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160
```

```
Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 29
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
```

```
                    180                 185                 190
Asn Ser Thr Tyr Arg Val Val Ser Val Leu Thr Val Leu His Gln Asp
                195                 200                 205
Trp Leu Asn Gly Lys Glu Tyr Lys Cys Lys Val Ser Asn Lys Ala Leu
            210                 215                 220
Pro Val Pro Ile Glu Lys Thr Ile Ser Lys Ala Lys Gly Gln Pro Arg
225                 230                 235                 240
Glu Pro Gln Val Tyr Thr Leu Pro Pro Ser Arg Glu Glu Met Thr Lys
                245                 250                 255
Asn Gln Val Ser Leu Thr Cys Leu Val Lys Gly Phe Tyr Pro Ser Asp
                260                 265                 270
Ile Ala Val Glu Trp Glu Ser Asn Gly Gln Pro Glu Asn Asn Tyr Lys
            275                 280                 285
Thr Thr Pro Pro Val Leu Asp Ser Asp Gly Ser Phe Phe Leu Tyr Ser
        290                 295                 300
Lys Leu Thr Val Asp Lys Ser Arg Trp Gln Gln Gly Asn Val Phe Ser
305                 310                 315                 320
Cys Ser Val Met His Glu Ala Leu His Asn His Tyr Thr Gln Lys Ser
                325                 330                 335
Leu Ser Leu Ser Pro Gly Lys
            340

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Thr Ala Pro Trp Val Ala Leu Ala Leu Leu Trp Gly Ser Leu Cys
1               5                   10                  15

Ala Gly Ser

<210> SEQ ID NO 31
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
        50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
                100                 105                 110
```

```
Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Asp Val Ser His Glu Asp Pro
            180                 185                 190

Glu Val Lys Phe Asn Trp Tyr Val Asp Gly Val Glu Val His Asn Ala
    195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
    275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
    355                 360                 365

<210> SEQ ID NO 32
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc   120
aactgggagc tggagcgcac caaccagagc ggcctggagc gctgcgaagg cgagcaggac   180
aagcggctgc actgctacgc ctcctggcgc aacagctctg gcaccatcga gctcgtgaag   240
aagggctgct ggctagatga cttcaactgc tacgataggc aggagtgtgt ggccactgag   300
gagaaccccc aggtgtactt ctgctgctgt gaaggcaact tctgcaacga gcgcttcact   360
catttgccag aggctggggg cccggaagtc acgtacgagc caccccgac agcccccacc   420 ggtggtggaa ctcacacatg cccaccgtgc ccagcacctg aactcctggg gggaccgtca   480
gtcttcctct tccccccaaa acccaaggac accctcatga tctcccggac ccctgaggtc   540
acatgcgtgg tggtggacgt gagccacgaa gaccctgagg tcaagttcaa ctggtacgtg   600
```

```
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gtccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                        1107
```

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 33

Gly Arg Gly Glu Ala Glu
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide <400> SEQUENCE: 34

Ile Leu Gly Arg Ser Glu Thr Gln Glu
1               5

<210> SEQ ID NO 35

<400> SEQUENCE: 35

000

<210> SEQ ID NO 36
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 36

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 37
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His

```
                    85                  90                  95
Leu Pro Glu Ala Gly Gly Pro Glu Val Thr Tyr Glu Pro Pro Thr
                100                 105                 110

Ala Pro Thr
        115

<210> SEQ ID NO 38
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asp Ala Met Lys Arg Gly Leu Cys Cys Val Leu Leu Cys Gly
1               5                   10                  15

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
        50                  55                  60

Cys Tyr Ala Ser Trp Arg Asn Ser Ser Gly Thr Ile Glu Leu Val Lys
65              70                  75                  80

Lys Gly Cys Trp Asp Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
                100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Ala Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320
```

Ser Asp Gly Ser Phe Phe Leu Tyr Ser Lys Leu Thr Val Asp Lys Ser
            325                 330                 335

Arg Trp Gln Gln Gly Asn Val Phe Ser Cys Ser Val Met His Glu Ala
        340                 345                 350

Leu His Asn His Tyr Thr Gln Lys Ser Leu Ser Leu Ser Pro Gly Lys
        355                 360                 365

<210> SEQ ID NO 39
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
atggatgcaa tgaagagagg gctctgctgt gtgctgctgc tgtgtggagc agtcttcgtt    60
tcgcccggcg cctctgggcg tggggaggct gagacacggg agtgcatcta ctacaacgcc   120
aactgggagc tggagcgcac caaccagagc ggcctggagc gctgcgaagg cgagcaggac   180
aagcggctgc actgctacgc ctcctggcgc aacagctctg gcaccatcga gctcgtgaag   240
aagggctgct gggatgatga cttcaactgc tacgataggc aggagtgtgt ggccactgag   300
gagaaccccc aggtgtactt ctgctgctgt gaaggcaact tctgcaacga gcgcttcact   360
catttgccag aggctggggg cccggaagtc acgtacgagc accccccgac agcccccacc   420
ggtggtggaa ctcacacatg cccaccgtgc ccagcacctg aactcctggg gggaccgtca   480
gtcttcctct tccccccaaa acccaaggac accctcatga tctcccggac ccctgaggtc   540
acatgcgtgg tggtggacgt gagccacgaa gaccctgagg tcaagttcaa ctggtacgtg   600
gacggcgtgg aggtgcataa tgccaagaca aagccgcggg aggagcagta caacagcacg   660
taccgtgtgg tcagcgtcct caccgtcctg caccaggact ggctgaatgg caaggagtac   720
aagtgcaagg tctccaacaa agccctccca gcccccatcg agaaaaccat ctccaaagcc   780
aaagggcagc ccgagaacc acaggtgtac accctgcccc catcccggga ggagatgacc   840
aagaaccagg tcagcctgac ctgcctggtc aaaggcttct atcccagcga catcgccgtg   900
gagtgggaga gcaatgggca gccggagaac aactacaaga ccacgcctcc cgtgctggac   960
tccgacggct ccttcttcct ctatagcaag ctcaccgtgg acaagagcag gtggcagcag  1020
gggaacgtct tctcatgctc cgtgatgcat gaggctctgc acaaccacta cacgcagaag  1080
agcctctccc tgtccccggg taaatga                                      1107
```

<210> SEQ ID NO 40
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
tcatttaccc ggggacaggg agaggctctt ctgcgtgtag tggttgtgca gagcctcatg    60
catcacggag catgagaaga cgttcccctg ctgccacctg ctcttgtcca cggtgagctt   120
gctatagagg aagaaggagc cgtcggagtc cagcacggga ggcgtggtct tgtagttgtt   180
ctccggctgc ccattgctct cccactccac ggcgatgtcg ctgggataga agcctttgac   240
caggcaggtc aggctgacct ggttcttggt catctcctcc cgggatgggg gcagggtgta   300
```

```
cacctgtggt tctcggggct gcccttggc tttggagatg gttttctcga tgggggctgg    360
gagggctttg ttggagacct tgcacttgta ctccttgcca ttcagccagt cctggtgcag    420
gacggtgagg acgctgacca cacggtacgt gctgttgtac tgctcctccc gcggctttgt    480
cttggcatta tgcacctcca cgccgtccac gtaccagttg aacttgacct cagggtcttc    540
gtggctcacg tccaccacca cgcatgtgac ctcagggggtc cgggagatca tgagggtgtc    600
cttgggtttt gggggaaga ggaagactga cggtcccccc aggagttcag gtgctgggca    660
cggtgggcat gtgtgagttc caccaccggt gggggctgtc gggggtggct cgtacgtgac    720
ttccgggccc ccagcctctg gcaaatgagt gaagcgctcg ttgcagaagt tgccttcaca    780
gcagcagaag tacacctggg ggttctcctc agtggccaca cactcctgcc tatcgtagca    840
gttgaagtca tcatcccagc agccttctt cacgagctcg atggtgccag agctgttgcg    900
ccaggaggcg tagcagtgca gccgcttgtc ctgctcgcct tcgcagcgct ccaggccgct    960
ctggttggtg cgctccagct cccagttggc gttgtagtag atgcactccc gtgtctcagc    1020
ctccccacgc cagaggcgc cgggcgaaac gaagactgct ccacacagca gcagcacaca    1080
gcagagccct ctcttcattg catccat                                        1107
```

<210> SEQ ID NO 41
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Asp Ala Met Lys Arg Gly Leu Cys Cys Val Leu Leu Cys Gly
1               5                   10                  15

Ala Val Phe Val Ser Pro Gly Ala Ala Glu Thr Arg Glu Cys Ile Tyr
                20                  25                  30

Tyr Asn Ala Asn Trp Glu Leu Glu Arg Thr Asn Gln Ser Gly Leu Glu
            35                  40                  45

Arg Cys Glu Gly Glu Gln Asp Lys Arg Leu His Cys Tyr Ala Ser Trp
        50                  55                  60

Arg Asn Ser Ser Gly Thr Ile Glu Leu Val Lys Lys Gly Cys Trp Asp
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
```

```
             210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 42
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atggatgcaa tgaagagagg gctctgctgt gtgctgctgc tgtgtggagc agtcttcgtt      60
tcgcccggcg ccgctgagac acgggagtgc atctactaca acgccaactg ggagctggag     120
cgcaccaacc agagcggcct ggagcgctgc gaaggcgagc aggacaagcg gctgcactgc     180
tacgcctcct ggcgcaacag ctctggcacc atcgagctcg tgaagaaggg ctgctgggac     240
gatgacttca actgctacga taggcaggag tgtgtggcca ctgaggagaa cccccaggtg     300
tacttctgct gctgtgaagg caacttctgc aacgagcgct tcactcattt gccagaggct     360
gggggcccgg aagtcacgta cgagccaccc ccgacaggtg gtggaactca cacatgccca     420
ccgtgcccag cacctgaact cctgggggga ccgtcagtct tcctcttccc cccaaaaccc     480
aaggacaccc tcatgatctc ccggacccct gaggtcacat gcgtggtggt ggacgtgagc     540
cacgaagacc ctgaggtcaa gttcaactgg tacgtggacg gcgtggaggt gcataatgcc     600
aagacaaagc cgcgggagga gcagtacaac agcacgtacc gtgtggtcag cgtcctcacc     660
gtcctgcacc aggactggct gaatggcaag gagtacaagt gcaaggtctc caacaaagcc     720
ctcccagccc ccatcgagaa aaccatctcc aaagccaaag gcagccccg agaaccacag     780 gtgtacaccc tgcccccatc ccgggaggag atgaccaaga accaggtcag cctgacctgc     840
ctggtcaaag gcttctatcc cagcgacatc gccgtggagt gggagagcaa tgggcagccg     900
gagaacaact acaagaccac gcctcccgtg ctggactccg acggctcctt cttcctctat     960
agcaagctca ccgtggacaa gagcaggtgg cagcaggga acgtcttctc atgctccgtg    1020
atgcatgagg ctctgcacaa ccactacacg cagaagagcc tctccctgtc cccgggtaaa    1080
tga                                                                  1083
```

<210> SEQ ID NO 43
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

```
tcatttaccc ggggacaggg agaggctctt ctgcgtgtag tggttgtgca gagcctcatg      60
catcacggag catgagaaga cgttccctg ctgccacctg ctcttgtcca cggtgagctt     120
gctatagagg aagaaggagc cgtcggagtc cagcacggga ggcgtggtct tgtagttgtt     180
ctccggctgc ccattgctct cccactccac ggcgatgtcg ctgggataga agcctttgac     240
caggcaggtc aggctgacct ggttcttggt catctcctcc cgggatgggg gcagggtgta     300
cacctgtggt tctcggggct gccctttggc tttggagatg gttttctcga tggggctgg      360
gagggctttg ttggagacct tgcacttgta ctccttgcca ttcagccagt cctggtgcag     420
gacggtgagg acgctgacca cacggtacgt gctgttgtac tgctcctccc gcggctttgt     480
cttggcatta tgcacctcca cgccgtccac gtaccagttg aacttgacct cagggtcttc     540
gtggctcacg tccaccacca cgcatgtgac ctcaggggtc cggagatca tgagggtgtc      600
cttgggtttt ggggggaaga ggaagactga cggtccccc aggagttcag gtgctgggca      660
cggtgggcat gtgtgagttc caccacctgt cgggggtggc tcgtacgtga cttccgggcc     720
cccagcctct ggcaaatgag tgaagcgctc gttgcagaag ttgccttcac agcagcagaa     780
gtacacctgg gggttctcct cagtggccac acactcctgc ctatcgtagc agttgaagtc     840
atcgtcccag cagccttct tcacgagctc gatggtgcca gagctgttgc gccaggaggc     900
gtagcagtgc agccgcttgt cctgctcgcc ttcgcagcgc tccaggccgc tctggttggt     960
gcgctccagc tcccagttgg cgttgtagta gatgcactcc cgtgtctcag cggcgccggg    1020
cgaaacgaag actgctccac acagcagcag cacacagcag agccctctct tcattgcatc    1080
cat                                                                   1083
```

<210> SEQ ID NO 44
<211> LENGTH: 335
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Gly Gly Gly Thr His
            100                 105                 110
```

```
Thr Cys Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr
            100                 105

<210> SEQ ID NO 46
<211> LENGTH: 1083
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 46

```
atggatgcaa tgaagagagg gctctgctgt gtgctgctgc tgtgtggagc agtcttcgtt      60
tcgcccggcg ccgccgaaac ccgcgaatgt atttattaca atgctaattg ggaactcgaa     120
cggacgaacc aatccgggct cgaacggtgt gaggggaac aggataaacg cctccattgc      180
tatgcgtcgt ggaggaactc ctccgggacg attgaactgg tcaagaaagg gtgctgggac     240
gacgatttca attgttatga ccgccaggaa tgtgtcgcga ccgaagagaa tccgcaggtc     300
tatttctgtt gttgcgaggg gaatttctgt aatgaacggt ttacccacct ccccgaagcc     360
ggcgggcccg aggtgaccta tgaacccccg cccaccggtg gtggaactca cacatgccca     420
ccgtgcccag cacctgaact cctgggggga ccgtcagtct tcctcttccc cccaaaaccc     480
aaggacaccc tcatgatctc ccggacccct gaggtcacat gcgtggtggt ggacgtgagc     540
cacgaagacc ctgaggtcaa gttcaactgg tacgtggacg gcgtggaggt gcataatgcc     600
aagacaaagc cgcggggagga gcagtacaac agcacgtacc gtgtggtcag cgtcctcacc     660
gtcctgcacc aggactggct gaatggcaag gagtacaagt gcaaggtctc caacaaagcc     720
ctcccagccc ccatcgagaa aaccatctcc aaagccaaag gcagccccg agaaccacag     780
gtgtacaccc tgcccccatc ccgggaggag atgaccaaga accaggtcag cctgacctgc     840
ctggtcaaag gcttctatcc cagcgacatc gccgtggagt gggagagcaa tgggcagccg     900
gagaacaact acaagaccac gcctcccgtg ctggactccg acggctcctt cttcctctat     960
agcaagctca ccgtggacaa gagcaggtgg cagcagggga acgtcttctc atgctccgtg    1020
atgcatgagg ctctgcacaa ccactacacg cagaagagcc tctccctgtc cccgggtaaa    1080
tga                                                                  1083
```

<210> SEQ ID NO 47
<211> LENGTH: 1083
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 47

```
tcatttaccc gggacagggg agaggctctt ctgcgtgtag tggttgtgca gagcctcatg      60
catcacggag catgagaaga cgttcccctg ctgccacctg ctcttgtcca cggtgagctt     120
gctatagagg aagaaggagc cgtcggagtc cagcacggga ggcgtggtct tgtagttgtt     180
ctccggctgc ccattgctct cccactccac ggcgatgtcg ctgggataga agcctttgac     240
caggcaggtc aggctgacct ggttcttggt catctcctcc cgggatgggg gcagggtgta     300
cacctgtggt tctcggggct gccctttggc tttggagatg gttttctcga tggggctgg      360
gagggctttg ttggagacct tgcacttgta ctccttgcca ttcagccagt cctggtgcag     420
gacggtgagg acgctgacca cacggtacgt gctgttgtac tgctcctccc gcggcttttgt     480
cttggcatta tgcacctcca cgccgtccac gtaccagttg aacttgacct cagggtcttc     540
gtggctcacg tccaccacca gcatgtgac ctcaggggtc cgggagatca tgagggtgtc      600
cttgggtttt ggggggaaga ggaagactga cggtccccc aggagttcag gtgctgggca     660
cggtgggcat gtgtgagttc caccaccggt gggcggggt tcataggtca cctcgggccc     720
```

```
gccggcttcg gggaggtggg taaaccgttc attacagaaa ttcccctcgc aacaacagaa    780
atagacctgc ggattctctt cggtcgcgac acattcctgg cggtcataac aattgaaatc    840
gtcgtcccag cacccttct tgaccagttc aatcgtcccg gaggagttcc tccacgacgc     900
atagcaatgg aggcgtttat cctgttcccc ctcacaccgt tcgagcccgg attggttcgt    960
ccgttcgagt tcccaattag cattgtaata aatacattcg cgggtttcgg cggcgccggg   1020
cgaaacgaag actgctccac acagcagcag cacacagcag agccctctct tcattgcatc   1080
cat                                                                 1083

<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gaaacccgcg aatgtattta ttacaatgct aattgggaac tcgaacggac gaaccaatcc     60
gggctcgaac ggtgtgaggg ggaacaggat aaacgcctcc attgctatgc gtcgtggagg    120
aactcctccg ggacgattga actggtcaag aaagggtgct gggacgacga tttcaattgt    180
tatgaccgcc aggaatgtgt cgcgaccgaa gagaatccgc aggtctattt ctgttgttgc    240
gaggggaatt tctgtaatga acggtttacc cacctccccg aagccggcgg gcccgaggtg    300
acctatgaac ccccgcccac c                                              321

<210> SEQ ID NO 49
<211> LENGTH: 141
<212> TYPE: PRT
<213> ORGANISM: Homo sapiens

<400> SEQUENCE: 49

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 50
<211> LENGTH: 141
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 50

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu
    130                 135                 140

<210> SEQ ID NO 51
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Gly Pro Trp Ala Ser Thr Thr Ile
            100                 105                 110

Pro Ser Gly Gly Pro Glu Ala Thr Ala Ala Gly Asp Gln Gly Ser
        115                 120                 125

Gly Ala Leu Trp Leu Cys Leu Glu Gly Pro Ala His Glu Thr Gly Gly
    130                 135                 140

Gly Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

-continued

```
Asp Pro Glu Val Lys Phe Asn Trp Tyr Val Asp Gly Val Glu Val His
            195                 200                 205

Asn Ala Lys Thr Lys Pro Arg Glu Glu Gln Tyr Asn Ser Thr Tyr Arg
        210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Gly Gly Gly Gly
1               5

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Gly Gly Gly
1

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Gly Gly Gly Gly
1               5
```

<210> SEQ ID NO 55

<400> SEQUENCE: 55

000

<210> SEQ ID NO 56
<211> LENGTH: 116
<212> TYPE: PRT
<213> ORGANISM: Homo sapiens

<400> SEQUENCE: 56

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115
```

<210> SEQ ID NO 57
<211> LENGTH: 150
<212> TYPE: PRT
<213> ORGANISM: Rattus sp.

<400> SEQUENCE: 57

```
Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150
```

<210> SEQ ID NO 58
<211> LENGTH: 150

<212> TYPE: PRT
<213> ORGANISM: Sus sp.

<400> SEQUENCE: 58

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 59
<211> LENGTH: 150
<212> TYPE: PRT
<213> ORGANISM: Mus sp.

<400> SEQUENCE: 59

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
130                 135                 140

Pro Ile Gly Gly Leu Ser
145                 150

<210> SEQ ID NO 60
<211> LENGTH: 150
<212> TYPE: PRT
<213> ORGANISM: Homo sapiens

```
<400> SEQUENCE: 60

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 61
<211> LENGTH: 150
<212> TYPE: PRT
<213> ORGANISM: Bos sp.

<400> SEQUENCE: 61

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150

<210> SEQ ID NO 62
<211> LENGTH: 150
<212> TYPE: PRT
<213> ORGANISM: Xenopus sp.

<400> SEQUENCE: 62

Met Gly Ala Ser Val Ala Leu Thr Phe Leu Leu Leu Leu Ala Thr Phe
```

```
                1               5                   10                  15
Arg Ala Gly Ser Gly His Asp Glu Val Glu Thr Arg Glu Cys Ile Tyr
                    20                  25                  30

Tyr Asn Ala Asn Trp Glu Leu Glu Lys Thr Asn Gln Ser Gly Val Glu
                    35                  40                  45

Arg Leu Val Glu Gly Lys Lys Asp Lys Arg Leu His Cys Tyr Ala Ser
            50                  55                  60

Trp Arg Asn Asn Ser Gly Phe Ile Glu Leu Val Lys Lys Gly Cys Trp
65                      70                  75                  80

Leu Asp Asp Phe Asn Cys Tyr Asp Arg Gln Glu Cys Ile Ala Lys Glu
                    85                  90                  95

Glu Asn Pro Gln Val Phe Phe Cys Cys Cys Glu Gly Asn Tyr Cys Asn
                    100                 105                 110

Lys Lys Phe Thr His Leu Pro Glu Val Glu Thr Phe Asp Pro Lys Pro
                    115                 120                 125

Gln Pro Ser Ala Ser Val Leu Asn Ile Leu Ile Tyr Ser Leu Leu Pro
            130                 135                 140

Ile Val Gly Leu Ser Met
145                 150
```

<210> SEQ ID NO 63
<211> LENGTH: 150
<212> TYPE: PRT
<213> ORGANISM: Homo sapiens

<400> SEQUENCE: 63

```
Met Gly Ala Ala Ala Lys Leu Ala Phe Ala Val Phe Leu Ile Ser Cys
1                   5                   10                  15

Ser Ser Gly Ala Ile Leu Gly Arg Ser Glu Thr Gln Glu Cys Leu Phe
                    20                  25                  30

Phe Asn Ala Asn Trp Glu Lys Asp Arg Thr Asn Gln Thr Gly Val Glu
                    35                  40                  45

Pro Cys Tyr Gly Asp Lys Asp Lys Arg Arg His Cys Phe Ala Thr Trp
            50                  55                  60

Lys Asn Ile Ser Gly Ser Ile Glu Ile Val Lys Gln Gly Cys Trp Leu
65                      70                  75                  80

Asp Asp Ile Asn Cys Tyr Asp Arg Thr Asp Cys Val Glu Lys Lys Asp
                    85                  90                  95

Ser Pro Glu Val Tyr Phe Cys Cys Cys Glu Gly Asn Met Cys Asn Glu
                    100                 105                 110

Lys Phe Ser Tyr Phe Pro Glu Met Glu Val Thr Gln Pro Thr Ser Asn
                    115                 120                 125

Pro Val Thr Pro Lys Pro Pro Tyr Tyr Asn Ile Leu Leu Tyr Ser Leu
            130                 135                 140

Val Pro Leu Met Leu Ile
145                 150
```

<210> SEQ ID NO 64
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Thr His Thr Cys Pro Pro Cys Pro Ala Pro Glu Leu Leu Gly Gly Pro

```
            1               5                  10                 15
Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
                35                  40                  45

Pro Glu Val Lys Phe Asn Trp Tyr Val Asp Gly Val Glu Val His Asn
            50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
                115                 120                 125

Leu Pro Pro Ser Arg Glu Glu Met Thr Lys Asn Gln Val Ser Leu Thr
            130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
                180                 185                 190

Ser Arg Trp Gln Gln Gly Asn Val Phe Ser Cys Ser Val Met His Glu
            195                 200                 205

Ala Leu His Asn His Tyr Thr Gln Lys Ser Leu Ser Leu Ser Pro Gly
            210                 215                 220

Lys
225

<210> SEQ ID NO 65
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
            100                 105                 110

Ser Lys Thr Lys Gly Gln Pro Arg Glu Pro Gln Val Tyr Thr Leu Pro
            115                 120                 125
```

```
Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 66

His His His His His His
1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: May encompass 2 to 10 "Gly" residues; See
      specification as filed for detailed description of substitutions
      and preferred embodiments

<400> SEQUENCE: 67

Gly Gly Gly Gly Gly Gly Gly Gly Gly Gly
1               5                   10

<210> SEQ ID NO 68
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
atggatgcaa tgaagagagg gctctgctgt gtgctgctgc tgtgtggagc agtcttcgtt      60
tcgcccggcg cctctgggcg tggggaggct gagacacggg agtgcatcta ctacaacgcc     120
aactgggagc tggagcgcac caaccagagc ggcctggagc gctgcgaagg cgagcaggac     180
aagcggctgc actgctacgc ctcctggcgc aacagctctg gcaccatcga gctcgtgaag     240
aagggctgct gggacgatga cttcaactgc tacgataggc aggagtgtgt ggccactgag     300
gagaaccccc aggtgtactt ctgctgctgt gaaggcaact tctgcaacga gcgcttcact     360
catttgccag aggctggggg cccggaagtc acgtacgagc accccccgac agccccacc      420 ggtggtggaa ctcacacatg cccaccgtgc ccagcacctg aactcctggg gggaccgtca     480
```

```
gtcttcctct tcccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gtccccatcg agaaaaccat ctccaaagcc    780
aaagggcagc cccgagaacc acaggtgtac accctgcccc catcccggga ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctggac    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaatga                                       1107
```

<210> SEQ ID NO 69
<211> LENGTH: 154
<212> TYPE: PRT
<213> ORGANISM: Artificial Sequence
<220> FEATURE:
<223> OTHER INFORMATION: Description of Artificial Sequence: Synthetic
     consensus polypeptide
<220> FEATURE:
<221> NAME/KEY: MOD_RES
<222> LOCATION: (8)..(8)
<223> OTHER INFORMATION: Thr, Ala or not present
<220> FEATURE:
<221> NAME/KEY: MOD_RES
<222> LOCATION: (121)..(121)
<223> OTHER INFORMATION: Pro, Ala, Val or Met

<400> SEQUENCE: 69

```
Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150
```